United States Patent
Park et al.

(10) Patent No.: US 12,173,070 B2
(45) Date of Patent: Dec. 24, 2024

(54) ANTI-PD-L1/ANTI-LAG3 BISPECIFIC ANTIBODIES AND USES THEREOF

(71) Applicant: ABL BIO INC., Seongnam-Si (KR)

(72) Inventors: Eunyoung Park, Seongnam-Si (KR); Yangsoon Lee, Seongnam-Si (KR); Uijung Jung, Seongnam-Si (KR); YoungKwang Kim, Seongnam-Si (KR); Yeun Ju Kim, Seongnam-Si (KR); Youngdon Pak, Seongnam-Si (KR); Sang Hoon Lee, Seongnam-Si (KR); Weon-Kyoo You, Seongnam-Si (KR); Jaeho Jung, Seongnam-Si (KR); Lei Fang, Shanghai (CN); Wenqing Jiang, Shanghai (CN)

(73) Assignee: ABL BIO INC., Seongnam-Si (KR)

( * ) Notice: Subject to any disclaimer, the term of this patent is extended or adjusted under 35 U.S.C. 154(b) by 612 days.

(21) Appl. No.: 17/269,784

(22) PCT Filed: Aug. 21, 2019

(86) PCT No.: PCT/CN2019/101747
§ 371 (c)(1),
(2) Date: Feb. 19, 2021

(87) PCT Pub. No.: WO2020/038397
PCT Pub. Date: Feb. 27, 2020

(65) Prior Publication Data
US 2022/0363763 A1     Nov. 17, 2022

(30) Foreign Application Priority Data
Aug. 21, 2018 (WO) ................ PCT/CN2018/101547
May 22, 2019 (WO) ................ PCT/CN2019/087943

(51) Int. Cl.
*C07K 16/28* (2006.01)
*A61K 39/00* (2006.01)
*A61P 35/00* (2006.01)

(52) U.S. Cl.
CPC .......... *C07K 16/2827* (2013.01); *A61P 35/00* (2018.01); *A61K 2039/505* (2013.01);
(Continued)

(58) Field of Classification Search
CPC ............ C07K 16/2827; C07K 2317/31; C07K 2317/565; C07K 2317/76; A61P 35/00; A61K 2039/505
See application file for complete search history.

(56) References Cited

U.S. PATENT DOCUMENTS

| | | | |
|---|---|---|---|
| 10,059,769 B2 * | 8/2018 | Fang | ........................ A61P 31/08 |
| 2017/0355756 A1 * | 12/2017 | Julien | ...................... A61P 25/00 |

FOREIGN PATENT DOCUMENTS

| | | |
|---|---|---|
| JP | 2017-535528 A | 11/2017 |
| KR | 10-2018-0039182 A | 4/2018 |

(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Jeffrey Stucker
*Assistant Examiner* — Selam Berhane
(74) *Attorney, Agent, or Firm* — Sughrue Mion, PLLC

(57) ABSTRACT

The present disclosure provides an anti-PD-L1/anti-LAG3 bispecific antibody capable to effectively block the interactions between PD-L1 and its receptor PD-1 and between LAG3 and its ligand (e.g., a MHC class II molecule and (Continued)

FGL1). The bispecific antibody may have high binding affinity to both of a PD-L1 protein (e.g., a human PD-L1 protein) and a LAG3 protein (e.g., a human LAG3 protein). Also provided are antibodies and fragments that have specificity to the PD-L1 or LAG3 protein alone, or antibodies and fragments having additional specificity to one or more other antigens.

9 Claims, 45 Drawing Sheets

Specification includes a Sequence Listing.

(52) U.S. Cl.
CPC .... *C07K 2317/31* (2013.01); *C07K 2317/565* (2013.01); *C07K 2317/76* (2013.01)

(56) References Cited

FOREIGN PATENT DOCUMENTS

| WO | WO-2008068048 A2 | * | 6/2008 | ............ A61P 31/10 |
|---|---|---|---|---|
| WO | 2016/061142 A1 | | 4/2016 | |
| WO | WO-2017215590 A1 | * | 12/2017 | ............ A61K 35/17 |
| WO | 2018/153340 A1 | | 8/2018 | |
| WO | 2019/185029 A1 | | 10/2019 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Doody et al., "Abstract PR06: A LAG-3/PD-L1 bispecific antibody inhibits tumour growth in two syngeneic colon carcinoma models" Cancer Immunology Research, 2016, (1 Page Total).

Korean Office Action dated May 24, 2023 in Korean Application No. 10-2021-7008267.

Jacqueline Doody et al., "A LAG-3/PD-L1 bispecific antibody inhibits tumor growth in two syngeneic colon carcinoma models", Cancer Immunology Research, Nov. 30, 2016, 2 pages, vol. 4, No. 11 Suppl.

Eva Dahlén et al., "Bispecific antibodies in cancer immunotherapy", Therapeutic Advances in Vaccines and Immunotherapy, Mar. 28, 2018, pp. 3-17, vol. 6, No. 1.

Written Opinion for PCT/CN2019/101747, dated Nov. 21, 2019.

International Search Report for PCT/CN2019/101747, dated Nov. 21, 2019.

Communication ("Notice of Reasons for Refusal") dated Apr. 13, 2022 in Japanese Patent Application No. 2021-510096.

Communication ("Decision to Grant a Patent") dated Oct. 18, 2022 in Japanese Patent Application No. 2021-510096.

Kraman et al, "Abstract 5651: A LAG-3/PD-L1 bispecific antibody inhibits tumor growth in two syngeneic colon carcinoma models"; Cancer Research, Jul. 1, 2017, vol. 77 (13_Supplement): 5651.

Office Action issued Apr. 19, 2022 in Japanese Application No. 2021-510096.

Matthew Kraman, et al. "A LAG-3/PD-L1 bispecific antibody inhibits tumour growth in two syngeneic colon carcinoma models" Poster 128, Nov. 2016, (1 page).

Jacqueline Doody, et al. "Abstract B091: A LAG-3/PD-L1 bispecific antibody inhibits tumor growth in two syngeneic colon carcinoma models" Cancer Immunology Research, vol. 4, No. 11, Sep. 2016, (5 pages).

Mustapha Faroudi, et al. "Abstract 2399: LAG-3/PD-L1 mAb 2 can overcome PD-L1-mediated compensatory upregulation of LAG-3 induced by single-agent checkpoint blockade" Cancer Research, 2019, (4 pages).

Seng-Ryong Woo, et al. "Immune Inhibitory Molecules LAG-3 and PD-1 Synergistically Regulate T-cell Function to Promote Tumoral Immune Escape", Cancer Research, vol. 72, No. 4, Dec. 2011, pp. 917-927, (26 pages).

Extended European Search Report dated Sep. 5, 2023 in Application No. 19851296.4.

* cited by examiner

IC50=21.40 nM

|  | 25F7 | B3807 |
|---|---|---|
| EC50 (nM) | 0.22 | 0.06 |

SEQUENCE LISTING

```
<160> NUMBER OF SEQ ID NOS: 555

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Thr Ile Ser Asp Gly Gly Gly Tyr Ile Tyr Tyr Ser Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Glu Phe Gly Lys Arg Tyr Ala Leu Asp Tyr
```

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

```
Lys Ala Ser Gln Asp Val Thr Pro Ala Val Ala
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

```
Ser Thr Ser Ser Arg Tyr Thr
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
Gln Gln His Tyr Thr Thr Pro Leu Thr
1               5
```

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

```
Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Ser Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Ile Cys
                85                  90                  95

Ala Arg Glu Phe Gly Lys Arg Tyr Ala Leu Asp Tyr Trp Gly Gln Gly
            100                 105                 110

Thr Ser Val Thr Val Ser Ser
        115
```

<210> SEQ ID NO 8
<211> LENGTH: 119
<212> TYPE: PRT

<213> ORGANISM: Artificial Sequence
<220> FEATURE:
<223> OTHER INFORMATION: Synthetic

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

```
Asp Met Ser Trp Val Arg Gln Ala Pro Gly Lys Ser Leu Glu Trp Val
         35                  40                  45

Ala Thr Ile Ser Asp Gly Gly Tyr Ile Tyr Tyr Ser Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Ile Cys
             85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115
```

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Asp Met Ser Trp Ile Arg Gln Ala Pro Gly Lys Gly Leu Glu Trp Val
         35                  40                  45

Ser Thr Ile Ser Asp Gly Gly Tyr Ile Tyr Tyr Ser Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115
```

<210> SEQ ID NO 12
<211> LENGTH: 119
<212> TYPE: PRT
<213> ORGANISM: Artificial Sequence
<220> FEATURE:
<223> OTHER INFORMATION: Synthetic

<400> SEQUENCE: 12

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Asp Met Ser Trp Ile Arg Gln Ala Pro Gly Lys Gly Leu Glu Trp Val
         35                  40                  45

Ala Thr Ile Ser Asp Gly Gly Tyr Ile Tyr Tyr Ser Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
```

```
                85                  90                  95
Ala Arg Glu Phe Gly Lys Arg Tyr Ala Leu Asp Tyr Trp Gln Gly
            100                 105                 110

Thr Thr Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gln Gly
            100                 105                 110

Thr Thr Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: Synthetic

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gln Gly
            100                 105                 110

Thr Thr Val Thr Val Ser Ser
        115

<210> SEQ ID NO 15
<211> LENGTH: 119
```

```
<212> TYPE: PRT
<213> ORGANISM: Artificial Sequence
<220> FEATURE:
<223> OTHER INFORMATION: Synthetic

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Ile Cys
            85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115
```

```
<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115
```

```
<210> SEQ ID NO 19
<211> LENGTH: 119
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Ser Leu Glu Trp Val
        35                  40                  45

Ala Thr Ile Ser Glu Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Asp Glu Asp Thr Ala Val Tyr Ile Cys
            85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
            85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Val Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
            85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 22

<211> LENGTH: 119
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
            115

<210> SEQ ID NO 25
<211> LENGTH: 119
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
            115

<210> SEQ ID NO 26
<211> LENGTH: 119
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Thr Pro Glu Lys Ser Leu Glu Trp Val
        35                  40                  45

Ala Thr Ile Ser Asp Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Arg Ala Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Leu Val Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ser Pro Lys Leu Leu Ile
        35                  40                  45

Tyr Ser Thr Ser Ser Arg Tyr Thr Gly Val Pro Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105
```

<210> SEQ ID NO 30
<211> LENGTH: 108
<212> TYPE: PRT
<213> ORGANISM: Artificial Sequence
<220> FEATURE:
<223> OTHER INFORMATION: Synthetic

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
                85                  90                  95

Thr Phe Gly Gln Gly Thr Lys Leu Glu Ile Lys Arg
            100                 105
```

<210> SEQ ID NO 31
<211> LENGTH: 108
<212> TYPE: PRT
<213> ORGANISM: Artificial Sequence
<220> FEATURE:
<223> OTHER INFORMATION: Synthetic

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Asp Arg Phe Thr Gly
 50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln His Tyr Thr Thr Pro Leu
            85                  90                  95

Thr Phe Gly Gln Gly Thr Lys Leu Glu Ile Lys Arg
            100                 105

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
            85                  90                  95

Thr Phe Gly Gln Gly Thr Lys Leu Glu Ile Lys Arg
            100                 105

<210> SEQ ID NO 33
<211> LENGTH: 108
<212> TYPE: PRT
<213> ORGANISM: Artificial Sequence
<220> FEATURE:
<223> OTHER INFORMATION: Synthetic

<400> SEQUENCE: 33

Asp Ile Gln Met Thr Gln Ser Pro Ser Ser Leu Ser Ala Ser Val Gly
1               5                   10                  15

Asp Arg Val Thr Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Leu
            85                  90                  95

Thr Phe Gly Gln Gly Thr Lys Leu Glu Ile Lys Arg
            100                 105

<210> SEQ ID NO 34
<211> LENGTH: 357
<212> TYPE: DNA
<213> ORGANISM: Artificial Sequence
<220> FEATURE:
<223> OTHER INFORMATION: Synthetic

<400> SEQUENCE: 34

| | |
|---|---|
| gaggtgaagc tggtggagag cggcggagat ctggtgaagc ctggcggcag cctgaagctg | 60 |
| agctgtgccg ccagcggctt caccttcagc agctacgaca tgagctgggt gaggcagacc | 120 |
| cccgagaaga gcctggagtg ggtggccacc atcagcgatg gcggcggcta catctactac | 180 |
| agcgacagcg tgaagggcag gttcaccatc agcagggaca cgccaagaa caacctgtac | 240 |
| ctgcagatga gcagcctgag gagcgaggac accgccctgt acatctgcgc cagggagttc | 300 |
| ggcaagaggt acgccctgga ctactgggga cagggcacca cgtgaccgt gagcagc | 357 |

```
<210> SEQ ID NO 35
<211> LENGTH: 357
<212> TYPE: DNA
<213> ORGANISM: Artificial Sequence
<220> FEATURE:
<223> OTHER INFORMATION: Synthetic

<400> SEQUENCE: 35
```

| | |
|---|---|
| gaggtgcagc tggtggagag cggaggagga ctggtgaagc ccggaggcag cctgagactg | 60 |
| agctgcgctg ccagcggctt caccttcagc agctacgaca tgagctgggt gagacaggcc | 120 |
| cctggcaaag gcctggagtg ggtgagcacc atctccgatg gcggcggcta catctattac | 180 |
| tccgacagcg tgaagggcag gttcaccatc agcagggaca cgccaagaa cagcctgtac | 240 |
| ctgcagatga acagcctgag ggccgaggac accgccgtgt actactgcgc cagggagttc | 300 |
| ggcaaaaggt acgccctgga ctactggggc cagggcacaa ccgtgaccgt gagcagc | 357 |

```
<210> SEQ ID NO 36
<211> LENGTH: 357
<212> TYPE: DNA
<213> ORGANISM: Artificial Sequence
<220> FEATURE:
<223> OTHER INFORMATION: Synthetic

<400> SEQUENCE: 36
```

| | |
|---|---|
| gaggtgcagc tggtggagag cggaggagga ctggtgaagc ccggaggcag cctgagactg | 60 |
| agctgcgctg ccagcggctt caccttcagc agctacgaca tgagctgggt gagacaggcc | 120 |
| cctggcaaag gcctggagtg ggtggccacc atctccgatg gcggcggcta catctattac | 180 |
| tccgacagcg tgaagggcag gttcaccatc agcagggaca cgccaagaa cagcctgtac | 240 |
| ctgcagatga acagcctgag ggccgaggac accgccgtgt actactgcgc cagggagttc | 300 |
| ggcaaaaggt acgccctgga ctactggggc cagggcacaa ccgtgaccgt gagcagc | 357 |

```
<210> SEQ ID NO 37
<211> LENGTH: 357
<212> TYPE: DNA
<213> ORGANISM: Artificial Sequence
<220> FEATURE:
<223> OTHER INFORMATION: Synthetic

<400> SEQUENCE: 37
```

| | |
|---|---|
| gaggtgcagc tggtggagag cggaggagga ctggtgaagc ccggaggcag cctgagactg | 60 |
| agctgcgctg ccagcggctt caccttcagc agctacgaca tgagctgggt gagacaggcc | 120 |
| cctggcaaaa gcctggagtg ggtggccacc atctccgatg gcggcggcta catctattac | 180 |
| tccgacagcg tgaagggcag gttcaccatc agcagggaca cgccaagaa cagcctgtac | 240 |
| ctgcagatga acagcctgag ggccgaggac accgccgtgt acatctgcgc cagggagttc | 300 |
| ggcaaaaggt acgccctgga ctactggggc cagggcacaa ccgtgaccgt gagcagc | 357 |

```
<210> SEQ ID NO 38
<211> LENGTH: 357
<212> TYPE: DNA
<213> ORGANISM: Artificial Sequence
<220> FEATURE:
<223> OTHER INFORMATION: Synthetic

<400> SEQUENCE: 38
gaggtgcagc tggtggagag cggaggagga ctggtgaagc ccggaggcag cctgagactg     60
agctgcgctg ccagcggctt caccttcagc agctacgaca tgagctggat cagacaggcc    120
cctggcaaag gcctggagtg ggtgagcacc atctccgatg gcggcggcta catctattac    180
tccgacagcg tgaagggcag gttcaccatc agcagggaca cgccaagaa cagcctgtac     240 ctgcagatga acagcctgag ggccgaggac accgccgtgt actactgcgc cagggagttc    300
ggcaaaaggt acgccctgga ctactggggc cagggcacaa ccgtgaccgt gagcagc       357

<210> SEQ ID NO 39
<211> LENGTH: 357
<212> TYPE: DNA
<213> ORGANISM: Artificial Sequence
<220> FEATURE:
<223> OTHER INFORMATION: Synthetic

<400> SEQUENCE: 39
gaggtgcagc tggtggagag cggaggagga ctggtgaagc ccggaggcag cctgagactg     60
agctgcgctg ccagcggctt caccttcagc agctacgaca tgagctggat cagacaggcc    120
cctggcaaag gcctggagtg ggtggccacc atctccgatg gcggcggcta catctattac    180
tccgacagcg tgaagggcag gttcaccatc agcagggaca cgccaagaa cagcctgtac     240 ctgcagatga acagcctgag ggccgaggac accgccgtgt actactgcgc cagggagttc    300
ggcaaaaggt acgccctgga ctactggggc cagggcacaa ccgtgaccgt gagcagc       357

<210> SEQ ID NO 40
<211> LENGTH: 357
<212> TYPE: DNA
<213> ORGANISM: Artificial Sequence
<220> FEATURE:
<223> OTHER INFORMATION: Synthetic

<400> SEQUENCE: 40
gaggtgcagc tggtggagag cggaggagga ctggtgaagc ccggaggcag cctgagactg     60
agctgcgctg ccagcggctt caccttcagc agctacgaca tgagctgggt gagacaggcc    120
cctggcaaaa gcctggagtg ggtggccacc atctccgatg gcggcggcta catctattac    180
tccgacagcg tgaagggcag gttcaccatc agcagggaca cgccaagaa cagcctgtac     240 ctgcagatga acagcctgag ggccgaggac accgccgtgt acatctgcgc cagggagttc    300
ggcaaaaggt acgccctgga ctactggggc cagggcacaa ccgtgaccgt gagcagc       357

<210> SEQ ID NO 41
<211> LENGTH: 357
<212> TYPE: DNA
<213> ORGANISM: Artificial Sequence
<220> FEATURE:
<223> OTHER INFORMATION: Synthetic

<400> SEQUENCE: 41
gaggtgcagc tgctggagag cggaggagga ctggtgcaac ccggaggcag cctgagactg     60
agctgcgctg ccagcggctt caccttcagc agctacgaca tgagctgggt gagacaggcc    120
```

```
cctggcaaag gcctggagtg ggtgagcacc atctccgatg gcggcggcta catctattac    180
tccgacagcg tgaagggcag gttcaccatc agcagggaca acagcaagaa caccctgtac    240
ctgcagatga acagcctgag ggccgaggac accgccgtgt actactgcgc cagggagttc    300
ggcaaaaggt acgccctgga ctactggggc cagggcacaa ccgtgaccgt gagcagc       357
```

<210> SEQ ID NO 42
<211> LENGTH: 357
<212> TYPE: DNA
<213> ORGANISM: Artificial Sequence
<220> FEATURE:
<223> OTHER INFORMATION: Synthetic

<400> SEQUENCE: 42

```
gaggtgcagc tgctggagag cggaggagga ctggtgcaac ccggaggcag cctgagactg    60
agctgcgctg ccagcggctt caccttcagc agctacgaca tgagctgggt gagacaggcc    120
cctggcaaaa gcctggagtg ggtggccacc atctccgatg gcggcggcta catctattac    180
tccgacagcg tgaagggcag gttcaccatc agcagggaca acagcaagaa caccctgtac    240
ctgcagatga acagcctgag ggccgaggac accgccgtgt acatctgcgc cagggagttc    300
ggcaaaaggt acgccctgga ctactggggc cagggcacaa ccgtgaccgt gagcagc       357
```

<210> SEQ ID NO 43
<211> LENGTH: 357
<212> TYPE: DNA
<213> ORGANISM: Artificial Sequence
<220> FEATURE:
<223> OTHER INFORMATION: Synthetic

<400> SEQUENCE: 43

```
gaggtgcagc tggtggagag cggaggagga ctggtgcaac ccggaggcag cctgagactg    60
agctgcgctg ccagcggctt caccttcagc agctacgaca tgagctgggt gagacaggcc    120
cctggcaaag gcctggagtg ggtgagcacc atctccgatg gcggcggcta catctattac    180
tccgacagcg tgaagggcag gttcaccatc agcagggaca acgccaagaa cagcctgtac    240
ctgcagatga acagcctgag ggatgaggac accgccgtgt actactgcgc cagggagttc    300
ggcaaaaggt acgccctgga ctactggggc cagggcacaa ccgtgaccgt gagcagc       357
```

<210> SEQ ID NO 44
<211> LENGTH: 357
<212> TYPE: DNA
<213> ORGANISM: Artificial Sequence
<220> FEATURE:
<223> OTHER INFORMATION: Synthetic

<400> SEQUENCE: 44

```
gaggtgcagc tggtggagag cggaggagga ctggtgcaac ccggaggcag cctgagactg    60
agctgcgctg ccagcggctt caccttcagc agctacgaca tgagctgggt gagacaggcc    120
cctggcaaag gcctggagtg ggtggccacc atctccgatg gcggcggcta catctattac    180
tccgacagcg tgaagggcag gttcaccatc agcagggaca acgccaagaa cagcctgtac    240
ctgcagatga acagcctgag ggatgaggac accgccgtgt actactgcgc cagggagttc    300
ggcaaaaggt acgccctgga ctactggggc cagggcacaa ccgtgaccgt gagcagc       357
```

<210> SEQ ID NO 45
<211> LENGTH: 357
<212> TYPE: DNA
<213> ORGANISM: Artificial Sequence

```
<220> FEATURE:
<223> OTHER INFORMATION: Synthetic

<400> SEQUENCE: 45
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg gcggcggcta catctattac     180
tccgacagcg tgaagggcag gttcaccatc agcagggaca acgccaagaa cagcctgtac     240
ctgcagatga acagcctgag ggatgaggac accgccgtgt acatctgcgc cagggagttc     300
ggcaaaaggt acgccctgga ctactggggc cagggcacaa ccgtgaccgt gagcagc        357

<210> SEQ ID NO 46
<211> LENGTH: 357
<212> TYPE: DNA
<213> ORGANISM: Artificial Sequence
<220> FEATURE:
<223> OTHER INFORMATION: Synthetic

<400> SEQUENCE: 46
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgaag gcggcggcta catctattac     180
tccgacagcg tgaagggcag gttcaccatc agcagggaca acgccaagaa cagcctgtac     240
ctgcagatga acagcctgag ggatgaggac accgccgtgt acatctgcgc cagggagttc     300
ggcaaaaggt acgccctgga ctactggggc cagggcacaa ccgtgaccgt gagcagc        357

<210> SEQ ID NO 47
<211> LENGTH: 357
<212> TYPE: DNA
<213> ORGANISM: Artificial Sequence
<220> FEATURE:
<223> OTHER INFORMATION: Synthetic

<400> SEQUENCE: 47
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg cggcggcta catctattac      180 tccgacagcg tgaagggcag gttcaccatc agcagggaca acgccaagaa cagcctgtac     240
ctgcagatga acagcctgag ggatgaggac accgccgtgt acatctgcgc cagggagttc     300
ggcaaaaggt acgccctgga ctactggggc cagggcacaa ccgtgaccgt gagcagc        357

<210> SEQ ID NO 48
<211> LENGTH: 357
<212> TYPE: DNA
<213> ORGANISM: Artificial Sequence
<220> FEATURE:
<223> OTHER INFORMATION: Synthetic

<400> SEQUENCE: 48
gaggtgcagc tggtggagag cggaggagga ctggtgcaac ccggaggcag cctgagactg      60
agctgcgctg ccagcggctt caccttcagc agctacgaca tgagctgggt gagacaggcc     120
cctggcaaaa gcctggagtg ggtggccacc atctccgatg ttggcggcta catctattac     180
tccgacagcg tgaagggcag gttcaccatc agcagggaca acgccaagaa cagcctgtac     240
```

```
ctgcagatga acagcctgag ggatgaggac accgccgtgt acatctgcgc cagggagttc    300
ggcaaaaggt acgccctgga ctactggggc cagggcacaa ccgtgaccgt gagcagc       357
```

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49

```
gaggtgcagc tggtggagtc cggaggaggc ctggtgcaac tggaggctc cctgaggctg    60 tcctgtgccg cttccggctt caccttcagc tcctacgata tgagctgggt gaggcaggct    120
cctggaaagg gcctggagtg ggtggccacc atctccgacg gaggcggcta catctactac    180
tccgactccg tgaagggcag gttcaccatc tcccgggaca acgccaagaa ctccctgtac    240
ctgcagatga actctctcag ggctgaggac accgccgtgt attactgcgc cagggagttt    300
ggcaagaggt acgccctgga ttactggggc cagggcacac tggtgacagt gagctcc       357
```

<210> SEQ ID NO 50
<211> LENGTH: 357
<212> TYPE: DNA
<213> ORGANISM: Artificial Sequence
<220> FEATURE:
<223> OTHER INFORMATION: Synthetic

<400> SEQUENCE: 50

```
gaggtgcagc tggtggagtc cggaggaggc ctggtgcaac tggaggctc cctgaggctg    60 tcctgtgccg cttccggctt caccttcagc tcctacgata tgagctgggt gaggcaggct    120
cctggaaagg gcctggagtg ggtggccacc atctccgacg gaggcggcta catctactac    180
tccgactccg tgaagggcag gttcaccatc tcccgggaca acgccaagaa ctccctgtac    240
ctgcagatga actctctcag ggctgaggac accgccgtgt atatctgcgc cagggagttt    300
ggcaagaggt acgccctgga ttactggggc cagggcacac tggtgacagt gagctcc       357
```

<210> SEQ ID NO 51
<211> LENGTH: 357
<212> TYPE: DNA
<213> ORGANISM: Artificial Sequence
<220> FEATURE:
<223> OTHER INFORMATION: Synthetic

<400> SEQUENCE: 51

```
gaggtgcagc tggtggagtc cggaggaggc ctggtgcaac tggaggctc cctgaggctg    60 tcctgtgccg cttccggctt caccttcagc tcctacgata tgagctgggt gaggcaggct    120
cctggaaagg gcctggagtg ggtggccacc atctccgacg gaggcggcta catctactac    180
tccgactccg tgaagggcag gttcaccatc tcccgggaca acgccaagaa caacctgtac    240
ctgcagatga actctctcag ggctgaggac accgccgtgt atatctgcgc cagggagttt    300
ggcaagaggt acgccctgga ttactggggc cagggcacac tggtgacagt gagctcc       357
```

<210> SEQ ID NO 52
<211> LENGTH: 357
<212> TYPE: DNA
<213> ORGANISM: Artificial Sequence
<220> FEATURE:
<223> OTHER INFORMATION: Synthetic

<400> SEQUENCE: 52

```
gaggtgcagc tggtggagtc cggaggaggc ctggtgcaac ctggaggctc cctgaggctg    60
tcctgtgccg cttccggctt caccttcagc tcctacgata tgagctgggt gaggcagacc   120
cctgagaaga gcctggagtg ggtggccacc atctccgacg gaggcggcta catctactac   180
tccgactccg tgaagggcag gttcaccatc tcccgggaca cgccaagaa caacctgtac    240 ctgcagatga actctctcag ggctgaggac accgccgtgt atatctgcgc agggagttt   300 ggcaagaggt acgccctgga ttactggggc cagggcacac tggtgacagt gagctcc      357
```

<210> SEQ ID NO 53
<211> LENGTH: 357
<212> TYPE: DNA
<213> ORGANISM: Artificial Sequence
<220> FEATURE:
<223> OTHER INFORMATION: Synthetic

<400> SEQUENCE: 53

```
gaggtgcagc tggtggagtc cggaggaggc ctggtgcaac ctggaggctc cctgaggctg    60
tcctgtgccg cttccggctt caccttcagc tcctacgata tgagctgggt gaggcaggct   120
cctggaaagg gcctggagtg ggtggccacc atctccgacg gaggcggcta catctactac   180
tccgactccg tgaagggcag gttcaccatc tcccgggaca cgccaagaa ctccctgtac    240 ctgcagatga actctctcag ggctgaggac accgccgtgt atatctgcgc agggagttt   300 ggcaagaggt acgccctgga ttactggggc cagggcacaa ccgtgacagt gagctcc      357
```

<210> SEQ ID NO 54
<211> LENGTH: 321
<212> TYPE: DNA
<213> ORGANISM: Artificial Sequence
<220> FEATURE:
<223> OTHER INFORMATION: Synthetic

<400> SEQUENCE: 54

```
gacatcgtga tgacccagag ccacaagttc atgagcacca gcgtgggcga tagggtgagc    60
atcagctgca aggccagcca ggatgtgacc cctgccgtgg cctggtacca gcagaagccc   120
ggccagagcc ccaagctgct gatctacagc accagcagca ggtacaccgg cgtgcccgac   180
aggttcacag gaagcggcag cggcaccgac ttcaccttca ccatcagcag cgtgcaggcc   240
gaggacctgg ccgtgtacta ctgccagcag cactacacca cccctctgac cttcggcgcc   300
ggcaccaagc tggagctgaa g                                            321
```

<210> SEQ ID NO 55
<211> LENGTH: 321
<212> TYPE: DNA
<213> ORGANISM: Artificial Sequence
<220> FEATURE:
<223> OTHER INFORMATION: Synthetic

<400> SEQUENCE: 55

```
gacatccaga tgacccagag ccctagcagc ctgagcgcta gcgtgggcga cagggtgacc    60
atcacctgca aggccagcca ggatgtgacc cctgccgtgg cctggtacca gcagaagccc   120
ggcaaggccc ccaagctgct gatctacagc accagcagca ggtacaccgg cgtgcccagc   180
aggtttagcg gaagcggcag cggcaccgac ttcaccttca ccatcagcag cctgcagccc   240
gaggacatcg ccacctacta ctgccagcag cactacacca cccctctgac cttcggccag   300
ggcaccaagc tggagatcaa g                                            321
```

<210> SEQ ID NO 56
<211> LENGTH: 321
<212> TYPE: DNA
<213> ORGANISM: Artificial Sequence
<220> FEATURE:
<223> OTHER INFORMATION: Synthetic

<400> SEQUENCE: 56

```
gacatccaga tgacccagag ccctagcagc ctgagcgcta gcgtgggcga cagggtgacc      60
atcacctgca aggccagcca ggatgtgacc cctgccgtgg cctggtacca gcagaagccc     120
ggcaagtccc ccaagctgct gatctacagc accagcagca ggtacaccgg cgtgcccagc     180
aggtttagcg gaagcggcag cggcaccgac ttcaccttca ccatcagcag cctgcagccc     240
gaggacatcg ccacctacta ctgccagcag cactacacca cccctctgac cttcggccag     300
ggcaccaagc tggagatcaa g                                                321
```

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
ggcaaggctc ctaagctcct gatctacagc acatcctccc ggtacaccgg agtgccctcc     180
aggtttagcg gcagcggctc cggcaccgat ttcaccctga ccatttcctc cctgcagccc     240
gaggacttcg ccacctacta ctgccagcag cactacacca ccccctgac cttcggccag      300
ggcaccaagc tggagatcaa gcgg                                             324
```

<210> SEQ ID NO 58
<211> LENGTH: 324
<212> TYPE: DNA
<213> ORGANISM: Artificial Sequence
<220> FEATURE:
<223> OTHER INFORMATION: Synthetic

<400> SEQUENCE: 58

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
ggcaaggctc ctaagctcct gatctacagc acatcctccc ggtacaccgg agtgcccgac     180
aggtttaccg gcagcggctc cggcaccgat ttcaccctga ccatttcctc cctgcagccc     240
gaggacttcg ccacctacta ctgccagcag cactacacca ccccctgac cttcggccag      300
ggcaccaagc tggagatcaa gcgg                                             324
```

<210> SEQ ID NO 59
<211> LENGTH: 324
<212> TYPE: DNA
<213> ORGANISM: Artificial Sequence
<220> FEATURE:
<223> OTHER INFORMATION: Synthetic

<400> SEQUENCE: 59

```
gacattcaga tgacccagtc ccctagcagc ctgtccgctt ccgtgggcga cagggtgacc      60
atcacctgca aggccagcca ggacgtgaca cctgctgtgg cctggtatca acagaagcct     120
```

```
ggccagagcc ctaagctcct gatctacagc acatcctccc ggtacaccgg agtgcccgac    180
aggtttaccg gcagcggctc cggcaccgat ttcaccctga ccattcctc cctgcagccc    240 gaggacttcg ccacctacta ctgccagcag cactacacca caccctgac cttcggccag    300 ggcaccaagc tggagatcaa gcgg                                          324
```

<210> SEQ ID NO 60
<211> LENGTH: 324
<212> TYPE: DNA
<213> ORGANISM: Artificial Sequence
<220> FEATURE:
<223> OTHER INFORMATION: Synthetic

<400> SEQUENCE: 60

```
gacattcaga tgacccagtc ccctagcagc ctgtccgctt ccgtgggcga cagggtgacc     60
atcagctgca aggccagcca ggacgtgaca cctgctgtgg cctggtatca acagaagcct    120
ggccagagcc ctaagctcct gatctacagc acatcctccc ggtacaccgg agtgcccgac    180
aggtttaccg gcagcggctc cggcaccgat ttcaccctga ccattcctc cctgcagccc    240 gaggacttcg ccacctacta ctgccagcag cactacacca caccctgac cttcggccag    300 ggcaccaagc tggagatcaa gcgg                                          324
```

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Thr Tyr Asp Met Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

Cys Tyr Asp Met Ser
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Ser Phe Asp Met Ser
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic

<400> SEQUENCE: 64

Ser His Asp Met Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

Ser Trp Asp Met Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

Ser Tyr Asp Met Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

Ser Tyr Asp Met Cys
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Thr Ile Ser Asp Gly Gly Ala Tyr Ile Tyr Tyr Ser Asp Ser Val Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Thr Ile Ser Asp Gly Gly Pro Tyr Ile Tyr Tyr Ser Asp Ser Val Lys
1               5                   10                  15

Gly

<210> SEQ ID NO 70
<211> LENGTH: 17
<212> TYPE: PRT
<213> ORGANISM: Artificial Sequence
<220> FEATURE:

<223> OTHER INFORMATION: Synthetic

<400> SEQUENCE: 70

Thr Ile Ser Asp Gly Gly Gly Phe Ile Tyr Tyr Ser Asp Ser Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic

<400> SEQUENCE: 71

Thr Ile Ser Asp Gly Gly Gly His Ile Tyr Tyr Ser Asp Ser Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Thr Ile Ser Asp Gly Gly Gly Trp Ile Tyr Tyr Ser Asp Ser Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic

<400> SEQUENCE: 73

Thr Ile Ser Asp Gly Gly Gly Tyr Ile Tyr Tyr Ser Asp Thr Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic

<400> SEQUENCE: 74

Thr Ile Ser Asp Gly Gly Gly Tyr Ile Tyr Tyr Ser Asp Cys Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic

<400> SEQUENCE: 75

```
Thr Ile Ser Asp Gly Gly Gly Tyr Ile Tyr Tyr Ser Asp Ser Leu Lys
1               5                   10                  15
Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic

<400> SEQUENCE: 76

Thr Ile Ser Asp Gly Gly Gly Tyr Ile Tyr Tyr Ser Asp Ser Ile Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Thr Ile Ser Asp Gly Gly Gly Tyr Ile Tyr Tyr Ser Asp Ser Met Lys
1               5                   10                  15
Gly

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Gln Phe Gly Lys Arg Tyr Ala Leu Asp Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic

<400> SEQUENCE: 79

Asp Phe Gly Lys Arg Tyr Ala Leu Asp Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Asn Phe Gly Lys Arg Tyr Ala Leu Asp Tyr
1               5                   10

<210> SEQ ID NO 81
<211> LENGTH: 10
<212> TYPE: PRT
<213> ORGANISM: Artificial Sequence
```

<220> FEATURE:
<223> OTHER INFORMATION: Synthetic

<400> SEQUENCE: 81

Glu Tyr Gly Lys Arg Tyr Ala Leu Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic

<400> SEQUENCE: 82

Glu His Gly Lys Arg Tyr Ala Leu Asp Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Glu Trp Gly Lys Arg Tyr Ala Leu Asp Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Glu Phe Ala Lys Arg Tyr Ala Leu Asp Tyr
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic

<400> SEQUENCE: 85

Glu Phe Pro Lys Arg Tyr Ala Leu Asp Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Glu Phe Gly Arg Arg Tyr Ala Leu Asp Tyr
1               5                   10

<210> SEQ ID NO 87
<211> LENGTH: 10
<212> TYPE: PRT
<213> ORGANISM: Artificial Sequence
<220> FEATURE:

<223> OTHER INFORMATION: Synthetic

<400> SEQUENCE: 87

Glu Phe Gly Lys Lys Tyr Ala Leu Asp Tyr
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic

<400> SEQUENCE: 88

Glu Phe Gly Lys Arg Phe Ala Leu Asp Tyr
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic

<400> SEQUENCE: 89

Glu Phe Gly Lys Arg His Ala Leu Asp Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic

<400> SEQUENCE: 90

Glu Phe Gly Lys Arg Trp Ala Leu Asp Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

Lys Ala Thr Gln Asp Val Thr Pro Ala Val Ala
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

Lys Ala Cys Gln Asp Val Thr Pro Ala Val Ala
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Thr Thr Ser Ser Arg Tyr Thr
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Cys Thr Ser Ser Arg Tyr Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Ser Ser Ser Ser Arg Tyr Thr
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Ser Met Ser Ser Arg Tyr Thr
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Ser Val Ser Ser Arg Tyr Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Ser Thr Thr Ser Arg Tyr Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic

```
<400> SEQUENCE: 99

Ser Thr Cys Ser Arg Tyr Thr
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Ser Thr Ser Thr Arg Tyr Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Ser Thr Ser Cys Arg Tyr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ser Thr Ser Ser Lys Tyr Thr
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Ser Thr Ser Ser Arg Phe Thr
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ser Thr Ser Ser Arg His Thr
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105
```

```
Ser Thr Ser Ser Arg Trp Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic

<400> SEQUENCE: 106

Glu Gln His Tyr Thr Thr Pro Leu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Asp Gln His Tyr Thr Thr Pro Leu Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

Asn Gln His Tyr Thr Thr Pro Leu Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic

<400> SEQUENCE: 109

Gln Glu His Tyr Thr Thr Pro Leu Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic

<400> SEQUENCE: 110

Gln Asp His Tyr Thr Thr Pro Leu Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111
```

Gln Asn His Tyr Thr Thr Pro Leu Thr
1               5

<210> SEQ ID NO 112
<211> LENGTH: 357
<212> TYPE: DNA
<213> ORGANISM: Artificial Sequence
<220> FEATURE:
<223> OTHER INFORMATION: Synthetic

<400> SEQUENCE: 112

```
gaagtgaaac tggtggagtc tgggggagac ttagtgaagc ctggagggtc cctgaaactc    60
tcctgtgcag cctctggatt cactttcagt agctatgaca tgtcttgggt tcgccagact   120
ccggagaaga gtctggagtg ggtcgcaacc attagtgatg gtggtggtta catctactat   180
tcagacagtg tgaaggggcg atttaccatc tccagagaca tgccaagaa caacctgtac    240
ctgcaaatga gcagtctgag gtctgaggac acggccttgt atatttgtgc aagagaattt   300
ggtaagcgct atgctttgga ctactgggt caaggaacct cagtcaccgt ctcctca       357
```

<210> SEQ ID NO 113
<211> LENGTH: 116
<212> TYPE: PRT
<213> ORGANISM: Artificial Sequence
<220> FEATURE:
<223> OTHER INFORMATION: Synthetic

<400> SEQUENCE: 113

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Ser Leu Glu Trp Val
        35                  40                  45

Ala Thr Ile Ser Asp Gly Gly Gly Tyr Ile Tyr Tyr Ser Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Ile Cys
                85                  90                  95

Ala Arg Glu Phe Gly Lys Arg Tyr Ala Leu Asp Tyr Trp Gly Gln Gly
            100                 105                 110

Thr Ser Val Thr
        115

<210> SEQ ID NO 114
<211> LENGTH: 321
<212> TYPE: DNA
<213> ORGANISM: Artificial Sequence
<220> FEATURE:
<223> OTHER INFORMATION: Synthetic

<400> SEQUENCE: 114

```
gacattgtga tgacccagtc tcacaaattc atgtccacat cggtaggaga cagggtcagc    60
atctcctgca aggccagtca ggatgtgact cctgctgtcg cctggtatca acagaagcca   120
ggacaatctc ctaaactact gatttactcc acatcctccc ggtacactgg agtccctgat   180
cgcttcactg gcagtggatc tgggacggat ttcactttca ccatcagcag tgtgcaggct   240
gaagacctgg cagtttatta ctgtcagcaa cattatacta ctccgctcac gttcggtgct   300
```
gggaccaagc tggagctgaa a                                              321

<210> SEQ ID NO 115
<211> LENGTH: 107
<212> TYPE: PRT
<213> ORGANISM: Artificial Sequence
<220> FEATURE:
<223> OTHER INFORMATION: Synthetic

<400> SEQUENCE: 115

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Thr Pro Ala
            20                  25                  30

Val Ala Trp Tyr Gln Gln Lys Pro Gly Gln Ser Pro Lys Leu Leu Ile
        35                  40                  45

Tyr Ser Thr Ser Ser Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 116
<211> LENGTH: 5
<212> TYPE: PRT
<213> ORGANISM: Artificial Sequence
<220> FEATURE:
<223> OTHER INFORMATION: Synthetic

<400> SEQUENCE: 116

Ser Tyr Ala Ile Ser
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic

<400> SEQUENCE: 117

Ser Tyr Ala Met Ser
1               5

<210> SEQ ID NO 118
<211> LENGTH: 17
<212> TYPE: PRT
<213> ORGANISM: Artificial Sequence
<220> FEATURE:
<223> OTHER INFORMATION: Synthetic

<400> SEQUENCE: 118

Gly Ile Ile Pro Ile Phe Gly Thr Ala Asn Tyr Ala Gln Lys Phe Gln
1               5                   10                  15

Gly

<210> SEQ ID NO 119
<211> LENGTH: 17
<212> TYPE: PRT
<213> ORGANISM: Artificial Sequence

```
<220> FEATURE:
<223> OTHER INFORMATION: Synthetic

<400> SEQUENCE: 119

Ala Ile Ser Gly Ser Gly Gly Ser Thr Tyr Tyr Ala Asp Ser Val Lys
1               5                   10                  15
Gly

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Ala Arg Gly Ser Ser Trp Phe Asp Tyr
1               5

<210> SEQ ID NO 121
<211> LENGTH: 12
<212> TYPE: PRT
<213> ORGANISM: Artificial Sequence
<220> FEATURE:
<223> OTHER INFORMATION: Synthetic

<400> SEQUENCE: 121

Ala Ser Ser Tyr His Gly Gly Gly Tyr His Arg Tyr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Thr Thr Ser Lys Tyr Ser Gly Ser Ala Leu Arg Tyr
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic

<400> SEQUENCE: 123

Ala Arg Asp Arg Thr Gly Ala Phe Asp Tyr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Ala Arg His Glu Thr Val Ala Gly Ser Phe Asp Tyr
1               5                   10

<210> SEQ ID NO 125
<211> LENGTH: 15
<212> TYPE: PRT
```

-continued

<213> ORGANISM: Artificial Sequence
<220> FEATURE:
<223> OTHER INFORMATION: Synthetic

<400> SEQUENCE: 125

Ala Arg Thr Gly Tyr Tyr Gly Gly Asn Ser Gly Ala Phe Asp Ile
1               5                   10                  15

<210> SEQ ID NO 126
<211> LENGTH: 13
<212> TYPE: PRT
<213> ORGANISM: Artificial Sequence
<220> FEATURE:
<223> OTHER INFORMATION: Synthetic

<400> SEQUENCE: 126

Ala Arg Ala Gly Thr Gly Met Asp Leu Val Phe Asn Ser
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Synthetic

<400> SEQUENCE: 127

Ala Arg Gly Leu Ala Arg Gly Asp Leu Asn Phe Gly Tyr
1               5                   10

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Thr Arg Glu Pro His Phe Asp Tyr
1               5

<210> SEQ ID NO 129
<211> LENGTH: 14
<212> TYPE: PRT
<213> ORGANISM: Artificial Sequence
<220> FEATURE:
<223> OTHER INFORMATION: Synthetic

<400> SEQUENCE: 129

Thr Thr Ala Ala Pro Gly Ser Tyr Tyr Leu Val Phe His Tyr
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Synthetic

<400> SEQUENCE: 130

Ala Arg Asp Ala Gly Pro Val Gly Tyr Tyr Gly Met Asp Val
1               5                   10

<210> SEQ ID NO 131
<211> LENGTH: 13
<212> TYPE: PRT
<213> ORGANISM: Artificial Sequence

```
<220> FEATURE:
<223> OTHER INFORMATION: Synthetic

<400> SEQUENCE: 131

Ala Gly Asp Gly Leu Tyr Gly Ser Gly Ser Phe Gly Tyr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Ala Lys Asp Ile Arg Trp Phe Tyr Gly Met Asp Val
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic

<400> SEQUENCE: 133

Ala Arg His Glu Ser Gly Ile Ala Gly Gly His Phe Asp Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic

<400> SEQUENCE: 134

Ala Lys Asp Ile Arg Trp Tyr Tyr Gly Met Asp Val
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Synthetic

<400> SEQUENCE: 135

Ala Lys Gly Val Arg Gly Thr Tyr Gln Ile Gly Tyr Tyr Gly Met Asp
1               5                   10                  15

Val

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Ala Arg Gln Gly Thr Ala Met Ala Leu Asp Tyr
1               5                   10

<210> SEQ ID NO 137
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 137

Val Arg Asp Leu Gln Asp Trp Asn Tyr Gly Gly Ala Ala Tyr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

Ala Arg Asp Asp Tyr Tyr Tyr Gly Gln Phe Asp Ser
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthetic

<400> SEQUENCE: 139

Ala Arg Glu Ile Thr Gly Thr Ser Tyr Thr Ala Leu Asp Ser
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic

<400> SEQUENCE: 140

Ala Arg Gly His Ile Asp Gly Gln Ala Ala Gly Asp Tyr
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic

<400> SEQUENCE: 141

Ala Ala Ser Thr Leu Arg Val Pro Asn Pro Pro Tyr
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic

<400> SEQUENCE: 142

Ala Arg Ser Gly Asp Arg Tyr Asp Phe Trp Ser Gly Tyr
1               5                   10

<210> SEQ ID NO 143
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 143

Thr Arg Gly Gln Asp Ser Thr Trp Tyr Ser Ser Phe Asp Tyr
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Ala Ala Ser Thr Leu Arg Leu Pro Asn Pro Pro Tyr
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Synthetic

<400> SEQUENCE: 145

Ala Thr Thr Gln Thr Ser Phe Tyr Ser His Gly Met Asp Val
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthetic

<400> SEQUENCE: 146

Ala Arg Val Arg Lys Thr Pro Phe Trp Gly Ala Leu Asp Ser
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic

<400> SEQUENCE: 147

Ala Arg Gly Phe Thr Tyr Gly Asp Phe Ile Phe Asp Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic

<400> SEQUENCE: 148

Ala Arg Asp Val Arg Gly Val Thr Tyr Leu Gly Met Asp Val
1               5                   10

<210> SEQ ID NO 149
<211> LENGTH: 14
<212> TYPE: PRT
<213> ORGANISM: Artificial Sequence
<220> FEATURE:
```

<223> OTHER INFORMATION: Synthetic

<400> SEQUENCE: 149

Ala Arg Val Arg Lys Thr Pro Phe Trp Gly Thr Leu Asp Ser
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Synthetic

<400> SEQUENCE: 150

Ala Arg Val Arg Arg Thr Pro Phe Trp Gly Ala Leu Asp Ser
1               5                   10

<210> SEQ ID NO 151
<211> LENGTH: 18
<212> TYPE: PRT
<213> ORGANISM: Artificial Sequence
<220> FEATURE:
<223> OTHER INFORMATION: Synthetic

<400> SEQUENCE: 151

Ala Lys Arg Lys Gly Leu Gly Ser Pro Thr Asp Tyr Tyr Tyr Gly Met
1               5                   10                  15

Asp Val

<210> SEQ ID NO 152
<211> LENGTH: 14
<212> TYPE: PRT
<213> ORGANISM: Artificial Sequence
<220> FEATURE:
<223> OTHER INFORMATION: Synthetic

<400> SEQUENCE: 152

Val Arg Pro Glu Tyr Asp Thr Tyr Tyr Tyr Gly Met Asp Val
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Ala Lys Gly Gly Gly Ser Tyr Asp Tyr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Ala Arg Ala Leu Asn Gly Met Asp Val
1               5

<210> SEQ ID NO 155
<211> LENGTH: 20
<212> TYPE: PRT
<213> ORGANISM: Artificial Sequence

```
<220> FEATURE:
<223> OTHER INFORMATION: Synthetic

<400> SEQUENCE: 155

Thr Arg Pro Leu Gln Gly Ile Ala Ala Ala Asp Ser Tyr Tyr Tyr Tyr
1               5                   10                  15

Ala Met Asp Val
            20

<210> SEQ ID NO 156
<211> LENGTH: 13
<212> TYPE: PRT
<213> ORGANISM: Artificial Sequence
<220> FEATURE:
<223> OTHER INFORMATION: Synthetic

<400> SEQUENCE: 156

Ala Arg Leu His Ser Tyr Leu Ser Glu Glu Phe Asp Pro
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Synthetic

<400> SEQUENCE: 157

Ala Lys Leu Ser Ala Val Asn Thr Tyr Ile Asp Asp
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Synthetic

<400> SEQUENCE: 158

Ala Arg Val Thr Lys Thr Pro Phe Trp Gly Thr Leu Asp Tyr
1               5                   10

<210> SEQ ID NO 159
<211> LENGTH: 14
<212> TYPE: PRT
<213> ORGANISM: Artificial Sequence
<220> FEATURE:
<223> OTHER INFORMATION: Synthetic

<400> SEQUENCE: 159

Ala Arg Val Ser Gln Ser Pro Val Trp Gly Tyr Phe Asp Tyr
1               5                   10

<210> SEQ ID NO 160
<211> LENGTH: 15
<212> TYPE: PRT
<213> ORGANISM: Artificial Sequence
<220> FEATURE:
<223> OTHER INFORMATION: Synthetic

<400> SEQUENCE: 160

Ala Lys Asp Gly Tyr Tyr Asp Phe Trp Ser Gly Tyr Ser Asp Tyr
1               5                   10                  15

<210> SEQ ID NO 161
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 161

Gln Ala Asn Gln Asp Ile His His Tyr Leu Asn
1               5                   10

<210> SEQ ID NO 162
<211> LENGTH: 17
<212> TYPE: PRT
<213> ORGANISM: Artificial Sequence
<220> FEATURE:
<223> OTHER INFORMATION: Synthetic

<400> SEQUENCE: 162

Lys Ser Ser Gln Ser Val Leu Tyr Ser Ser Asn Lys Asn Tyr Leu
1               5                   10                  15

Ala

<210> SEQ ID NO 163
<211> LENGTH: 17
<212> TYPE: PRT
<213> ORGANISM: Artificial Sequence
<220> FEATURE:
<223> OTHER INFORMATION: Synthetic

<400> SEQUENCE: 163

Lys Ser Ser Gln Ser Val Leu Tyr Ser Asn Asn Lys Asn Tyr Leu
1               5                   10                  15

Ala

<210> SEQ ID NO 164
<211> LENGTH: 16
<212> TYPE: PRT
<213> ORGANISM: Artificial Sequence
<220> FEATURE:
<223> OTHER INFORMATION: Synthetic

<400> SEQUENCE: 164

Arg Ser Ser Gln Asn Leu Leu His Ser Asp Gly Tyr Asn Tyr Leu Asn
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Synthetic

<400> SEQUENCE: 165

Lys Ser Ser Gln Ser Val Leu Tyr Thr Ser Asn Asn Lys Asn Tyr Leu
1               5                   10                  15

Ala

<210> SEQ ID NO 166
<211> LENGTH: 11
<212> TYPE: PRT
<213> ORGANISM: Artificial Sequence
<220> FEATURE:
<223> OTHER INFORMATION: Synthetic

<400> SEQUENCE: 166

Gln Ala Ser Gln Asp Ile Asn Arg Tyr Leu Ser
```

```
1               5                  10

<210> SEQ ID NO 167
<211> LENGTH: 11
<212> TYPE: PRT
<213> ORGANISM: Artificial Sequence
<220> FEATURE:
<223> OTHER INFORMATION: Synthetic

<400> SEQUENCE: 167

Gln Ala Ser Gln Asp Ile Ser Asn Tyr Leu Asn
1               5                  10

<210> SEQ ID NO 168
<211> LENGTH: 11
<212> TYPE: PRT
<213> ORGANISM: Artificial Sequence
<220> FEATURE:
<223> OTHER INFORMATION: Synthetic

<400> SEQUENCE: 168

Arg Ala Ser Gln Thr Ile Ser Ser His Leu Asn
1               5                  10

<210> SEQ ID NO 169
<211> LENGTH: 11
<212> TYPE: PRT
<213> ORGANISM: Artificial Sequence
<220> FEATURE:
<223> OTHER INFORMATION: Synthetic

<400> SEQUENCE: 169

Arg Ala Ser Gln Gly Ile Ala Gly Trp Leu Ala
1               5                  10

<210> SEQ ID NO 170
<211> LENGTH: 11
<212> TYPE: PRT
<213> ORGANISM: Artificial Sequence
<220> FEATURE:
<223> OTHER INFORMATION: Synthetic

<400> SEQUENCE: 170

Arg Ala Ser Gln Gly Val Ser Ser Trp Leu Ala
1               5                  10

<210> SEQ ID NO 171
<211> LENGTH: 17
<212> TYPE: PRT
<213> ORGANISM: Artificial Sequence
<220> FEATURE:
<223> OTHER INFORMATION: Synthetic

<400> SEQUENCE: 171

Lys Ser Ser Gln Ser Leu Phe Tyr His Ser Asn Asn His Asn Tyr Leu
1               5                  10                  15

Ala

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172
```

Arg Ala Ser Gln Gly Ile Ser Ser Ser Leu Ala
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Synthetic

<400> SEQUENCE: 173

Gln Ala Ser Arg Asp Ile Ser Asn Ser Leu Ser
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic

<400> SEQUENCE: 174

Arg Ala Ser Gln Ser Ile Ser Arg Tyr Leu Asn
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic

<400> SEQUENCE: 175

Arg Ala Ser Arg Ser Ile Ser Asn Trp Leu Ala
1               5                   10

<210> SEQ ID NO 176
<211> LENGTH: 17
<212> TYPE: PRT
<213> ORGANISM: Artificial Sequence
<220> FEATURE:
<223> OTHER INFORMATION: Synthetic

<400> SEQUENCE: 176

Lys Ser Ser Gln Ser Val Phe Tyr Arg Ser Asn Gln Lys Asn Tyr Leu
1               5                   10                  15
Ala

<210> SEQ ID NO 177
<211> LENGTH: 11
<212> TYPE: PRT
<213> ORGANISM: Artificial Sequence
<220> FEATURE:
<223> OTHER INFORMATION: Synthetic

<400> SEQUENCE: 177

Arg Ala Ser Gln Ser Val Ser Ser Tyr Leu Ala
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Synthetic

<400> SEQUENCE: 178

Arg Ala Ser Arg Gly Ile Ser Ser Trp Leu Ala
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic

<400> SEQUENCE: 179

Arg Ala Ser Gln Gly Ile Ser Ser Trp Leu Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

Arg Ala Ser Gln Ser Ile Ser Ser Tyr Leu Asn
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Synthetic

<400> SEQUENCE: 181

Arg Ala Ser Gln Ala Ile Ser Asn Leu Leu Ala
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthetic

<400> SEQUENCE: 182

Arg Ala Ser Gln Gly Ile Ser Thr Trp Leu Ala
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Synthetic

<400> SEQUENCE: 183

Arg Ala Ser Gln Gly Ile Ala Ser Asn Leu Ala
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic

<400> SEQUENCE: 184

Arg Ala Ser Gln Gly Val Ser Ser Tyr Leu Ala
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Synthetic

<400> SEQUENCE: 185

Arg Ala Ser Gln Ser Ile Tyr Thr Tyr Leu Asn
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic

<400> SEQUENCE: 186

Arg Ala Ser Gln Phe Val Ser Asp Trp Leu Ala
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

Arg Ala Ser Gln Thr Ile Ser Thr Trp Leu Ala
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic

<400> SEQUENCE: 188

Arg Ala Ser Gln Gly Ile Ser Ser Tyr Leu Ala
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic

<400> SEQUENCE: 189

Arg Ala Ser Gln Ser Ile Gly Tyr Trp Leu Ala
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic

<400> SEQUENCE: 190

Arg Ala Thr Gln Ser Ile Ser Ser Trp Leu Ala

```
1               5               10
```

<210> SEQ ID NO 191
<211> LENGTH: 11
<212> TYPE: PRT
<213> ORGANISM: Artificial Sequence
<220> FEATURE:
<223> OTHER INFORMATION: Synthetic

<400> SEQUENCE: 191

```
Arg Ala Ser Gln Gly Val Arg Asn Trp Leu Ala
1               5                   10
```

<210> SEQ ID NO 192
<211> LENGTH: 11
<212> TYPE: PRT
<213> ORGANISM: Artificial Sequence
<220> FEATURE:
<223> OTHER INFORMATION: Synthetic

<400> SEQUENCE: 192

```
Arg Ala Ser Gln Ser Ile Asn Asn Tyr Leu Ala
1               5                   10
```

<210> SEQ ID NO 193
<211> LENGTH: 11
<212> TYPE: PRT
<213> ORGANISM: Artificial Sequence
<220> FEATURE:
<223> OTHER INFORMATION: Synthetic

<400> SEQUENCE: 193

```
Arg Ala Ser Gln Asp Ile Thr Ser Trp Leu Ala
1               5                   10
```

<210> SEQ ID NO 194
<211> LENGTH: 11
<212> TYPE: PRT
<213> ORGANISM: Artificial Sequence
<220> FEATURE:
<223> OTHER INFORMATION: Synthetic

<400> SEQUENCE: 194

```
Arg Ala Ser Gln Gly Ile Tyr Asp Tyr Leu Ala
1               5                   10
```

<210> SEQ ID NO 195
<211> LENGTH: 11
<212> TYPE: PRT
<213> ORGANISM: Artificial Sequence
<220> FEATURE:
<223> OTHER INFORMATION: Synthetic

<400> SEQUENCE: 195

```
Arg Ala Ser Glu Gly Ile Ser Gly Trp Leu Ala
1               5                   10
```

<210> SEQ ID NO 196
<211> LENGTH: 7
<212> TYPE: PRT
<213> ORGANISM: Artificial Sequence
<220> FEATURE:
<223> OTHER INFORMATION: Synthetic

<400> SEQUENCE: 196

```
Asp Ala Ser Ile Leu Gln Ser
1               5
```

<210> SEQ ID NO 197
<211> LENGTH: 7
<212> TYPE: PRT
<213> ORGANISM: Artificial Sequence
<220> FEATURE:
<223> OTHER INFORMATION: Synthetic

<400> SEQUENCE: 197

Trp Ala Ser Thr Arg Glu Ser
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Leu Gly Ser Asn Arg Ala Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Asp Ala Ser Asn Leu Glu Thr
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic

<400> SEQUENCE: 200

Ala Ala Ser Ser Leu Gln Ser
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic

<400> SEQUENCE: 201

Ala Ala Ser Thr Leu Gln Ser
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic

<400> SEQUENCE: 202

Ala Ala Phe Ser Leu Gln Ser
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic

<400> SEQUENCE: 203

Gly Ala Ser Ser Arg Ala Thr
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic

<400> SEQUENCE: 204

Gly Ile Ser Ser Arg Ala Thr
1               5

<210> SEQ ID NO 205
<211> LENGTH: 7
<212> TYPE: PRT
<213> ORGANISM: Artificial Sequence
<220> FEATURE:
<223> OTHER INFORMATION: Synthetic

<400> SEQUENCE: 205

Ala Val Ser Thr Leu Gln Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic

<400> SEQUENCE: 206

Asp Ile Ser Thr Leu Gln Asn
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic

<400> SEQUENCE: 207

Gly Ala Ser Thr Leu Gln Ser
1               5

<210> SEQ ID NO 208
<211> LENGTH: 7
<212> TYPE: PRT
<213> ORGANISM: Artificial Sequence
<220> FEATURE:
<223> OTHER INFORMATION: Synthetic

<400> SEQUENCE: 208

Gly Ala Ser Ser Leu Gln Ser
1               5

```
<210> SEQ ID NO 209
<211> LENGTH: 7
<212> TYPE: PRT
<213> ORGANISM: Artificial Sequence
<220> FEATURE:
<223> OTHER INFORMATION: Synthetic

<400> SEQUENCE: 209

Ala Ala Ser Thr Leu Glu Ser
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic

<400> SEQUENCE: 210

Asp Ala Ser Ser Leu Gln Ser
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic

<400> SEQUENCE: 211

Lys Ala Ser Asn Leu Gln Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic

<400> SEQUENCE: 212

Thr Ala Ser Thr Leu Gln Asn
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic

<400> SEQUENCE: 213

Arg Ala Ser Ser Leu Gln Ser
1               5

<210> SEQ ID NO 214
<211> LENGTH: 7
<212> TYPE: PRT
<213> ORGANISM: Artificial Sequence
<220> FEATURE:
<223> OTHER INFORMATION: Synthetic

<400> SEQUENCE: 214

Ala Ala Ser His Leu Gln Ser
1               5

<210> SEQ ID NO 215
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 215

Asp Ala Ser Thr Leu Gln Ser
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic

<400> SEQUENCE: 216

Ala Ala Ser Asn Leu Glu Arg
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic

<400> SEQUENCE: 217

Ala Ala Ser Ser Leu Glu Thr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic

<400> SEQUENCE: 218

Gln Gln Ala Asp Ser Phe Pro Ile Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic

<400> SEQUENCE: 219

Gln Gln Ser Tyr Ser Thr Pro Trp Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic

<400> SEQUENCE: 220

Gln Gln Tyr Tyr Ser Thr Pro Trp Thr
1               5

<210> SEQ ID NO 221
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 221

Gln Gln Ser Phe Thr Thr Pro Trp Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic

<400> SEQUENCE: 222

Gln Gln Tyr Asp Asn Leu Pro Pro Thr
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic

<400> SEQUENCE: 223

Gln Gln Ser Tyr Gly Ser Pro Val Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Gly Asn Ser Phe Pro Phe Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic

<400> SEQUENCE: 225

Gln Gln Ala Lys Ser Phe Pro Leu Thr
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic

<400> SEQUENCE: 226

Gln Gln Val Lys Ser Phe Pro Leu Thr
1               5

<210> SEQ ID NO 227
<211> LENGTH: 9
<212> TYPE: PRT
```

<213> ORGANISM: Artificial Sequence
<220> FEATURE:
<223> OTHER INFORMATION: Synthetic

<400> SEQUENCE: 227

Gln Gln Tyr Tyr Asn Thr Pro Trp Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Synthetic

<400> SEQUENCE: 228

Gln Gln Thr Lys Asn Phe Pro Leu Thr
1               5

<210> SEQ ID NO 229
<211> LENGTH: 11
<212> TYPE: PRT
<213> ORGANISM: Artificial Sequence
<220> FEATURE:
<223> OTHER INFORMATION: Synthetic

<400> SEQUENCE: 229

Arg Ala Ser Gln Asp Ile Val Asn Trp Leu Ala
1               5                   10

<210> SEQ ID NO 230
<211> LENGTH: 9
<212> TYPE: PRT
<213> ORGANISM: Artificial Sequence
<220> FEATURE:
<223> OTHER INFORMATION: Synthetic

<400> SEQUENCE: 230

Gln Gln Thr Lys Ser Phe Pro Leu Thr
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic

<400> SEQUENCE: 231

Gln Gln Ser Tyr Asn Thr Pro Arg Thr
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Ser Tyr Arg Ala Pro Trp Thr
1               5

<210> SEQ ID NO 233
<211> LENGTH: 9
<212> TYPE: PRT
<213> ORGANISM: Artificial Sequence

```
<220> FEATURE:
<223> OTHER INFORMATION: Synthetic

<400> SEQUENCE: 233

Gln Gln Ala Asn Asn Phe Pro Leu Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic

<400> SEQUENCE: 234

Gln Gln Gly Asn Ser Phe Pro Leu Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic

<400> SEQUENCE: 235

Gln Gln Ser Lys Asn Phe Pro Val Thr
1               5

<210> SEQ ID NO 236
<211> LENGTH: 9
<212> TYPE: PRT
<213> ORGANISM: Artificial Sequence
<220> FEATURE:
<223> OTHER INFORMATION: Synthetic

<400> SEQUENCE: 236

Gln Gln Ala Asn Ser Phe Pro Leu Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic

<400> SEQUENCE: 237

Gln Gln Leu Glu Ser Tyr Pro Leu Thr
1               5

<210> SEQ ID NO 238
<211> LENGTH: 8
<212> TYPE: PRT
<213> ORGANISM: Artificial Sequence
<220> FEATURE:
<223> OTHER INFORMATION: Synthetic

<400> SEQUENCE: 238

Gln Gln Tyr Tyr Ser Ser Pro Thr
1               5

<210> SEQ ID NO 239
<211> LENGTH: 9
<212> TYPE: PRT
<213> ORGANISM: Artificial Sequence
<220> FEATURE:
```

<223> OTHER INFORMATION: Synthetic

<400> SEQUENCE: 239

Gln Gln Leu Lys Thr Phe Pro Leu Thr
1               5

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Thr Asn Trp Phe Pro Leu Thr
1               5

<210> SEQ ID NO 241
<211> LENGTH: 9
<212> TYPE: PRT
<213> ORGANISM: Artificial Sequence
<220> FEATURE:
<223> OTHER INFORMATION: Synthetic

<400> SEQUENCE: 241

Gln Gln Ala Gln Ser Phe Pro Ile Thr
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic

<400> SEQUENCE: 242

Gln Gln Ala His Ser Phe Pro Leu Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Synthetic

<400> SEQUENCE: 243

Leu Gln Asp Tyr His Phe Pro Leu Thr
1               5

<210> SEQ ID NO 244
<211> LENGTH: 9
<212> TYPE: PRT
<213> ORGANISM: Artificial Sequence
<220> FEATURE:
<223> OTHER INFORMATION: Synthetic

<400> SEQUENCE: 244

Gln Gln Gly His Ser Phe Pro Leu Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Synthetic

<400> SEQUENCE: 245

Gln Gln Ser Tyr Ile Phe Pro Leu Thr
1               5

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Gln Gln Tyr Asp Thr Tyr Trp Thr
1               5

<210> SEQ ID NO 247
<211> LENGTH: 10
<212> TYPE: PRT
<213> ORGANISM: Artificial Sequence
<220> FEATURE:
<223> OTHER INFORMATION: Synthetic

<400> SEQUENCE: 247

Gln Gln Leu Asn Ser Tyr Pro Leu Phe Thr
1               5                   10

<210> SEQ ID NO 248
<211> LENGTH: 8
<212> TYPE: PRT
<213> ORGANISM: Artificial Sequence
<220> FEATURE:
<223> OTHER INFORMATION: Synthetic

<400> SEQUENCE: 248

Gln Gln Tyr Ser Ser Tyr Trp Thr
1               5

<210> SEQ ID NO 249
<211> LENGTH: 9
<212> TYPE: PRT
<213> ORGANISM: Artificial Sequence
<220> FEATURE:
<223> OTHER INFORMATION: Synthetic

<400> SEQUENCE: 249

Leu Gln His Asn Thr Tyr Pro Phe Thr
1               5

<210> SEQ ID NO 250
<211> LENGTH: 9
<212> TYPE: PRT
<213> ORGANISM: Artificial Sequence
<220> FEATURE:
<223> OTHER INFORMATION: Synthetic

<400> SEQUENCE: 250

Gln Gln Gly His Ser Phe Pro Leu Thr
1               5

<210> SEQ ID NO 251
<211> LENGTH: 9
<212> TYPE: PRT
<213> ORGANISM: Artificial Sequence
<220> FEATURE:
<223> OTHER INFORMATION: Synthetic

<400> SEQUENCE: 251

Gln Gln Ala His Ser Phe Pro Phe Thr
1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic

<400> SEQUENCE: 252

Gln Gln Ala Asn Met Phe Pro Leu Thr
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic

<400> SEQUENCE: 253

Gln Gln Ala Asp Ser Phe Pro Phe Thr
1               5

<210> SEQ ID NO 254
<211> LENGTH: 116
<212> TYPE: PRT
<213> ORGANISM: Artificial Sequence
<220> FEATURE:
<223> OTHER INFORMATION: Synthetic

<400> SEQUENCE: 254

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Trp Phe Asp Tyr Trp Gly Gln Gly Thr Leu Val
            100                 105                 110

Thr Val Ser Ser
        115

<210> SEQ ID NO 255
<211> LENGTH: 119
<212> TYPE: PRT
<213> ORGANISM: Artificial Sequence
<220> FEATURE:
<223> OTHER INFORMATION: Synthetic

<400> SEQUENCE: 255

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

```
                    20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Tyr His Gly Gly Tyr His Arg Tyr Trp Gly Gln Gly
            100                 105                 110

Thr Leu Val Thr Val Ser Ser
        115

<210> SEQ ID NO 256
<211> LENGTH: 119
<212> TYPE: PRT
<213> ORGANISM: Artificial Sequence
<220> FEATURE:
<223> OTHER INFORMATION: Synthetic

<400> SEQUENCE: 256

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Ser Lys Tyr Ser Gly Ser Ala Leu Arg Tyr Trp Gly Gln Gly
            100                 105                 110

Thr Leu Val Thr Val Ser Ser
        115

<210> SEQ ID NO 257
<211> LENGTH: 117
<212> TYPE: PRT
<213> ORGANISM: Artificial Sequence
<220> FEATURE:
<223> OTHER INFORMATION: Synthetic

<400> SEQUENCE: 257

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Arg Thr Gly Ala Phe Asp Tyr Trp Gly Gln Gly Thr Leu
            100                 105                 110

Val Thr Val Ser Ser
        115

<210> SEQ ID NO 258
<211> LENGTH: 119
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Thr Val Ala Gly Ser Phe Asp Tyr Trp Gly Gln Gly
            100                 105                 110

Thr Leu Val Thr Val Ser Ser
        115

<210> SEQ ID NO 259
<211> LENGTH: 122
<212> TYPE: PRT
<213> ORGANISM: Artificial Sequence
<220> FEATURE:
<223> OTHER INFORMATION: Synthetic

<400> SEQUENCE: 259

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Tyr Gly Asn Ser Gly Ala Phe Asp Ile Trp
            100                 105                 110

Gly Gln Gly Thr Met Val Thr Val Ser Ser
        115                 120

<210> SEQ ID NO 260
```

```
<211> LENGTH: 120
<212> TYPE: PRT
<213> ORGANISM: Artificial Sequence
<220> FEATURE:
<223> OTHER INFORMATION: Synthetic

<400> SEQUENCE: 260

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Thr Gly Met Asp Leu Val Phe Asn Ser Trp Gly Gln
            100                 105                 110

Gly Thr Leu Val Thr Val Ser Ser
        115                 120

<210> SEQ ID NO 261
<211> LENGTH: 120
<212> TYPE: PRT
<213> ORGANISM: Artificial Sequence
<220> FEATURE:
<223> OTHER INFORMATION: Synthetic

<400> SEQUENCE: 261

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Ala Arg Gly Asp Leu Asn Phe Gly Tyr Trp Gly Gln
            100                 105                 110

Gly Thr Leu Val Thr Val Ser Ser
        115                 120

<210> SEQ ID NO 262
<211> LENGTH: 115
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Pro His Phe Asp Tyr Trp Gly Gln Gly Thr Leu Val Thr
            100                 105                 110

Val Ser Ser
        115

<210> SEQ ID NO 263
<211> LENGTH: 121
<212> TYPE: PRT
<213> ORGANISM: Artificial Sequence
<220> FEATURE:
<223> OTHER INFORMATION: Synthetic

<400> SEQUENCE: 263

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Ala Ala Pro Gly Ser Tyr Tyr Leu Val Phe His Tyr Trp Gly
            100                 105                 110

Gln Gly Thr Leu Val Thr Val Ser Ser
        115                 120

<210> SEQ ID NO 264
<211> LENGTH: 121
<212> TYPE: PRT
<213> ORGANISM: Artificial Sequence
<220> FEATURE:
<223> OTHER INFORMATION: Synthetic

<400> SEQUENCE: 264

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Pro Val Gly Tyr Tyr Gly Met Asp Val Trp Gly
            100                 105                 110

Gln Gly Thr Thr Val Thr Val Ser Ser
        115                 120

<210> SEQ ID NO 265
<211> LENGTH: 120
<212> TYPE: PRT
<213> ORGANISM: Artificial Sequence
<220> FEATURE:
<223> OTHER INFORMATION: Synthetic

<400> SEQUENCE: 265

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Asp Gly Leu Tyr Gly Ser Gly Ser Phe Gly Tyr Trp Gly Gln
            100                 105                 110

Gly Thr Pro Val Thr Val Ser Ser
        115                 120

<210> SEQ ID NO 266
<211> LENGTH: 120
<212> TYPE: PRT
<213> ORGANISM: Artificial Sequence
<220> FEATURE:
<223> OTHER INFORMATION: Synthetic

<400> SEQUENCE: 266

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Ile Arg Trp Phe Tyr Gly Met Asp Val Trp Gly Gln Gly
            100                 105                 110

Thr Thr Val Thr Val Ser Ser Trp
        115                 120

<210> SEQ ID NO 267
<211> LENGTH: 121
<212> TYPE: PRT
<213> ORGANISM: Artificial Sequence
<220> FEATURE:
<223> OTHER INFORMATION: Synthetic

<400> SEQUENCE: 267

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Ser Gly Ile Ala Gly Gly His Phe Asp Tyr Trp Gly
            100                 105                 110

Gln Gly Thr Leu Val Thr Val Ser Ser
        115                 120

<210> SEQ ID NO 268
<211> LENGTH: 120
<212> TYPE: PRT
<213> ORGANISM: Artificial Sequence
<220> FEATURE:
<223> OTHER INFORMATION: Synthetic

<400> SEQUENCE: 268

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Pro Val Tyr Tyr Gly Met Asp Val Trp Gly
            100                 105                 110

Gln Gly Thr Thr Val Thr Val Ser
        115                 120

<210> SEQ ID NO 269
<211> LENGTH: 119
<212> TYPE: PRT
<213> ORGANISM: Artificial Sequence
<220> FEATURE:
<223> OTHER INFORMATION: Synthetic

<400> SEQUENCE: 269

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Ile Arg Trp Tyr Tyr Gly Met Asp Val Trp Gly Gln Gly
            100                 105                 110

Thr Thr Val Thr Val Ser Ser
            115

<210> SEQ ID NO 270
<211> LENGTH: 124
<212> TYPE: PRT
<213> ORGANISM: Artificial Sequence
<220> FEATURE:
<223> OTHER INFORMATION: Synthetic

<400> SEQUENCE: 270

Gln Val Gln Leu Val Gln Ser Gly Ala Glu Val Lys Lys Pro Gly Ser
1               5                   10                  15

Ser Val Lys Val Phe Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Val Arg Gly Thr Tyr Gln Ile Gly Tyr Tyr Gly Met Asp
            100                 105                 110

Val Trp Gly Gln Gly Thr Thr Val Thr Val Ser Ser
            115                 120

<210> SEQ ID NO 271
<211> LENGTH: 118
<212> TYPE: PRT
<213> ORGANISM: Artificial Sequence
<220> FEATURE:
<223> OTHER INFORMATION: Synthetic

<400> SEQUENCE: 271

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr

Met Glu Leu Ser Ser Leu Arg Ser Glu Asp Thr Ala Val Tyr Tyr Cys
            85                  90                  95

Ala Arg Gln Gly Thr Ala Met Ala Leu Asp Tyr Trp Gly Gln Gly Thr
            100                 105                 110

Leu Val Thr Val Ser Ser
        115

<210> SEQ ID NO 272
<211> LENGTH: 121
<212> TYPE: PRT
<213> ORGANISM: Artificial Sequence
<220> FEATURE:
<223> OTHER INFORMATION: Synthetic

<400> SEQUENCE: 272

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Val Arg Asp Leu Gln Asp Trp Asn Tyr Gly Gly Ala Ala Tyr Trp Gly
            100                 105                 110

Gln Gly Thr Leu Val Thr Val Ser Ser
        115                 120

<210> SEQ ID NO 273
<211> LENGTH: 119
<212> TYPE: PRT
<213> ORGANISM: Artificial Sequence
<220> FEATURE:
<223> OTHER INFORMATION: Synthetic

<400> SEQUENCE: 273

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Asp Tyr Tyr Tyr Gly Gln Phe Asp Ser Trp Gly Gln Gly
            100                 105                 110

Thr Leu Val Thr Val Ser Ser
        115

<210> SEQ ID NO 274
<211> LENGTH: 121
<212> TYPE: PRT
<213> ORGANISM: Artificial Sequence
<220> FEATURE:
<223> OTHER INFORMATION: Synthetic

<400> SEQUENCE: 274

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Thr Gly Thr Ser Tyr Thr Ala Leu Asp Ser Trp Gly
            100                 105                 110

Gln Gly Thr Leu Val Thr Val Ser Ser
        115                 120

<210> SEQ ID NO 275
<211> LENGTH: 120
<212> TYPE: PRT
<213> ORGANISM: Artificial Sequence
<220> FEATURE:
<223> OTHER INFORMATION: Synthetic

<400> SEQUENCE: 275

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Ile Asp Gly Gln Ala Ala Gly Asp Tyr Trp Gly Gln
            100                 105                 110

Gly Thr Leu Val Thr Val Ser Ser
        115                 120

<210> SEQ ID NO 276
<211> LENGTH: 119
<212> TYPE: PRT
<213> ORGANISM: Artificial Sequence
<220> FEATURE:
<223> OTHER INFORMATION: Synthetic

<400> SEQUENCE: 276

Gln Val Gln Leu Val Gln Ser Gly Ala Glu Val Lys Lys Pro Gly Ser

```
    1               5                   10                  15
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Leu Arg Val Pro Asn Pro Pro Tyr Trp Gly Gln Gly
            100                 105                 110

Thr Leu Val Thr Val Ser Ser
            115

<210> SEQ ID NO 277
<211> LENGTH: 120
<212> TYPE: PRT
<213> ORGANISM: Artificial Sequence
<220> FEATURE:
<223> OTHER INFORMATION: Synthetic

<400> SEQUENCE: 277

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asp Arg Tyr Asp Phe Trp Ser Gly Tyr Trp Gly Gln
            100                 105                 110

Gly Thr Leu Val Thr Val Ser Ser
            115                 120

<210> SEQ ID NO 278
<211> LENGTH: 119
<212> TYPE: PRT
<213> ORGANISM: Artificial Sequence
<220> FEATURE:
<223> OTHER INFORMATION: Synthetic

<400> SEQUENCE: 278

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60
```

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Leu Arg Val Pro Asn Pro Pro Tyr Trp Gly Gln Gly
            100                 105                 110

Thr Leu Val Thr Val Ser Ser
            115
```

<210> SEQ ID NO 279
<211> LENGTH: 121
<212> TYPE: PRT
<213> ORGANISM: Artificial Sequence
<220> FEATURE:
<223> OTHER INFORMATION: Synthetic

<400> SEQUENCE: 279

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Gly Pro Val Tyr Tyr Gly Met Asp Val Trp Gly
            100                 105                 110

Gln Gly Thr Met Val Thr Val Ser Ser
            115                 120
```

<210> SEQ ID NO 280
<211> LENGTH: 121
<212> TYPE: PRT
<213> ORGANISM: Artificial Sequence
<220> FEATURE:
<223> OTHER INFORMATION: Synthetic

<400> SEQUENCE: 280

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Gln Asp Ser Thr Trp Tyr Ser Ser Phe Asp Tyr Trp Gly
            100                 105                 110

Gln Gly Thr Leu Val Thr Val Ser Ser
            115                 120
```

```
<210> SEQ ID NO 281
<211> LENGTH: 119
<212> TYPE: PRT
<213> ORGANISM: Artificial Sequence
<220> FEATURE:
<223> OTHER INFORMATION: Synthetic

<400> SEQUENCE: 281
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Leu Arg Leu Pro Asn Pro Pro Tyr Trp Gly Gln Gly
            100                 105                 110

Thr Leu Val Thr Val Ser Ser
        115

```
<210> SEQ ID NO 282
<211> LENGTH: 121
<212> TYPE: PRT
<213> ORGANISM: Artificial Sequence
<220> FEATURE:
<223> OTHER INFORMATION: Synthetic

<400> SEQUENCE: 282
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Gln Thr Ser Phe Tyr Ser His Gly Met Asp Val Trp Gly
            100                 105                 110

Gln Gly Thr Thr Val Thr Val Ser Ser
        115                 120

```
<210> SEQ ID NO 283
<211> LENGTH: 119
<212> TYPE: PRT
<213> ORGANISM: Artificial Sequence
<220> FEATURE:
<223> OTHER INFORMATION: Synthetic

<400> SEQUENCE: 283
```

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
            115

<210> SEQ ID NO 284
<211> LENGTH: 120
<212> TYPE: PRT
<213> ORGANISM: Artificial Sequence
<220> FEATURE:
<223> OTHER INFORMATION: Synthetic

<400> SEQUENCE: 284

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Thr Tyr Gly Asp Phe Ile Phe Asp Tyr Trp Gly Gln
            100                 105                 110

Gly Thr Leu Val Thr Val Ser Ser
        115                 120

<210> SEQ ID NO 285
<211> LENGTH: 121
<212> TYPE: PRT
<213> ORGANISM: Artificial Sequence
<220> FEATURE:
<223> OTHER INFORMATION: Synthetic

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Arg Gly Val Thr Tyr Leu Gly Met Asp Val Trp Gly
            100                 105                 110

Gln Gly Thr Thr Val Thr Val Ser Ser
        115                 120

<210> SEQ ID NO 286
<211> LENGTH: 119
<212> TYPE: PRT
<213> ORGANISM: Artificial Sequence
<220> FEATURE:
<223> OTHER INFORMATION: Synthetic

<400> SEQUENCE: 286

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Thr Leu Asp Ser Trp Gly Arg Gly
            100                 105                 110

Thr Leu Val Thr Val Ser Ser
        115

<210> SEQ ID NO 287
<211> LENGTH: 119
<212> TYPE: PRT
<213> ORGANISM: Artificial Sequence
<220> FEATURE:
<223> OTHER INFORMATION: Synthetic

<400> SEQUENCE: 287

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Arg Thr Pro Phe Trp Gly Ala Leu Asp Ser Trp Gly Arg Gly
            100                 105                 110

Thr Leu Val Thr Val Ser Ser

```
<210> SEQ ID NO 288
<211> LENGTH: 119
<212> TYPE: PRT
<213> ORGANISM: Artificial Sequence
<220> FEATURE:
<223> OTHER INFORMATION: Synthetic

<400> SEQUENCE: 288

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
        115

<210> SEQ ID NO 289
<211> LENGTH: 123
<212> TYPE: PRT
<213> ORGANISM: Artificial Sequence
<220> FEATURE:
<223> OTHER INFORMATION: Synthetic

<400> SEQUENCE: 289

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Lys Gly Leu Gly Ser Pro Thr Asp Tyr Tyr Tyr Gly Met Asp Val
            100                 105                 110

Trp Gly Gln Gly Thr Thr Val Thr Val Ser Ser
        115                 120

<210> SEQ ID NO 290
<211> LENGTH: 119
<212> TYPE: PRT
<213> ORGANISM: Artificial Sequence
<220> FEATURE:
<223> OTHER INFORMATION: Synthetic

<400> SEQUENCE: 290
```

-continued

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
            115

<210> SEQ ID NO 291
<211> LENGTH: 119
<212> TYPE: PRT
<213> ORGANISM: Artificial Sequence
<220> FEATURE:
<223> OTHER INFORMATION: Synthetic

<400> SEQUENCE: 291

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Thr Leu Asp Ser Trp Gly Arg Gly
            100                 105                 110

Ser Leu Val Thr Val Ser Ser
            115

<210> SEQ ID NO 292
<211> LENGTH: 119
<212> TYPE: PRT
<213> ORGANISM: Artificial Sequence
<220> FEATURE:
<223> OTHER INFORMATION: Synthetic

<400> SEQUENCE: 292

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly

```
                    50                  55                  60
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Val Arg
                 85                  90                  95

Pro Glu Tyr Asp Thr Tyr Tyr Tyr Gly Met Asp Val Trp Gly Gln Gly
                100                 105                 110

Thr Thr Val Thr Val Ser Ser
            115

<210> SEQ ID NO 293
<211> LENGTH: 114
<212> TYPE: PRT
<213> ORGANISM: Artificial Sequence
<220> FEATURE:
<223> OTHER INFORMATION: Synthetic

<400> SEQUENCE: 293

Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                 20                  25                  30

Ser Trp Val Arg Gln Ala Pro Gly Lys Gly Leu Glu Trp Val Ser Ala
             35                  40                  45

Ile Ser Gly Ser Gly Gly Ser Thr Tyr Tyr Ala Asp Ser Val Lys Gly
         50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Gly Gly Gly Ser Tyr Asp Tyr Trp Gly Gln Gly Thr Leu Val Thr Val
                100                 105                 110

Ser Ser

<210> SEQ ID NO 294
<211> LENGTH: 114
<212> TYPE: PRT
<213> ORGANISM: Artificial Sequence
<220> FEATURE:
<223> OTHER INFORMATION: Synthetic

<400> SEQUENCE: 294

Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
                 20                  25                  30

Ser Trp Val Arg Gln Ala Pro Gly Lys Gly Leu Glu Trp Val Ser Ala
             35                  40                  45

Ile Ser Gly Ser Gly Gly Ser Thr Tyr Tyr Ala Asp Ser Val Lys Gly
         50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ala Leu Asn Gly Met Asp Val Trp Gly Gln Gly Thr Met Val Thr Val
                100                 105                 110

Ser Ser
```

<210> SEQ ID NO 295
<211> LENGTH: 125
<212> TYPE: PRT
<213> ORGANISM: Artificial Sequence
<220> FEATURE:
<223> OTHER INFORMATION: Synthetic

<400> SEQUENCE: 295

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Thr Arg
                85                  90                  95

Pro Leu Gln Gly Ile Ala Ala Ala Asp Ser Tyr Tyr Tyr Tyr Ala Met
            100                 105                 110

Asp Val Trp Gly Gln Gly Thr Thr Val Thr Val Ser Ser
        115                 120                 125
```

<210> SEQ ID NO 296
<211> LENGTH: 118
<212> TYPE: PRT
<213> ORGANISM: Artificial Sequence
<220> FEATURE:
<223> OTHER INFORMATION: Synthetic

<400> SEQUENCE: 296

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu His Ser Tyr Leu Ser Glu Glu Phe Asp Pro Trp Gly Gln Gly Thr
            100                 105                 110

Leu Val Thr Val Ser Ser
        115
```

<210> SEQ ID NO 297
<211> LENGTH: 119
<212> TYPE: PRT
<213> ORGANISM: Artificial Sequence
<220> FEATURE:
<223> OTHER INFORMATION: Synthetic

<400> SEQUENCE: 297

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Val Arg Lys Thr Pro Phe Trp Gly Ala Leu Asp Ser Trp Gly Arg Gly
            100                 105                 110

Thr Leu Val Thr Val Ser Ser
            115

<210> SEQ ID NO 298
<211> LENGTH: 117
<212> TYPE: PRT
<213> ORGANISM: Artificial Sequence
<220> FEATURE:
<223> OTHER INFORMATION: Synthetic

<400> SEQUENCE: 298

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Leu Ser Ala Val Asn Thr Tyr Ile Asp Asp Trp Gly Gln Gly Thr Leu
            100                 105                 110

Val Thr Val Ser Ser
        115

<210> SEQ ID NO 299
<211> LENGTH: 119
<212> TYPE: PRT
<213> ORGANISM: Artificial Sequence
<220> FEATURE:
<223> OTHER INFORMATION: Synthetic

<400> SEQUENCE: 299

Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

```
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Thr Lys Thr Pro Phe Trp Gly Thr Leu Asp Tyr Trp Gly Gln Gly
            100                 105                 110

Thr Leu Val Thr Val Ser Ser
            115

<210> SEQ ID NO 300
<211> LENGTH: 119
<212> TYPE: PRT
<213> ORGANISM: Artificial Sequence
<220> FEATURE:
<223> OTHER INFORMATION: Synthetic

<400> SEQUENCE: 300

Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
             20                  25                  30

Ser Trp Val Arg Gln Ala Pro Gly Lys Gly Leu Glu Trp Val Ser Ala
         35                  40                  45

Ile Ser Gly Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Arg Arg Thr Pro Phe Trp Gly Ala Leu Asp Ser Trp Gly Arg Gly
            100                 105                 110

Thr Leu Val Thr Val Ser Ser
            115

<210> SEQ ID NO 301
<211> LENGTH: 119
<212> TYPE: PRT
<213> ORGANISM: Artificial Sequence
<220> FEATURE:
<223> OTHER INFORMATION: Synthetic

<400> SEQUENCE: 301

Gln Leu Leu Glu Ser Gly Gly Gly Leu Val Gln Pro Gly Gly Ser Leu
 1               5                  10                  15

Arg Leu Ser Cys Ala Ala Ser Gly Phe Thr Phe Ser Ser Tyr Ala Met
             20                  25                  30

Ser Trp Val Arg Gln Ala Pro Gly Lys Gly Leu Glu Trp Val Ser Ala
         35                  40                  45

Ile Ser Gly Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Val Ser Gln Ser Pro Val Trp Gly Tyr Phe Asp Tyr Trp Gly Gln Gly
            100                 105                 110

Met Leu Val Thr Val Ser Ser
```

<210> SEQ ID NO 302
<211> LENGTH: 120
<212> TYPE: PRT
<213> ORGANISM: Artificial Sequence
<220> FEATURE:
<223> OTHER INFORMATION: Synthetic

<400> SEQUENCE: 302

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ala Met
            20                  25                  30

Ser Trp Val Arg Gln Ala Pro Gly Lys Gly Leu Glu Trp Val Ser Ala
        35                  40                  45

Ile Ser Gly Ser Gly Gly Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Gly Tyr Tyr Asp Phe Trp Ser Gly Tyr Ser Asp Tyr Trp Gly Gln
            100                 105                 110

Gly Thr Leu Val Thr Val Ser Ser
        115                 120
```

<210> SEQ ID NO 303
<211> LENGTH: 108
<212> TYPE: PRT
<213> ORGANISM: Artificial Sequence
<220> FEATURE:
<223> OTHER INFORMATION: Synthetic

<400> SEQUENCE: 303

```
Asp Ile Gln Leu Thr Gln Ser Pro Ser Ser Leu Ser Ala Phe Val Gly
1               5                   10                  15

Asp Arg Val Thr Ile Thr Cys Gln Ala Asn Gln Asp Ile His His Tyr
            20                  25                  30

Leu Asn Trp Tyr Gln Gln Lys Pro Gly Lys Ala Pro Lys Leu Leu Ile
        35                  40                  45

Tyr Asp Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Ile
                85                  90                  95

Thr Phe Gly Gln Gly Thr Arg Leu Glu Ile Lys Arg
            100                 105
```

<210> SEQ ID NO 304
<211> LENGTH: 114
<212> TYPE: PRT
<213> ORGANISM: Artificial Sequence
<220> FEATURE:
<223> OTHER INFORMATION: Synthetic

<400> SEQUENCE: 304

```
Glu Ile Val Leu Thr Gln Ser Pro Asp Ser Leu Ala Val Ser Leu Gly
1               5                   10                  15
```

Glu Arg Ala Thr Ile Asn Cys Lys Ser Ser Gln Ser Val Leu Tyr Ser
            20                  25                  30

Ser Ser Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Thr Pro Trp Thr Phe Gly Pro Gly Thr Lys Leu Glu Ile
            100                 105                 110

Lys Arg

<210> SEQ ID NO 305
<211> LENGTH: 114
<212> TYPE: PRT
<213> ORGANISM: Artificial Sequence
<220> FEATURE:
<223> OTHER INFORMATION: Synthetic

<400> SEQUENCE: 305

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly His
        35                  40                  45

Pro Pro Lys Leu Leu Val Tyr Trp Ala Ser Thr Arg Glu Ser Gly Val
50                  55                  60

Pro Ala Arg Phe Ser Ala Ser Gly Ser Gly Thr Asp Phe Thr Leu Ala
65                  70                  75                  80

Ile Ser Asn Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys Arg

<210> SEQ ID NO 306
<211> LENGTH: 113
<212> TYPE: PRT
<213> ORGANISM: Artificial Sequence
<220> FEATURE:
<223> OTHER INFORMATION: Synthetic

<400> SEQUENCE: 306

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Asn Leu Leu His Ser
            20                  25                  30

Asp Gly Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Thr Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
             85                  90                  95

Tyr Ser Thr Pro Trp Thr Phe Gly Gln Gly Thr Lys Val Glu Ile Lys
            100                 105                 110

Arg

<210> SEQ ID NO 307
<211> LENGTH: 114
<212> TYPE: PRT
<213> ORGANISM: Artificial Sequence
<220> FEATURE:
<223> OTHER INFORMATION: Synthetic

<400> SEQUENCE: 307

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Pro Trp Thr Phe Gly Gln Gly Thr Lys Leu Glu Ile
            100                 105                 110

Lys Arg

<210> SEQ ID NO 308
<211> LENGTH: 114
<212> TYPE: PRT
<213> ORGANISM: Artificial Sequence
<220> FEATURE:
<223> OTHER INFORMATION: Synthetic

<400> SEQUENCE: 308

Ala Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Ser Ala Thr Tyr Tyr Cys Gln Gln
                85                  90                  95

Ser Phe Thr Thr Pro Trp Thr Phe Gly Gln Gly Thr Lys Val Glu Ile
            100                 105                 110

Lys Arg

<210> SEQ ID NO 309
<211> LENGTH: 108
<212> TYPE: PRT
<213> ORGANISM: Artificial Sequence
<220> FEATURE:
<223> OTHER INFORMATION: Synthetic

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Ser Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Ala Ser Gly Thr Asp Phe Thr Phe Ala Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Thr Phe Gly Gln Gly Thr Arg Leu Glu Ile Lys Arg
            100                 105

<210> SEQ ID NO 310
<211> LENGTH: 108
<212> TYPE: PRT
<213> ORGANISM: Artificial Sequence
<220> FEATURE:
<223> OTHER INFORMATION: Synthetic

<400> SEQUENCE: 310

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Gly Ser Pro Val
                85                  90                  95

Thr Phe Gly Gln Gly Thr Lys Leu Glu Ile Lys Arg
            100                 105

<210> SEQ ID NO 311
<211> LENGTH: 108
<212> TYPE: PRT
<213> ORGANISM: Artificial Sequence
<220> FEATURE:
<223> OTHER INFORMATION: Synthetic

<400> SEQUENCE: 311

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

```
Ser Gly Ser Gly Thr Glu Phe Thr Leu Thr Ile Ser Ser Leu Arg Pro
 65                  70                  75                  80

Glu Asp Phe Ala Thr Tyr Phe Cys Gln Gln Ala Asp Ser Phe Pro Ile
                 85                  90                  95

Thr Phe Gly Gln Gly Thr Arg Leu Glu Ile Lys Arg
            100                 105
```

<210> SEQ ID NO 312
<211> LENGTH: 108
<212> TYPE: PRT
<213> ORGANISM: Artificial Sequence
<220> FEATURE:
<223> OTHER INFORMATION: Synthetic

<400> SEQUENCE: 312

```
Asp Ile Gln Leu Thr Gln Ser Pro Ser Ser Leu Ser Ala Ser Val Gly
  1               5                  10                  15

Asp Arg Val Thr Ile Thr Cys Arg Ala Ser Gln Thr Ile Ser Ser His
                 20                  25                  30

Leu Asn Trp Tyr Gln Gln Lys Pro Gly Lys Ala Pro Lys Val Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Gly Asn Ser Phe Pro Phe
                 85                  90                  95

Thr Phe Gly Pro Gly Thr Lys Val Glu Ile Lys Arg
            100                 105
```

<210> SEQ ID NO 313
<211> LENGTH: 108
<212> TYPE: PRT
<213> ORGANISM: Artificial Sequence
<220> FEATURE:
<223> OTHER INFORMATION: Synthetic

<400> SEQUENCE: 313

```
Ala Ile Arg Met Thr Gln Ser Pro Ser Thr Leu Ser Ala Ser Val Gly
  1               5                  10                  15

Asp Arg Val Thr Ile Thr Cys Arg Ala Ser Gln Gly Ile Ala Gly Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Ala Ser Gly Thr Asp Phe Thr Leu Thr Ile Ser Asn Leu Gln Pro
 65                  70                  75                  80

Glu Asp Phe Ala Thr Tyr Tyr Cys Gln Gln Ala Lys Ser Phe Pro Leu
                 85                  90                  95

Thr Phe Gly Gly Gly Thr Lys Val Glu Ile Lys Arg
            100                 105
```

<210> SEQ ID NO 314
<211> LENGTH: 113
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Thr Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Thr Pro Trp Thr Phe Gly Gln Gly Thr Lys Leu Glu Ile
            100                 105                 110

Lys

<210> SEQ ID NO 315
<211> LENGTH: 108
<212> TYPE: PRT
<213> ORGANISM: Artificial Sequence
<220> FEATURE:
<223> OTHER INFORMATION: Synthetic

<400> SEQUENCE: 315

Asp Ile Val Met Thr Gln Ser Pro Ser Ser Val Ser Ala Phe Val Gly
1               5                   10                  15

Asp Arg Val Thr Ile Thr Cys Arg Ala Ser Gln Gly Val Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Arg Gly Tyr Gly Thr Glu Phe Thr Leu Thr Ile Ser Ser Leu Gln Pro
65                  70                  75                  80

Glu Asp Leu Ala Thr Tyr Tyr Cys Gln Gln Val Lys Ser Phe Pro Leu
                85                  90                  95

Thr Phe Gly Gly Gly Thr Lys Val Asp Ile Lys Arg
            100                 105

<210> SEQ ID NO 316
<211> LENGTH: 114
<212> TYPE: PRT
<213> ORGANISM: Artificial Sequence
<220> FEATURE:
<223> OTHER INFORMATION: Synthetic

<400> SEQUENCE: 316

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
            20                  25                  30

Ser Asn Asn His Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val
50                  55                  60

Pro Asp Arg Phe Thr Gly Ser Gly Ser Gly Thr Asp Phe Thr Leu Thr

```
                65                  70                  75                  80
Ile Ser Ser Leu Gln Ala Glu Asp Val Ala Val Tyr Tyr Cys Gln Gln
                    85                  90                  95

Tyr Tyr Asn Thr Pro Trp Thr Phe Gly Gln Gly Thr Lys Val Glu Ile
                100                 105                 110

Lys Arg

<210> SEQ ID NO 317
<211> LENGTH: 108
<212> TYPE: PRT
<213> ORGANISM: Artificial Sequence
<220> FEATURE:
<223> OTHER INFORMATION: Synthetic

<400> SEQUENCE: 317

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Gly Ile Ala Gly Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Ala Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys Arg
                100                 105

<210> SEQ ID NO 318
<211> LENGTH: 108
<212> TYPE: PRT
<213> ORGANISM: Artificial Sequence
<220> FEATURE:
<223> OTHER INFORMATION: Synthetic

<400> SEQUENCE: 318

Asp Ile Val Met Thr Gln Ser Pro Ser Ser Val Ser Ala Phe Val Gly
1               5                   10                  15

Asp Arg Val Thr Ile Thr Cys Arg Ala Ser Gln Gly Val Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Arg Gly Tyr Gly Thr Glu Phe Thr Leu Thr Ile Ser Ser Leu Gln Pro
65                  70                  75                  80

Glu Asp Leu Ala Thr Tyr Tyr Cys Gln Gln Val Lys Ser Phe Pro Leu
                85                  90                  95

Thr Phe Gly Gly Gly Thr Lys Val Asp Ile Lys Arg
                100                 105

<210> SEQ ID NO 319
<211> LENGTH: 108
<212> TYPE: PRT
<213> ORGANISM: Artificial Sequence
<220> FEATURE:
<223> OTHER INFORMATION: Synthetic
```

<400> SEQUENCE: 319

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Asn Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Lys Asn Phe Pro Leu
                85                  90                  95

Thr Phe Gly Gln Gly Thr Arg Leu Glu Ile Lys Arg
            100                 105

<210> SEQ ID NO 320
<211> LENGTH: 114
<212> TYPE: PRT
<213> ORGANISM: Artificial Sequence
<220> FEATURE:
<223> OTHER INFORMATION: Synthetic

<400> SEQUENCE: 320

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Arg Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Ala Asp Phe Ser Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Leu Glu Ile
            100                 105                 110

Lys Arg

<210> SEQ ID NO 321
<211> LENGTH: 108
<212> TYPE: PRT
<213> ORGANISM: Artificial Sequence
<220> FEATURE:
<223> OTHER INFORMATION: Synthetic

<400> SEQUENCE: 321

Val Ile Trp Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Asn Ser
            20                  25                  30

Leu Ser Trp His Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Lys Ser Phe Pro Leu
                85                  90                  95

Thr Phe Gly Gly Gly Thr Lys Val Glu Ile Lys Arg
            100                 105

<210> SEQ ID NO 322
<211> LENGTH: 108
<212> TYPE: PRT
<213> ORGANISM: Artificial Sequence
<220> FEATURE:
<223> OTHER INFORMATION: Synthetic

<400> SEQUENCE: 322

Glu Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Arg Tyr
                20                  25                  30

Leu Asn Trp Tyr Gln Gln Lys Pro Gly Gln Ala Pro Lys Leu Leu Ile
            35                  40                  45

Tyr Ala Ala Phe Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Arg
                85                  90                  95

Thr Phe Gly Gln Gly Thr Lys Leu Glu Ile Lys Arg
            100                 105

<210> SEQ ID NO 323
<211> LENGTH: 107
<212> TYPE: PRT
<213> ORGANISM: Artificial Sequence
<220> FEATURE:
<223> OTHER INFORMATION: Synthetic

<400> SEQUENCE: 323

Asp Val Val Met Thr Gln Ser Pro Ser Thr Val Ser Ala Ser Val Gly
1               5                   10                  15

Asp Arg Ile Thr Ile Thr Cys Arg Ala Ser Arg Ser Ile Ser Asn Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys
            100                 105

<210> SEQ ID NO 324
<211> LENGTH: 114
<212> TYPE: PRT
<213> ORGANISM: Artificial Sequence
<220> FEATURE:
<223> OTHER INFORMATION: Synthetic

<400> SEQUENCE: 324

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Arg
            20                  25                  30

Ser Asn Gln Lys Asn Tyr Leu Ala Trp Tyr Gln Gln Lys Pro Gly Gln
        35                  40                  45

Thr Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Arg Ala Pro Trp Thr Phe Gly Gln Gly Thr Lys Val Glu Ile
            100                 105                 110

Lys Arg

<210> SEQ ID NO 325
<211> LENGTH: 108
<212> TYPE: PRT
<213> ORGANISM: Artificial Sequence
<220> FEATURE:
<223> OTHER INFORMATION: Synthetic

<400> SEQUENCE: 325

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ile Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Leu Glu Ile Lys Arg
            100                 105

<210> SEQ ID NO 326
<211> LENGTH: 108
<212> TYPE: PRT
<213> ORGANISM: Artificial Sequence
<220> FEATURE:
<223> OTHER INFORMATION: Synthetic

<400> SEQUENCE: 326

Glu Ile Val Leu Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ala Lys Ser Phe Pro Leu
                    85                  90                  95

Thr Phe Gly Gly Gly Thr Lys Val Glu Ile Lys Arg
                100                 105

<210> SEQ ID NO 327
<211> LENGTH: 108
<212> TYPE: PRT
<213> ORGANISM: Artificial Sequence
<220> FEATURE:
<223> OTHER INFORMATION: Synthetic

<400> SEQUENCE: 327

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ile Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Leu Glu Ile Lys Arg
                100                 105

<210> SEQ ID NO 328
<211> LENGTH: 108
<212> TYPE: PRT
<213> ORGANISM: Artificial Sequence
<220> FEATURE:
<223> OTHER INFORMATION: Synthetic

<400> SEQUENCE: 328

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys Arg
                100                 105

<210> SEQ ID NO 329
<211> LENGTH: 108
<212> TYPE: PRT
<213> ORGANISM: Artificial Sequence
<220> FEATURE:
<223> OTHER INFORMATION: Synthetic

<400> SEQUENCE: 329
```

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Val Ser Thr Leu Gln Ser Gly Val Pro Ser Arg Phe Ser Gly
    50                  55                  60

Ser Gly Ser Gly Thr Val Phe Thr Leu Thr Ile Ser Ser Leu Gln Pro
65              70                  75                  80

Glu Asp Phe Ala Thr Tyr Phe Cys Gln Gln Gly Asn Ser Phe Pro Leu
                85                  90                  95

Thr Phe Gly Gly Gly Thr Lys Val Glu Ile Lys Arg
            100                 105

<210> SEQ ID NO 330
<211> LENGTH: 108
<212> TYPE: PRT
<213> ORGANISM: Artificial Sequence
<220> FEATURE:
<223> OTHER INFORMATION: Synthetic

<400> SEQUENCE: 330

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ala Ile Ser Asn Leu
            20                  25                  30

Leu Ala Trp Tyr Gln Gln Lys Pro Gly Lys Pro Pro Asn Leu Leu Ile
        35                  40                  45

Tyr Asp Ile Ser Thr Leu Gln Asn Gly Val Pro Ser Arg Phe Ser Gly
    50                  55                  60

Ser Gly Ser Gly Thr Asp Phe Thr Leu Thr Ile Asn Ser Leu Gln Pro
65              70                  75                  80

Glu Asp Phe Ala Ile Tyr Tyr Cys Gln Gln Ser Lys Asn Phe Pro Val
                85                  90                  95

Thr Phe Gly Gly Gly Thr Lys Val Glu Ile Lys Arg
            100                 105

<210> SEQ ID NO 331
<211> LENGTH: 108
<212> TYPE: PRT
<213> ORGANISM: Artificial Sequence
<220> FEATURE:
<223> OTHER INFORMATION: Synthetic

<400> SEQUENCE: 331

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Ala Asp Tyr Thr Leu Thr Ile Ser Ser Leu Gln Pro
65              70                  75                  80

Glu Asp Phe Ala Thr Tyr Tyr Cys Gln Gln Ala Asn Ser Phe Pro Leu

```
                    85                  90                  95

Thr Phe Ala Gly Gly Thr Lys Leu Glu Ile Lys Arg
                100                 105

<210> SEQ ID NO 332
<211> LENGTH: 108
<212> TYPE: PRT
<213> ORGANISM: Artificial Sequence
<220> FEATURE:
<223> OTHER INFORMATION: Synthetic

<400> SEQUENCE: 332

Asp Ile Gln Leu Thr Gln Ser Pro Ser Ser Leu Ser Ala Ser Pro Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Lys Ser Gly Thr Glu Tyr Thr Leu Thr Ile Ser Ser Leu Gln Pro
65                  70                  75                  80

Glu Asp Phe Ala Thr Tyr Tyr Cys Gln Gln Leu Glu Ser Tyr Pro Leu
                85                  90                  95

Thr Phe Gly Gly Gly Thr Lys Val Glu Ile Lys Arg
                100                 105

<210> SEQ ID NO 333
<211> LENGTH: 113
<212> TYPE: PRT
<213> ORGANISM: Artificial Sequence
<220> FEATURE:
<223> OTHER INFORMATION: Synthetic

<400> SEQUENCE: 333

Ala Ile Arg Met Thr Gln Ser Pro Asp Ser Leu Val Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Ser
65                  70                  75                  80

Ile Ser Ser Leu Gln Ala Glu Asp Val Ala Val Tyr Tyr Cys Gln Gln
                85                  90                  95

Tyr Tyr Ser Ser Pro Thr Phe Gly Gly Gly Thr Lys Val Glu Ile Lys
                100                 105                 110

Arg

<210> SEQ ID NO 334
<211> LENGTH: 108
<212> TYPE: PRT
<213> ORGANISM: Artificial Sequence
<220> FEATURE:
<223> OTHER INFORMATION: Synthetic

<400> SEQUENCE: 334
```

Asp Val Val Met Thr Gln Ser Pro Phe Phe Leu Ser Ala Ser Val Gly
1               5                   10                  15

Asp Arg Val Thr Ile Thr Cys Arg Ala Ser Gln Gly Ile Ala Ser Asn
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Thr Gly
50                  55                  60

Ser Gly Ser Gly Thr Glu Phe Thr Leu Thr Val Thr Ser Leu Gln Pro
65                  70                  75                  80

Glu Asp Phe Ala Thr Tyr Tyr Cys Gln Gln Leu Lys Thr Phe Pro Leu
                85                  90                  95

Thr Phe Gly Gly Gly Thr Lys Val Glu Ile Lys Arg
            100                 105

<210> SEQ ID NO 335
<211> LENGTH: 108
<212> TYPE: PRT
<213> ORGANISM: Artificial Sequence
<220> FEATURE:
<223> OTHER INFORMATION: Synthetic

<400> SEQUENCE: 335

Val Ile Trp Met Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Asn Trp Phe Pro Leu
                85                  90                  95

Thr Phe Gly Pro Gly Thr Arg Leu Glu Ile Lys Arg
            100                 105

<210> SEQ ID NO 336
<211> LENGTH: 108
<212> TYPE: PRT
<213> ORGANISM: Artificial Sequence
<220> FEATURE:
<223> OTHER INFORMATION: Synthetic

<400> SEQUENCE: 336

Asp Ile Gln Met Thr Gln Ser Pro Ser Ser Leu Ser Thr Ser Ala Gly
1               5                   10                  15

Asp Thr Val Thr Ile Thr Cys Arg Ala Ser Gln Ser Ile Tyr Thr Tyr
            20                  25                  30

Leu Asn Trp Tyr Gln Gln Lys Pro Gly Lys Ala Pro Asn Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gln Ser Phe Pro Ile
                85                  90                  95

```
Thr Phe Gly Gln Gly Thr Arg Leu Glu Ile Lys Arg
            100                 105
```

```
<210> SEQ ID NO 337
<211> LENGTH: 108
<212> TYPE: PRT
<213> ORGANISM: Artificial Sequence
<220> FEATURE:
<223> OTHER INFORMATION: Synthetic

<400> SEQUENCE: 337
```

```
Val Ile Trp Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Phe Pro Leu
                85                  90                  95

Thr Phe Gly Gly Gly Thr Lys Val Glu Ile Lys Arg
            100                 105
```

```
<210> SEQ ID NO 338
<211> LENGTH: 108
<212> TYPE: PRT
<213> ORGANISM: Artificial Sequence
<220> FEATURE:
<223> OTHER INFORMATION: Synthetic

<400> SEQUENCE: 338
```

```
Ala Ile Gln Leu Thr Gln Ser Pro Ser Thr Leu Ser Ala Ser Val Gly
1               5                   10                  15

Asp Arg Val Thr Ile Thr Cys Arg Ala Ser Gln Phe Val Ser Asp Trp
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Leu Gln Asp Tyr His Phe Pro Leu
                85                  90                  95

Thr Phe Gly Gly Gly Thr Lys Leu Glu Ile Lys Arg
            100                 105
```

```
<210> SEQ ID NO 339
<211> LENGTH: 108
<212> TYPE: PRT
<213> ORGANISM: Artificial Sequence
<220> FEATURE:
<223> OTHER INFORMATION: Synthetic

<400> SEQUENCE: 339
```

```
Asp Val Val Met Thr Gln Ser Pro Ser Ser Val Ser Ala Ser Val Gly
1               5                   10                  15
```

Asp Arg Val Thr Ile Thr Cys Arg Ala Ser Gln Asp Ile Val Asn Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Ala Pro Ser Arg Phe Ser Ala
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly His Ser Phe Pro Leu
                85                  90                  95

Thr Phe Gly Pro Gly Thr Lys Leu Glu Ile Lys Arg
            100                 105

<210> SEQ ID NO 340
<211> LENGTH: 108
<212> TYPE: PRT
<213> ORGANISM: Artificial Sequence
<220> FEATURE:
<223> OTHER INFORMATION: Synthetic

<400> SEQUENCE: 340

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Thr Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Tyr Gly Thr Glu Phe Thr Leu Thr Ile Ser Gly Leu Gln Pro
65                  70                  75                  80

Glu Asp Phe Ala Thr Tyr Tyr Cys Gln Gln Ser Tyr Ile Phe Pro Leu
                85                  90                  95

Thr Phe Gly Arg Gly Thr Lys Val Glu Ile Lys Arg
            100                 105

<210> SEQ ID NO 341
<211> LENGTH: 107
<212> TYPE: PRT
<213> ORGANISM: Artificial Sequence
<220> FEATURE:
<223> OTHER INFORMATION: Synthetic

<400> SEQUENCE: 341

Ala Ile Arg Met Thr Gln Ser Pro Ser Phe Val Ser Ala Ser Val Gly
1               5                   10                  15

Asp Arg Val Thr Ile Ala Cys Arg Ala Ser Gln Thr Ile Ser Thr Trp
            20                  25                  30

Leu Ala Trp Tyr Gln Gln Lys Pro Gly Lys Ala Pro Lys Val Leu Ile
        35                  40                  45

Ser Lys Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys Arg
            100                 105

<210> SEQ ID NO 342
<211> LENGTH: 107
<212> TYPE: PRT
<213> ORGANISM: Artificial Sequence
<220> FEATURE:
<223> OTHER INFORMATION: Synthetic

<400> SEQUENCE: 342

Ala Ile Arg Met Thr Gln Ser Pro Ser Phe Val Ser Ala Ser Val Gly
1               5                   10                  15

Asp Arg Val Thr Ile Ala Cys Arg Ala Ser Gln Thr Ile Ser Thr Trp
            20                  25                  30

Leu Ala Trp Tyr Gln Gln Lys Pro Gly Lys Ala Pro Lys Val Leu Ile
        35                  40                  45

Ser Lys Ala Ser Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys Arg
            100                 105

<210> SEQ ID NO 343
<211> LENGTH: 109
<212> TYPE: PRT
<213> ORGANISM: Artificial Sequence
<220> FEATURE:
<223> OTHER INFORMATION: Synthetic

<400> SEQUENCE: 343

Asp Ile Val Met Thr Gln Ser Pro Ser Phe Val Ser Ala Ser Val Gly
1               5                   10                  15

Asp Thr Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Phe Thr Phe Gly Pro Gly Thr Lys Val Glu Ile Lys Arg
            100                 105

<210> SEQ ID NO 344
<211> LENGTH: 107
<212> TYPE: PRT
<213> ORGANISM: Artificial Sequence
<220> FEATURE:
<223> OTHER INFORMATION: Synthetic

<400> SEQUENCE: 344

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Tyr Trp
            20                  25                  30

-continued

```
Leu Ala Trp Tyr Gln Gln Lys Pro Gly Lys Ala Pro Lys Leu Leu Ile
             35                  40                  45

Tyr Arg Ala Ser Ser Leu Gln Ser Gly Val Pro Ser Arg Phe Ser Gly
 50                  55                  60

Ser Gly Ser Ala Thr Glu Phe Thr Leu Thr Ile Thr Ser Leu Gln Pro
 65                  70                  75                  80

Asp Asp Phe Ala Thr Tyr Phe Cys Gln Gln Tyr Ser Ser Tyr Trp Thr
                 85                  90                  95

Phe Gly Gln Gly Thr Lys Val Glu Ile Lys Arg
                100                 105
```

<210> SEQ ID NO 345
<211> LENGTH: 108
<212> TYPE: PRT
<213> ORGANISM: Artificial Sequence
<220> FEATURE:
<223> OTHER INFORMATION: Synthetic

<400> SEQUENCE: 345

```
Glu Ile Val Leu Thr Gln Ser Pro Ser Ser Leu Ser Ala Ser Val Gly
 1               5                  10                  15

Asp Thr Val Thr Ile Thr Cys Arg Ala Thr Gln Ser Ile Ser Ser Trp
                 20                  25                  30

Leu Ala Trp Tyr Gln Gln Lys Pro Gly Lys Ala Pro Gln Arg Leu Ile
             35                  40                  45

Ser Gly Ala Ser Thr Leu Gln Ser Gly Val Pro Ser Arg Phe Ser Gly
 50                  55                  60

Ser Gly Ser Gly Thr Glu Phe Thr Leu Thr Ile Ser Gly Leu Gln Pro
 65                  70                  75                  80

Glu Asp Phe Ala Thr Tyr Tyr Cys Leu Gln His Asn Thr Tyr Pro Phe
                 85                  90                  95

Thr Phe Gly Gln Gly Thr Lys Val Glu Ile Lys Arg
                100                 105
```

<210> SEQ ID NO 346
<211> LENGTH: 108
<212> TYPE: PRT
<213> ORGANISM: Artificial Sequence
<220> FEATURE:
<223> OTHER INFORMATION: Synthetic

<400> SEQUENCE: 346

```
Asp Ile Val Met Thr Gln Ser Pro Ser Ser Val Ser Ala Ser Val Gly
 1               5                  10                  15

Asp Arg Val Thr Ile Thr Cys Arg Ala Ser Gln Gly Val Arg Asn Trp
                 20                  25                  30

Leu Ala Trp Tyr Gln Gln Lys Pro Gly Lys Ala Pro Lys Leu Leu Ile
             35                  40                  45

Tyr Ala Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Thr
 65                  70                  75                  80

Asp Asp Phe Ala Thr Tyr Tyr Cys Gln Gln Gly His Ser Phe Pro Leu
                 85                  90                  95

Thr Phe Gly Gly Gly Thr Lys Val Glu Ile Lys Arg
                100                 105
```

<210> SEQ ID NO 347

```
<211> LENGTH: 108
<212> TYPE: PRT
<213> ORGANISM: Artificial Sequence
<220> FEATURE:
<223> OTHER INFORMATION: Synthetic

<400> SEQUENCE: 347

Asp Ile Val Met Thr Gln Ser Pro Ser Ser Val Ala Ser Val Gly
1               5                   10                  15

Asp Arg Val Thr Ile Thr Cys Arg Ala Ser Gln Gly Val Arg Asn Trp
            20                  25                  30

Leu Ala Trp Tyr Gln Gln Lys Pro Gly Lys Ala Pro Lys Leu Leu Ile
        35                  40                  45

Tyr Ala Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Thr
65                  70                  75                  80

Asp Asp Phe Ala Thr Tyr Tyr Cys Gln Gln Gly His Ser Phe Pro Leu
                85                  90                  95

Thr Phe Gly Gly Gly Thr Lys Val Glu Ile Lys Arg
            100                 105

<210> SEQ ID NO 348
<211> LENGTH: 108
<212> TYPE: PRT
<213> ORGANISM: Artificial Sequence
<220> FEATURE:
<223> OTHER INFORMATION: Synthetic

<400> SEQUENCE: 348

Val Ile Trp Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Gly Gly Ser Gly Thr Asp Phe Thr Leu Thr Ile Asn Ser Leu Gln Pro
65                  70                  75                  80

Asp Asp Phe Ala Ser Tyr Tyr Cys Gln Gln Ala His Ser Phe Pro Phe
                85                  90                  95

Thr Phe Gly Gly Gly Thr Lys Leu Glu Ile Lys Arg
            100                 105

<210> SEQ ID NO 349
<211> LENGTH: 108
<212> TYPE: PRT
<213> ORGANISM: Artificial Sequence
<220> FEATURE:
<223> OTHER INFORMATION: Synthetic

<400> SEQUENCE: 349

Glu Ile Val Met Thr Gln Ser Pro Ser Ser Val Ser Ala Ser Val Gly
1               5                   10                  15

Asp Arg Val Thr Ile Thr Cys Arg Ala Ser Gln Asp Ile Thr Ser Trp
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Thr Gly Leu Gln Pro
65                  70                  75                  80

Glu Asp Phe Ala Thr Tyr Tyr Cys Gln Gln Ala Asn Met Phe Pro Leu
                85                  90                  95

Thr Phe Gly Gly Gly Thr Lys Val Glu Ile Lys Arg
            100                 105
```

<210> SEQ ID NO 350
<211> LENGTH: 108
<212> TYPE: PRT
<213> ORGANISM: Artificial Sequence
<220> FEATURE:
<223> OTHER INFORMATION: Synthetic

<400> SEQUENCE: 350

```
Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asp Tyr
            20                  25                  30

Leu Ala Trp Tyr Gln Gln Lys Pro Gly Lys Ala Pro Ser Leu Leu Ile
        35                  40                  45

Tyr Ala Ala Ser Asn Leu Glu Arg Gly Val Pro Ser Arg Phe Ser Gly
    50                  55                  60

Ser Gly Ser Gly Lys Tyr Phe Ile Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105
```

<210> SEQ ID NO 351
<211> LENGTH: 108
<212> TYPE: PRT
<213> ORGANISM: Artificial Sequence
<220> FEATURE:
<223> OTHER INFORMATION: Synthetic

<400> SEQUENCE: 351

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Gly Ile Ser Gly Trp
            20                  25                  30

Leu Ala Trp Tyr Gln Gln Ile Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Phe
                85                  90                  95

Thr Phe Gly Pro Gly Thr Lys Val Glu Ile Lys Arg
            100                 105
```

<210> SEQ ID NO 352
<211> LENGTH: 116
<212> TYPE: PRT
<213> ORGANISM: Artificial Sequence
<220> FEATURE:
<223> OTHER INFORMATION: Synthetic

<400> SEQUENCE: 352

Gln Val Gln Leu Gln Gln Ser Gly Ser Glu Leu Val Arg Pro Gly Thr
1               5                   10                  15

Ser Val Lys Ile Ser Cys Lys Ala Ser Gly Tyr Thr Phe Thr Asn Tyr
            20                  25                  30

Trp Leu Gly Trp Ile Lys Gln Arg Pro Gly His Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Ser Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Pro Asn Leu Pro Gly Asp Tyr Trp Gly Gln Gly Thr Ser Val
            100                 105                 110

Thr Val Ser Ser
            115

<210> SEQ ID NO 353
<211> LENGTH: 112
<212> TYPE: PRT
<213> ORGANISM: Artificial Sequence
<220> FEATURE:
<223> OTHER INFORMATION: Synthetic

<400> SEQUENCE: 353

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Gly Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 354
<211> LENGTH: 10
<212> TYPE: PRT
<213> ORGANISM: Artificial Sequence
<220> FEATURE:
<223> OTHER INFORMATION: Synthetic

<400> SEQUENCE: 354

Gly Tyr Thr Phe Thr Asn Tyr Trp Leu Gly
1               5                   10

<210> SEQ ID NO 355
<211> LENGTH: 17
<212> TYPE: PRT
<213> ORGANISM: Artificial Sequence
<220> FEATURE:

<223> OTHER INFORMATION: Synthetic

<400> SEQUENCE: 355

Asp Ile Tyr Pro Gly Gly Asp Tyr Ile Asn Tyr Asn Glu Lys Phe Lys
1               5                   10                  15
Gly

<210> SEQ ID NO 356
<211> LENGTH: 7
<212> TYPE: PRT
<213> ORGANISM: Artificial Sequence
<220> FEATURE:
<223> OTHER INFORMATION: Synthetic

<400> SEQUENCE: 356

Pro Asn Leu Pro Gly Asp Tyr
1               5

<210> SEQ ID NO 357
<211> LENGTH: 16
<212> TYPE: PRT
<213> ORGANISM: Artificial Sequence
<220> FEATURE:
<223> OTHER INFORMATION: Synthetic

<400> SEQUENCE: 357

Arg Ser Ser Lys Ser Leu Leu His Ser Asn Gly Ile Thr Tyr Leu Tyr
1               5                   10                  15

<210> SEQ ID NO 358
<211> LENGTH: 7
<212> TYPE: PRT
<213> ORGANISM: Artificial Sequence
<220> FEATURE:
<223> OTHER INFORMATION: Synthetic

<400> SEQUENCE: 358

Gln Val Ser Asn Leu Ala Ser
1               5

<210> SEQ ID NO 359
<211> LENGTH: 9
<212> TYPE: PRT
<213> ORGANISM: Artificial Sequence
<220> FEATURE:
<223> OTHER INFORMATION: Synthetic

<400> SEQUENCE: 359

Ala Gln Asn Leu Glu Leu Pro Trp Thr
1               5

<210> SEQ ID NO 360
<211> LENGTH: 116
<212> TYPE: PRT
<213> ORGANISM: Artificial Sequence
<220> FEATURE:
<223> OTHER INFORMATION: Synthetic

<400> SEQUENCE: 360

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
            50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 361
<211> LENGTH: 116
<212> TYPE: PRT
<213> ORGANISM: Artificial Sequence
<220> FEATURE:
<223> OTHER INFORMATION: Synthetic

<400> SEQUENCE: 361

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Ile Asn Tyr Asn Glu Lys Phe
            50                  55                  60

Lys Gly Arg Val Thr Met Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 362
<211> LENGTH: 116
<212> TYPE: PRT
<213> ORGANISM: Artificial Sequence
<220> FEATURE:
<223> OTHER INFORMATION: Synthetic

<400> SEQUENCE: 362

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Ile Asn Tyr Asn Glu Lys Phe
            50                  55                  60

Lys Gly Arg Val Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val

-continued

```
              100                 105                 110

Thr Val Ser Ser
        115

<210> SEQ ID NO 363
<211> LENGTH: 116
<212> TYPE: PRT
<213> ORGANISM: Artificial Sequence
<220> FEATURE:
<223> OTHER INFORMATION: Synthetic

<400> SEQUENCE: 363

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 364
<211> LENGTH: 116
<212> TYPE: PRT
<213> ORGANISM: Artificial Sequence
<220> FEATURE:
<223> OTHER INFORMATION: Synthetic

<400> SEQUENCE: 364

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 365
<211> LENGTH: 116
<212> TYPE: PRT
<213> ORGANISM: Artificial Sequence
<220> FEATURE:
```

<223> OTHER INFORMATION: Synthetic

<400> SEQUENCE: 365

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 366
<211> LENGTH: 116
<212> TYPE: PRT
<213> ORGANISM: Artificial Sequence
<220> FEATURE:
<223> OTHER INFORMATION: Synthetic

<400> SEQUENCE: 366

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 367
<211> LENGTH: 116
<212> TYPE: PRT
<213> ORGANISM: Artificial Sequence
<220> FEATURE:
<223> OTHER INFORMATION: Synthetic

<400> SEQUENCE: 367

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met

```
                 35                  40                  45

Gly Asp Ile Tyr Pro Gly Gly Asp Tyr Ile Asn Tyr Asn Glu Lys Phe
         50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
                100                 105                 110

Thr Val Ser Ser
        115

<210> SEQ ID NO 368
<211> LENGTH: 116
<212> TYPE: PRT
<213> ORGANISM: Artificial Sequence
<220> FEATURE:
<223> OTHER INFORMATION: Synthetic

<400> SEQUENCE: 368

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Ile Asn Tyr Asn Glu Lys Phe
         50                  55                  60

Lys Gly Arg Val Thr Met Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
                100                 105                 110

Thr Val Ser Ser
        115

<210> SEQ ID NO 369
<211> LENGTH: 116
<212> TYPE: PRT
<213> ORGANISM: Artificial Sequence
<220> FEATURE:
<223> OTHER INFORMATION: Synthetic

<400> SEQUENCE: 369

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Ile Asn Tyr Asn Glu Lys Phe
         50                  55                  60

Lys Gly Arg Val Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95
```

Ala Arg Pro Asn Leu Pro Gly Asp Tyr Trp Gly Gln Gly Thr Thr Val
            100                 105                 110

Thr Val Ser Ser
        115

<210> SEQ ID NO 370
<211> LENGTH: 116
<212> TYPE: PRT
<213> ORGANISM: Artificial Sequence
<220> FEATURE:
<223> OTHER INFORMATION: Synthetic

<400> SEQUENCE: 370

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 371
<211> LENGTH: 116
<212> TYPE: PRT
<213> ORGANISM: Artificial Sequence
<220> FEATURE:
<223> OTHER INFORMATION: Synthetic

<400> SEQUENCE: 371

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 372
<211> LENGTH: 116
<212> TYPE: PRT
<213> ORGANISM: Artificial Sequence

```
<220> FEATURE:
<223> OTHER INFORMATION: Synthetic

<400> SEQUENCE: 372

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 373
<211> LENGTH: 116
<212> TYPE: PRT
<213> ORGANISM: Artificial Sequence
<220> FEATURE:
<223> OTHER INFORMATION: Synthetic

<400> SEQUENCE: 373

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 374
<211> LENGTH: 112
<212> TYPE: PRT
<213> ORGANISM: Artificial Sequence
<220> FEATURE:
<223> OTHER INFORMATION: Synthetic

<400> SEQUENCE: 374

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30
```

```
Asn Gly Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
            100                 105                 110

<210> SEQ ID NO 375
<211> LENGTH: 116
<212> TYPE: PRT
<213> ORGANISM: Artificial Sequence
<220> FEATURE:
<223> OTHER INFORMATION: Synthetic

<400> SEQUENCE: 375

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
         50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Lys Asp His Trp Gly Gln Gly Thr Thr Val
            100                 105                 110

Thr Val Ser Ser
        115

<210> SEQ ID NO 376
<211> LENGTH: 112
<212> TYPE: PRT
<213> ORGANISM: Artificial Sequence
<220> FEATURE:
<223> OTHER INFORMATION: Synthetic

<400> SEQUENCE: 376

Asp Ile Val Met Thr Gln Ser Pro Leu Ser Leu Pro Val Thr Pro Gly
  1               5                  10                  15

Glu Pro Ala Ser Ile Ser Cys Arg Ser Ser Lys Ser Leu Leu His Ser
                 20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
            100                 105                 110
```

<210> SEQ ID NO 377
<211> LENGTH: 116
<212> TYPE: PRT
<213> ORGANISM: Artificial Sequence
<220> FEATURE:
<223> OTHER INFORMATION: Synthetic

<400> SEQUENCE: 377

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asp Leu Pro Gly Asp Tyr Trp Gly Gln Gly Thr Thr Val
            100                 105                 110

Thr Val Ser Ser
        115

<210> SEQ ID NO 378
<211> LENGTH: 112
<212> TYPE: PRT
<213> ORGANISM: Artificial Sequence
<220> FEATURE:
<223> OTHER INFORMATION: Synthetic

<400> SEQUENCE: 378

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 379
<211> LENGTH: 116
<212> TYPE: PRT
<213> ORGANISM: Artificial Sequence
<220> FEATURE:
<223> OTHER INFORMATION: Synthetic

<400> SEQUENCE: 379

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Lys Asp Tyr Trp Gly Gln Gly Thr Thr Val
            100                 105                 110

Thr Val Ser Ser
        115

<210> SEQ ID NO 380
<211> LENGTH: 112
<212> TYPE: PRT
<213> ORGANISM: Artificial Sequence
<220> FEATURE:
<223> OTHER INFORMATION: Synthetic

<400> SEQUENCE: 380

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 381
<211> LENGTH: 116
<212> TYPE: PRT
<213> ORGANISM: Artificial Sequence
<220> FEATURE:
<223> OTHER INFORMATION: Synthetic

<400> SEQUENCE: 381

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Pro Asn Leu Pro Lys Asp Tyr Trp Gly Gln Gly Thr Thr Val
            100                 105                 110

Thr Val Ser Ser
        115

<210> SEQ ID NO 382
<211> LENGTH: 112
<212> TYPE: PRT
<213> ORGANISM: Artificial Sequence
<220> FEATURE:
<223> OTHER INFORMATION: Synthetic

<400> SEQUENCE: 382

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 383
<211> LENGTH: 116
<212> TYPE: PRT
<213> ORGANISM: Artificial Sequence
<220> FEATURE:
<223> OTHER INFORMATION: Synthetic

<400> SEQUENCE: 383

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Arg Asp Tyr Trp Gly Gln Gly Thr Thr Val
            100                 105                 110

Thr Val Ser Ser
        115

<210> SEQ ID NO 384
<211> LENGTH: 112
<212> TYPE: PRT
<213> ORGANISM: Artificial Sequence
<220> FEATURE:
<223> OTHER INFORMATION: Synthetic
```

<400> SEQUENCE: 384

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 385
<211> LENGTH: 116
<212> TYPE: PRT
<213> ORGANISM: Artificial Sequence
<220> FEATURE:
<223> OTHER INFORMATION: Synthetic

<400> SEQUENCE: 385

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Arg Asp Tyr Trp Gly Gln Gly Thr Thr Val
            100                 105                 110

Thr Val Ser Ser
        115

<210> SEQ ID NO 386
<211> LENGTH: 112
<212> TYPE: PRT
<213> ORGANISM: Artificial Sequence
<220> FEATURE:
<223> OTHER INFORMATION: Synthetic

<400> SEQUENCE: 386

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 387
<211> LENGTH: 116
<212> TYPE: PRT
<213> ORGANISM: Artificial Sequence
<220> FEATURE:
<223> OTHER INFORMATION: Synthetic

<400> SEQUENCE: 387

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Gly Leu Pro Gln Asp Tyr Trp Gly Gln Gly Thr Thr Val
            100                 105                 110

Thr Val Ser Ser
        115

<210> SEQ ID NO 388
<211> LENGTH: 112
<212> TYPE: PRT
<213> ORGANISM: Artificial Sequence
<220> FEATURE:
<223> OTHER INFORMATION: Synthetic

<400> SEQUENCE: 388

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 389
<211> LENGTH: 116
<212> TYPE: PRT

```
<213> ORGANISM: Artificial Sequence
<220> FEATURE:
<223> OTHER INFORMATION: Synthetic

<400> SEQUENCE: 389

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asp Leu Pro Lys Tyr Trp Gly Gln Gly Thr Thr Val
                100                 105                 110

Thr Val Ser Ser
            115

<210> SEQ ID NO 390
<211> LENGTH: 112
<212> TYPE: PRT
<213> ORGANISM: Artificial Sequence
<220> FEATURE:
<223> OTHER INFORMATION: Synthetic

<400> SEQUENCE: 390

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
                100                 105                 110

<210> SEQ ID NO 391
<211> LENGTH: 116
<212> TYPE: PRT
<213> ORGANISM: Artificial Sequence
<220> FEATURE:
<223> OTHER INFORMATION: Synthetic

<400> SEQUENCE: 391

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45
```

Gly Asp Ile Tyr Pro Gly Gly Asp Tyr Ile Asn Tyr Asn Glu Lys Phe
            50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 392
<211> LENGTH: 112
<212> TYPE: PRT
<213> ORGANISM: Artificial Sequence
<220> FEATURE:
<223> OTHER INFORMATION: Synthetic

<400> SEQUENCE: 392

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Asn
                 85                  90                  95

Leu Glu Leu Pro Trp Thr Phe Gly Gly Gly Thr Lys Val Glu Ile Lys
            100                 105                 110

<210> SEQ ID NO 393
<211> LENGTH: 116
<212> TYPE: PRT
<213> ORGANISM: Artificial Sequence
<220> FEATURE:
<223> OTHER INFORMATION: Synthetic

<400> SEQUENCE: 393

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
            100                 105                 110

Thr Val Ser Ser

```
                115

<210> SEQ ID NO 394
<211> LENGTH: 112
<212> TYPE: PRT
<213> ORGANISM: Artificial Sequence
<220> FEATURE:
<223> OTHER INFORMATION: Synthetic

<400> SEQUENCE: 394

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Met Pro Trp Thr Phe Gly Gly Gly Thr Lys Val Glu Ile Lys
            100                 105                 110

<210> SEQ ID NO 395
<211> LENGTH: 116
<212> TYPE: PRT
<213> ORGANISM: Artificial Sequence
<220> FEATURE:
<223> OTHER INFORMATION: Synthetic

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 396
<211> LENGTH: 112
<212> TYPE: PRT
<213> ORGANISM: Artificial Sequence
<220> FEATURE:
<223> OTHER INFORMATION: Synthetic

<400> SEQUENCE: 396

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Asn
                85                  90                  95

Leu Glu Met Pro Trp Thr Phe Gly Gly Gly Thr Lys Val Glu Ile Lys
            100                 105                 110
```

<210> SEQ ID NO 397
<211> LENGTH: 116
<212> TYPE: PRT
<213> ORGANISM: Artificial Sequence
<220> FEATURE:
<223> OTHER INFORMATION: Synthetic

<400> SEQUENCE: 397

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115
```

<210> SEQ ID NO 398
<211> LENGTH: 112
<212> TYPE: PRT
<213> ORGANISM: Artificial Sequence
<220> FEATURE:
<223> OTHER INFORMATION: Synthetic

<400> SEQUENCE: 398

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
```

```
                    85                  90                  95

Leu Glu Glu Pro Trp Thr Phe Gly Gly Gly Thr Lys Val Glu Ile Lys
                100                 105                 110
```

<210> SEQ ID NO 399
<211> LENGTH: 116
<212> TYPE: PRT
<213> ORGANISM: Artificial Sequence
<220> FEATURE:
<223> OTHER INFORMATION: Synthetic

<400> SEQUENCE: 399

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
                100                 105                 110

Thr Val Ser Ser
        115
```

<210> SEQ ID NO 400
<211> LENGTH: 112
<212> TYPE: PRT
<213> ORGANISM: Artificial Sequence
<220> FEATURE:
<223> OTHER INFORMATION: Synthetic

<400> SEQUENCE: 400

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
                100                 105                 110
```

<210> SEQ ID NO 401
<211> LENGTH: 116
<212> TYPE: PRT
<213> ORGANISM: Artificial Sequence
<220> FEATURE:
<223> OTHER INFORMATION: Synthetic

<400> SEQUENCE: 401

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
            115

<210> SEQ ID NO 402
<211> LENGTH: 112
<212> TYPE: PRT
<213> ORGANISM: Artificial Sequence
<220> FEATURE:
<223> OTHER INFORMATION: Synthetic

<400> SEQUENCE: 402

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 403
<211> LENGTH: 116
<212> TYPE: PRT
<213> ORGANISM: Artificial Sequence
<220> FEATURE:
<223> OTHER INFORMATION: Synthetic

<400> SEQUENCE: 403

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr

-continued

```
              65                  70                  75                  80
Met Glu Leu Ser Arg Leu Arg Ser Asp Asp Thr Ala Val Tyr Tyr Cys
                    85                  90                  95

Ala Arg Pro Asn Leu Pro Lys Asp His Trp Gly Gln Gly Thr Thr Val
                100                 105                 110

Thr Val Ser Ser
        115

<210> SEQ ID NO 404
<211> LENGTH: 112
<212> TYPE: PRT
<213> ORGANISM: Artificial Sequence
<220> FEATURE:
<223> OTHER INFORMATION: Synthetic

<400> SEQUENCE: 404

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Glu Pro Trp Thr Phe Gly Gly Gly Thr Lys Val Glu Ile Lys
                100                 105                 110

<210> SEQ ID NO 405
<211> LENGTH: 116
<212> TYPE: PRT
<213> ORGANISM: Artificial Sequence
<220> FEATURE:
<223> OTHER INFORMATION: Synthetic

<400> SEQUENCE: 405

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
                100                 105                 110

Thr Val Ser Ser
        115

<210> SEQ ID NO 406
<211> LENGTH: 112
```

```
<212> TYPE: PRT
<213> ORGANISM: Artificial Sequence
<220> FEATURE:
<223> OTHER INFORMATION: Synthetic

<400> SEQUENCE: 406

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 407
<211> LENGTH: 116
<212> TYPE: PRT
<213> ORGANISM: Artificial Sequence
<220> FEATURE:
<223> OTHER INFORMATION: Synthetic

<400> SEQUENCE: 407

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 408
<211> LENGTH: 112
<212> TYPE: PRT
<213> ORGANISM: Artificial Sequence
<220> FEATURE:
<223> OTHER INFORMATION: Synthetic

<400> SEQUENCE: 408

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
```

```
                35                  40                  45
Pro Gln Leu Leu Ile Tyr Gln Val Ser Asn Leu Ala Arg Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 409
<211> LENGTH: 116
<212> TYPE: PRT
<213> ORGANISM: Artificial Sequence
<220> FEATURE:
<223> OTHER INFORMATION: Synthetic

<400> SEQUENCE: 409

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 410
<211> LENGTH: 112
<212> TYPE: PRT
<213> ORGANISM: Artificial Sequence
<220> FEATURE:
<223> OTHER INFORMATION: Synthetic

<400> SEQUENCE: 410

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Lys Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110
```

<210> SEQ ID NO 411
<211> LENGTH: 116
<212> TYPE: PRT
<213> ORGANISM: Artificial Sequence
<220> FEATURE:
<223> OTHER INFORMATION: Synthetic

<400> SEQUENCE: 411

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Ile Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 412
<211> LENGTH: 112
<212> TYPE: PRT
<213> ORGANISM: Artificial Sequence
<220> FEATURE:
<223> OTHER INFORMATION: Synthetic

<400> SEQUENCE: 412

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Val Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 413
<211> LENGTH: 116
<212> TYPE: PRT
<213> ORGANISM: Artificial Sequence
<220> FEATURE:
<223> OTHER INFORMATION: Synthetic

<400> SEQUENCE: 413

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr

```
            20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Val Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
                100                 105                 110

Thr Val Ser Ser
            115

<210> SEQ ID NO 414
<211> LENGTH: 112
<212> TYPE: PRT
<213> ORGANISM: Artificial Sequence
<220> FEATURE:
<223> OTHER INFORMATION: Synthetic

<400> SEQUENCE: 414

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Leu Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
                100                 105                 110

<210> SEQ ID NO 415
<211> LENGTH: 116
<212> TYPE: PRT
<213> ORGANISM: Artificial Sequence
<220> FEATURE:
<223> OTHER INFORMATION: Synthetic

<400> SEQUENCE: 415

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Trp Trp Ile Lys Gln Ala Pro Gly Gln Gly Leu Glu Trp Ile
            35                  40                  45

Gly Asp Ile Phe Pro Gly Gly Asp Tyr Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Pro Asn Leu Pro Gly Asp Tyr Trp Gly Gln Gly Thr Thr Val
                100                 105                 110

Thr Val Ser Ser
        115

<210> SEQ ID NO 416
<211> LENGTH: 112
<212> TYPE: PRT
<213> ORGANISM: Artificial Sequence
<220> FEATURE:
<223> OTHER INFORMATION: Synthetic

<400> SEQUENCE: 416

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Asp Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
                100                 105                 110

<210> SEQ ID NO 417
<211> LENGTH: 116
<212> TYPE: PRT
<213> ORGANISM: Artificial Sequence
<220> FEATURE:
<223> OTHER INFORMATION: Synthetic

<400> SEQUENCE: 417

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
                100                 105                 110

Thr Val Ser Ser
        115

<210> SEQ ID NO 418
<211> LENGTH: 112
<212> TYPE: PRT
<213> ORGANISM: Artificial Sequence
<220> FEATURE:
<223> OTHER INFORMATION: Synthetic
```

```
<400> SEQUENCE: 418

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 419
<211> LENGTH: 116
<212> TYPE: PRT
<213> ORGANISM: Artificial Sequence
<220> FEATURE:
<223> OTHER INFORMATION: Synthetic

<400> SEQUENCE: 419

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 420
<211> LENGTH: 112
<212> TYPE: PRT
<213> ORGANISM: Artificial Sequence
<220> FEATURE:
<223> OTHER INFORMATION: Synthetic

<400> SEQUENCE: 420

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 421
<211> LENGTH: 116
<212> TYPE: PRT
<213> ORGANISM: Artificial Sequence
<220> FEATURE:
<223> OTHER INFORMATION: Synthetic

<400> SEQUENCE: 421

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 422
<211> LENGTH: 112
<212> TYPE: PRT
<213> ORGANISM: Artificial Sequence
<220> FEATURE:
<223> OTHER INFORMATION: Synthetic

<400> SEQUENCE: 422

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr His Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 423
<211> LENGTH: 116
<212> TYPE: PRT
<213> ORGANISM: Artificial Sequence

```
<220> FEATURE:
<223> OTHER INFORMATION: Synthetic

<400> SEQUENCE: 423

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Trp Trp Ile Lys Gln Ala Pro Gly Gln Gly Leu Glu Trp Ile
            35                  40                  45

Gly Asp Ile Tyr Pro Gly Gly Asp Leu Ile Asn Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
                100                 105                 110

Thr Val Ser Ser
            115

<210> SEQ ID NO 424
<211> LENGTH: 112
<212> TYPE: PRT
<213> ORGANISM: Artificial Sequence
<220> FEATURE:
<223> OTHER INFORMATION: Synthetic

<400> SEQUENCE: 424

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr His Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
                100                 105                 110

<210> SEQ ID NO 425
<211> LENGTH: 116
<212> TYPE: PRT
<213> ORGANISM: Artificial Sequence
<220> FEATURE:
<223> OTHER INFORMATION: Synthetic

<400> SEQUENCE: 425

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Ser Trp Ile Lys Gln Ala Pro Gly Gln Gly Leu Glu Trp Ile
            35                  40                  45
```

Gly Asp Ile Tyr Pro Gly Gly Asp His Ile Asn Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
             100                 105                 110

Thr Val Ser Ser
        115

<210> SEQ ID NO 426
<211> LENGTH: 112
<212> TYPE: PRT
<213> ORGANISM: Artificial Sequence
<220> FEATURE:
<223> OTHER INFORMATION: Synthetic

<400> SEQUENCE: 426

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
             20                  25                  30

Asn Ala Ile Thr Tyr Leu Tyr Trp Tyr Leu Gln Lys Pro Gly Gln Ser
         35                  40                  45

Pro Gln Leu Leu Ile Tyr Gln Val Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Trp Thr Phe Gly Gly Gly Thr Lys Val Glu Ile Lys
             100                 105                 110

<210> SEQ ID NO 427
<211> LENGTH: 116
<212> TYPE: PRT
<213> ORGANISM: Artificial Sequence
<220> FEATURE:
<223> OTHER INFORMATION: Synthetic

<400> SEQUENCE: 427

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Trp Leu Trp Trp Ile Lys Gln Ala Pro Gly Gln Gly Leu Glu Trp Ile
         35                  40                  45

Gly Glu Ile Tyr Pro Gly Gly Asp Tyr Ile Thr Tyr Asn Glu Lys Phe
     50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Gly Asp Tyr Trp Gly Gln Gly Thr Thr Val
             100                 105                 110

Thr Val Ser Ser
        115

-continued

<210> SEQ ID NO 428
<211> LENGTH: 112
<212> TYPE: PRT
<213> ORGANISM: Artificial Sequence
<220> FEATURE:
<223> OTHER INFORMATION: Synthetic

<400> SEQUENCE: 428

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 429
<211> LENGTH: 116
<212> TYPE: PRT
<213> ORGANISM: Artificial Sequence
<220> FEATURE:
<223> OTHER INFORMATION: Synthetic

<400> SEQUENCE: 429

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 430
<211> LENGTH: 112
<212> TYPE: PRT
<213> ORGANISM: Artificial Sequence
<220> FEATURE:
<223> OTHER INFORMATION: Synthetic

<400> SEQUENCE: 430

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Asp Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

<210> SEQ ID NO 431
<211> LENGTH: 116
<212> TYPE: PRT
<213> ORGANISM: Artificial Sequence
<220> FEATURE:
<223> OTHER INFORMATION: Synthetic

<400> SEQUENCE: 431

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 432
<211> LENGTH: 112
<212> TYPE: PRT
<213> ORGANISM: Artificial Sequence
<220> FEATURE:
<223> OTHER INFORMATION: Synthetic

<400> SEQUENCE: 432

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

```
Leu Glu Leu Pro Trp Thr Phe Gly Gly Gly Thr Lys Val Glu Ile Lys
                100                 105                 110
```

<210> SEQ ID NO 433
<211> LENGTH: 116
<212> TYPE: PRT
<213> ORGANISM: Artificial Sequence
<220> FEATURE:
<223> OTHER INFORMATION: Synthetic

<400> SEQUENCE: 433

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
                100                 105                 110

Thr Val Ser Ser
            115
```

<210> SEQ ID NO 434
<211> LENGTH: 112
<212> TYPE: PRT
<213> ORGANISM: Artificial Sequence
<220> FEATURE:
<223> OTHER INFORMATION: Synthetic

<400> SEQUENCE: 434

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
                100                 105                 110
```

<210> SEQ ID NO 435
<211> LENGTH: 116
<212> TYPE: PRT
<213> ORGANISM: Artificial Sequence
<220> FEATURE:
<223> OTHER INFORMATION: Synthetic

<400> SEQUENCE: 435

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Val Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 436
<211> LENGTH: 112
<212> TYPE: PRT
<213> ORGANISM: Artificial Sequence
<220> FEATURE:
<223> OTHER INFORMATION: Synthetic

<400> SEQUENCE: 436

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 437
<211> LENGTH: 116
<212> TYPE: PRT
<213> ORGANISM: Artificial Sequence
<220> FEATURE:
<223> OTHER INFORMATION: Synthetic

<400> SEQUENCE: 437

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Val Tyr Asn Glu Lys Phe
        50                  55                  60

Lys Gly Lys Ala Thr Leu Thr Ala Asp Thr Ser Ile Ser Thr Ala Tyr
65                  70                  75                  80

```
Met Glu Leu Ser Arg Leu Arg Ser Asp Asp Thr Ala Val Tyr Tyr Cys
            85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 438
<211> LENGTH: 112
<212> TYPE: PRT
<213> ORGANISM: Artificial Sequence
<220> FEATURE:
<223> OTHER INFORMATION: Synthetic

<400> SEQUENCE: 438

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 439
<211> LENGTH: 116
<212> TYPE: PRT
<213> ORGANISM: Artificial Sequence
<220> FEATURE:
<223> OTHER INFORMATION: Synthetic

<400> SEQUENCE: 439

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Val Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Pro Asn Leu Pro Gly Asp Tyr Trp Gly Gln Gly Thr Thr Val
            100                 105                 110

Thr Val Ser Ser
            115

<210> SEQ ID NO 440
<211> LENGTH: 112
<212> TYPE: PRT
```

<213> ORGANISM: Artificial Sequence
<220> FEATURE:
<223> OTHER INFORMATION: Synthetic

<400> SEQUENCE: 440

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Asn
                85                  90                  95

Leu Glu Leu Pro Trp Thr Phe Gly Gly Gly Thr Lys Val Glu Ile Lys
            100                 105                 110

<210> SEQ ID NO 441
<211> LENGTH: 116
<212> TYPE: PRT
<213> ORGANISM: Artificial Sequence
<220> FEATURE:
<223> OTHER INFORMATION: Synthetic

<400> SEQUENCE: 441

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 442
<211> LENGTH: 112
<212> TYPE: PRT
<213> ORGANISM: Artificial Sequence
<220> FEATURE:
<223> OTHER INFORMATION: Synthetic

<400> SEQUENCE: 442

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

```
Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110
```

<210> SEQ ID NO 443
<211> LENGTH: 116
<212> TYPE: PRT
<213> ORGANISM: Artificial Sequence
<220> FEATURE:
<223> OTHER INFORMATION: Synthetic

<400> SEQUENCE: 443

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Ile Lys Gln Ala Pro Gly Gln Gly Leu Glu Trp Ile
            35                  40                  45

Gly Asp Ile Tyr Pro Gly Gly Asp Tyr Ile Val Tyr Asn Glu Lys Phe
        50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115
```

<210> SEQ ID NO 444
<211> LENGTH: 112
<212> TYPE: PRT
<213> ORGANISM: Artificial Sequence
<220> FEATURE:
<223> OTHER INFORMATION: Synthetic

<400> SEQUENCE: 444

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Gln Gly Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110
```

<210> SEQ ID NO 445
<211> LENGTH: 116
<212> TYPE: PRT
<213> ORGANISM: Artificial Sequence
<220> FEATURE:
<223> OTHER INFORMATION: Synthetic

<400> SEQUENCE: 445

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
        115
```

<210> SEQ ID NO 446
<211> LENGTH: 112
<212> TYPE: PRT
<213> ORGANISM: Artificial Sequence
<220> FEATURE:
<223> OTHER INFORMATION: Synthetic

<400> SEQUENCE: 446

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Tyr
                85                  90                  95

Leu Glu Leu Pro Trp Thr Phe Gly Gly Gly Thr Lys Val Glu Ile Lys
            100                 105                 110
```

<210> SEQ ID NO 447
<211> LENGTH: 116
<212> TYPE: PRT
<213> ORGANISM: Artificial Sequence
<220> FEATURE:
<223> OTHER INFORMATION: Synthetic

<400> SEQUENCE: 447

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30
```

```
Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Lys Asp His Trp Gly Gln Gly Thr Thr Val
                100                 105                 110

Thr Val Ser Ser
            115
```

<210> SEQ ID NO 448
<211> LENGTH: 112
<212> TYPE: PRT
<213> ORGANISM: Artificial Sequence
<220> FEATURE:
<223> OTHER INFORMATION: Synthetic

<400> SEQUENCE: 448

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                 20                  25                  30

Asn Ala Ile Thr Tyr Leu Tyr Trp Tyr Leu Gln Lys Pro Gly Gln Ser
             35                  40                  45

Pro Gln Leu Leu Ile Tyr Gln Val Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Tyr
                 85                  90                  95

Leu Glu Leu Pro Trp Thr Phe Gly Gly Gly Thr Lys Val Glu Ile Lys
                100                 105                 110
```

<210> SEQ ID NO 449
<211> LENGTH: 116
<212> TYPE: PRT
<213> ORGANISM: Artificial Sequence
<220> FEATURE:
<223> OTHER INFORMATION: Synthetic

<400> SEQUENCE: 449

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Leu Phe Thr Asn Tyr
                 20                  25                  30

Trp Leu Gly Trp Ile Lys Gln Ala Pro Gly Gln Gly Leu Glu Trp Ile
             35                  40                  45

Gly Asp Ile Tyr Pro Gly Gly Asp Tyr Ile Val Tyr Asn Glu Lys Phe
 50                  55                  60

Lys Gly Lys Ala Thr Leu Thr Ala Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Pro Asn Leu Pro Lys Asp His Trp Gly Gln Gly Thr Thr Val
```

```
                       100                 105                 110

Thr Val Ser Ser
            115

<210> SEQ ID NO 450
<211> LENGTH: 112
<212> TYPE: PRT
<213> ORGANISM: Artificial Sequence
<220> FEATURE:
<223> OTHER INFORMATION: Synthetic

<400> SEQUENCE: 450

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

<210> SEQ ID NO 451
<211> LENGTH: 116
<212> TYPE: PRT
<213> ORGANISM: Artificial Sequence
<220> FEATURE:
<223> OTHER INFORMATION: Synthetic

<400> SEQUENCE: 451

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Lys Asp His Trp Gly Gln Gly Thr Thr Val
            100                 105                 110

Thr Val Ser Ser
            115

<210> SEQ ID NO 452
<211> LENGTH: 112
<212> TYPE: PRT
<213> ORGANISM: Artificial Sequence
<220> FEATURE:
<223> OTHER INFORMATION: Synthetic

<400> SEQUENCE: 452
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Ala Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Tyr
                85                  90                  95

Leu Glu Leu Pro Trp Thr Phe Gly Gly Gly Thr Lys Val Glu Ile Lys
            100                 105                 110
```

<210> SEQ ID NO 453
<211> LENGTH: 10
<212> TYPE: PRT
<213> ORGANISM: Artificial Sequence
<220> FEATURE:
<223> OTHER INFORMATION: Synthetic

<400> SEQUENCE: 453

```
Gly Tyr Thr Phe Glu Asn Tyr Trp Leu Gly
1               5                   10
```

<210> SEQ ID NO 454
<211> LENGTH: 10
<212> TYPE: PRT
<213> ORGANISM: Artificial Sequence
<220> FEATURE:
<223> OTHER INFORMATION: Synthetic

<400> SEQUENCE: 454

```
Gly Tyr Met Phe Thr Asn Tyr Trp Leu Gly
1               5                   10
```

<210> SEQ ID NO 455
<211> LENGTH: 10
<212> TYPE: PRT
<213> ORGANISM: Artificial Sequence
<220> FEATURE:
<223> OTHER INFORMATION: Synthetic

<400> SEQUENCE: 455

```
Gly Tyr Thr Phe Asp Asn Tyr Trp Leu Gly
1               5                   10
```

<210> SEQ ID NO 456
<211> LENGTH: 10
<212> TYPE: PRT
<213> ORGANISM: Artificial Sequence
<220> FEATURE:
<223> OTHER INFORMATION: Synthetic

<400> SEQUENCE: 456

```
Gly Tyr Thr Phe Gly Asn Tyr Trp Leu Gly
1               5                   10
```

<210> SEQ ID NO 457
<211> LENGTH: 10
<212> TYPE: PRT
<213> ORGANISM: Artificial Sequence

```
<220> FEATURE:
<223> OTHER INFORMATION: Synthetic

<400> SEQUENCE: 457

Gly Tyr Thr Phe Thr Asn Tyr Trp Leu Trp
1               5                   10

<210> SEQ ID NO 458
<211> LENGTH: 10
<212> TYPE: PRT
<213> ORGANISM: Artificial Sequence
<220> FEATURE:
<223> OTHER INFORMATION: Synthetic

<400> SEQUENCE: 458

Gly Tyr Leu Phe Thr Asn Tyr Trp Leu Gly
1               5                   10

<210> SEQ ID NO 459
<211> LENGTH: 10
<212> TYPE: PRT
<213> ORGANISM: Artificial Sequence
<220> FEATURE:
<223> OTHER INFORMATION: Synthetic

<400> SEQUENCE: 459

Gly Tyr Thr Phe Thr Asn Tyr Trp Leu Ser
1               5                   10

<210> SEQ ID NO 460
<211> LENGTH: 10
<212> TYPE: PRT
<213> ORGANISM: Artificial Sequence
<220> FEATURE:
<223> OTHER INFORMATION: Synthetic

<400> SEQUENCE: 460

Gly Phe Thr Phe Thr Asn Tyr Trp Leu Gly
1               5                   10

<210> SEQ ID NO 461
<211> LENGTH: 17
<212> TYPE: PRT
<213> ORGANISM: Artificial Sequence
<220> FEATURE:
<223> OTHER INFORMATION: Synthetic

<400> SEQUENCE: 461

Asp Ile Tyr Pro Gly Gly Asp Tyr Ile Val Tyr Asn Glu Lys Phe Lys
1               5                   10                  15

Gly

<210> SEQ ID NO 462
<211> LENGTH: 17
<212> TYPE: PRT
<213> ORGANISM: Artificial Sequence
<220> FEATURE:
<223> OTHER INFORMATION: Synthetic

<400> SEQUENCE: 462

Asp Ile Tyr Pro Gly Gly Asp Ile Ile Asn Tyr Asn Glu Lys Phe Lys
1               5                   10                  15

Gly

<210> SEQ ID NO 463
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 463

Asp Ile Tyr Pro Gly Gly Asp Val Ile Asn Tyr Asn Glu Lys Phe Lys
1               5                   10                  15
Gly

<210> SEQ ID NO 464
<211> LENGTH: 17
<212> TYPE: PRT
<213> ORGANISM: Artificial Sequence
<220> FEATURE:
<223> OTHER INFORMATION: Synthetic

<400> SEQUENCE: 464

Asp Ile Phe Pro Gly Gly Asp Tyr Ile Asn Tyr Asn Glu Lys Phe Lys
1               5                   10                  15
Gly

<210> SEQ ID NO 465
<211> LENGTH: 17
<212> TYPE: PRT
<213> ORGANISM: Artificial Sequence
<220> FEATURE:
<223> OTHER INFORMATION: Synthetic

<400> SEQUENCE: 465

Asp Ile Tyr Pro Gly Gly Asp Leu Ile Asn Tyr Asn Glu Lys Phe Lys
1               5                   10                  15
Gly

<210> SEQ ID NO 466
<211> LENGTH: 17
<212> TYPE: PRT
<213> ORGANISM: Artificial Sequence
<220> FEATURE:
<223> OTHER INFORMATION: Synthetic

<400> SEQUENCE: 466

Asp Ile Tyr Pro Gly Gly Asp His Ile Asn Tyr Asn Glu Lys Phe Lys
1               5                   10                  15
Gly

<210> SEQ ID NO 467
<211> LENGTH: 17
<212> TYPE: PRT
<213> ORGANISM: Artificial Sequence
<220> FEATURE:
<223> OTHER INFORMATION: Synthetic

<400> SEQUENCE: 467

Glu Ile Tyr Pro Gly Gly Asp Tyr Ile Thr Tyr Asn Glu Lys Phe Lys
1               5                   10                  15
Gly

<210> SEQ ID NO 468
<211> LENGTH: 7
<212> TYPE: PRT
<213> ORGANISM: Artificial Sequence
<220> FEATURE:
```

<223> OTHER INFORMATION: Synthetic

<400> SEQUENCE: 468

Pro Asn Leu Pro Lys Asp His
1               5

<210> SEQ ID NO 469
<211> LENGTH: 7
<212> TYPE: PRT
<213> ORGANISM: Artificial Sequence
<220> FEATURE:
<223> OTHER INFORMATION: Synthetic

<400> SEQUENCE: 469

Pro Asp Leu Pro Gly Asp Tyr
1               5

<210> SEQ ID NO 470
<211> LENGTH: 7
<212> TYPE: PRT
<213> ORGANISM: Artificial Sequence
<220> FEATURE:
<223> OTHER INFORMATION: Synthetic

<400> SEQUENCE: 470

Pro Gly Leu Pro Lys Asp Tyr
1               5

<210> SEQ ID NO 471
<211> LENGTH: 7
<212> TYPE: PRT
<213> ORGANISM: Artificial Sequence
<220> FEATURE:
<223> OTHER INFORMATION: Synthetic

<400> SEQUENCE: 471

Pro Asn Leu Pro Lys Asp Tyr
1               5

<210> SEQ ID NO 472
<211> LENGTH: 7
<212> TYPE: PRT
<213> ORGANISM: Artificial Sequence
<220> FEATURE:
<223> OTHER INFORMATION: Synthetic

<400> SEQUENCE: 472

Pro Asn Leu Pro Arg Asp Tyr
1               5

<210> SEQ ID NO 473
<211> LENGTH: 7
<212> TYPE: PRT
<213> ORGANISM: Artificial Sequence
<220> FEATURE:
<223> OTHER INFORMATION: Synthetic

<400> SEQUENCE: 473

Pro Gly Leu Pro Arg Asp Tyr
1               5

<210> SEQ ID NO 474
<211> LENGTH: 7
<212> TYPE: PRT
<213> ORGANISM: Artificial Sequence
<220> FEATURE:
<223> OTHER INFORMATION: Synthetic

<400> SEQUENCE: 474

Pro Gly Leu Pro Gln Asp Tyr
1               5

<210> SEQ ID NO 475
<211> LENGTH: 7
<212> TYPE: PRT
<213> ORGANISM: Artificial Sequence
<220> FEATURE:
<223> OTHER INFORMATION: Synthetic

<400> SEQUENCE: 475

Pro Asp Leu Pro Lys Asp Tyr
1               5

<210> SEQ ID NO 476
<211> LENGTH: 7
<212> TYPE: PRT
<213> ORGANISM: Artificial Sequence
<220> FEATURE:
<223> OTHER INFORMATION: Synthetic

<400> SEQUENCE: 476

Gln Val Ser Asn Leu Ala Arg
1               5

<210> SEQ ID NO 477
<211> LENGTH: 7
<212> TYPE: PRT
<213> ORGANISM: Artificial Sequence
<220> FEATURE:
<223> OTHER INFORMATION: Synthetic

<400> SEQUENCE: 477

Gln Lys Ser Asn Leu Ala Ser
1               5

<210> SEQ ID NO 478
<211> LENGTH: 7
<212> TYPE: PRT
<213> ORGANISM: Artificial Sequence
<220> FEATURE:
<223> OTHER INFORMATION: Synthetic

<400> SEQUENCE: 478

Gln Val Ser Asn Leu Ala Val
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic

<400> SEQUENCE: 479

Gln Val Ser Asn Leu Ala Leu
1               5

<210> SEQ ID NO 480
<211> LENGTH: 7
<212> TYPE: PRT
<213> ORGANISM: Artificial Sequence
<220> FEATURE:
<223> OTHER INFORMATION: Synthetic

<400> SEQUENCE: 480

Gln Val Asp Asn Leu Ala Ser
1               5

<210> SEQ ID NO 481
<211> LENGTH: 7
<212> TYPE: PRT
<213> ORGANISM: Artificial Sequence
<220> FEATURE:
<223> OTHER INFORMATION: Synthetic

<400> SEQUENCE: 481

Gln Val Ser Asn Leu Ala Thr
1               5

<210> SEQ ID NO 482
<211> LENGTH: 7
<212> TYPE: PRT
<213> ORGANISM: Artificial Sequence
<220> FEATURE:
<223> OTHER INFORMATION: Synthetic

<400> SEQUENCE: 482

His Val Ser Asn Leu Ala Ser
1               5

<210> SEQ ID NO 483
<211> LENGTH: 7
<212> TYPE: PRT
<213> ORGANISM: Artificial Sequence
<220> FEATURE:
<223> OTHER INFORMATION: Synthetic

<400> SEQUENCE: 483

Gln Val Ser Asn Arg Ala Ser
1               5

<210> SEQ ID NO 484
<211> LENGTH: 9
<212> TYPE: PRT
<213> ORGANISM: Artificial Sequence
<220> FEATURE:
<223> OTHER INFORMATION: Synthetic

<400> SEQUENCE: 484

Gly Gln Asn Leu Glu Leu Pro Trp Thr
1               5

<210> SEQ ID NO 485
<211> LENGTH: 9
<212> TYPE: PRT
<213> ORGANISM: Artificial Sequence
<220> FEATURE:
<223> OTHER INFORMATION: Synthetic

<400> SEQUENCE: 485

Ala Gln Asn Leu Glu Met Pro Trp Thr
1               5

<210> SEQ ID NO 486
<211> LENGTH: 9
<212> TYPE: PRT
<213> ORGANISM: Artificial Sequence
<220> FEATURE:
<223> OTHER INFORMATION: Synthetic

<400> SEQUENCE: 486

```
Gly Gln Asn Leu Glu Met Pro Trp Thr
1               5
```

<210> SEQ ID NO 487
<211> LENGTH: 9
<212> TYPE: PRT
<213> ORGANISM: Artificial Sequence
<220> FEATURE:
<223> OTHER INFORMATION: Synthetic

<400> SEQUENCE: 487

```
Ala Gln Tyr Leu Glu Glu Pro Trp Thr
1               5
```

<210> SEQ ID NO 488
<211> LENGTH: 9
<212> TYPE: PRT
<213> ORGANISM: Artificial Sequence
<220> FEATURE:
<223> OTHER INFORMATION: Synthetic

<400> SEQUENCE: 488

```
Ala Gln Tyr Leu Glu Leu Pro Trp Thr
1               5
```

<210> SEQ ID NO 489
<211> LENGTH: 9
<212> TYPE: PRT
<213> ORGANISM: Artificial Sequence
<220> FEATURE:
<223> OTHER INFORMATION: Synthetic

<400> SEQUENCE: 489

```
Gly Gln Tyr Leu Glu Leu Pro Trp Thr
1               5
```

<210> SEQ ID NO 490
<211> LENGTH: 16
<212> TYPE: PRT
<213> ORGANISM: Artificial Sequence
<220> FEATURE:
<223> OTHER INFORMATION: Synthetic

<400> SEQUENCE: 490

```
Arg Ser Ser Lys Ser Leu Leu His Ser Gln Gly Ile Thr Tyr Leu Tyr
1               5                   10                  15
```

<210> SEQ ID NO 491
<211> LENGTH: 116
<212> TYPE: PRT
<213> ORGANISM: Artificial Sequence
<220> FEATURE:
<223> OTHER INFORMATION: Synthetic

<400> SEQUENCE: 491

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
        35                  40                  45

Gly Asp Ile Tyr Pro Gly Gly Asp Tyr Ile Val Tyr Asn Glu Lys Phe
    50                  55                  60

Lys Gly Lys Ala Thr Leu Thr Ala Asp Thr Ser Ile Ser Thr Ala Tyr
```

```
                65                  70                  75                  80
Met Glu Leu Ser Arg Leu Arg Ser Asp Asp Thr Ala Val Tyr Tyr Cys
                    85                  90                  95

Ala Arg Pro Asn Leu Pro Lys Asp His Trp Gly Gln Gly Thr Thr Val
                100                 105                 110

Thr Val Ser Ser
        115

<210> SEQ ID NO 492
<211> LENGTH: 112
<212> TYPE: PRT
<213> ORGANISM: Artificial Sequence
<220> FEATURE:
<223> OTHER INFORMATION: Synthetic

<400> SEQUENCE: 492

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Ala Ile Thr Tyr Leu Tyr Trp Tyr Leu Gln Lys Pro Gly Gln Ser
            35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
                100                 105                 110

<210> SEQ ID NO 493
<211> LENGTH: 119
<212> TYPE: PRT
<213> ORGANISM: Artificial Sequence
<220> FEATURE:
<223> OTHER INFORMATION: Synthetic

<400> SEQUENCE: 493

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
                100                 105                 110

Thr Thr Val Thr Val Ser Ser
        115

<210> SEQ ID NO 494
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 494

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 495
<211> LENGTH: 119
<212> TYPE: PRT
<213> ORGANISM: Artificial Sequence
<220> FEATURE:
<223> OTHER INFORMATION: Synthetic

<400> SEQUENCE: 495

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 496
<211> LENGTH: 107
<212> TYPE: PRT
<213> ORGANISM: Artificial Sequence
<220> FEATURE:
<223> OTHER INFORMATION: Synthetic

<400> SEQUENCE: 496

Asp Ile Gln Met Thr Gln Ser Pro Ser Ser Leu Ser Ala Ser Val Gly
1               5                   10                  15

Asp Arg Val Thr Ile Thr Cys Lys Ala Lys Gln Asp Val Thr Pro Ala
            20                  25                  30

Val Ala Trp Tyr Gln Gln Lys Pro Gly Lys Ala Pro Lys Leu Leu Ile
```

```
            35                  40                  45

Tyr Ser Thr Ser Ser Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln His Tyr Thr Thr Pro Leu
                85                  90                  95

Thr Phe Gly Gln Gly Thr Lys Leu Glu Ile Lys
            100                 105

<210> SEQ ID NO 497
<211> LENGTH: 119
<212> TYPE: PRT
<213> ORGANISM: Artificial Sequence
<220> FEATURE:
<223> OTHER INFORMATION: Synthetic

<400> SEQUENCE: 497

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Ser Trp Gly Gln Gly
            100                 105                 110

Thr Thr Val Thr Val Ser Ser
        115

<210> SEQ ID NO 498
<211> LENGTH: 107
<212> TYPE: PRT
<213> ORGANISM: Artificial Sequence
<220> FEATURE:
<223> OTHER INFORMATION: Synthetic

<400> SEQUENCE: 498

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Trp Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Leu
                85                  90                  95

Thr Phe Gly Gln Gly Thr Lys Leu Glu Ile Lys
            100                 105
```

```
<210> SEQ ID NO 499
<211> LENGTH: 119
<212> TYPE: PRT
<213> ORGANISM: Artificial Sequence
<220> FEATURE:
<223> OTHER INFORMATION: Synthetic

<400> SEQUENCE: 499
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Ile Phe Asn Arg Tyr Ala Leu Asp Tyr Trp Gly Gln Gly
            100                 105                 110

Thr Thr Val Thr Val Ser Ser
        115

```
<210> SEQ ID NO 500
<211> LENGTH: 107
<212> TYPE: PRT
<213> ORGANISM: Artificial Sequence
<220> FEATURE:
<223> OTHER INFORMATION: Synthetic

<400> SEQUENCE: 500
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

```
<210> SEQ ID NO 501
<211> LENGTH: 119
<212> TYPE: PRT
<213> ORGANISM: Artificial Sequence
<220> FEATURE:
<223> OTHER INFORMATION: Synthetic

<400> SEQUENCE: 501
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                 20                  25                  30
Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser
            115

<210> SEQ ID NO 502
<211> LENGTH: 107
<212> TYPE: PRT
<213> ORGANISM: Artificial Sequence
<220> FEATURE:
<223> OTHER INFORMATION: Synthetic

<400> SEQUENCE: 502

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 503
<211> LENGTH: 119
<212> TYPE: PRT
<213> ORGANISM: Artificial Sequence
<220> FEATURE:
<223> OTHER INFORMATION: Synthetic

<400> SEQUENCE: 503

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
            35                  40                  45

Ala Thr Ile Ser Asp Ala Gly Gly Tyr Ile Tyr Tyr Arg Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95
```

```
Ala Arg Glu Leu His Phe Arg Tyr Ala Leu Asp Tyr Trp Gly Gln Gly
                100                 105                 110

Thr Thr Val Thr Val Ser Ser
            115

<210> SEQ ID NO 504
<211> LENGTH: 107
<212> TYPE: PRT
<213> ORGANISM: Artificial Sequence
<220> FEATURE:
<223> OTHER INFORMATION: Synthetic

<400> SEQUENCE: 504

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 505
<211> LENGTH: 119
<212> TYPE: PRT
<213> ORGANISM: Artificial Sequence
<220> FEATURE:
<223> OTHER INFORMATION: Synthetic

<400> SEQUENCE: 505

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Tyr Phe Arg Tyr Ala Leu Asp Tyr Trp Gly Gln Gly
                100                 105                 110

Thr Thr Val Thr Val Ser Ser
            115

<210> SEQ ID NO 506
<211> LENGTH: 107
<212> TYPE: PRT
<213> ORGANISM: Artificial Sequence
<220> FEATURE:
<223> OTHER INFORMATION: Synthetic
```

<400> SEQUENCE: 506

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 507
<211> LENGTH: 119
<212> TYPE: PRT
<213> ORGANISM: Artificial Sequence
<220> FEATURE:
<223> OTHER INFORMATION: Synthetic

<400> SEQUENCE: 507

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Leu His Arg Tyr Ala Leu Asp Tyr Trp Gly Gln Gly
            100                 105                 110

Thr Thr Val Thr Val Ser Ser
        115

<210> SEQ ID NO 508
<211> LENGTH: 107
<212> TYPE: PRT
<213> ORGANISM: Artificial Sequence
<220> FEATURE:
<223> OTHER INFORMATION: Synthetic

<400> SEQUENCE: 508

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 509
<211> LENGTH: 119
<212> TYPE: PRT
<213> ORGANISM: Artificial Sequence
<220> FEATURE:
<223> OTHER INFORMATION: Synthetic

<400> SEQUENCE: 509

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Arg Gly Arg Tyr Ala Leu Asp Tyr Trp Gly Gln Gly
            100                 105                 110

Thr Thr Val Thr Val Ser Ser
        115

<210> SEQ ID NO 510
<211> LENGTH: 107
<212> TYPE: PRT
<213> ORGANISM: Artificial Sequence
<220> FEATURE:
<223> OTHER INFORMATION: Synthetic

<400> SEQUENCE: 510

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 511
<211> LENGTH: 119
<212> TYPE: PRT
<213> ORGANISM: Artificial Sequence
<220> FEATURE:
<223> OTHER INFORMATION: Synthetic

<400> SEQUENCE: 511

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 512
<211> LENGTH: 107
<212> TYPE: PRT
<213> ORGANISM: Artificial Sequence
<220> FEATURE:
<223> OTHER INFORMATION: Synthetic

<400> SEQUENCE: 512

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Asp Ala Pro Leu
                85                  90                  95

Thr Phe Gly Gln Gly Thr Lys Leu Glu Ile Lys
            100                 105

<210> SEQ ID NO 513
<211> LENGTH: 10
<212> TYPE: PRT
<213> ORGANISM: Artificial Sequence
<220> FEATURE:
<223> OTHER INFORMATION: Synthetic

<400> SEQUENCE: 513

Glu Phe Gly Lys Arg Tyr Ala Leu Asp Ser
1               5                   10

<210> SEQ ID NO 514
<211> LENGTH: 10
<212> TYPE: PRT
<213> ORGANISM: Artificial Sequence
<220> FEATURE:

```
<223> OTHER INFORMATION: Synthetic

<400> SEQUENCE: 514

Glu Ile Phe Asn Arg Tyr Ala Leu Asp Tyr
1               5                   10

<210> SEQ ID NO 515
<211> LENGTH: 10
<212> TYPE: PRT
<213> ORGANISM: Artificial Sequence
<220> FEATURE:
<223> OTHER INFORMATION: Synthetic

<400> SEQUENCE: 515

Glu Leu Pro Trp Arg Tyr Ala Leu Asp Tyr
1               5                   10

<210> SEQ ID NO 516
<211> LENGTH: 10
<212> TYPE: PRT
<213> ORGANISM: Artificial Sequence
<220> FEATURE:
<223> OTHER INFORMATION: Synthetic

<400> SEQUENCE: 516

Glu Leu His Phe Arg Tyr Ala Leu Asp Tyr
1               5                   10

<210> SEQ ID NO 517
<211> LENGTH: 10
<212> TYPE: PRT
<213> ORGANISM: Artificial Sequence
<220> FEATURE:
<223> OTHER INFORMATION: Synthetic

<400> SEQUENCE: 517

Glu Leu Tyr Phe Arg Tyr Ala Leu Asp Tyr
1               5                   10

<210> SEQ ID NO 518
<211> LENGTH: 10
<212> TYPE: PRT
<213> ORGANISM: Artificial Sequence
<220> FEATURE:
<223> OTHER INFORMATION: Synthetic

<400> SEQUENCE: 518

Glu Leu Leu His Arg Tyr Ala Leu Asp Tyr
1               5                   10

<210> SEQ ID NO 519
<211> LENGTH: 10
<212> TYPE: PRT
<213> ORGANISM: Artificial Sequence
<220> FEATURE:
<223> OTHER INFORMATION: Synthetic

<400> SEQUENCE: 519

Glu Leu Arg Gly Arg Tyr Ala Leu Asp Tyr
1               5                   10

<210> SEQ ID NO 520
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 520

Lys Ala Lys Gln Asp Val Thr Pro Ala Val Ala
1               5                  10

<210> SEQ ID NO 521
<211> LENGTH: 11
<212> TYPE: PRT
<213> ORGANISM: Artificial Sequence
<220> FEATURE:
<223> OTHER INFORMATION: Synthetic

<400> SEQUENCE: 521

Lys Ala Ser Gln Asp Val Trp Pro Ala Val Ala
1               5                  10

<210> SEQ ID NO 522
<211> LENGTH: 9
<212> TYPE: PRT
<213> ORGANISM: Artificial Sequence
<220> FEATURE:
<223> OTHER INFORMATION: Synthetic

<400> SEQUENCE: 522

Met Gln His Tyr Thr Thr Pro Leu Thr
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic

<400> SEQUENCE: 523

Gln Gln His Ser Thr Thr Pro Leu Thr
1               5

<210> SEQ ID NO 524
<211> LENGTH: 9
<212> TYPE: PRT
<213> ORGANISM: Artificial Sequence
<220> FEATURE:
<223> OTHER INFORMATION: Synthetic

<400> SEQUENCE: 524

Gln Gln His Ser Asp Ala Pro Leu Thr
1               5

<210> SEQ ID NO 525
<211> LENGTH: 17
<212> TYPE: PRT
<213> ORGANISM: Artificial Sequence
<220> FEATURE:
<223> OTHER INFORMATION: Synthetic

<400> SEQUENCE: 525

Thr Ile Ser Asp Ala Gly Gly Tyr Ile Tyr Tyr Ser Asp Ser Val Lys
1               5                   10                  15

Gly

<210> SEQ ID NO 526
<211> LENGTH: 17
<212> TYPE: PRT
<213> ORGANISM: Artificial Sequence
<220> FEATURE:
```

<223> OTHER INFORMATION: Synthetic

<400> SEQUENCE: 526

Thr Ile Ser Asp Ala Gly Gly Tyr Ile Tyr Tyr Arg Asp Ser Val Lys
1               5                   10                  15

Gly

<210> SEQ ID NO 527
<211> LENGTH: 17
<212> TYPE: PRT
<213> ORGANISM: Artificial Sequence
<220> FEATURE:
<223> OTHER INFORMATION: Synthetic

<400> SEQUENCE: 527

Thr Ile Ser Asp Gly Gly Gly Tyr Ile Tyr Tyr Arg Asp Ser Val Lys
1               5                   10                  15

Gly

<210> SEQ ID NO 528
<211> LENGTH: 449
<212> TYPE: PRT
<213> ORGANISM: Artificial Sequence
<220> FEATURE:
<223> OTHER INFORMATION: Synthetic

<400> SEQUENCE: 528

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 529
<211> LENGTH: 18
<212> TYPE: PRT
<213> ORGANISM: Artificial Sequence
<220> FEATURE:
<223> OTHER INFORMATION: Synthetic

<400> SEQUENCE: 529

Gly Ser Gly Ser Gly Ser Gly Ser Gly Ser Gly Ser Gly Ser Gly Ser
1               5                   10                  15

Gly Ser

<210> SEQ ID NO 530
<211> LENGTH: 113
<212> TYPE: PRT
<213> ORGANISM: Artificial Sequence
<220> FEATURE:
<223> OTHER INFORMATION: Synthetic

<400> SEQUENCE: 530

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Ala Gln Asn
                    85                  90                  95

Leu Glu Leu Pro Trp Thr Phe Gly Cys Gly Thr Lys Val Glu Ile Lys
            100                 105                 110

Arg

<210> SEQ ID NO 531
<211> LENGTH: 20
<212> TYPE: PRT
<213> ORGANISM: Artificial Sequence
<220> FEATURE:
<223> OTHER INFORMATION: Synthetic

<400> SEQUENCE: 531

Gly Gly Gly Gly Ser Gly Gly Gly Gly Ser Gly Gly Gly Gly Ser Gly
1               5                   10                  15

Gly Gly Ser
        20

<210> SEQ ID NO 532
<211> LENGTH: 116
<212> TYPE: PRT
<213> ORGANISM: Artificial Sequence
<220> FEATURE:
<223> OTHER INFORMATION: Synthetic

<400> SEQUENCE: 532

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Cys Leu Glu Trp Ile
        35                  40                  45

Gly Asp Ile Tyr Pro Gly Gly Asp Tyr Ile Asn Tyr Asn Glu Lys Phe
    50                  55                  60

Lys Gly Lys Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Pro Asn Leu Pro Gly Asp Tyr Trp Gly Gln Gly Thr Thr Val
            100                 105                 110

Thr Val Ser Ser
        115

<210> SEQ ID NO 533
<211> LENGTH: 2151
<212> TYPE: DNA
<213> ORGANISM: Artificial Sequence
<220> FEATURE:
<223> OTHER INFORMATION: Synthetic

<400> SEQUENCE: 533
gaggtgcagc tggtggagag cggaggagga ctggtgcaac ccggaggcag cctgagactg      60
agctgcgctg ccagcggctt caccttcagc agctacgaca tgagctgggt gagacaggcc    120
cctggcaaaa gcctggagtg ggtggccacc atctccgatg cgggcggcta catctattac    180
tccgacagcg tgaagggcag gttcaccatc agcagggaca cgccaagaa  cagcctgtac    240 ctgcagatga acagcctgag ggatgaggac accgccgtgt acatctgcgc cagggagttc    300
```

```
ggcaaaaggt acgccctgga ctactggggc cagggcacaa ccgtgaccgt gagcagcgct    360
agcaccaagg gcccctctgt gttccctctg gccccttcct ctaaatccac ctctggcgga    420
accgctgctc tgggctgtct ggtcaaggac tacttccctg agcccgtgac cgtgtcttgg    480
aattctggcg ctctgaccag cggagtgcac acctttccag ctgtgctgca gtcctccggc    540
ctgtactctc tgtcctctgt cgtgacagtg ccttccagct ctctgggcac ccagacctac    600
atctgcaact gaaccacaa gccctccaac accaaggtgg acaagaaggt ggaacccaag    660
tcctgcgaca gacccacac ctgtcctcca gtcctgctc cagaactgct gggcggaccc    720
tccgtgttcc tgttccctcc aaagcctaag acaccctga tgatctcccg gaccccctgaa    780 gtgacctgcg tggtggtgga tgtgtcccac gaggatcccg aagtgaagtt caattggtac    840
gtggacggcg tggaagtgca aacgccaag accaagccta gagaggaaca gtacgcctcc    900
acctaccggg tggtgtccgt gctgaccgtt ctgcaccagg attggctgaa cggcaaagag    960
tacaagtgca aggtgtccaa caaggccctg cctgcccta tcgaaaagac catctctaag    1020
gccaagggcc agccccggga acctcaagtg tacaccttgc ctcccagccg ggaagagatg    1080
accaagaacc aggtgtccct gacctgcctg gttaagggct tctacccctc cgatatcgcc    1140
gtggaatggg agtctaatgg ccagcctgag aacaactaca gaccacacc tcctgtgctg    1200 gactccgacg gctcattctt cctgtactcc aagctgaccg tggacaagtc cagatggcag    1260
cagggcaacg tgttctcctg ctccgtgatg cacgaggccc tgcacaatca ctacacccag    1320
aagtccctgt ctctgtcccc tggcaaaggc tccggatctg gttctggatc cggaagcggt    1380
tctggcagcg gctctggatc tgacatcgtg atgacccagt ctccactgag cctgcctgtg    1440
acacctggcg agcctgcttc catctcctgc cggtcctcta gtccctgct gcactctaac    1500 ggcatcacct acctgtactg gtatctgcag aagcccggcc agtctcctca gctgctgatc    1560
taccaggtgt ccaacctggc ttctggcgtg cccgatagat ctccggtag cggatctgga    1620 accgacttca ccctgaagat ctccagagtg gaagccgagg acgtgggcgt gtactactgt    1680
gcccagaacc tggaactgcc ctggaccttt ggctgtggca ccaaggtgga aatcaagaga    1740
ggcggcggag gatctggcgg aggtggaagc ggaggcggag gaagcggtgg cggcggatct    1800
gaagttcagt tggttcagtc tggcgccgaa gtgaagaaac ctggcgcctc tgtgaaggtg    1860
tcctgcaagg cttccggcta cacctttacc aactactggc tcggctggat caagcaggcc    1920
cctggacagt gtctggaatg gatcggcgac atctaccctg cggcgacta catcaactac    1980 aacgagaagt tcaagggcaa agctaccctg accgccgaca cctctatctc caccgcctac    2040
atggaactgt cccggctgag atctgacgac accgccgtgt actattgcgc cagacctaac    2100
ctgcctggcg actattgggg ccagggcaca acagtgaccg tgtcctctta a    2151
```

<210> SEQ ID NO 534
<211> LENGTH: 214
<212> TYPE: PRT
<213> ORGANISM: Artificial Sequence
<220> FEATURE:
<223> OTHER INFORMATION: Synthetic

<400> SEQUENCE: 534

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30
```

```
Val Ala Trp Tyr Gln Gln Lys Pro Gly Lys Ala Pro Lys Leu Leu Ile
         35                  40                  45

Tyr Ser Thr Ser Ser Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Thr Thr Pro Leu
                 85                  90                  95

Thr Phe Gly Gln Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 535
<211> LENGTH: 645
<212> TYPE: DNA
<213> ORGANISM: Artificial Sequence
<220> FEATURE:
<223> OTHER INFORMATION: Synthetic

<400> SEQUENCE: 535

```
gacatccaga tgacccagag ccctagcagc ctgagcgcta gcgtgggcga cagggtgacc    60
atcacctgca aggccagcca ggatgtgacc cctgccgtgg cctggtacca gcagaagccc   120
ggcaaggccc ccaagctgct gatctacagc accagcagca ggtacaccgg cgtgcccagc   180
aggtttagcg gaagcggcag cggcaccgac ttcaccttca ccatcagcag cctgcagccc   240
gaggacatcg ccacctacta ctgccagcag cactacacca cccctctgac cttcggccag   300
ggcaccaagc tggagatcaa gagaaccgtg gccgctccct ccgtgttcat cttcccacca   360
tctgacgagc agctgaagtc cggcaccgct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctact ccctgtcctc taccctgacc   540
ctgtccaagg ccgactacga gaagcacaag gtgtacgcct gcgaagtgac ccaccaggga   600
ctgtctagcc ccgtgaccaa gtccttcaac agaggcgagt gctga               645
```

<210> SEQ ID NO 536
<211> LENGTH: 113
<212> TYPE: PRT
<213> ORGANISM: Artificial Sequence
<220> FEATURE:
<223> OTHER INFORMATION: Synthetic

<400> SEQUENCE: 536

```
Asp Ile Val Met Thr Gln Ser Pro Leu Ser Leu Pro Val Thr Pro Gly
```

```
               1               5                  10                 15
            Glu Pro Ala Ser Ile Ser Cys Arg Ser Ser Lys Ser Leu Leu His Ser
                            20                 25                 30

Gln Gly Ile Thr Tyr Leu Tyr Trp Tyr Leu Gln Lys Pro Gly Gln Ser
                    35                 40                 45

Pro Gln Leu Leu Ile Tyr Gln Val Ser Asn Leu Ala Ser Gly Val Pro
                50                 55                 60

Asp Arg Phe Ser Gly Ser Gly Ser Gly Thr Asp Phe Thr Leu Lys Ile
            65                 70                 75                 80

Ser Arg Val Glu Ala Glu Asp Val Gly Val Tyr Tyr Cys Ala Gln Tyr
                            85                 90                 95

Leu Glu Leu Pro Trp Thr Phe Gly Cys Gly Thr Lys Val Glu Ile Lys
                    100                105                110

Arg

<210> SEQ ID NO 537
<211> LENGTH: 116
<212> TYPE: PRT
<213> ORGANISM: Artificial Sequence
<220> FEATURE:
<223> OTHER INFORMATION: Synthetic

<400> SEQUENCE: 537

Glu Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Thr Asn Tyr
                            20                 25                 30

Trp Leu Gly Trp Ile Lys Gln Ala Pro Gly Gln Cys Leu Glu Trp Ile
                    35                 40                 45

Gly Asp Ile Tyr Pro Gly Gly Asp Tyr Ile Val Tyr Asn Glu Lys Phe
                50                 55                 60

Lys Gly Lys Ala Thr Leu Thr Ala Asp Thr Ser Ile Ser Thr Ala Tyr
            65                 70                 75                 80

Met Glu Leu Ser Arg Leu Arg Ser Asp Asp Thr Ala Val Tyr Tyr Cys
                            85                 90                 95

Ala Arg Pro Asn Leu Pro Lys Asp His Trp Gly Gln Gly Thr Thr Val
                    100                105                110

Thr Val Ser Ser
                    115

<210> SEQ ID NO 538
<211> LENGTH: 2151
<212> TYPE: DNA
<213> ORGANISM: Artificial Sequence
<220> FEATURE:
<223> OTHER INFORMATION: Synthetic

<400> SEQUENCE: 538
gaggtgcagc tggtggagag cggaggagga ctggtgcaac ccggaggcag cctgagactg     60
agctgcgctg ccagcggctt caccttcagc agctacgaca tgagctgggt gagacaggcc    120
cctggcaaaa gctggagtg gtggccacc atctccgatg cggcggcta catctattac    180 tccgacagcg tgaagggcag gttcaccatc agcagggaca cgccaagaa cagcctgtac    240 ctgcagatga acagcctgag ggatgaggac accgccgtgt acatctgcgc cagggagttc    300
ggcaaaaggt acgccctgga ctactgggc cagggcacaa ccgtgaccgt gagcagcgct    360
agcaccaagg gccctctgt gttccctctg gcccttcct ctaaatccac ctctggcgga    420
```

```
accgctgctc tgggctgtct ggtcaaggac tacttccctg agcccgtgac cgtgtcttgg    480
aattctggcg ctctgaccag cggagtgcac acctttccag ctgtgctgca gtcctccggc    540
ctgtactctc tgtcctctgt cgtgacagtg ccttccagct ctctgggcac ccagacctac    600
atctgcaacg tgaaccacaa gccctccaac accaaggtgg acaagaaggt ggaacccaag    660
tcctgcgaca gacccacac ctgtcctcca tgtcctgctc cagaactgct gggcggaccc     720
tccgtgttcc tgttccctcc aaagcctaag gacaccctga tgatctcccg gacccctgaa    780
gtgacctgcg tggtggtgga tgtgtcccac gaggatcccg aagtgaagtt caattggtac    840
gtggacggcg tggaagtgca aacgccaag accaagccta gagaggaaca gtacgcctcc     900
acctaccggg tggtgtccgt gctgaccgtt ctgcaccagg attggctgaa cggcaaagag    960
tacaagtgca aggtgtccaa caaggccctg cctgcccta tcgaaaagac catctctaag    1020
gccaagggcc agccccggga acctcaagtg tacaccttgc ctcccagccg ggaagagatg   1080
accaagaacc aggtgtccct gacctgcctg gttaagggct tctaccccctc cgatatcgcc   1140 gtggaatggg agtctaacgg ccagcccgag aacaactaca agaccacccc tcctgtgctg   1200
gactccgacg gctcattctt cctgtactcc aagctgaccg tggacaagtc tcggtggcag   1260
cagggcaacg tgttctcctg ctctgtgatg cacgaggccc tgcacaacca ctacacccag   1320
aagtccctgt ccctgtctcc cggcaaaggc tccggatctg gttctggatc cggaagcggt   1380
tctggcagcg gctctggatc tgacattgtg atgacccaga gcccctgag cctccccgtg    1440 accctggag aacccgccag cataagctgc agatcctcca aaagcctgct gcactcccag    1500 ggaataaccct acctgtattg gtacctgcag aaacccggcc aatcccccca actcctgata   1560
taccaagtgt ccaacctggc ctccggcgtg cccgacagat ctccggctc cggcagcgt     1620 accgacttca ccctcaaaat ctccagagtg gaagcagaag acgtcggcgt gtactactgc   1680
gcccagtacc tggaactgcc ctggaccttc ggctgtggca ccaaggtgga atcaagaga    1740 ggcggcggag gaagcggagg cggcggttct ggtggtggcg gtagcggagg tggtggatct   1800
gaggtgcagc tggtgcagag cggagcagag gtgaagaagc caggggccag cgtgaaggtg   1860
agctgtaagg ctagtgggta cacatttaca aactattggc tgggatggat taagcaggcc   1920
ccaggccaat gcctggagtg gataggagac atataccccg gaggagacta tatcgtgtac   1980
aacgagaagt tcaagggcaa ggccacactc accgctgata caagcatcag caccgcctac   2040
atggagctga ccgactgag aagcgacgac acagcagtgt attactgcgc cagacccaac   2100
ctgcccaagg accactgggg acaaggcacc accgtgaccg tgagcagctg a            2151
```

<210> SEQ ID NO 539
<211> LENGTH: 449
<212> TYPE: PRT
<213> ORGANISM: Artificial Sequence
<220> FEATURE:
<223> OTHER INFORMATION: Synthetic

<400> SEQUENCE: 539

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
             85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 540
<211> LENGTH: 2151

<212> TYPE: DNA
<213> ORGANISM: Artificial Sequence
<220> FEATURE:
<223> OTHER INFORMATION: Synthetic

<400> SEQUENCE: 540

```
gaagtgcagc tggttgaatc tggcggcgga ttggttcagc ctggcggatc tctgagactg     60
tcttgtgccg cctccggctt caccttctcc agctacgata tgtcctgggt ccgacaggcc    120
cctggcaagt ctttggaatg ggtcgccacc atctctgacg ctggcggcta catctactac    180
cgggactctg tgaagggcag attcaccatc agccgggaca cgccaagaa ctccctgtac     240
ctgcagatga acagcctgcg cgacgaggat accgccgtgt acatctgtgc tagagagctg    300
ccttggagat acgccctgga ttattgggc agggcacca cagtgaccgt gtcctctgct      360
tctaccaagg gacccagcgt gttccctctg gctccttcca gcaagtctac ctctggcgga    420
acagctgctc tgggctgcct ggtcaaggac tactttcctg agcctgtgac agtgtcctgg    480
aactctggcg ctctgacatc tggcgtgcac acctttccag cagtgctgca gtcctccggc    540
ctgtactctc tgtcctctgt cgtgaccgtg ccttccagct ctctgggcac ccagacctac    600
atctgcaacg tgaaccacaa gccctccaac accaaggtgg acaagaaggt ggaacccaag    660
tcctgcgaca gacccacac ctgtcctcca tgtcctgctc cagaactgct gggcggaccc      720
tccgtgttcc tgttccctcc aaagcctaag gacaccctga tgatctcccg gacccctgaa    780
gtgacctgcg tggtggtgga tgtgtcccac gaggatcccg aagtgaagtt caattggtac    840
gtggacggcg tggaagtgca caacgccaag accaagccta gagaggaaca gtacgcctcc    900
acctaccggg tggtgtccgt gctgaccgtt ctgcaccagg attggctgaa cggcaaagag    960
tacaagtgca aggtgtccaa caaggccctg cctgccccta tcgaaaagac catctctaag   1020
gccaagggcc agccccggga acctcaagtg tacaccttgc ctcccagccg ggaagagatg   1080
accaagaacc aggtgtccct gacctgcctg gttaagggct ctaccccctc cgatatcgcc   1140
gtggaatggg agtctaatgg ccagcctgag aacaactaca agaccacacc tcctgtgctg   1200
gactccgacg gctcattctt cctgtactcc aagctgaccg tggacaagtc cagatggcag   1260
cagggcaacg tgttctcctg ctccgtgatg cacgaggccc tgcacaatca ctacacccag   1320
aagtccctgt ctctgtcccc tggcaaaggc tccggatctg gttctggatc cggaagcggt   1380
tctggcagcg gctctggatc tgacatcgtg atgacccagt ctccactgag cctgcctgtg   1440
acacctggcg agcctgcttc catctcctgc cggtcctcta gtccctgct gcactctaac    1500
ggcatcacct acctgtactg gtatctgcag aagcccggcc agtctcctca gctgctgatc   1560
taccaggtgt ccaacctggc ttctggcgtg cccgatagat ctccggtag cggatctgga    1620
accgacttca ccctgaagat ctccagagtg gaagccgagg acgtgggcgt gtactactgt   1680
gcccagaacc tggaactgcc ctggaccttt ggctgtggca ccaaggtgga aatcaagaga   1740
ggcggcggag gatctggcgg aggtggaagc ggaggcggag gaagcggtgg cggcggatct   1800
gaagttcagt tggttcagtc tggcgccgaa gtgaagaaac ctggcgcctc tgtgaaggtg   1860
tcctgcaagg cttccggcta caccttttacc aactactggc tcggctggat caagcaggcc   1920
cctggacagt gtctggaatg gatcggcgac atctaccctg cggcgactta catcaactac   1980
aacgagaagt tcaagggcaa agctaccctg accgccgaca cctctatctc caccgcctac   2040
atggaactgt cccggctgag atctgacgac accgccgtgt actattgcgc cagacctaac   2100
ctgcctggcg actattgggg ccagggcaca acagtgaccg tgtcctctta a             2151
```

<210> SEQ ID NO 541
<211> LENGTH: 2151
<212> TYPE: DNA
<213> ORGANISM: Artificial Sequence
<220> FEATURE:
<223> OTHER INFORMATION: Synthetic

<400> SEQUENCE: 541

| | | | | | |
|---|---|---|---|---|---|
| gaagtgcagc | tggttgaatc | tggcggcgga | ttggttcagc | ctggcggatc | tctgagactg | 60 |
| tcttgtgccg | cctccggctt | caccttctcc | agctacgata | tgtcctgggt | ccgacaggcc | 120 |
| cctggcaagt | ctttggaatg | ggtcgccacc | atctctgacg | ctggcggcta | catctactac | 180 |
| cgggactctg | tgaagggcag | attcaccatc | agccgggaca | acgccaagaa | ctccctgtac | 240 |
| ctgcagatga | acagcctgcg | cgacgaggat | accgccgtgt | acatctgtgc | tagagagctg | 300 |
| ccttggagat | acgccctgga | ttattgggc | cagggcacca | cagtgaccgt | gtcctctgct | 360 |
| tctaccaagg | gacccagcgt | gttccctctg | gctccttcca | gcaagtctac | ctctggcgga | 420 |
| acagctgctc | tgggctgcct | ggtcaaggac | tactttcctg | agcctgtgac | agtgtcctgg | 480 |
| aactctggcg | ctctgacatc | tggcgtgcac | acctttccag | cagtgctgca | gtcctccggc | 540 |
| ctgtactctc | tgtcctctgt | cgtgaccgtg | ccttccagct | ctctgggcac | ccagacctac | 600 |
| atctgcaacg | tgaaccacaa | gccctccaac | accaaggtgg | acaagaaggt | ggaacccaag | 660 |
| tcctgcgaca | gacccacac | ctgtcctcca | tgtcctgctc | cagaactgct | gggcggaccc | 720 |
| tccgtgttcc | tgttccctcc | aaagcctaag | gacaccctga | tgatctcccg | gacccctgaa | 780 |
| gtgacctgcg | tggtggtgga | tgtgtcccac | gaggatcccg | aagtgaagtt | caattggtac | 840 |
| gtggacggcg | tggaagtgca | caacgccaag | accaagccta | gagaggaaca | gtacgcctcc | 900 |
| acctaccggg | tggtgtccgt | gctgaccgtt | ctgcaccagg | attggctgaa | cggcaaagag | 960 |
| tacaagtgca | aggtgtccaa | caaggccctg | cctgcccta | tcgaaaagac | catctctaag | 1020 |
| gccaagggca | gccccggga | acctcaagtg | tacaccttgc | ctcccagccg | ggaagagatg | 1080 |
| accaagaacc | aggtgtccct | gacctgcctg | gttaagggct | tctaccccte | cgatatcgcc | 1140 |
| gtggaatggg | agtctaacgg | ccagcccgag | aacaactaca | agaccacccc | tcctgtgctg | 1200 |
| gactccgacg | gctcattctt | cctgtactcc | aagctgaccg | tggacaagtc | tcggtggcag | 1260 |
| cagggcaacg | tgttctcctg | ctctgtgatg | cacgaggccc | tgcacaacca | ctacacccag | 1320 |
| aagtccctgt | ccctgtctcc | cggcaaaggc | tccggatctg | gttctggatc | cggaagcggt | 1380 |
| tctggcagcg | gctctggatc | tgacattgtg | atgacccaga | gccccctgag | cctccccgtg | 1440 |
| accccctggag | aacccgccag | cataagctgc | agatcctcca | aaagcctgct | gcactcccag | 1500 |
| ggaataacct | acctgtattg | gtacctgcag | aaacccggcc | aatcccccca | actcctgata | 1560 |
| taccaagtgt | ccaacctggc | ctccggcgtg | cccgacagat | tctccggctc | cggcagcggt | 1620 |
| accgacttca | ccctcaaaat | ctccagagtg | gaagcagaag | acgtcggcgt | gtactactgc | 1680 |
| gcccagtacc | tggaactgcc | ctggaccttc | ggctgtggca | ccaaggtgga | aatcaagaga | 1740 |
| ggcggcggag | gaagcggagg | cggcggttct | ggtggtggcg | gtagcggagg | tggtggatct | 1800 |
| gaggtgcagc | tggtgcagag | cggagcagag | gtgaagaagc | caggggccag | cgtgaaggtg | 1860 |
| agctgtaagg | ctagtgggta | cacatttaca | aactattggc | tgggatggat | taagcaggcc | 1920 |
| ccaggccaat | gcctggagtg | gataggagac | atataccccg | gaggagacta | tcgtgtgtac | 1980 |
| aacgagaagt | tcaagggcaa | ggccacactc | accgctgata | caagcatcag | caccgcctac | 2040 |
| atggagctga | gcctgactgag | aagcgacgac | acagcagtgt | attactgcgc | cagacccaac | 2100 | ctgcccaagg accactgggg acaaggcacc accgtgaccg tgagcagctg a                2151

<210> SEQ ID NO 542
<211> LENGTH: 443
<212> TYPE: PRT
<213> ORGANISM: Artificial Sequence
<220> FEATURE:
<223> OTHER INFORMATION: Synthetic

<400> SEQUENCE: 542

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Leu Gly Trp Ile Lys Gln Ala Pro Gly Gln Gly Leu Glu Trp Ile
        35                  40                  45
Gly Asp Ile Tyr Pro Gly Gly Asp Tyr Ile Asn Tyr Asn Glu Lys Phe
    50                  55                  60
Lys Gly Lys Ala Thr Leu Thr Ala Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Pro Asn Leu Pro Gly Asp Tyr Trp Gly Gln Gly Thr Thr Val
            100                 105                 110
Thr Val Ser Ser Ala Ser Thr Lys Gly Pro Ser Val Phe Pro Leu Ala
        115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly Pro Pro Cys Pro Pro
    210                 215                 220
Cys Pro Ala Pro Glu Phe Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
```

```
Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440

<210> SEQ ID NO 543
<211> LENGTH: 15
<212> TYPE: PRT
<213> ORGANISM: Artificial Sequence
<220> FEATURE:
<223> OTHER INFORMATION: Synthetic

<400> SEQUENCE: 543

Gly Gly Gly Gly Ser Gly Gly Gly Gly Ser Gly Gly Gly Gly Ser
1               5                   10                  15

<210> SEQ ID NO 544
<211> LENGTH: 108
<212> TYPE: PRT
<213> ORGANISM: Artificial Sequence
<220> FEATURE:
<223> OTHER INFORMATION: Synthetic

<400> SEQUENCE: 544

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Cys Gly Thr Lys Leu Glu Ile Lys Arg
            100                 105

<210> SEQ ID NO 545
<211> LENGTH: 119
<212> TYPE: PRT
<213> ORGANISM: Artificial Sequence
<220> FEATURE:
<223> OTHER INFORMATION: Synthetic

<400> SEQUENCE: 545

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
```

```
                35                  40                  45
Ala Thr Ile Ser Asp Ala Gly Gly Tyr Ile Tyr Tyr Ser Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Phe Gly Lys Arg Tyr Ala Leu Asp Tyr Trp Gly Gln Gly
            100                 105                 110

Thr Thr Val Thr Val Ser Ser
        115

<210> SEQ ID NO 546
<211> LENGTH: 2118
<212> TYPE: DNA
<213> ORGANISM: Artificial Sequence
<220> FEATURE:
<223> OTHER INFORMATION: Synthetic

<400> SEQUENCE: 546
gaggtgcagc tggtgcagag cggagcagag gtgaagaagc caggggccag cgtgaaggtg      60
agctgtaagg ctagtgggta cacatttaca aactattggc tgggatggat taagcaggcc     120
ccaggccaag gactggagtg gataggagac atataccccg gaggagacta tatcaattac     180
aacgagaagt tcaagggcaa ggccacactc accgctgata caagcatcag caccgcctac     240
atggagctga ccgactgag aagcgacgac acagcagtgt attactgcgc cagacccaac     300
ctgcccggcg actactgggg acaaggcacc accgtgaccg tgtcttccgc tagcaccaag     360
ggcccctccg tgttccctct ggcccccatgc tcccggtcca cctccgagtc caccgccgct     420
ctgggctgtc tggtgaagga ctacttccct gagcccgtga ccgtgagctg gaactctggc     480
gccctgacct ccggcgtgca caccttccct gccgtgctgc agtcctccgg cctgtactcc     540
ctgtcctccg tggtgaccgt gccttcctcc tccctgggca ccaagaccta cacctgcaac     600
gtggaccaca gccttccaa caccaaggtg gacaagcggg tggagtccaa gtacggccct     660
ccttgccctc cctgccctgc ccctgagttc ctggcggac cctccgtgtt cctgttccct     720
cctaagccta aggacaccct gatgatctcc cggaccctg aggtgacctg cgtggtggtg     780
gacgtgtccc aggaagatcc tgaggtccag ttcaattggt acgtggatgg cgtggaggtg     840
cacaacgcca agaccaagcc tcgggaggaa cagttcaact ccacctaccg ggtggtgtct     900
gtgctgaccg tgctgcacca ggactggctg aacggcaagg aatacaagtg caaggtcagc     960
aacaagggcc tgcccctcctc catcgagaaa accatctcca aggccaaggg ccagcctcgc    1020
gagcctcagg tgtacaccct gcctcctagc caggaagaga tgaccaagaa tcaggtgtcc    1080
ctgacatgcc tggtgaaggg cttctacccct tccgatatcg ccgtggagtg ggagagcaac    1140
ggccagccag agaacaacta caagaccacc cctcctgtgc tggactccga cggctccttc    1200
ttcctgtact ccaggctgac cgtggacaag tcccggtggc aggaaggcaa cgtctttttc    1260
tgctccgtga tgcacgaggc cctgcacaac cactacaccc agaagtccct gtccctgtct    1320
ctgggcaagg gtggaggtgg gtctgggggt ggcgggtcag gtgaggagg ttcagacatc    1380 cagatgaccc agagccctag cagcctgagc gctagcgtgg gcgacagggt gaccatcacc    1440
tgcaaggcca gccaggatgt gacccctgcc gtggcctggt accagcagaa gcccggcaag    1500
gcccccaagc tgctgatcta cagcaccagc agcaggtaca ccggcgtgcc cagcaggttt    1560
```

```
agcggaagcg gcagcggcac cgacttcacc ttcaccatca gcagcctgca gcccgaggac    1620
atcgccacct actactgcca gcagcactac accacccctc tgaccttcgg ctgtggcacc    1680
aagctggaga tcaagagagg tggaggcggc tcaggggggg gtggatcagg gggaggagga    1740
tcagggggag gcggtagtga ggtgcagctg gtggagagcg gaggaggact ggtgcaaccc    1800
ggaggcagcc tgagactgag ctgcgctgcc agcggcttca ccttcagcag ctacgacatg    1860
agctgggtga acaggcccc tggcaaatgt ctggagtggg tggccaccat ctccgatgcg    1920
ggcggctaca tctattactc cgacagcgtg aagggcaggt tcaccatcag cagggacaac    1980
gccaagaaca ccctgtacct gcagatgaac agcctgaggg atgaggacac cgccgtgtac    2040
atctgcgcca gggagttcgg caaaaggtac gccctggact actggggcca gggcacaacc    2100
gtgaccgtga gcagctga                                                  2118
```

<210> SEQ ID NO 547
<211> LENGTH: 219
<212> TYPE: PRT
<213> ORGANISM: Artificial Sequence
<220> FEATURE:
<223> OTHER INFORMATION: Synthetic

<400> SEQUENCE: 547

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 548
<211> LENGTH: 660
<212> TYPE: DNA
<213> ORGANISM: Artificial Sequence
<220> FEATURE:
<223> OTHER INFORMATION: Synthetic

<400> SEQUENCE: 548

```
gacattgtga tgacccagag cccctgagc ctccccgtga cccctggaga acccgccagc    60
ataagctgca gatcctccaa aagcctgctg cactccaacg gaataaccta cctgtattgg   120
tacctgcaga aacccggcca atcccccaa ctcctgatat accaagtgtc caacctggcc   180
tccggcgtgc ccgacagatt ctccggctcc ggcagcggta ccgacttcac cctcaaaatc   240
tccagagtgg aagcagaaga cgtcggcgtg tactactgcg cccagaatct ggaactgccc   300
tggaccttcg gcggcggcac caaggtggaa atcaagagaa ccgtggccgc tccctccgtg   360
ttcatcttcc caccatctga cgagcagctg aagtccggca ccgcttctgt cgtgtgcctg   420
ctgaacaact tctaccctcg ggaagccaag gtgcagtgga aggtggacaa tgccctgcag   480
tccggcaact cccaagagtc tgtgaccgag caggactcca aggacagcac ctactccctg   540
tcctctaccc tgaccctgtc caaggccgac tacgagaagc acaaggtgta cgcctgcgaa   600
gtgacccacc agggactgtc tagccccgtg accaagtcct caacagagg cgagtgctga    660
```

<210> SEQ ID NO 549
<211> LENGTH: 119
<212> TYPE: PRT
<213> ORGANISM: Artificial Sequence
<220> FEATURE:
<223> OTHER INFORMATION: Synthetic

<400> SEQUENCE: 549

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met Ser Trp Val Arg Gln Ala Pro Gly Lys Cys Leu Glu Trp Val
        35                  40                  45
Ala Thr Ile Ser Asp Ala Gly Gly Tyr Ile Tyr Tyr Arg Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Asp Glu Asp Thr Ala Val Tyr Ile Cys
                85                  90                  95
Ala Arg Glu Leu Pro Trp Arg Tyr Ala Leu Asp Tyr Trp Gly Gln Gly
            100                 105                 110
Thr Thr Val Thr Val Ser Ser
        115
```

<210> SEQ ID NO 550
<211> LENGTH: 2118
<212> TYPE: DNA
<213> ORGANISM: Artificial Sequence
<220> FEATURE:
<223> OTHER INFORMATION: Synthetic

<400> SEQUENCE: 550

```
gaggtgcagc tggtgcagag cggagcagag gtgaagaagc caggggccag cgtgaaggtg    60
agctgtaagg ctagtgggta cacatttaca aactattggc tgggatggat taagcaggcc   120
ccaggccaag gactggagtg gataggagac atatacccccg aggagactta tcaattac    180
aacgagaagt tcaagggcaa ggccacactc accgctgata caagcatcag caccgcctac   240
atggagctga gccgactgag aagcgacgac acagcagtgt attactgcgc cagacccaac   300
```

-continued

```
ctgcccggcg actactgggg acaaggcacc accgtgaccg tgtcttccgc tagcaccaag    360
ggcccctccg tgttccctct ggccccatgc tcccggtcca cctccgagtc caccgccgct    420
ctgggctgtc tggtgaagga ctacttccct gagcccgtga ccgtgagctg gaactctggc    480
gccctgacct ccggcgtgca caccttccct gccgtgctgc agtcctccgg cctgtactcc    540
ctgtcctccg tggtgaccgt gccttcctcc tccctgggca ccaagaccta cacctgcaac    600
gtggaccaca gccttccaa caccaaggtg acaagcggg tggagtccaa gtacggccct    660
ccttgccctc cctgccctgc ccctgagttc ctgggcggac cctccgtgtt cctgttccct    720
cctaagccta aggacaccct gatgatctcc cggacccctg aggtgacctg cgtggtggtg    780
gacgtgtccc aggaagatcc tgaggtccag ttcaattggt acgtggatgg cgtggaggtg    840
cacaacgcca agaccaagcc tcgggaggaa cagttcaact ccacctaccg ggtggtgtct    900
gtgctgaccg tgctgcacca ggactggctg aacggcaagg aatacaagtg caaggtcagc    960
aacaagggcc tgccctcctc catcgagaaa accatctcca aggccaaggg ccagcctcgc   1020
gagcctcagg tgtacaccct gcctcctagc caggaagaga tgaccaagaa tcaggtgtcc   1080
ctgacatgcc tggtgaaggg cttctaccct tccgatatcg ccgtggaatg ggagagcaat   1140
ggccagcctg agaacaacta caagacaacc cctcctgtgc tggactccga cggctccttc   1200
tttctgtact ctcgcctgac cgtggacaag tccagatggc aagagggcaa cgtgttctcc   1260
tgctccgtga tgcacgaggc cctgcacaat cactacaccc agaagtccct gtctctgtcc   1320
ctcggaaaag gcggcggagg atctggcgga ggcggtagcg gtggtggcgg atctgatatt   1380
cagatgaccc agtctccttc cagcctgtcc gcttctgtgg gcgacagagt gaccatcaca   1440
tgcaaggcca gcaggatgt gacccctgct gtggcttggt atcagcagaa gcctggcaag   1500
gccctaagc tgctgatcta ctccacctcc tccagataca caggcgtgcc ctccagattc   1560
tccggctctg gctctggcac cgactttacc tttacaatct ccagcctgca gcctgaggac   1620
attgccacct actactgcca gcagcactac accacacctc tgacctttgg ctgcggcacc   1680
aagctggaaa tcaagagagg tggcggagga agcggaggcg gcggttcagg tggcggtggt   1740
tcaggcggtg gtggatctga agttcagctg gtggaatctg gcggcggatt ggttcaacca   1800
ggcggctctc tgagactgtc ttgtgccgct tccggcttca ccttctccag ctacgacatg   1860
tcctgggtcc gacaggcccc tggaaagtgt ctggaatggg tcgccaccat ctctgacgct   1920
ggcggctaca tctactaccg ggactctgtg aagggcagat tcaccatcag ccgggacaat   1980
gccaagaact ccctgtacct gcagatgaac agtctgcgcg acgaggacac cgccgtgtac   2040
atctgtgcta gagagctgcc ttggcgctac gccctggatt attggggcca gggcacaaca   2100
gtgacagtgt cctcttga                                                 2118
```

<210> SEQ ID NO 551
<211> LENGTH: 443
<212> TYPE: PRT
<213> ORGANISM: Artificial Sequence
<220> FEATURE:
<223> OTHER INFORMATION: Synthetic

<400> SEQUENCE: 551

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Ile Lys Gln Ala Pro Gly Gln Gly Leu Glu Trp Ile
```

```
                35                  40                  45
Gly Asp Ile Tyr Pro Gly Gly Asp Tyr Ile Val Tyr Asn Glu Lys Phe
 50                  55                  60
Lys Gly Lys Ala Thr Leu Thr Ala Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Pro Asn Leu Pro Lys Asp His Trp Gly Gln Gly Thr Thr Val
                100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
    195                 200                 205
Lys Val Asp Lys Arg Val Glu Ser Lys Tyr Gly Pro Pro Cys Pro Pro
210                 215                 220
Cys Pro Ala Pro Glu Phe Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
    275                 280                 285
Glu Glu Gln Phe Asn Ser Thr Tyr Arg Val Val Ser Val Leu Thr Val
290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
    355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly Lys
    435                 440

<210> SEQ ID NO 552
```

<211> LENGTH: 2118
<212> TYPE: DNA
<213> ORGANISM: Artificial Sequence
<220> FEATURE:
<223> OTHER INFORMATION: Synthetic

<400> SEQUENCE: 552

| | | | | | |
|---|---|---|---|---|---|
| gaggtgcagc | tggtgcagag | cggagcagag | gtgaagaagc | caggggccag | cgtgaaggtg | 60 |
| agctgtaagg | ctagtgggta | cacatttaca | aactattggc | tgggatggat | taagcaggcc | 120 |
| ccaggccaag | gactggagtg | gataggagac | atatacccccg | gaggagacta | tatcgtgtac | 180 |
| aacgagaagt | tcaagggcaa | ggccacactc | accgctgata | caagcatcag | caccgcctac | 240 |
| atggagctga | gccgactgag | aagcgacgac | acagcagtgt | attactgcgc | cagacccaac | 300 |
| ctgcccaagg | accactgggg | acaaggcacc | accgtgaccg | tgtcttccgc | tagcaccaag | 360 |
| ggccccctccg | tgttccctct | ggccccatgc | tcccggtcca | cctccgagtc | caccgccgct | 420 |
| ctgggctgtc | tggtgaagga | ctacttccct | gagcccgtga | ccgtgagctg | gaactctggc | 480 |
| gccctgacct | ccggcgtgca | caccttccct | gccgtgctgc | agtcctccgg | cctgtactcc | 540 |
| ctgtcctccg | tggtgaccgt | gccttcctcc | tccctgggca | ccaagaccta | cacctgcaac | 600 |
| gtggaccaca | agccttccaa | caccaaggtg | gacaagcggg | tggagtccaa | gtacggccct | 660 |
| ccttgccctc | cctgccctgc | ccctgagttc | ctgggcggac | cctccgtgtt | cctgttccct | 720 |
| cctaagccta | aggacaccct | gatgatctcc | cggacccctg | aggtgacctg | cgtggtggtg | 780 |
| gacgtgtccc | aggaagatcc | tgaggtccag | ttcaattggt | acgtggatgg | cgtggaggtg | 840 |
| cacaacgcca | agaccaagcc | tcgggaggaa | cagttcaact | ccacctaccg | ggtggtgtct | 900 |
| gtgctgaccg | tgctgcacca | ggactggctg | aacggcaagg | aatacaagtg | caaggtcagc | 960 |
| aacaaggggcc | tgccctcctc | catcgagaaa | accatctcca | aggccaaggg | ccagcctcgc | 1020 |
| gagcctcagg | tgtacaccct | gcctcctagc | caggaagaga | tgaccaagaa | tcaggtgtcc | 1080 |
| ctgacatgcc | tggtgaaggg | cttctaccct | tccgatatcg | ccgtggagtg | ggagagcaac | 1140 |
| ggccagccag | agaacaacta | caagaccacc | cctcctgtgc | tggactccga | cggctccttc | 1200 |
| ttcctgtact | ccaggctgac | cgtggacaag | tcccggtggc | aggaaggcaa | cgtcttttcc | 1260 |
| tgctccgtga | tgcacgaggc | cctgcacaac | cactacaccc | agaagtccct | gtccctgtct | 1320 |
| ctgggcaagg | gtggaggtgg | gtctgggggt | ggcgggtcag | gtggaggagg | ttcagacatc | 1380 |
| cagatgaccc | agagccctag | cagcctgagc | gctagcgtgg | gcgacagggt | gaccatcacc | 1440 |
| tgcaaggcca | gccaggatgt | gacccctgcc | gtggcctggt | accagcagaa | gcccggcaag | 1500 |
| gcccccaagc | tgctgatcta | cagcaccagc | agcaggtaca | ccggcgtgcc | cagcaggttt | 1560 |
| agcggaagcg | gcagcggcac | cgacttcacc | ttcaccatca | gcagcctgca | gcccgaggac | 1620 |
| atcgccacct | actactgcca | gcagcactac | accacccctc | tgaccttcgg | ctgtggcacc | 1680 |
| aagctggaga | tcaagagagg | tggaggcggc | tcagggggg | gtggatcagg | ggaggagga | 1740 |
| tcagggggag | gcggtagtga | ggtgcagctg | gtggagagcg | gaggaggact | ggtgcaaccc | 1800 |
| ggaggcagcc | tgagactgag | ctgcgctgcc | agcggcttca | ccttcagcag | ctacgacatg | 1860 |
| agctgggtga | gcaggccccc | tggcaaatgt | ctggagtggg | tggccaccat | ctccgatgcg | 1920 |
| ggcggctaca | tctattactc | cgacagcgtg | aagggcaggt | tcaccatcag | cagggacaac | 1980 |
| gccaagaaca | gcctgtacct | gcagatgaac | agcctgaggg | atgaggacac | cgccgtgtac | 2040 |
| atctgcgcca | gggagttcgg | caaaaggtac | gccctggact | actggggcca | gggcacaacc | 2100 |
| gtgaccgtga | gcagctga | | | | | 2118 |

<210> SEQ ID NO 553
<211> LENGTH: 219
<212> TYPE: PRT
<213> ORGANISM: Artificial Sequence
<220> FEATURE:
<223> OTHER INFORMATION: Synthetic

<400> SEQUENCE: 553

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Gln Gly Ile Thr Tyr Leu Tyr Trp Tyr Leu Gln Lys Pro Gly Gln Ser
        35                  40                  45

Pro Gln Leu Leu Ile Tyr Gln Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Tyr
                85                  90                  95

Leu Glu Leu Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 554
<211> LENGTH: 660
<212> TYPE: DNA
<213> ORGANISM: Artificial Sequence
<220> FEATURE:
<223> OTHER INFORMATION: Synthetic

<400> SEQUENCE: 554

```
gacattgtga tgacccagag cccccctgagc ctccccgtga cccctggaga acccgccagc    60
ataagctgca gatcctccaa aagcctgctg cactcccagg gaataaccta cctgtattgg   120
tacctgcaga aacccggcca atcccccccaa ctcctgatat accaagtgtc caacctggcc   180
tccggcgtgc ccgacagatt ctccggctcc ggcagcggta ccgacttcac cctcaaaatc   240
tccagagtgg aagcagaaga cgtcggcgtg tactactgcg cccagtacct ggaactgccc   300
tggaccttcg gcggcggcac caaggtggaa atcaagagaa ccgtggccgc tcctccgtg    360 ttcatcttcc caccatctga cgagcagctg aagtccggca ccgcttctgt cgtgtgcctg   420
ctgaacaact ctaccctcg ggaagccaag gtgcagtgga aggtggacaa tgccctgcag   480
```

| | |
|---|---|
| tccggcaact cccaagagtc tgtgaccgag caggactcca aggacagcac ctactccctg | 540 |
| tcctctaccc tgaccctgtc caaggccgac tacgagaagc acaaggtgta cgcctgcgaa | 600 |
| gtgacccacc agggactgtc tagccccgtg accaagtcct caacagagg cgagtgctga | 660 |

<210> SEQ ID NO 555
<211> LENGTH: 2118
<212> TYPE: DNA
<213> ORGANISM: Artificial Sequence
<220> FEATURE:
<223> OTHER INFORMATION: Synthetic

<400> SEQUENCE: 555

| | |
|---|---|
| gaggtgcagc tggtgcagag cggagcagag gtgaagaagc caggggccag cgtgaaggtg | 60 |
| agctgtaagg ctagtgggta cacatttaca aactattggc tgggatggat taagcaggcc | 120 |
| ccaggccaag gactggagtg gataggagac atatacccg gaggagacta tatcgtgtac | 180 |
| aacgagaagt tcaagggcaa ggccacactc accgctgata caagcatcag caccgcctac | 240 |
| atggagctga gccgactgag aagcgacgac acagcagtgt attactgcgc cagacccaac | 300 |
| ctgcccaagg accactgggg acaaggcacc accgtgaccg tgtcttccgc tagcaccaag | 360 |
| ggcccctccg tgttccctct ggccccatgc tcccggtcca cctccgagtc caccgccgct | 420 |
| ctgggctgtc tggtgaagga ctacttccct gagcccgtga ccgtgagctg gaactctggc | 480 |
| gccctgacct ccggcgtgca caccttccct gccgtgctgc agtcctccgg cctgtactcc | 540 |
| ctgtcctccg tggtgaccgt gccttcctcc tccctgggca ccaagaccta cacctgcaac | 600 |
| gtggaccaca agccttccaa caccaaggtg gacaagcggg tggagtccaa gtacggccct | 660 |
| ccttgccctc cctgccctgc ccctgagttc ctgggcggac cctccgtgtt cctgttccct | 720 |
| cctaagccta aggacaccct gatgatctcc cggacccctg aggtgacctg cgtggtggtg | 780 |
| gacgtgtccc aggaagatcc tgaggtccag ttcaattggt acgtggatgg cgtggaggtg | 840 |
| cacaacgcca agaccaagcc tcgggaggaa cagttcaact ccacctaccg ggtggtgtct | 900 |
| gtgctgaccg tgctgcacca ggactggctg aacggcaagg aatacaagtg caaggtcagc | 960 |
| aacaagggcc tgcccctcctc catcgagaaa accatctcca aggccaaggg ccagcctcgc | 1020 |
| gagcctcagg tgtacaccct gcctcctagc caggaagaga tgaccaagaa tcaggtgtcc | 1080 |
| ctgacatgcc tggtgaaggg cttctaccct tccgatatcg ccgtggaatg ggagagcaat | 1140 |
| ggccagcctg agaacaacta caagacaacc cctcctgtgc tggactccga cggctccttc | 1200 |
| tttctgtact ctcgcctgac cgtggacaag tccagatggc aagagggcaa cgtgttctcc | 1260 |
| tgctccgtga tgcacgaggc cctgcacaat cactacaccc agaagtccct gtctctgtcc | 1320 |
| ctcggaaaag cggcggagg atctggcgga ggcggtagcg gtggtggcgg atctgatatt | 1380 |
| cagatgaccc agtctccttc cagcctgtcc gcttctgtgg gcgacagagt gaccatcaca | 1440 |
| tgcaaggcca gcaggatgt gacccctgct gtggcttggt atcagcagaa gcctggcaag | 1500 |
| gcccctaagc tgctgatcta ctccacctcc tccagataca caggcgtgcc ctccagattc | 1560 |
| tccggctctg gctctggcac cgactttacc tttacaatct ccagcctgca gcctgaggac | 1620 |
| attgccacct actactgcca gcagcactac accacacctc tgacctttgg ctgcggcacc | 1680 |
| aagctggaaa tcaagagagg tggcggagga agcggaggcg gcggttcagg tggcggtggt | 1740 |
| tcaggcggtg gtggatctga agttcagctg gtggaatctg gcggcggatt ggttcaacca | 1800 |
| ggcggctctc tgagactgtc ttgtgccgct tccggcttca ccttctccag ctacgacatg | 1860 |
| tcctgggtcc gacaggcccc tggaaagtgt ctggaatggg tcgccaccat ctctgacgct | 1920 |

```
ggcggctaca tctactaccg ggactctgtg aagggcagat tcaccatcag ccgggacaat    1980
gccaagaact ccctgtacct gcagatgaac agtctgcgcg acgaggacac cgccgtgtac    2040
atctgtgcta gagagctgcc ttggcgctac gccctggatt attggggcca gggcacaaca    2100
gtgacagtgt cctcttga                                                  2118
```

ANTI-PD-L1/ANTI-LAG3 BISPECIFIC ANTIBODIES AND USES THEREOF

CROSS-REFERENCE TO RELATED APPLICATIONS

This application is a National Stage of International Application No. PCT/CN2019/101747 filed Aug. 21, 2019, claiming priority based on International Application No. PCT/CN2018/101547 filed Aug. 21, 2018 and International Application No. PCT/CN2019/087943 filed May 22, 2019, the entire disclosures of which are incorporated herein by reference.

BACKGROUND

Programmed death-ligand 1 (PD-L1), also known as cluster of differentiation 274 (CD274) or B7 homolog 1 (B7-H1), is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

It has been shown that upregulation of PD-L1 may allow cancers to evade the host immune system. An analysis of tumor specimens from patients with renal cell carcinoma found that high tumor expression of PD-L1 was associated with increased tumor aggressiveness and an increased risk of death. Many PD-L1 inhibitors are in development as immuno-oncology therapies and are showing good results in clinical trials.

In addition to treatment of cancers, PD-L1 inhibition has also shown promises in treating infectious diseases. In a mouse model of intracellular infection, *L. monocytogenes* induced PD-L1 protein expression in T cells, NK cells, and macrophages. PD-L1 blockade (e.g., using blocking antibodies) resulted in increased mortality for infected mice. Blockade reduced TNFα and nitric oxide production by macrophages, reduced granzyme B production by NK cells, and decreased proliferation of *L. monocytogenes* antigen-specific CD8 T cells (but not CD4 T cells). This evidence suggests that PD-L1 acts as a positive costimulatory molecule in intracellular infection.

Lymphocyte Activation Gene-3 (LAG-3) (also known as CD223) is a member of the immunoglobulin (Ig) superfamily, is closely related to CD4, and variously impacts T cell function. LAG-3 is expressed on activated T cells, exhausted T cells, tumor infiltrating T cells, and regulatory T cells (Tregs). Upon binding with major histocompatibility complex 2 (MHC class II), the LAG-3/MHC class II interaction results in the negative regulation of T cell proliferation, activation, and homeostasis.

LAG-3 represents an important immune checkpoint in cancer, similarly to cytotoxic T lymphocyte antigen-4 (CTLA-4), programmed cell death ligand-1 (PD-L1), and programmed cell death-1 (PD-1). LAG-3 not only expresses on the activated/exhausted effector T cells but also on regulatory T cells. LAG3 antagonism can not only promote the activation of effector T cells, but also block the suppressive function of regulatory T cells. Therefore, LAG-3 represents a promising target for cancer immunotherapy and preclinical evidence suggests that an anti-LAG-3 antibody can promote an anti-tumor response.

In view of the above, a need exists for developing novel agents that modulate the activity of LAG-3 in a manner that stimulates an immune response that inhibits the growth of various cancers and tumor cells, as well as being useful in the treatment of autoimmune, inflammatory, or viral diseases.

SUMMARY

The present disclosure provides an anti-PD-L1/anti-LAG3 bispecific antibody capable to effectively block the interactions between PD-L1 and its receptor PD-1 and between LAG3 and its ligand (e.g., a MHC class II molecule). The bispecific antibody may have high binding affinity to both of a PD-L1 protein (e.g., a human PD-L1 protein) and a LAG3 protein (e.g., a human LAG3 protein).

The anti-PD-L1/anti-LAG3 bispecific antibody may comprise an anti-PD-L1 antibody or an antigen-binding fragment thereof as a PD-L1 targeting moiety, which is capable of specifically recognizing and/or binding to a PD-L1 protein, and an anti-LAG3 antibody or an antigen-binding fragment thereof as a LAG3 targeting moiety, which is capable of specifically recognizing and/or binding to a LAG3 protein.

The anti-PD-L1/anti-LAG3 bispecific antibody may comprise an anti-PD-L1 antibody or an antigen-binding fragment thereof as a PD-L1 targeting moiety.

In an embodiment, the anti-PD-L1 antibody or fragment thereof comprised in the bispecific antibody can specifically bind to an immunoglobulin C (IgC) domain of PD-L1 (e.g., human PD-L1) protein. In some embodiments, the IgC domain consists of amino acid residues 133-225 of a human PD-L1 protein. In some embodiments, the anti-PD-L1 antibody or fragment thereof can bind to at least one of amino acid residues Y134, K162, and N183 of a human PD-L1 protein. In some embodiments, the anti-PD-L1 antibody or fragment thereof does not bind to an immunoglobulin V (IgV) domain of the PD-L1 protein, and for example, the IgV domain consists of amino acid residues 19-127 of a human PD-L1 protein. For example, the human PD-L1 protein may be selected from the group consisting of proteins represented by GenBank Accession No. NP_001254635.1 NP_001300958.1, NP_054862.1, etc., but may not be limited thereto. These anti-PD-L1 antibodies may be useful for therapeutic purposes such as treating various types of cancer, infections (inflammations), etc., and can also be used for diagnostic and prognostic purposes. In an embodiment, the anti-PD-L1 antibody or fragment thereof is capable of specificity to a human PD-L1 protein.

The anti-PD-L1 antibody or fragment thereof may comprise (1) a VH CDR1 having an amino acid sequence selected from the group consisting of SEQ ID NO: 1 and SEQ ID NO: 61-67; (2) a VH CDR2 having an amino acid sequence selected from the group consisting of SEQ ID NO: 2, SEQ ID NO: 68-77, and 525-527; (3) a VH CDR3 having an amino acid sequence selected from the group consisting of SEQ ID NO: 3, SEQ ID NO: 78-90 and SEQ ID NO: 513-519; (4) a VL CDR1 having an amino acid sequence selected from the group consisting of SEQ ID NO: 4, SEQ ID NO: 91-92, and SEQ ID NO: 520-521; (5) a VL CDR2 having an amino acid sequence selected from the group consisting of SEQ ID NO: 5 and SEQ ID NO: 93-105; and (6) a VL CDR3 having an amino acid sequence selected from the group consisting of SEQ ID NO: 6, SEQ ID NO: 106-111, and SEQ ID NO: 522-524. For example, the anti-PD-L1 antibody or fragment thereof may comprise a VH CDR1 having an amino acid sequence of SEQ ID NO: 1; a VH CDR2 having an amino acid sequence of SEQ ID NO: 2; (3) a VH CDR3 having an amino acid sequence of SEQ ID NO: 3 or 515; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6.

The anti-PD-L1/anti-LAG3 bispecific antibody may comprise an anti-LAG3 antibody or an antigen-binding fragment thereof as a LAG3 targeting moiety. In an embodiment, the anti-LAG3 antibody or fragment thereof can specifically bind to LAG3 (e.g., human LAG3) protein; for example, the anti-LAG3 antibody or fragment thereof may bind to an extracellular domain of LAG-3.

For instance, the anti-LAG3 antibody or fragment thereof described herein may inhibit the binding of the LAG-3 protein to Galectin-3 (LGALS3) and C-type lectin domain family 4 member G (LSECtin) protein, in addition to inhibiting the binding to MHC class II molecules, which is a unique and considerable effect of the anti-LAG3 antibody or fragment thereof of the present disclosure, considering that existing anti-LAG-3 antibodies have only shown inhibitory effect to the binding to MHC class II molecules. In some embodiments, the antibodies and fragments thereof of the present disclosure are capable of reversing the inhibitory effect of regulatory T cells ($T_{regs}$) on effector T cells ($T_{effs}$). In some embodiments, the antibodies and fragments thereof of the present disclosure are capable of inhibiting the binding between LAG3 Fibrinogen-like Protein 1 (FGL1).

For example, the human LAG3 protein may be selected from the group consisting of proteins represented by GenBank Accession No. NP_002277.4, etc., but may not be limited thereto. These anti-LAG3 antibodies may be useful for therapeutic purposes such as treating various types of cancer, infections (inflammations), etc., and can also be used for diagnostic and prognostic purposes.

In an embodiment, the anti-LAG3 antibody or fragment thereof is capable of specificity to a human LAG3 protein. The anti-LAG3 antibody or fragment thereof may comprise (i) a VH CDR1 having an amino acid sequence selected from the group consisting of SEQ ID NOS: 116-117, 354, and 453-460; (ii) a VH CDR2 having an amino acid sequence selected from the group consisting of SEQ ID NOS: 118-119, 355, and 461-467; (iii) a VH CDR3 having an amino acid sequence selected from the group consisting of SEQ ID NOs: 120-160, 356, and 468-475; (iv) a VL CDR1 having an amino acid sequence selected from the group consisting of SEQ ID NOS: 163-195, 229, 357, and 490; (v) a VL CDR2 having an amino acid sequence selected from the group consisting of SEQ ID NOS: 196-217, 358, and 476-483; and (vi) a VL CDR3 having an amino acid sequence selected from the group consisting of SEQ ID NOS: 218-228, 230-253, 359, and 484-489. For example, the anti-LAG3 antibody or fragment thereof may comprise a VH CDR1 having an amino acid sequence of SEQ ID NO: 354; a VH CDR2 having an amino acid sequence of SEQ ID NO: 355 or 461; a VH CDR3 having an amino acid sequence of SEQ ID NO: 356 or 468; a VL CDR1 having an amino acid sequence of SEQ ID NO: 357 or 490; a VL CDR2 having an amino acid sequence of SEQ ID NO: 358; and a VL CDR3 having an amino acid sequence of SEQ ID NO: 359 or 488.

Also provided are antibodies and fragments that have specificity to the PD-L1 or LAG3 protein alone, or antibodies having additional specificity to one or more other antigens.

In one embodiment, provided is an antibody or antigen-binding fragment thereof having specificity to a human PD-L1 protein, comprising: (1) a VH CDR1 comprising an amino acid sequence selected from the group consisting of SEQ ID NO: 1 and 61-67; (2) a VH CDR2 comprising an amino acid sequence selected from the group consisting of SEQ ID NO: 2, 68-77, and 525-527; (3) a VH CDR3 comprising an amino acid sequence selected from the group consisting of SEQ ID NO: 3, 78-90, and 513-519; (4) a VL CDR1 comprising an amino acid sequence selected from the group consisting of SEQ ID NO: 4, 91-92, and 520-521; (5) a VL CDR2 comprising an amino acid sequence selected from the group consisting of SEQ ID NO: 5, and 93-105; and (6) a VL CDR3 comprising an amino acid sequence selected from the group consisting of SEQ ID NO: 6, 106-111, and 522-524.

In one embodiment, provided is an antibody or antigen-binding fragment thereof having specificity to a human LAG3 protein, comprising: (i) a VH CDR1 comprising an amino acid sequence selected from the group consisting of SEQ ID NO: 116-117, 354, and 453-460; (ii) a VH CDR2 comprising an amino acid sequence selected from the group consisting of SEQ ID NO: 118-119, 355, and 461-467; (iii) a VH CDR3 comprising an amino acid sequence selected from the group consisting of SEQ ID NO: 120-160, 356, and 468-475; (iv) a VL CDR1 comprising an amino acid sequence selected from the group consisting of SEQ ID NO: 163-195, 229, 357, and 490; (v) a VL CDR2 comprising an amino acid sequence selected from the group consisting of SEQ ID NO: 196-217, 358, and 476-483; and (vi) a VL CDR3 comprising an amino acid sequence selected from the group consisting of SEQ ID NO: 218-228, 230-253, 359, and 484-489.

Another embodiment provides a pharmaceutical composition comprising the bispecific antibody as described above. The pharmaceutical composition may further comprise a pharmaceutically acceptable carrier. The pharmaceutical composition may be used for treating and/or preventing a cancer or an infection.

Another embodiment provides a method of treating and/or preventing a cancer or an infection in a subject in need thereof, comprising administering to the subject a pharmaceutically effective amount of the bispecific antibody or the pharmaceutical composition. The method may further step of identifying the subject in need of treating and/or preventing a cancer or an infection, prior to the administering step.

Another embodiment provides a use of the bispecific antibody or the pharmaceutical composition in treating and/or preventing a cancer or an infection. Another embodiment provides a use of the bispecific antibody in preparing a pharmaceutical composition for treating and/or preventing a cancer or an infection.

In the pharmaceutical compositions, methods and/or uses provided herein, the cancer may be a solid cancer or blood cancer, preferably a solid cancer.

Another embodiment provides a composition for detection of PD-L1, LAG3, or both thereof simultaneously, in a biological sample, the composition comprising the bispecific antibody. Another embodiment provides a method of detection of PD-1, LAG3, or both thereof simultaneously, in a biological sample, the method comprising contacting the biological sample with the bispecific antibody; and detecting (measuring) an antigen-antibody reaction (binding) between the bispecific antibody and PD-L1, LAG3, or both thereof.

The method of detection may further comprise, after the detecting step, determining that PD-L1, LAG3, or both thereof are present in the biological sample when an antigen-antibody reaction is detected, and/or that PD-L1, LAG3, or both thereof are absent (not present) in the biological sample, when an antigen-antibody reaction is not detected.

Another embodiment provides a pharmaceutical composition for diagnosing a disease associated with PD-L1, LAG3, or both thereof, the composition comprising the bispecific antibody. In another embodiment, provided is a use of the bispecific antibody for diagnosing a disease associated with PD-L1, LAG3, or both thereof.

Another embodiment provides a method of diagnosing a disease associated with PD-L1, LAG3, or both thereof, the method comprising contacting a biological sample obtained from a patient with the bispecific antibody, and detecting antigen-antibody reaction or measuring a level of antigen-antibody reaction in the biological sample. In some embodiments, the method may further comprise contacting a normal sample with the bispecific antibody, and measuring a level of an antigen-antibody reaction in the normal sample. In addition, the method may further comprise comparing the level of the antigen-antibody reaction in the biological sample and in the normal sample, after the measuring step. In addition, after the detecting step or comparing step, the method may further comprise determining the patient as a patient with a disease associated with PD-L1, LAG3, or both thereof, when the antigen-antibody reaction is detected in the biological sample or the level of the antigen-antibody reaction in the biological sample is higher than that of the normal sample.

The disease associated with PD-L1, LAG3, or both thereof may be one associated with activation (e.g., abnormal activation or over-activation) and/or overproduction (overexpression) of PD-L1, LAG3, or both thereof. For example, the disease may be a cancer or an infection, as described above.

An embodiment provides a polynucleotide encoding the bispecific antibody. In particular, an embodiment provides a polynucleotide encoding a heavy chain of the bispecific antibody in an IgG-scFv form which comprises a full-length IgG and a scFv linked to a C-terminus and/or N-terminus of the full-length IgG. Other embodiment provides a polynucleotide encoding a light chain of the bispecific antibody in an IgG-scFv form. Another embodiment provides a recombinant vector comprising the polynucleotide encoding a heavy chain of the bispecific antibody, the polynucleotide encoding a light chain of the bispecific antibody, or both thereof. Another embodiment provides a recombinant cell transfected with the recombinant vector.

Another embodiment provides a method of preparing the bispecific antibody, comprising expressing the polynucleotide encoding a heavy chain of the bispecific antibody, the polynucleotide encoding a light chain of the bispecific antibody in a cell. The step of expressing the polynucleotide may be conducted by culturing the cell comprising the polynucleotide (for example, in a recombinant vector) under a condition allowing the expression of the polynucleotide. The method may further comprise isolating and/or purifying the bispecific antibody from the cell culture, after the step of expressing or culturing.

DETAILED DESCRIPTION

Definitions

Figure 1:
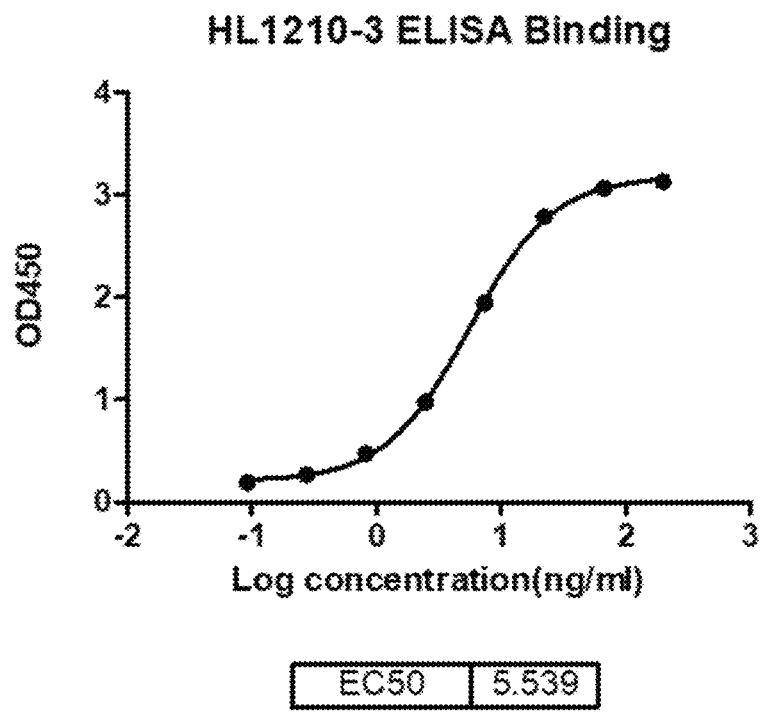
FIG. 1 shows that HL1210-3 can bind to human PD-L1 with high affinity.

It is to be noted that the term "a" or "an" entity refers to one or more of that entity for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides, "and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein, ""amino acid chain, "or any other term used to refer to a chain or chains of two or more amino acids, are included within the definition of "polypeptide, "and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least 70%, at least 75%, at least 80%, at least 85%, at least 90%, at least 95%, at least 98%, or at least 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency." In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgGI, IgG2, IgG3, IgG4, IgAI and IgA2) or subclass of immunoglobulin molecule.

Light chains are classified as either kappa or lambda (K, A). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363: 446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see bioinf.org.uk: Dr. Andrew C. R. Martin's Group; "Sequences of Proteins of Immunological Interest," Kabat, E., et al., U.S. Department of Health and Human Services, (1983); and Chothia and Lesk, J. Mol. Biol., 196: 901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196: 901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161: 4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." Preferably, the antibody binds to an antigen (or epitope) with "high affinity", namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $25\times10^{-9}$ M or less or even more preferably $1\times10^{-9}$ M or less.

As used herein, the terms "treat" or "treatment" may refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," may refer to any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

The present disclosure provides an anti-PD-L1/anti-LAG3 bispecific antibody capable to effectively block the interactions between PD-L1 and its receptor PD-1 and between LAG3 and its ligand (e.g., a MHC class II molecule). The bispecific antibody may have high binding affinity to both of a PD-L1 protein (e.g., a human PD-L1 protein) and a LAG3 protein (e.g., a human LAG3 protein).

The anti-PD-L1/anti-LAG3 bispecific antibody may comprise an anti-PD-L1 antibody or an antigen-binding fragment thereof as a PD-L1 targeting moiety, which is capable of specifically recognizing and/or binding to a PD-L1 protein, and an anti-LAG3 antibody or an antigen-binding fragment thereof as a LAG3 targeting moiety, which is capable of specifically recognizing and/or binding to a LAG3 protein.

Anti-PD-L1 Antibody

The anti-PD-L1/anti-LAG3 bispecific antibody may comprise an anti-PD-L1 antibody or an antigen-binding fragment thereof as a PD-L1 targeting moiety. The anti-PD-L1 antibody or antigen-binding fragment thereof may exhibit potent binding and inhibitory activities to PD-L1, and be useful for therapeutic and diagnostics uses.

The PD-L1 protein is a 40 kDa type 1 transmembrane protein. The PD-L1 protein may be a human PD-L1 protein, and the human PD-L1 protein may be selected from the group consisting of proteins represented by GenBank Accession No. NP_001254635.1, NP_001300958.1, NP_054862.1, etc., but may not be limited thereto. The human PD-L1 protein includes an extracellular portion including an N-terminal immunoglobulin V (IgV) domain (amino acids 19-127) and a C-terminal immunoglobulin C (IgC) domain (amino acids 133-225). Unlike pre-existing anti-PD-L1 antibodies, which bind to the IgV domain of PD-L1, thereby disrupting the binding between PD-1 and PD-L1, the anti-PD-L1 antibody or fragment thereof comprised in the bispecific antibody may not bind to an immunoglobulin V (IgV) domain of the PD-L1 protein but bind to the IgC domain of PD-L1, to effectively inhibit PD-L1, thereby improving therapeutic effects.

In particular, the anti-PD-L1 antibody or fragment thereof comprised in the bispecific antibody can specifically bind to an immunoglobulin C (IgC) domain of PD-L1 protein. In the case of human PD-L1 protein, the Ig C domain comprises or consists essentially of amino acid residues 133-225 of full-length of the human PD-L1 protein. More specifically, the anti-PD-L1 antibody or fragment thereof can bind to at least one selected from the amino acid residues Y134, K162, and N183 of human PD-L1 protein. In some embodiments, the anti-PD-L1 antibody or fragment thereof can bind to at least two selected from the amino acid residues Y134, K162, and N183 of human PD-L1 protein. In some embodiments, the anti-PD-L1 antibody or fragment thereof does not bind to an immunoglobulin V (IgV) domain of the PD-L1 protein, wherein the IgV domain consists of amino acid residues 19-127 of human PD-L1 protein.

In an embodiment, antibodies and fragments thereof are provided that are capable of specific binding to a human PD-L1 protein. These antibodies may be useful for therapeutic purposes such as treating various types of cancer, infections (inflammations), etc., and can also be used for diagnostic and prognostic purposes.

The anti-PD-L1 antibody or fragment thereof may comprise (1) a VH CDR1 having an amino acid sequence selected from the group consisting of SEQ ID NO: 1 and SEQ ID NO: 61-67; (2) a VH CDR2 having an amino acid sequence selected from the group consisting of SEQ ID NO: 2, SEQ ID NO: 68-77, and 525-527; (3) a VH CDR3 having an amino acid sequence selected from the group consisting of SEQ ID NO: 3, SEQ ID NO: 78-90 and SEQ ID NO: 513-519; (4) a VL CDR1 having an amino acid sequence selected from the group consisting of SEQ ID NO: 4, SEQ ID NO: 91-92, and SEQ ID NO: 520-521; (5) a VL CDR2 having an amino acid sequence selected from the group consisting of SEQ ID NO: 5 and SEQ ID NO: 93-105; and (6) a VL CDR3 having an amino acid sequence selected from the group consisting of SEQ ID NO: 6, SEQ ID NO: 106-111, and SEQ ID NO: 522-524.

TABLE 2

CDRs of anti-PD-L1 antibodies

| Name | Sequence | SEQ ID NO: |
|---|---|---|
| VH CDR1 | SYDMS | 1 |
| | TYDMS | 61 |
| | CYDMS | 62 |
| | SFDMS | 63 |
| | SHDMS | 64 |
| | SWDMS | 65 |
| | SYDMT | 66 |
| | SYDMC | 67 |
| VH CDR2 | TISDGGGYIYYSDSVKG | 2 |
| | TISDGGAYIYYSDSVKG | 68 |
| | TISDGGPYIYYSDSVKG | 69 |
| | TISDGGGFIYYSDSVKG | 70 |
| | TISDGGGHIYYSDSVKG | 71 |
| | TISDGGGWIYYSDSVKG | 72 |
| | TISDGGGYIYYSDTVKG | 73 |
| | TISDGGGYIYYSDCVKG | 74 |
| | TISDGGGYIYYSDSLKG | 75 |
| | TISDGGGYIYYSDSIKG | 76 |
| | TISDGGGYIYYSDSMKG | 77 |
| | TISDAGGYIYYSDSVKG | 525 |
| | TISDAGGYIYYRDSVKG | 526 |
| | TISDGGGYIYYRDSVKG | 527 |
| VH CDR3 | EFGKRYALDY | 3 |
| | QFGKRYALDY | 78 |
| | DFGKRYALDY | 79 |
| | NFGKRYALDY | 80 |
| | EYGKRYALDY | 81 |
| | EHGKRYALDY | 82 |
| | EWGKRYALDY | 83 |
| | EFAKRYALDY | 84 |
| | EFPKRYALDY | 85 |
| | EFGRRYALDY | 86 |
| | EFGKKYALDY | 87 |
| | EFGKRFALDY | 88 |
| | EFGKRHALDY | 89 |
| | EFGKRWALDY | 90 |
| | EFGKRYALDS | 513 |
| | EIFNRYALDY | 514 |
| | ELPWRYALDY | 515 |
| | ELHFRYALDY | 516 |

TABLE 2-continued

CDRs of anti-PD-L1 antibodies

| Name | Sequence | SEQ ID NO: |
|---|---|---|
| | ELYFRYALDY | 517 |
| | ELLHRYALDY | 518 |
| | ELRGRYALDY | 519 |
| VLCDR1 | KASQDVTPAVA | 4 |
| | KATQDVTPAVA | 91 |
| | KACQDVTPAVA | 92 |
| | KAKQDVTPAVA | 520 |
| | KASQDVWPAVA | 521 |
| VL CDR2 | STSSRYT | 5 |
| | TTSSRYT | 93 |
| | CTSSRYT | 94 |
| | SSSSRYT | 95 |
| | SMSSRYT | 96 |
| | SVSSRYT | 97 |
| | STTSRYT | 98 |
| | STCSRYT | 99 |
| | STSTRYT | 100 |
| | STSCRYT | 101 |
| | STSSKYT | 102 |
| | STSSRFT | 103 |
| | STSSRHT | 104 |
| | STSSRWT | 105 |
| VLCDR3 | QQHYTTPLT | 6 |
| | EQHYTTPLT | 106 |
| | DQHYTTPLT | 107 |
| | NQHYTTPLT | 108 |
| | QEHYTTPLT | 109 |
| | QDHYTTPLT | 110 |
| | QNHYTTPLT | 111 |
| | MQHYTTPLT | 522 |
| | QQHSTTPLT | 523 |
| | QQHSDAPLT | 524 |

In some embodiments, an antibody or fragment thereof includes no more than one, no more than two, or no more than three of the above substitutions. In some embodiments, the antibody or fragment thereof includes a VH CDR1 of SEQ ID NO: 1 or any one of SEQ ID NO: 61-67, a VH CDR2 of SEQ ID NO: 2, 525, 526 or 527, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2 or any one of SEQ ID NO: 68-77, 525, 526 or 527, a VH CDR3 of SEQ ID NO: 3, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, 525, 526 or 527, a VH CDR3 of SEQ ID NO: 3 or any one of SEQ ID NO: 78-90 and 513-519, a VL CDR1 of SEQ ID NO: 4, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, 525, 526 or 527, a VH CDR3 of SEQ ID NO: 3, a VL CDR1 of SEQ ID NO: 4 or any one of SEQ ID NO: 91-92 and 520-521, a VL CDR2 of SEQ ID NO: 5, and a VL CDR3 of SEQ ID NO: 6.

In some embodiments, the antibody or fragment thereof includes a VH CDR1 of SEQ ID NO: 1, a VH CDR2 of SEQ ID NO: 2, 525, 526 or 527, a VH CDR3 of SEQ ID NO: 3, a VL CDR1 of SEQ ID NO: 4, a VL CDR2 of SEQ ID NO: 5 or any one of SEQ ID NO: 93-105, and a VL CDR3 of SEQ ID NO: 6.

In some embodiments, the antibody or fragment thereof includes a VH CDR1 of SEQ ID NO: 1, a VH CDR2 of SEQ ID NO: 2, 525, 526 or 527, a VH CDR3 of SEQ ID NO: 3, a VL CDR1 of SEQ ID NO: 4, a VL CDR2 of SEQ ID NO: 5, and a VL CDR3 of SEQ ID NO: 6 or any one of SEQ ID NO: 106-111 and 522-524.

For example, the anti-PD-L1 antibody or fragment thereof may comprise a VH CDR1 having an amino acid sequence of SEQ ID NO: 1; a VH CDR2 having an amino acid sequence of SEQ ID NO: 2, 525, 526 or 527; (3) a VH CDR3 having an amino acid sequence of SEQ ID NO: 3 or 515; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6.

In some embodiments, an anti-PD-L1 antibody or fragment thereof is provided that comprises a VH CDR1 having an amino acid sequence of SEQ ID NO: 1; a VH CDR2 having an amino acid sequence of SEQ ID NO: 525; a VH CDR3 having an amino acid sequence of SEQ ID NO: 3; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6.

In some embodiments, an anti-PD-L1 antibody or fragment thereof is provided that comprises a VH CDR1 having an amino acid sequence of SEQ ID NO: 1; a VH CDR2 having an amino acid sequence of SEQ ID NO: 526; a VH CDR3 having an amino acid sequence of SEQ ID NO: 515; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6.

Non-limiting examples of VH (heavy chain variable region) are provided in SEQ ID NOS: 7-26, 113, 493, 495, 497, 499, 501, 503, 505, 507, 509, and 511, wherein SEQ ID NO: 113 is the mouse VH, SEQ ID NOs: 7-26 are humanized ones, and SEQ ID NO: 493, 495, 497, 499, 501, 503, 505, 507, 509, and 511 is an affinity-matured one of the humanized antibodies. Further, among the humanized VHs, SEQ ID NO: 9-15, 17-21 and 23-26 include one or more back-mutations to the mouse version. Likewise, non-limiting examples of VL (VK; light chain (kappa type) variable region) are provided in SEQ ID NOS: 27-33, 494, 496, 498, 500, 502, 504, 506, 508, 510, and 512. SEQ ID NO: 28 and 30 are the originally derived, CDR-grafted, and humanized sequences as shown in the examples, and SEQ ID NO: 29 and 31-33 are humanized VL with back-mutations.

The back-mutations may be useful for retaining certain characteristics of the anti-PD-L1 antibodies. In some embodiments, the anti-PD-L1 antibodies of the present disclosure, in particular the human or humanized ones, may include one or more of the back-mutations. In some embodiments, the back-mutation (i.e., included amino acid at the specified position) in a heavy chain variable region (VH) is one or more selected from (a) Ser at position 44, (b) Ala at position 49, (c) Ala at position 53, (d) Ile at position 91, (e) Glu at position 1, (f) Val at position 37, (g) Thr at position 40 (h) Val at position 53, (i) Glu at position 54, (j) Asn at position 77, (k) Arg at position 94, and (l) Thr at position 108, of the heavy chain variable region, according to Kabat numbering, and combinations thereof. In some embodiments, the VH back-mutations are selected from (a) Ser at position 44, (b) Ala at position 49, (c) Ala at position 53, and/or (d) Ile at position 91, of the heavy chain variable region, according to Kabat numbering, and combinations thereof.

In some embodiments, the back-mutation in a light chain variable region (VL) is one or more selected from (a) Ser at position 22, (b) Gin at position 42, (c) Ser at position 43, (d) Asp at position 60, and (e) Thr at position 63, of the light chain variable region, according to Kabat numbering, and combinations thereof.

In some embodiments, the anti-PD-L1 antibody of the present disclosure or fragment thereof may comprise a VH selected from SEQ ID NO: 7-26, 113, 493, 495, 497, 499, 501, 503, 505, 507, 509, and 511, a VL selected from SEQ ID NO: 27-33, 494, 496, 498, 500, 502, 504, 506, 508, 510, and 512, or their respective biological equivalents as described above. A biological equivalent of the VH and/or VL may have an amino acid sequence that includes the designated amino acids (e.g., CDRs) while having sequence identity of at least 80%, at least 85%, at least 90%, at least 95%, at least 96%, at least 97%, at least 98%, or at least 99%. A biological equivalent of SEQ ID NO: 20, for instance, can be a VH that has an overall 80%, 85%, 90%, 95%, 96%, 97%, 98% or 99% sequence identity to SEQ ID NO: 20 but retains the CDRs (SEQ ID NO: 1-6 or their variants), and optionally retains one or more, or all of the back-mutations.

Non-limiting examples of the antibody or fragment thereof may comprise a heavy chain variable region comprising or consisting essentially of the amino acid sequence of SEQ ID NO: 20 or 501, or a biological equivalent thereof, and a light chain variable region comprising or consisting essentially of the amino acid sequence of SEQ ID NO: 28 or 502, or a biological equivalent thereof.

In some embodiments, the anti-PD-L1 antibody or fragment thereof further comprises a heavy chain constant region, a light chain constant region, an Fc region, or the combination thereof. In some embodiments, the light chain constant region may be a kappa or lambda chain constant region. In some embodiments, the antibody is of an isotype of IgG, IgM, IgA, IgE or IgD, for example, human IgG, human IgM, human IgA, human IgE, or human IgD. In some embodiments, the isotype may be IgG, for example human IgG, such as, IgG1, IgG2, IgG3, or IgG4. In some embodiments, the fragment (antigen-binding fragment of the anti-PD-L1 antibody) may be any fragment comprising heavy chain CDRs and/or light chain CDRs of the antibody, and for example, it may be selected from the group consisting of Fab, Fab', F(ab')2, Fd (comprising a heavy chain variable region and a CH1 domain), Fv (a heavy chain variable region and/or a light chain variable region), single-chain Fv (scFv; comprising or consisting essentially of a heavy chain variable region and a light chain variable region, in any order, and a peptide linker between the heavy chain variable region and the light chain variable region), single-chain antibodies, disulfide-linked Fvs (sdFv), and the like.

Without limitation, the anti-PD-L1 antibody or fragment thereof is a chimeric antibody, a humanized antibody, or a fully human antibody. In one aspect, antibody or fragment thereof is not naturally occurring, or chemically or recombinantly synthesized.

Given that each of these antibodies can bind to PD-L1 such as human PD-L1, the CDR sequences or VH and VL sequences can be "mixed and matched" to create other anti-LAG-3 binding molecules of the disclosure. Preferably, when the CDR sequences or VH and VL chains are mixed and matched, for example, a VH sequence from a particular VH/VL pairing is replaced with a structurally similar VH sequence. Likewise, preferably a VL sequence from a particular VH/VL pairing is replaced with a structurally similar VL sequence.

Anti-LAG3 Antibody

The anti-PD-L1/anti-LAG3 bispecific antibody may comprise an anti-LAG3 antibody or an antigen-binding fragment thereof as a LAG3 targeting moiety.

In an embodiment, antibodies and fragments thereof are provided that can specifically bind to LAG3 (e.g., human LAG3) protein; for example, the anti-LAG3 antibody or fragment thereof may bind to an extracellular domain of LAG-3.

For example, the human LAG3 protein may be selected from the group consisting of proteins represented by GenBank Accession No. NP_002277.4, etc., but may not be limited thereto. These anti-LAG3 antibodies may be useful for therapeutic purposes such as treating various types of cancer, infections (inflammations), etc., and can also be used for diagnostic and prognostic purposes.

The term "LAG-3" or "LAG3" refers to Lymphocyte Activation Gene-3. The LAG3 protein, which belongs to immunoglobulin (Ig) superfamily, comprises a 503-amino acid type I transmembrane protein with four extracellular Ig-like domains, designated D1 to D4. As described herein, the term "LAG-3" includes variants, isoforms, homologs, orthologs, and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species but not all other species (e.g., cross-react with monkey LAG-3, but not mouse LAG-3). The term "human LAG-3" refers to human sequence LAG-3, such as the complete amino acid sequence of human LAG-3 having GenBank Accession No. NP 002277.4. The term "mouse LAG-3" refers to mouse sequence LAG-3, such as the complete amino acid sequence of mouse LAG-3 having GenBank Accession No. NP 032505. LAG-3 is also known in the art as, for example, CD223. The human LAG-3 sequence may differ from human LAG-3 of GenBank Accession No. NP 002277.4 by having, e.g., conserved mutations or mutations in non-conserved regions and the LAG-3 has substantially the same biological function as the human LAG-3 of GenBank Accession No. NP 002277.4. For example, a biological function of human LAG-3 is having an epitope in the extracellular domain of LAG-3 that is specifically bound by an antibody of the instant disclosure or a biological function of human LAG-3 is binding to MHC Class II molecules.

As demonstrated in the experimental examples, some of the anti-LAG-3 antibodies disclosed herein exhibited activities not shown with known anti-LAG-3 antibodies. For instance, the presently disclosed antibodies may inhibit the binding of the LAG-3 protein to Galectin-3 (LGALS3) and C-type lectin domain family 4 member G (LSECtin) protein, in addition to the binding to MHC class II molecules. Known anti-LAG-3 antibodies, by contrast, have only shown inhibitory effect to the binding to MHC class II molecules. In some embodiments, the antibodies and fragments thereof of the present disclosure are capable of reversing the inhibitory effect of regulatory T cells ($T_{regs}$) on effector T cells ($T_{effs}$). In some embodiments, the antibodies and fragments thereof of the present disclosure are capable of inhibiting the binding between LAG3 and Fibrinogen-like Protein 1 (FGL1).

These anti-LAG3 antibodies may be useful for therapeutic purposes such as treating various types of cancer, infections (inflammations), etc., and can also be used for diagnostic and prognostic purposes.

In an embodiment, an antibody or fragment thereof is provided that is capable of specificity to a human LAG3 protein. The anti-LAG3 antibody or fragment thereof may comprise (i) a VH CDR1 having an amino acid sequence selected from the group consisting of SEQ ID NOS: 116-117, 354, and 453-460; (ii) a VH CDR2 having an amino acid sequence selected from the group consisting of SEQ ID NOS: 118-119, 355, and 461-467; (iii) a VH CDR3 having an amino acid sequence selected from the group consisting of SEQ ID NOs: 120-160, 356, and 468-475; (iv) a VL CDR1 having an amino acid sequence selected from the group consisting of SEQ ID NOS: 163-195, 229, 357, and 490; (v) a VL CDR2 having an amino acid sequence selected from the group consisting of SEQ ID NOS: 196-217, 358, and 476-483; and (vi) a VL CDR3 having an amino acid sequence selected from the group consisting of SEQ ID NOS: 218-228, 230-253, 359, and 484-489. For example, the anti-LAG3 antibody or fragment thereof may comprise a VH CDR1 having an amino acid sequence of SEQ ID NO: 354; a VH CDR2 having an amino acid sequence of SEQ ID NO: 355 or 461; a VH CDR3 having an amino acid sequence of SEQ ID NO: 356 or 468; a VL CDR1 having an amino acid sequence of SEQ ID NO: 357 or 490; a VL CDR2 having an amino acid sequence of SEQ ID NO: 358; and a VL CDR3 having an amino acid sequence of SEQ ID NO: 359 or 488.

TABLE 3

CDRs of anti-LAG3 antibodies

| Name | Sequence | SEQ ID NO: |
| --- | --- | --- |
| VH CDR1 | SYAIS | 116 |
|  | SYAMS | 117 |
|  | GYTFTNYWLG | 354 |
|  | GYTFENYWLG | 453 |
|  | GYMFTNYWLG | 454 |
|  | GYTFDNYWLG | 455 |
|  | GYTFGNYWLG | 456 |
|  | GYTFTNYWLW | 457 |
|  | GYLFTNYWLG | 458 |
|  | GYTFTNYWLS | 459 |
|  | GFTFTNYWLG | 460 |
| VH CDR2 | GIIPIFGTANYAQKFQG | 118 |
|  | AISGSGGSTYYADSVKG | 119 |
|  | DIYPGGDYINYNEKFKG | 355 |
|  | DIYPGGDYIVYNEKFKG | 461 |
|  | DIYPGGDIINYNEKFKG | 462 |
|  | DIYPGGDVINYNEKFKG | 463 |
|  | DIFPGGDYINYNEKFKG | 464 |
|  | DIYPGGDLINYNEKFKG | 465 |
|  | DIYPGGDHINYNEKFKG | 466 |
|  | EIYPGGDYITYNEKFKG | 467 |
| VH CDR3 | ARGSSWFDY | 120 |
|  | ASSYHGGGYHRY | 121 |
|  | TTSKYSGSALRY | 122 |
|  | ARDRTGAFDY | 123 |
|  | ARHETVAGSFDY | 124 |
|  | ARTGYYGGNSGAFDI | 125 |
|  | ARAGTGMDLVFNS | 126 |
|  | ARGLARGDLNFGY | 127 |
|  | TREPHFDY | 128 |
|  | TTAAPGSYYLVFHY | 129 |
|  | ARDAGPVGYYGMDV | 130 |
|  | AGDGLYGSGSFGY | 131 |
|  | AKDIRWFYGMDV | 132 |
|  | ARHESGIAGGHFDY | 133 |

TABLE 3-continued

CDRs of anti-LAG3 antibodies

| Name | Sequence | SEQ ID NO: |
|---|---|---|
| | AKDIRWYYGMDV | 134 |
| | AKGVRGTYQIGYYGMDV | 135 |
| | ARQGTAMALDY | 136 |
| | VRDLQDWNYGGAAY | 137 |
| | ARDDYYYGQFDS | 138 |
| | AREITGTSYTALDS | 139 |
| | ARGHIDGQAAGDY | 140 |
| | AASTLRVPNPPY | 141 |
| | ARSGDRYDIAVSGY | 142 |
| | TRGQDSTWYSSFDY | 143 |
| | AASTLRLPNPPY | 144 |
| | ATTQTSFTSHGMDV | 145 |
| | ARVRKTPFWGALDS | 146 |
| | ARGFTYGDFIFDY | 147 |
| | ARDVRGVTYLGMDV | 148 |
| | ARVRKTPFWGTLDS | 149 |
| | ARVRRTPFWGALDS | 150 |
| | AKRKGLGSPTDYYYGMDV | 151 |
| | VRPEYDTYYYGMDV | 152 |
| | AKGGGSYDY | 153 |
| | ARALNGMDV | 154 |
| | TRPLQGIAAADSYYYYAMDV | 155 |
| | ARLHSYLSEEFDP | 156 |
| | AKLSAVNTYIDD | 157 |
| | ARVTKTPFWGTLDY | 158 |
| | ARVSQSPVWGYIDY | 159 |
| | AKDGYYDFWSGYSDY | 160 |
| | PNLPGDY | 356 |
| | PNLPKDH | 468 |
| | PDLPGDY | 469 |
| | PGLPKDY | 470 |
| | PNLPKDY | 471 |
| | PNLPRDY | 472 |
| | PGLPRDY | 473 |
| | PGLPQDY | 474 |
| | PDLPKDY | 475 |
| VL CDR1 | QANQDIHHYLN | 161 |
| | KSSQSVLYSSSNKNYLA | 162 |
| | KSSQSVLYSSNNKNYLA | 163 |
| | RSSQNLLHSDGYNYLN | 164 |
| | KSSQSVLYTSNNKNYLA | 165 |
| | QASQDINRYLS | 166 |
| | QASQDISNYLN | 167 |
| | QASQDISNYLN | 167 |
| | RASQTISSHLN | 168 |
| | RASQGIAGWLA | 169 |
| | RASQGVSSWLA | 170 |
| | KSSQSLFYHSNNHNYLA | 171 |
| | RASQGISSSLA | 172 |
| | QASRDISNSLS | 173 |
| | RASQSISRYLN | 174 |
| | RASRSISNWLA | 175 |
| | KSSQSVFYRSNQKNYLA | 176 |
| | RASQSVSSYLA | 177 |
| | RASRGISSWLA | 178 |
| | RASQGISSWLA | 179 |
| | RASQSISSYLN | 180 |
| | RASQAISNLLA | 181 |
| | RASQGISTWLA | 182 |
| | RASQGIASNLA | 183 |
| | RASQGVSSYLA | 184 |
| | RASQSIYTYLN | 185 |
| | RASQFVSDWLA | 186 |
| | RASQTISTWLA | 187 |
| | RASQGISSYLA | 188 |
| | RASQSIGYWLA | 189 |
| | RATQSISSWLA | 190 |
| | RASQGVRNWLA | 191 |
| | RASQSINNYLA | 192 |
| | RASQDITSWLA | 193 |
| | RASQGIYDYLA | 194 |
| | RASEGISGWLA | 195 |
| | RASQDIVNWLA | 229 |
| | RSSKSLLHSNGITYLY | 357 |
| | RSSKSLLHSQGITYLY | 490 |

TABLE 3-continued

CDRs of anti-LAG3 antibodies

| Name | Sequence | SEQ ID NO: |
|---|---|---|
| VL CDR2 | DASILQS | 196 |
| | WASTRES | 197 |
| | LGSNRAT | 198 |
| | DASNLET | 199 |
| | AASSLQS | 200 |
| | AASTLQS | 201 |
| | AAFSLQS | 202 |
| | GASSRAT | 203 |
| | GISSRAT | 204 |
| | AVSTLQS | 205 |
| | DISTLQN | 206 |
| | GASTLQS | 207 |
| | GASSLQS | 208 |
| | AASTLES | 209 |
| | DASSLQS | 210 |
| | KASNLQS | 211 |
| | TASTLQN | 212 |
| | RASSLQS | 213 |
| | AASHLQS | 214 |
| | DASTLQS | 215 |
| | AASNLER | 216 |
| | AASSLET | 217 |
| | QVSNLAS | 358 |
| | QVSNLAR | 476 |
| | QKSNLAS | 477 |
| | QVSNLAV | 478 |
| | QVSNLAL | 479 |
| | QVDNLAS | 480 |
| | QVSNLAT | 481 |
| | HVSNLAS | 482 |
| | QVSNRAS | 483 |
| VL CDR3 | QQADSFPIT | 218 |
| | QQSYSTPWT | 219 |
| | QQYYSTPWT | 220 |
| | QQSFTTPWT | 221 |
| | QQYDNLPPT | 222 |
| | QQSYGSPVT | 223 |
| | QQGNSFPFT | 224 |
| | QQAKSFPLT | 225 |
| | QQVKSFPLT | 226 |
| | QQYYNTPWT | 227 |
| | QQTKNFPLT | 228 |
| | QQTKSFPLT | 230 |
| | QQSYNTPRT | 231 |
| | QQSYRAPWT | 232 |
| | QQANNFPLT | 233 |
| | QQGNSFPLT | 234 |
| | QQSKNFPVT | 235 |
| | QQANSFPLT | 236 |
| | QQLESYPLT | 237 |
| | QQYYSSPT | 238 |
| | QQLKTFPLT | 239 |
| | QQTNWFPLT | 240 |
| | QQAQSFPIT | 241 |
| | QQAHSFPLT | 242 |
| | LQDYHFPLT | 243 |
| | QQGHSFPLT | 244 |
| | QQSYIFPLT | 245 |
| | QQYDTYWT | 246 |
| | QQLNSYPLFT | 247 |
| | QQYSSYWT | 248 |
| | LQHNTYPFT | 249 |
| | QQGHSFPLT | 250 |
| | QQAHSFPFT | 251 |
| | QQANMFPLT | 252 |
| | QQADSFPFT | 253 |
| | AQNLELPWT | 359 |
| | GQNLELPWT | 484 |
| | AQNLEMPWT | 485 |
| | GQNLEMPWT | 486 |
| | AQYLEEPWT | 487 |
| | AQYLELPWT | 488 |
| | GQYLELPWT | 489 |

In non-limiting examples, the antibody or fragment having specificity to LAG3 has a combination of VH CDR1, VH CDR2, VH CDR3, VL CDR1, VL CDR2, and VL CDR3 as shown in any of the antibodies listed in Table 27. For instance, the CDRs can be those from 147H 3807, which include a VH CDR1 of SEQ ID NO:354, a VH CDR2 of SEQ ID NO:461, a VH CDR3 of SEQ ID NO:468, a VL CDR1 of SEQ ID NO:490, a VL CDR2 of SEQ ID NO:358, and a VL CDR3 of SEQ ID NO:488. Variants of these antibodies are also provided, such as those having at least 75%, 80%, 85%, 90%, 95%, 98%, 99% or 99.5% sequence identity to the heavy chain/light chain variable regions and retaining the respective CDR sequences.

In one embodiment, for instance, provided is an antibody or antigen-binding fragment thereof, having specificity to a human LAG3 protein and comprising: a heavy chain variable region comprising the amino acid sequence of SEQ ID NO:443, or a polypeptide having at least 90% sequence identity to the amino acid sequence of SEQ ID NO:443 and having a VH CDR1 comprising the amino acid sequence of SEQ ID NO:354, a VH CDR2 comprising the amino acid sequence of SEQ ID NO:461, and a VH CDR3 comprising the amino acid sequence of SEQ ID NO:468, and a light chain variable region comprising the amino acid sequence of SEQ ID NO:444, or a polypeptide having at least 90% sequence identity to the amino acid sequence of SEQ ID NO:444 and having a VL CDR1 comprising the amino acid sequence of SEQ ID NO:490, a VL CDR2 comprising the amino acid sequence of SEQ ID NO:358, and a VL CDR3 comprising the amino acid sequence of SEQ ID NO:488.

In non-limiting examples of the anti-LAG3 antibody or fragment thereof,
(1) the heavy chain variable region may comprise or consist essentially of a polypeptide having an amino acid sequence selected from the group consisting of SEQ ID NOS: 254-302, 352, 360-373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451 and 491, or a polypeptide having a sequence identity of at least 80%, at least 85%, at least 90%, at least 95%, at least 96%, at least 97%, at least 98%, or at least 99% to the above described amino acid sequences; and/or
(2) the light chain variable region may comprise or consist essentially of a polypeptide having an amino acid sequence selected from the group consisting of SEQ ID NOS: 303-351, 353, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452 and 492, or a polypeptide having a sequence identity of at least 80%, at least 85%, at least 90%, at least 95%, at least 96%, at least 97%, at least 98%, or at least 99% to the above described amino acid sequences.

Non-limiting examples of the anti-LAG3 antibody or fragment thereof may comprise a heavy chain variable region comprising or consisting essentially of the amino acid sequence of SEQ ID NO: 352 or 443 and a light chain variable region comprising or consisting essentially of the amino acid sequence of SEQ ID NO: 353 or 444.

For a humanized antibody or fragment, certain back mutations can be incorporated. In some embodiments, the heavy chain variable region comprises one or more amino acid residues selected from the group consisting of:
(a) Ala (A) at position 71,
(b) Leu (L) at position 69,
(c) Lys (K) at position 66,
(d) Ala (A) at position 67,
(e) Ile (I) at position 48,
(f) Ile (I) at position 37,
(g) Lys (K) at position 38,
(h) Phe (F) at position 91, and
(i) Glu (E) at position 1, according to Kabat numbering, and combinations thereof.

In some embodiments, the heavy chain variable region comprises Ala (A) at position 71. In some embodiments, the heavy chain variable region comprises Leu (L) at position 69. In some embodiments, the heavy chain variable region comprises Lys (K) at position 66. In some embodiments, the heavy chain variable region comprises Ala (A) at position 67. In some embodiments, the heavy chain variable region comprises Ile (I) at position 48. In some embodiments, the heavy chain variable region comprises Ile (I) at position 37. In some embodiments, the heavy chain variable region comprises Lys (K) at position 38. In some embodiments, the heavy chain variable region comprises Phe (F) at position 91. In some embodiments, the heavy chain variable region comprises Glu (E) at position 1.

In some embodiments, the heavy chain variable region comprises one or more amino acid residues selected from the group consisting of
(a) Ala (A) at position 71,
(b) Leu (L) at position 69,
(c) Lys (K) at position 66,
(d) Ala (A) at position 67,
(e) Ile (I) at position 48,
(f) Ile (I) at position 37, and
(g) Lys (K) at position 38, according to Kabat numbering, and combinations thereof. In some embodiments, the heavy chain variable region comprises all of the above recited residues.

The antibodies of the disclosure are characterized by particular functional features or properties of the antibodies. For example, the antibodies specifically bind to human LAG-3 and may bind to LAG-3 from certain other species, e.g., monkey LAG-3, e.g., cynomolgus monkey, rhesus monkey, but may not substantially bind to LAG-3 from certain other species, e.g., mouse LAG-3. Preferably, an antibody of the disclosure binds to human LAG-3 with high affinity.

The ability of the antibody to stimulate an immune response, such as an antigen-specific T cell response, can be indicated by, for example, the ability of the antibody to stimulate interleukin-2 (IL-2) or interferon gamma (IFN-gamma) production in an antigen-specific T cell response. In certain embodiments, an antibody of the disclosure binds to human LAG-3 and exhibits an ability to stimulate an antigen-specific T cell response. In other embodiments, an antibody of the disclosure binds to human LAG-3 but does not exhibit an ability to stimulate an antigen-specific T cell response. Other means by which to evaluate the ability of the antibody to stimulate an immune response include the ability of the antibody to inhibit tumor growth, such as in an in vivo tumor graft model or the ability of the antibody to stimulate an autoimmune response, such as the ability to promote the development of an autoimmune disease in an autoimmune model, such as the ability to promote the development of diabetes in the NOD mouse model.

The binding of an antibody of the disclosure to LAG-3 can be assessed using one or more techniques well established in the art. For example, in a preferred embodiment, an antibody can be tested by a flow cytometry assay in which the antibody is reacted with a cell line that expresses human LAG-3, such as CHO cells that have been transfected to express LAG-3, e.g., human LAG-3, or monkey LAG-3, e.g., rhesus or cynomolgus monkey or mouse LAG-3 on their cell surface. Other suitable cells for use in flow cytometry assays include anti-CD3-stimulated CD4$^+$ activated T cells, which express native LAG-3. Additionally, or alternatively, the binding of the antibody, including the binding kinetics (e.g., $K_D$ value) can be tested in Biacore™ binding assays. Still other suitable binding assays include ELISA assays, for example using a recombinant LAG-3 protein. Preferably, an antibody of the disclosure binds to a LAG-3 protein with a $K_D$ of $5\times10^{-8}$ M or less, binds to a LAG-3 protein with a $K_D$ of $2\times10^{-8}$ M or less, binds to a LAG-3 protein with a $K_D$ of $5\times10^{-9}$ M or less, binds to a LAG-3 protein with a $K_D$ of $4\times10^{-9}$ M or less, binds to a LAG-3 protein with a $K_D$ of $3\times10^{-9}$ M or less, binds to a LAG-3 protein with a $K_D$ of $2\times10^{-9}$ M or less, binds to a LAG-3 protein with a $K_D$ of $125\times10^{-9}$ M or less, binds to a LAG-3 protein with a $K_D$ of $5\times10^{-10}$ M or less, or binds to a LAG-3 protein with a $K_D$ of $1\times10^{-10}$ M or less.

In some embodiments, the anti-LAG3 antibody or fragment thereof further comprises a heavy chain constant region, a light chain constant region, an Fc region, or the combination thereof. In some embodiments, the light chain constant region may be a kappa or lambda chain constant region. In some embodiments, the antibody is of an isotype of IgG, IgM, IgA, IgE or IgD, for example, human IgG, human IgM, human IgA, human IgE, or human IgD. In some embodiments, the isotype may be IgG, for example human IgG, such as, IgG1, IgG2, IgG3, or IgG4. In some embodiments, the fragment (antigen-binding fragment of the anti-PD-L1 antibody) may be any fragment comprising heavy chain CDRs and/or light chain CDRs of the antibody, and for example, it may be selected from the group consisting of Fab, Fab', F(ab')2, Fd (comprising a heavy chain variable region and a CH1 domain), Fv (a heavy chain variable region and/or a light chain variable region), single-chain Fv (scFv; comprising or consisting essentially of a heavy chain variable region and a light chain variable region, in any order, and a peptide linker between the heavy chain variable region and the light chain variable region), single-chain antibodies, disulfide-linked Fvs (sdFv), and the like.

Without limitation, the anti-LAG3 antibody or fragment thereof is a chimeric antibody, a humanized antibody, or a fully human antibody. In one aspect, antibody or fragment thereof is not naturally occurring, or chemically or recombinantly synthesized.

Given that each of these antibodies can bind to LAG-3 such as human LAG-3, the CDR sequences or the VH and VL sequences can be "mixed and matched" to create other anti-LAG-3 binding molecules of the disclosure. Preferably, when the CDRs sequences or VH and VL chains are mixed and matched, for example, a VH sequence from a particular VH/VL pairing is replaced with a structurally similar VH sequence. Likewise, preferably a VL sequence from a particular VH/VL pairing is replaced with a structurally similar VL sequence.

Anti-PD-L1/Anti-LAG3 Bispecific Antibody

Figure 32:
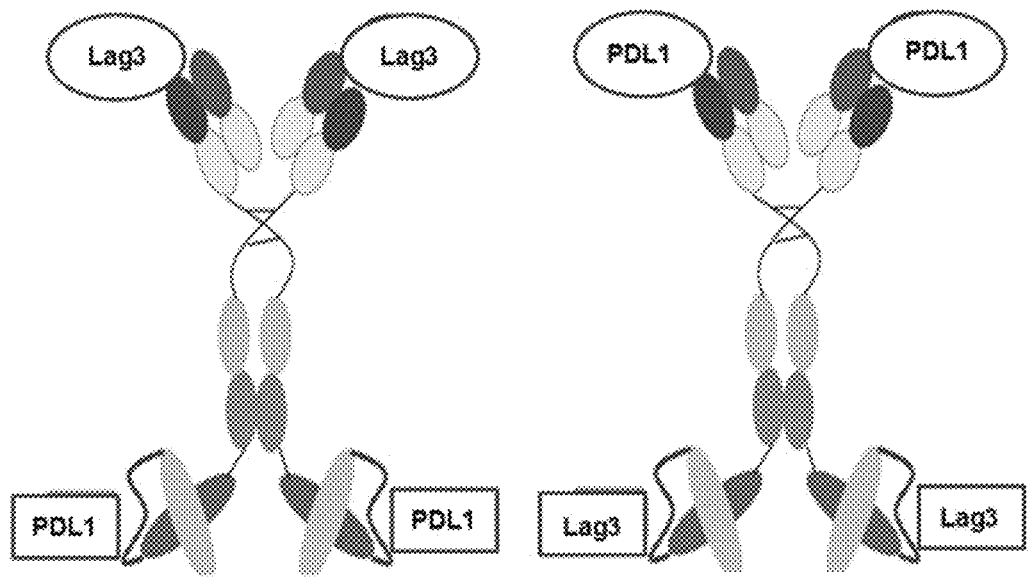
FIG. 32 schematically illustrates an anti-PD-L1/anti-LAG3 bispecific antibody according to an embodiment.

In the bispecific antibody comprising the PD-L1 targeting moiety and the LAG3 targeting moiety, one of the PD-L1 targeting moiety and the LAG3 targeting moiety can be a full-length antibody, and the other can be an antigen-binding fragment (e.g., scFv) comprising heavy chain CDRs, light chain CDRs, or a combination thereof. The full-length antibody targeting one of PD-L1 and LAG3 proteins, and the antigen-binding fragment targeting the other protein may be chemically linked (e.g., covalently linked) directly or via a peptide linker. The antigen-binding fragment (e.g., scFv) may be linked directly or via a peptide linker to N-terminus of the full-length antibody (e.g., N-terminus of a light chain or a heavy chain of the full-length antibody), C-terminus of the full-length antibody (e.g., C-terminus of a heavy chain (or Fc or CH3 domain) of the full-length antibody), or both thereof (see FIG. 32).

In an embodiment, the bispecific antibody may comprise a full-length anti-PD-L1 antibody, an antigen-binding fragment (e.g., scFv) of an anti-LAG3 antibody, and a peptide linker therebetween. In other embodiment, the bispecific antibody may comprise a full-length anti-LAG3 antibody, an antigen-binding fragment (e.g., scFv) of an anti-PD-L1 antibody, and a peptide linker therebetween.

In an embodiment, the scFv contained in the bispecific antibody may comprise a heavy chain variable region and a light chain variable region in any order. For example, the scFv contained in the bispecific antibody may comprise a heavy chain variable region and a light chain variable, in a direction from N-terminus to C-terminus, and optionally a peptide linker therebetween, or alternatively, the scFv contained in the bispecific antibody may comprise a light chain variable region and a heavy chain variable, in a direction from N-terminus to C-terminus, and optionally a peptide linker therebetween.

The use of a peptide linker for the bispecific antibody may lead to a high purity of the antibody.

As used herein, the term "peptide linker" may be those including any amino acids of 1 to 100, particularly 2 to 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the relevant art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as $(G_mS_l)n$ (m, l, and n, are independently an integer of about 1 to about 10, particularly an integer of about 2 to about 5). For example, the examples of the peptide liners are summarized as follows:

| | Examples | | | |
|---|---|---|---|---|
| Linker Function | Fusion Protein | Linker Type | Sequence$^a$ | Ref. |
| Increase Stabilitiy/Folding | scFv | flexible | (GGGGS)$_3$ | [46] |
| | G-CSF-Tf | flexible | (GGGGS)$_3$ | [20] |
| | HBsAg preS1 | flexible | (GGGGS)$_3$ | [85] |
| | Myc- Est2p | flexible | (Gly)$_8$ | [30] |

| Linker Function | Fusion Protein | Linker Type | Examples Sequence[a] | Ref. |
|---|---|---|---|---|
| | albumin-ANF | flexible | (Gly)$_6$ | [31] |
| | virus coat protein | rigid | (EAAAK)$_3$ | [50] |
| | beta-glucanase-xylanase | rigid | (EAAAK)$_a$ (n = 1-3) | [52] |
| Increase expression | hGH-Tf and Tf-hGH | rigid | A(EAAAK)$_a$ALEA(EAAAK)$_a$A | [18] |
| | G-CSF-Tf and Tf-G-CSF | rigid | A(EAAAK)$_a$ALEA(EAAAK)$_a$A | [18] |
| Improve biological activity | G-CSF-Tf | flexible | (GGGGS)$_3$ | [20] |
| | G-CSF-Tf | rigid | A(EAAAK)$_a$ALEA(EAAAK)$_a$A | [20] |
| | hGH-Tf | rigid | A(EAAAK)$_a$ALEA(EAAAK)$_a$A | [40] |
| | HSA-IFN-α2b | flexible | GGGGS | [17] |
| | HSA-IFN-α2b | rigid | PAPAP | [17] |
| | HSA-IFN-α2b | rigid | AEAAAKEAAAKA | [17] |
| | PGA-rTHS | flexible | (GGGGS)$_a$ (n = 1, 2, 4) | [55] |
| | interferon- -gp120 | rigid | (Ala-Pro)$_a$ (10-34 aa) | [54] |
| | GSF-S-S-TY | cleavable | disulfide | [39] |
| | IFN-α2b-HSA | cleavable | disulfide | [42] |
| Enable targeting | FIX-albumin | cleavable | VSQTSKLTR AETVFPDV[b] | [59] |
| | LAP-IFN- | cleavable | PLG LWA[c] | [64] |
| | MazE-MazF | cleavable | RVL AEA; EDVVCC SMSY; GGIEGR GS[c] | [68] |
| | Immunotoxins | cleavable | TRHQPR GWE; AGNRVRR SVG; RRRRRRR R R[d] | [72] |
| | Immunotoxin | cleavable | GFLG[c] | [77] |
| Alter PK | G-CSF-Tf and hGH-Tf | dipeptide | LE | [79] |
| | | rigid | A(EAAAK)$_a$ALEA(EAAAK)$_a$A | |
| | | cleavable | Disulfide | |

In another embodiment, both of the PD-L1 targeting moiety and the LAG3 targeting moiety may be a full-length antibody or an antigen-binding fragment comprising heavy chain CDRs, light chain CDRs, or a combination thereof.

In another embodiment, the bispecific antibody may be in a heterodimeric form, which comprises a first arm including a pair of a first heavy chain and a first light chain targeting one of PD-L1 and LAG3, and a second arm including a pair of a second heavy chain and a second light chain targeting the other one.

In an embodiment, the full-length antibody may be in a full-length immunoglobulin form (e.g., IgG, IgM, IgA, IgE or IgD, such as, human IgG, human IgM, human IgA, human IgE, or human IgD), and the antigen-binding fragment may be selected from the group consisting of Fab, Fab', F(ab')$_2$, Fd, Fv, scFv, single-chain antibodies, sdFv, and the like, as described above. For example, the full-length antibody may be in a full-length human IgG (human IgG1, human IgG2, human IgG3, or human IgG4) form, and the antigen-binding fragment may be scFv.

For example, an antibody described herein may comprise a flexible linker sequence, or may be modified to add a functional moiety (e.g., PEG, a drug, a toxin, or a label).

In some embodiments, a bi- or multi-specific antibody is provided, which includes anti-PD-L1 antibody or an antigen-binding fragment thereof and an anti-LAG3 antibody or an antigen-binding fragment thereof, wherein the anti-PD-L1 antibody or antigen-binding fragment thereof is capable of specifically binding to an immunoglobulin C (Ig C) domain of a human Programmed death-ligand 1 (PD-1) protein, wherein the Ig C domain consists of amino acid residues 133-225; and the anti-LAG3 antibody or antigen-binding fragment thereof is capable of binding to a MHC class II molecule and/or FGL1.

In some embodiments, the anti-PD-L1 antibody or antigen-binding fragment thereof includes a VH CDR1 comprising an amino acid sequence selected from the group consisting of SEQ ID NO: 1 and 61-67; a VH CDR2 comprising an amino acid sequence selected from the group consisting of SEQ ID NO: 2, 68-77, and 525-527; a VH CDR3 comprising an amino acid sequence selected from the group consisting of SEQ ID NO: 3, 78-90, and 513-519; a VL CDR1 comprising an amino acid sequence selected from the group consisting of SEQ ID NO: 4, 91-92, and 520-521; a VL CDR2 comprising an amino acid sequence selected from the group consisting of SEQ ID NO: 5, and 93-105; and a VL CDR3 comprising an amino acid sequence selected from the group consisting of SEQ ID NO: 6, 106-111, and 522-524, and the anti-LAG3 antibody or antigen-binding fragment thereof includes a VH CDR1 comprising an amino acid sequence selected from the group consisting of SEQ ID NO: 116-117, 354, and 453-460; a VH CDR2 comprising an amino acid sequence selected from the group consisting of SEQ ID NO: 118-119, 355, and 461-467; a VH CDR3 comprising an amino acid sequence selected from the group consisting of SEQ ID NO: 120-160, 356, and 468-475; a VL CDR1 comprising an amino acid sequence selected from the group consisting of SEQ ID NO: 163-195, 229, 357, and 490; a VL CDR2 comprising an amino acid sequence selected from the group consisting of SEQ ID NO: 196-217, 358, and 476-483; and a VL CDR3 comprising an amino acid sequence selected from the group consisting of SEQ ID NO: 218-228, 230-253, 359, and 484-489.

In some embodiments, the anti-PD-L1 antibody or antigen-binding fragment thereof includes a VH CDR1 having an amino acid sequence of SEQ ID NO: 1; a VH CDR2 having an amino acid sequence of SEQ ID NO: 525; a VH CDR3 having an amino acid sequence of SEQ ID NO: 3; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6, and the anti-LAG3 antibody or antigen-binding fragment thereof includes a VH CDR1 comprising the amino acid sequence of SEQ ID NO:354, a VH CDR2 comprising the amino acid sequence of SEQ ID NO:461, a VH CDR3 comprising the amino acid sequence of SEQ ID NO:468, a VL CDR1 comprising the amino acid sequence of SEQ ID NO:490, a VL CDR2 comprising the amino acid sequence of SEQ ID NO:358, and a VL CDR3 comprising the amino acid sequence of SEQ ID NO:488.

In some embodiments, the anti-PD-L1 antibody or antigen-binding fragment thereof includes a VH CDR1 having an amino acid sequence of SEQ ID NO: 1; a VH CDR2 having an amino acid sequence of SEQ ID NO: 526; a VH CDR3 having an amino acid sequence of SEQ ID NO: 515; a VL CDR1 having an amino acid sequence of SEQ ID NO: 4; a VL CDR2 having an amino acid sequence of SEQ ID NO: 5; and a VL CDR3 having an amino acid sequence of SEQ ID NO: 6, and the anti-LAG3 antibody or antigen-binding fragment thereof includes a VH CDR1 comprising the amino acid sequence of SEQ ID NO:354, a VH CDR2 comprising the amino acid sequence of SEQ ID NO:461, a VH CDR3 comprising the amino acid sequence of SEQ ID NO:468, a VL CDR1 comprising the amino acid sequence of SEQ ID NO:490, a VL CDR2 comprising the amino acid sequence of SEQ ID NO:358, and a VL CDR3 comprising the amino acid sequence of SEQ ID NO:488. Antibodies or variants described herein may comprise derivatives that are modified, e.g., by the covalent attachment of any type of molecule to the antibody such that covalent attachment does not prevent the antibody from binding to the antigen (e.g., an epitope). For example, but not by way of limitation, the antibodies can be modified, e.g., by at least one selected from the group consisting of glycosylation, acetylation, pegylation, phosphorylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

The antibodies or fragments thereof can be detectably labeled by tagging (coupling) with a conventional labeling material selected from chemiluminescent compounds, fluorescent compounds (e.g., fluorescence emitting metals), radioisotopes, dyes, etc. The presence of the tagged antibodies or fragments thereof can be detected by measuring a signal arising during a chemical reaction between the antibody (or fragment thereof) and the labeling material. Examples of particularly useful labeling material may be at least one selected from the group consisting of luminol, isoluminol, theromatic acridinium ester, imidazole, acridinium salt, oxalate ester, fluorescence emitting metals, and the like. For example, the fluorescence emitting metals may be $^{152}$Eu, or others of the lanthanide series. These metals can be attached to the antibody using such metal chelating groups as diethylenetriaminepentacetic acid (DTPA) or ethylenediaminetetraacetic acid (EDTA).

In certain embodiments, the prepared bispecific antibodies will not elicit a deleterious immune response in the animal to be treated, e.g., in a human. In one embodiment, the bispecific antibody may be modified to reduce their immunogenicity using any conventional techniques. For example, the bispecific antibody may be a humanized, primatized, deimmunized, or chimeric antibody. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues.

De-immunization can also be used to decrease the immunogenicity of an antibody. As used herein, the term "de-immunization" may include alteration of an antibody to modify T-cell epitopes (see, e.g., International Application Publication Nos. WO/9852976 A1 and WO/0034317 A2). For example, variable heavy chain and variable light chain sequences from the starting antibody are analyzed and a human T-cell epitope "map" from each V (variable) region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity and/or affinity of the bispecific antibody to each target protein can be determined by any conventional assay, for example, in vitro assays such as immunoprecipitation, radioimmunoassay (RIA), or enzyme-linked immunoabsorbent assay (ELISA), but not be limited thereto.

Alternatively, techniques described for the production of single-chain units (U.S. Pat. No. 4,694,778, etc.) can be adapted to produce single-chain units of the present disclosure. Single-chain units are formed by linking the heavy and light chain fragments of the Fv region via an amino acid bridge (peptide linker), resulting in a single-chain fusion peptide (scFv). Techniques for the assembly of functional Fv fragments in *E. coli* may also be used.

Examples of techniques which can be used to produce single-chain Fvs (scFvs) and antibodies include those described in U.S. Pat. Nos. 4,946,778, 5,258,498, etc.). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., U.S. Pat. Nos. 5,807,715, 4,816,567, and 4,816,397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions (See, e.g., Queen et al., U.S. Pat. No. 5,585,089, which are incorporated herein by reference in their entireties). Antibodies can be humanized using a variety of techniques known in the art including, for example, CDR-grafting (U.S. Pat. Nos. 5,225,539, 5,530,101, 5,585,089, etc., each of which is incorporated by reference in its entirety), veneering or resurfacing (EP 592,106; EP 519,596, each of which is incorporated by reference in its entirety), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887, 4,716,111, etc., each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the bispecific antibody may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278: 457-479 (1998) for a listing of human framework regions). For example, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen (or epitope). Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Alternatively, antibody-producing cell lines may be selected and cultured using techniques well known to the skilled artisan. Such techniques are described in a variety of laboratory manuals and primary publications.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Therapeutic Use of the Antibodies

Figure 33:
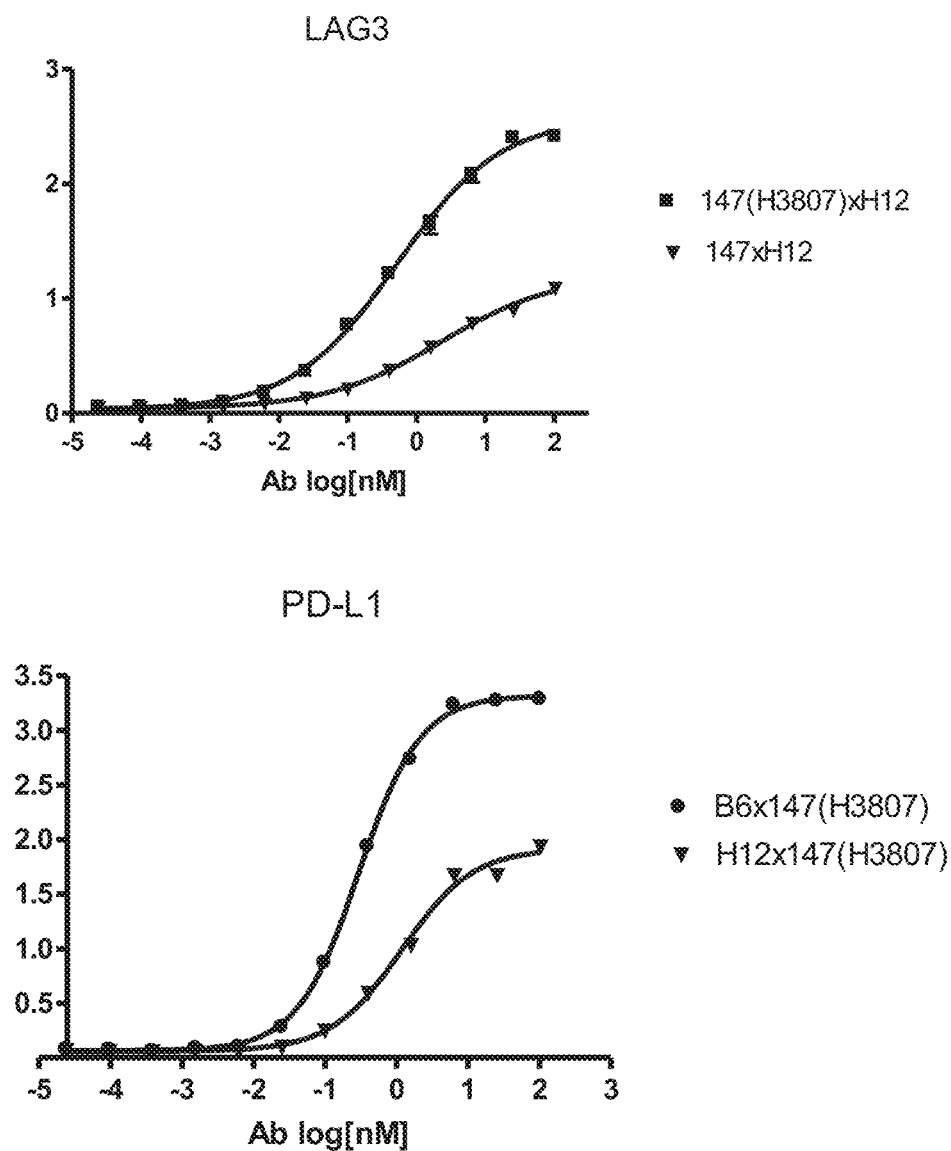
FIG. 33 shows graphs illustrating the binding of the anti-PD-L1/anti-LAG3 bispecific antibody according to an embodiment to human PD-L1 and human LAG3, measured by ELISA.

The bispecific antibody provided herein is capable of simultaneously blocking the activities of PD-L1 and LAG3, thereby exhibiting improved effects in immunotherapies and/or cancer therapies, for example, by activating immune response (see FIG. 33). Given the ability of the bispecific antibodies of the disclosure to inhibit the binding of LAG-3 to MHC Class II molecules and to stimulate antigen-specific T cell responses, the disclosure also provides a composition or in vitro and in vivo methods of using the antibodies of the disclosure to stimulate, enhance or upregulate antigen-specific T cell responses.

An embodiment provides a pharmaceutical composition comprising the bispecific antibody or the anti-PD-L1 or anti-LAG3 antibody as described above. The pharmaceutical composition may further comprise a pharmaceutically acceptable carrier. The pharmaceutical composition may be used for stimulating an immune response (e.g., an antigen-specific T cell response), and/or treating and/or preventing a disease associated with PD-L1, LAG3, or both thereof.

Another embodiment provides a method of stimulating an immune response (e.g., an antigen-specific T cell response), and/or treating and/or preventing a disease associated with PD-L1, LAG3, or both thereof, in a subject in need thereof, comprising administering to the subject a pharmaceutically effective amount of the bispecific antibody, the anti-PD-L1 or anti-LAG3 antibody, or the pharmaceutical composition.

The method may further step of identifying the subject in need of treating and/or preventing a disease associated with PD-L1, LAG3, or both thereof, prior to the administering step.

The disease associated with PD-L1, LAG3, or both thereof may be selected from cancers (or tumors), infectious diseases, autoimmune reactions, nervous system disorders, and the like.

In an embodiment, the subject may be selected from mammals including humans, for example, a mammal (e.g., a human) suffering from a cancer and/or infection mammalian cells. In other embodiment, the subject may be a cell separated (isolated) from a mammal, for example, a mammal suffering from the disease selected from cancers infectious diseases, autoimmune reactions, nervous system disorders, and the like (e.g., a cancer cell or a cell separated (isolated) from an infectious region in the mammal, or a T cell, such as a tumor-infiltrating T lymphocyte, a CD4+ T cell, a CD8+ T cell, or the combination thereof).

Another embodiment provides a use of the bispecific antibody, the anti-PD-L1 or anti-LAG3 antibody, or the pharmaceutical composition in treating and/or preventing a cancer or an infection. Another embodiment provides a use of the bispecific antibody, or the anti-PD-L1 or anti-LAG3 antibody, in preparing a pharmaceutical composition for treating and/or preventing a cancer or an infection.

In the pharmaceutical compositions, methods and/or uses provided herein, the disease associated with PD-L1, LAG3, or both thereof may be one associated with activation (e.g., abnormal activation or over-activation) and/or overproduction (overexpression) of PD-L1, LAG3, or both thereof. For example, the disease may be a cancer or an infection.

The cancer may be a solid cancer or blood cancer, preferably a solid cancer. The cancer may any tumor expressing PD-L1 protein, and may be selected from the group consisting of bladder cancer, liver cancer, colon cancer, rectal cancer, endometrial cancer, leukemia, lymphoma, pancreatic cancer, lung cancer (e.g., small cell lung cancer, non-small cell lung cancer etc.), breast cancer, urethral cancer, head and neck cancer, gastrointestinal cancer, stomach cancer, oesophageal cancer, ovarian cancer, renal cancer, melanoma, prostate cancer, thyroid cancer, and the like, but may not be limited thereto. In some embodiments, the cancer is selected from the group consisting of bladder cancer, liver cancer, pancreatic cancer, non-small cell lung cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, small cell lung cancer, and the like. The cancer may be a primary or metastatic cancer.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

The administration of the bispecific antibody or the anti-PD-L1 or anti-LAG3 antibody may be conducted through at least one selected from the group consisting of intraperitoneal, intravenous, subcutaneous, intradermal, intramuscular, intranasal, epidural, and oral routes, but not be limited thereto. The bispecific antibody or the anti-PD-L1 or anti-LAG3 antibody or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, parenterally, intracisternally, intravaginally, intraperitoneally, rectally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the bispecific antibodies, or the anti-PD-L1 or anti-LAG3 antibodies, or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the bispecific antibodies or the anti-PD-L1 or anti-LAG3 antibodies or composition can be delivered in a vesicle, in particular a liposome. In yet another embodiment, the bispecific antibodies or the anti-PD-L1 or anti-LAG3 antibodies or composition can be delivered in a controlled release system. In one embodiment, for the controlled release system, any pharmaceutically acceptable pumps, and/or polymeric materials may be used.

The pharmaceutically effective amount of the bispecific antibodies or the anti-PD-L1 or anti-LAG3 antibodies for treating, inhibiting, ameliorating, and/or preventing an inflammatory, immune or malignant disease, disorder, or condition, can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

The methods of treating an infectious or malignant disease (e.g., cancer), condition or disorder comprising administration of the bispecific antibody or the anti-PD-L1 or anti-LAG3 antibody are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of the bispecific antibody or the anti-PD-L1 or anti-LAG3 antibody include the effect of the bispecific antibody or the anti-PD-L1 or anti-LAG3 antibody on a cell line or a patient tissue sample. The effect of the bispecific antibody or the anti-PD-L1 or anti-LAG3 antibody on the cell line and/or tissue sample can be determined utilizing techniques known to those of skill in the art, such as the assays disclosed elsewhere herein. In accordance with the disclosure, in vitro assays which can be used to determine whether administration of the bispecific antibody or the anti-PD-L1 or anti-LAG3 antibody is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis, construction of a nucleic acid as part of a retroviral or other vector, etc.

The pharmaceutical compositions may comprise an effective amount of the bispecific antibody or the anti-PD-L1 or anti-LAG3 antibody, and an acceptable carrier. In some embodiments, the composition further includes a second anticancer agent (e.g., an immune checkpoint inhibitor).

In a specific embodiment, the term "pharmaceutically acceptable" may refer to approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" may refer to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Diagnostic Use of the Antibody

Over-expression and/or over-activation of PD-L1 and/or LAG3 is observed in a biological sample (e.g., cells, tissues, blood, serum, etc.) from a patient suffering from a certain cancer and/or infection (for example, tumor cell or tissue, blood or serum from an infectious patient), and/or patients having PD-L1- and/or LAG3-over-expressing cells are likely responsive to treatments with the bispecific antibody or the anti-PD-L1 or anti-LAG3 antibody. Accordingly, the bispecific antibody or the anti-PD-L1 or anti-LAG3 antibody of the present disclosure can also be used for diagnostic and prognostic purposes.

An embodiment provides a pharmaceutical composition for diagnosing a disease associated with PD-L1, LAG3, or both thereof, the composition comprising the bispecific antibody or the anti-PD-L1 or anti-LAG3 antibody. In another embodiment, provided is a use of the bispecific antibody or the anti-PD-L1 or anti-LAG3 antibody for diagnosing a disease associated with PD-L1, LAG3, or both thereof.

Another embodiment provides a method of diagnosing a disease associated with PD-L1, LAG3, or both thereof, the method comprising contacting a biological sample obtained from a patient with the bispecific antibody or the anti-PD-L1 or anti-LAG3 antibody, and detecting antigen-antibody reaction or measuring a level of antigen-antibody reaction in the biological sample. In this method, when the antigen-antibody reaction is detected in the biological sample or the level of the antigen-antibody reaction in the biological sample is higher than that of a normal sample, the patient from whom the biological sample is obtained may be determined as a patient with a disease associated with PD-L1, LAG3, or both thereof. Therefore, in some embodiments, the method may further comprise contacting a normal sample with the bispecific antibody or the anti-PD-L1 or anti-LAG3 antibody, and measuring a level of an antigen-antibody reaction in the normal sample. In addition, the method may further comprise comparing the level of the antigen-antibody reaction in the biological sample and in the normal sample, after the measuring step. In addition, after the detecting step or comparing step, the method may further comprise determining the patient as a patient with a disease associated with PD-L1, LAG3, or both thereof, when the antigen-antibody reaction is detected in the biological sample or the level of the antigen-antibody reaction in the biological sample is higher than that of the normal sample.

The disease associated with PD-L1, LAG3, or both thereof may be one associated with activation (e.g., abnormal activation or over-activation) and/or overproduction (overexpression) of PD-L1, LAG3, or both thereof. For example, the disease may be a cancer or an infection, as described above.

In the diagnosing composition and method, the biological sample may be at least one selected from the group consisting of a cell, a tissue, body fluid (e.g., blood, serum, lymph, etc.) and the like, obtained (separated) from a patient to be diagnosed. The normal sample may be at least one selected from the group consisting of a cell, a tissue, body fluid (e.g., blood, serum, lymph, urine, etc.) and the like, obtained (separated) from a patient having no disease associated with PD-L1, LAG3, or both thereof. The patient may be selected from a mammal, such as a human. Upon optional pre-treatment of the sample, the sample can be incubated with the bispecific antibody or the anti-PD-L1 or anti-LAG3 antibody of the present disclosure under conditions allowing the antibody to interact with a PD-L1 and/or LAG3 protein potentially present in the sample.

Presence and/or level (concentration) of the PD-L1 and/or LAG3 protein in the sample can be used for identifying a patient who is suitable for a treatment with the bispecific antibody or the anti-PD-L1 or anti-LAG3 antibody, or a patient who is responsive or susceptive to the treatment with the bispecific antibody or the anti-PD-L1 or anti-LAG3 antibody.

An embodiment provides a pharmaceutical composition identifying a patient who is suitable for a treatment with the bispecific antibody or the anti-PD-L1 or anti-LAG3 antibody, or a patient who is responsive or susceptive to the treatment with the bispecific antibody or the anti-PD-L1 or anti-LAG3 antibody, the composition comprising the bispecific antibody or the anti-PD-L1 or anti-LAG3 antibody. In another embodiment, provided is a use of the bispecific antibody or the anti-PD-L1 or anti-LAG3 antibody for identifying a patient who is suitable for a treatment with the bispecific antibody or the anti-PD-L1 or anti-LAG3 antibody, or a patient who is responsive or susceptive to the treatment with the bispecific antibody or the anti-PD-L1 or anti-LAG3 antibody. Another embodiment provides a method of identifying a patient who is suitable for a treatment with the bispecific antibody or the anti-PD-L1 or anti-LAG3 antibody, or a patient who is responsive or susceptive to the treatment with the bispecific antibody or the anti-PD-L1 or anti-LAG3 antibody, the method comprising contacting a biological sample obtained from a patient with the bispecific antibody or the anti-PD-L1 or anti-LAG3 antibody, and detecting antigen-antibody reaction or measuring a level of antigen-antibody reaction in the biological sample.

An embodiment provides a composition for detection of PD-L1, LAG3, or both thereof simultaneously, in a biological sample, the composition comprising the bispecific antibody or the anti-PD-L1 or anti-LAG3 antibody. Another embodiment provides a method of detection of PD-L1, LAG3, or both thereof simultaneously, in a biological sample, the method comprising contacting the biological sample with the bispecific antibody or the anti-PD-L1 or anti-LAG3 antibody; and detecting (measuring) an antigen-antibody reaction (binding) between the bispecific antibody or the anti-PD-L1 or anti-LAG3 antibody and PD-L1, LAG3, or both thereof.

In the detecting composition and the detecting method, the term "detection of PD-L1, LAG3, or both thereof" may refer to, but not be limited to, detection of presence (and/or absence) and/or level of PD-L1, LAG3, or both thereof in the biological sample.

In the method of detection, when an antigen-antibody reaction is detected, it can be determined that PD-L1, LAG3, or both thereof are present in the biological sample, and when an antigen-antibody reaction is not detected, it can be determined that PD-L1, LAG3, or both thereof are absent (not present) in the biological sample. Therefore, the method of detection may further comprise, after the detecting step, determining that PD-L1, LAG3, or both thereof are present in the biological sample when an antigen-antibody reaction is detected, and/or that PD-L1, LAG3, or both thereof are absent (not present) in the biological sample, when an antigen-antibody reaction is not detected.

In the method of detection, the level of PD-L1, LAG3, or both thereof may be determined according to the degree of the antigen-antibody reaction (e.g., the amount of antigen-antibody complex formed by the antigen-antibody reaction, the intensity of any signal obtained by the antigen-antibody reaction, and the like, which can be measured by any conventional means).

The biological sample may comprise at least one selected from the group consisting of a cell (e.g., a tumor cell), a tissue (e.g., a tumor tissue), body fluid (e.g., blood, serum, etc.), and the like, obtained or isolated from a mammal such as a human. The steps of the method of detection may be conducted in virto.

In the diagnosing method and/or detecting method, the step of detecting the antigen-antibody reaction or measuring a level of the antigen-antibody reaction may be performed by any general method known to the relevant art, such as general enzymatic reactions, fluorescent reactions, luminescent reactions, and/or detection of radiation. For example, the step may be performed by a method selected from, but not limited to, the group consisting of immunochromatography, immunohistochemistry (IHC), enzyme linked immunosorbent assay (ELISA), radioimmunoassay (RIA), enzyme immunoassay (EIA), fluorescence immunoassay (FIA), luminescence immunoassay (LIA), western blotting, microarray, flow cytometry, surface plasmon resonance (SPR), and the like, but not be limited thereto.

Polynucleotides Encoding the Antibodies and Methods of Preparing the Antibodies

An embodiment provides a polynucleotide encoding the bispecific antibody or the anti-PD-L1 or anti-LAG3 antibody. In particular, an embodiment provides a polynucleotide encoding a heavy chain of the bispecific antibody in an IgG-scFv form. Other embodiment provides a polynucleotide encoding a light chain of the bispecific antibody in the IgG-scFv form. The IgG-scFv form may refer to a kind of a bispecific antibody comprising a full-length IgG antibody targeting (binding to) one of PD-L1 and LAG3 proteins and a scFv fragment targeting (binding to) the other one, wherein the scFv is linked to a C-terminus and/or N-terminus of the full-length IgG antibody directly (without a peptide linker) or via a peptide linker.

In an embodiment, when the bispecific antibody in an IgG-scFv form comprises a full-length IgG antibody against PD-L1 and a scFv fragment against LAG3, the polynucleotide encoding a heavy chain of the bispecific antibody may encode a heavy chain of the full-length IgG antibody against PD-L1 and a scFv fragment against LAG3 that is linked to a C-terminus and/or N-terminus of the full-length IgG antibody directly or via a peptide linker; and the polynucleotide encoding a light chain of the bispecific antibody may encode a light chain of the full-length IgG antibody against PD-L1.

In another embodiment, when the bispecific antibody in an IgG-scFv form comprises a full-length IgG antibody against LAG3 and a scFv fragment against PD-L1, the polynucleotide encoding a heavy chain of the bispecific antibody may encode a heavy chain of the full-length IgG antibody against LAG3 and a scFv fragment against PD-L1 that is linked to a C-terminus and/or N-terminus of the full-length IgG antibody directly or via a peptide linker; and the polynucleotide encoding a light chain of the bispecific antibody may encode a light chain of the full-length IgG antibody against LAG3.

Another embodiment provides a recombinant vector comprising the polynucleotide encoding a heavy chain of the bispecific antibody, the polynucleotide encoding a light chain of the bispecific antibody, or both thereof. Another embodiment provides a recombinant cell transfected with the recombinant vector.

Another embodiment provides a method of preparing the bispecific antibody, comprising expressing the polynucleotide encoding a heavy chain of the bispecific antibody, the polynucleotide encoding a light chain of the bispecific antibody in a cell. The step of expressing the polynucleotide may be conducted by culturing the cell comprising the polynucleotide (for example, in a recombinant vector) under a condition allowing the expression of the polynucleotide. The method may further comprise isolating and/or purifying the bispecific antibody from the cell culture, after the step of expressing or culturing.

EXAMPLES

Hereafter, the present invention will be described in detail by examples.

The following examples are intended merely to illustrate the invention and are not construed to restrict the invention.

Example 1: Preparation of Anti-PD-L1 Monoclonal Antibodies 1.1. Preparation of Anti-Human-PD-L1 Mouse Monoclonal Antibodies and Analysis Thereof Anti-human-PD-L1 mouse monoclonal antibodies were generated using the hybridoma technology.

Antigen: human PD-L1-Fc protein and human PD-L1 highly expressed CHOK1 cell line (PDL1-CHOK1 cell line).

Immunization: To generate mouse monoclonal antibodies to human PD-L1, 6-8 week female BALB/c mice were firstly immunized with $1.5 \times 10^7$ PDL1-CHOK1 cells. Day 14 and 33 post first immunization, the immunized mice were re-immunized with $1.5 \times 10^7$ PDL1-CHOK1 cells respectively. To select mice producing antibodies that bound PD-L1 protein, sera from immunized mice were tested by ELISA. Briefly, microtiter plates were coated with human PD-L1 protein at 1 µg/ml in PBS, 100 µl/well at room temperature (RT) overnight, then blocked with 100 µl/well of 5% BSA. Dilutions of plasma from immunized mice were added to each well and incubated for 1-2 hours at RT. The plates were washed with PBS/Tween® (polysorbate) and then incubate with anti-mouse IgG antibody conjugated with Horse Radish Peroxidase (HRP) for 1 hour at RT. After washing, the plates were developed with ABTS substrate and analyzed by spectrophotometer at OD 405 nm. Mice with sufficient titers of anti-PDL1 IgG were boosted with 50 µg human PDL1-Fc protein at Day 54 post-immunization.

The resulting mice were used for fusions. The hybridoma supernatants were tested for anti-PD-L1 IgGs by ELISA.

The amino acid and polynucleotide sequences of the variable regions of Hybridoma HL1210-3 are provided in Table 5 below.

TABLE 5

HL1210-3 variable sequences

| Name | Sequence | SEQ ID NO: |
|---|---|---|
| HL1210-3 VH | GAAGTGAAACTGGTGGAGTCTGGGGGAGACTTAGTGAAGC<br>CTGGAGGGTCCCTGAAACTCTCCTGTGCAGCCTCTGGATT<br>CACTTTCAGTAGCTATGACATGTCTTGGGTTCGCCAGACT<br>CCGGAGAAGAGTCTGGAGTGGGTCGCAACCATTAGTGATG<br>GTGGTGGTTACATCTACTATTCAGACAGTGTGAAGGGGCG<br>ATTTAGCATCTCCAGAGACAATGCCAAGAACAACCTGTAC<br>CTGCAAATGAGCAGTCTGAGGTCTGAGGACACGGCCTTGT<br>ATATTTGTGCAAGAGAATTTGGTAAGCGCTATGCTTTGGA<br>CTACTGGGGTCAAGGAACCTCAGTCACCGTCTCCTCA | 112 |
| HL1210-3 VH | EVKLVESGGDLVKPGGSLKLSCAASGFTFSSYDMSWVRQT<br>PEKSLEWVATISDGGGYIYYSDSVKGRFTISRDNAKNNLY<br>LQMSSLRSEDTALYICAREFGKRYALDYWGQGTSVT | 113 |
| HL1210-3 VL | GACATTGTGATGACCCAGTCTCACAAATTCATGTCCACAT<br>CGGTAGGAGACAGGGTCAGCATCTCCTGCAAGGCCAGTCA<br>GGATGTGACTCCTGCTGTCGCCTGGTATCAACAGAAGCCA<br>GGACAATCTCCTAAACTACTGATTTACTCCACATCCTCCC<br>GGTACACTGGAGTCCCTGATCGCTTCACTGGCAGTGGATC<br>TGGGACGGATTTCACTTTCACCATCAGCAGTGTGCAGGCT<br>GAAGACCTGGCAGTTTATTACTGTCAGCAACATTATACTA<br>CTCCGCTCACGTTCGGTGCTGGGACCAAGCTGGAGCTGAA<br>A | 114 |
| HL1210-3 VL | DIVMTQSHKFMSTSVGDRVSISCKASQDVTPAVAWYQQKP<br>GQSPKLLIYSTSSRYTGVPDRFTGSGSGTDFTFTISSVQA<br>EDLAVYYCQQHYTTPLTFGAGTKLELK | 115 |

1.2. Activities of HL1210-3 Mouse mAb

To evaluate the binding activity of hybridoma clone HL1210-3, the purified mAb from this clone were subjected to ELISA test. Briefly, microtiter plates were coated with human PD-L1-Fc protein at 0.1 μg/ml in PBS, 100 μl/well at 4° C. overnight, then blocked with 100 μl/well of 5% BSA. Three-fold dilutions of HL1210-3 antibodies starting from 0.2 μg/ml were added to each well and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. As shown in FIG. 1, HL1210-3 can bind to human PD-L1 with high activity ($EC_{50}$=5.539 ng/ml).

To evaluate the activity of HL1210-3 mouse mAb to block human PD-L1 binding to its receptor PD-i, a receptor blocking assay was performed by using recombinant human PD-L1.

Figure 2:
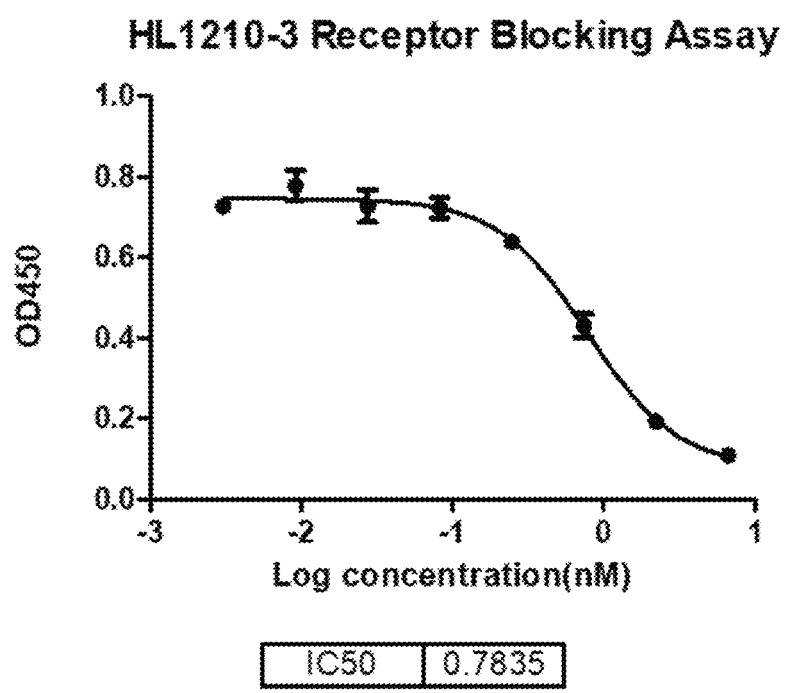
FIG. 2 shows that HL1210-3 can efficiently inhibit the binding of human PD-L1 to human PD1.

To evaluate the blocking effect of HL1210-3 mouse mAb on recombinant human PD-L1 to bind to its receptor PD-i, the ELISA based receptor blocking assay was employed. Briefly, microtiter plates were coated with human PD-L1-Fc protein at 1 μg/ml in PBS, 100 μl/well at 4° C. overnight, then blocked with 100 μl/well of 5% BSA. 50 μl biotin-labeled human PD-1-Fc protein and 3-fold dilutions of HL1210-3 antibodies starting from 2 μg/ml at 50 μl were added to each well and incubated for 1 hour at 37° C. The plates were washed with PBS/Tween® and then incubated with Streptavidin-HRP for 1 hour at 37° C. After washing, the plates were developed with TMB substrate and analyzed by spectrophotometer at OD 450-630 nm. As shown in FIG. 2, HL1210-3 can efficiently inhibit the binding of human PD-L1 to human PD1 at $IC_{50}$=0.7835 nM.

In addition, a receptor blocking assay was also performed by using mammalian cell expressed human PD-L1.

Figure 3:
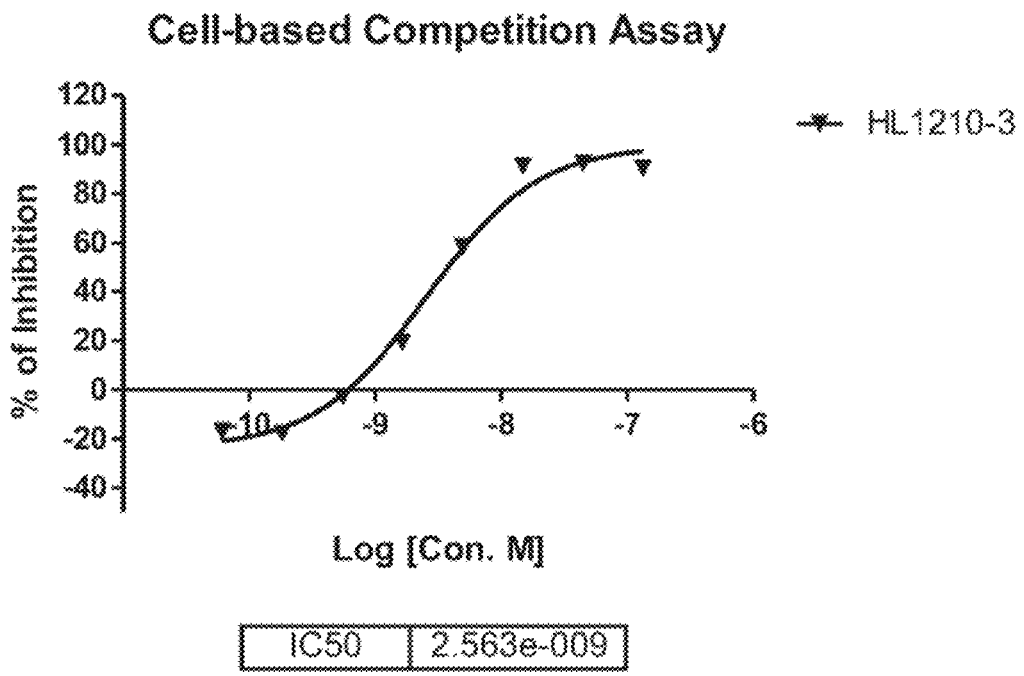
FIG. 3 shows the HL1210-3 antibody can highly efficiently inhibit the binding of PD-1 on PD-L1 expressed on mammalian cells.

To evaluate the blocking effect of HL1210-3 mouse mAb on human PD-L1 expressed on mammalian cells to bind to its receptor PD-1, the FACS-based receptor blocking assay was used. Briefly, PDL1-CHOK1 cells were firstly incubated with 3-fold serious diluted HL1210-3 mouse mAb starting at 20 μg/ml at RT for 1 hour. After wash by FACS buffer (PBS with 2% FBS), the biotin-labeled huPD-1 was added to each well and incubated at RT for 1 hour. Then, the Streptavidin-PE was added to each well for 0.5 hour post twice wash with FACS buffer. The mean florescence intensity (MFI) of PE was evaluated by FACSAria™ III flow cytometer. As shown in FIG. 3, the HL1210-3 antibody can highly efficiently inhibit the binding of PD-1 on PD-L1 expressed on mammalian cells at IC50 of 2.56 nM with 92.6% top inhibition rate.

$$\% \text{ of inhibition} = \left(1 - \frac{MFI \text{ of testing antibody}}{MFI \text{ of vehicle contori}}\right) \times 100\%$$

1.3. Effects of HL1210-3 Mouse mAb

Figure 4:
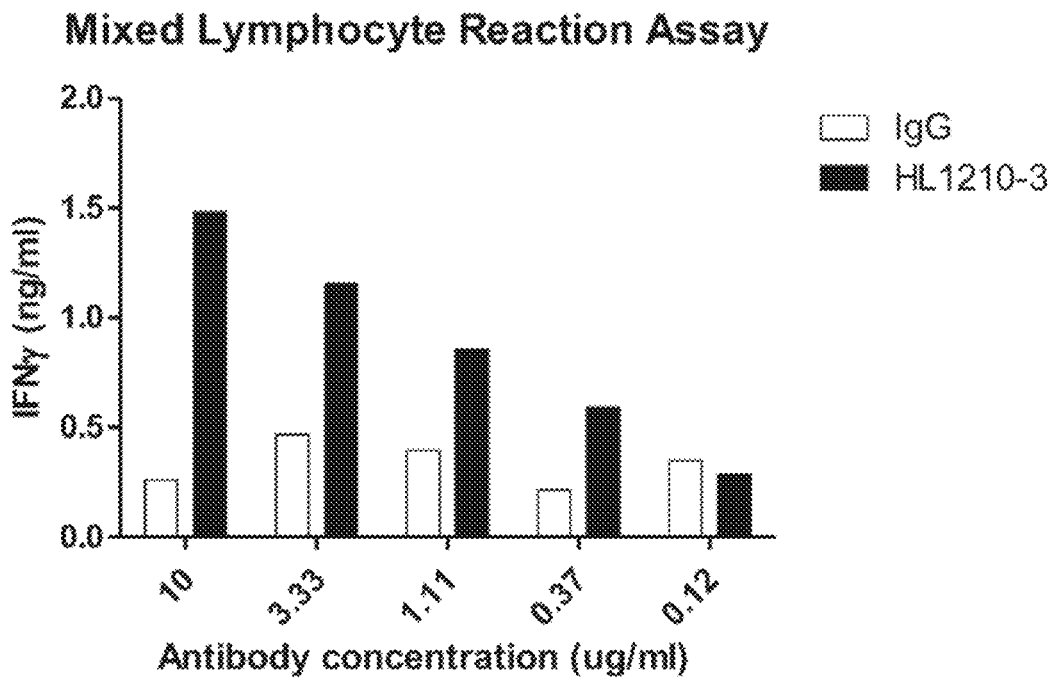
FIG. 4 shows that the tested anti-PD-L1 antibodies can promote human T cell response.

To evaluate the effect of HL1210-3 mouse mAb to promote human T cell immune response, the response of human T cells assessed in a mixed lymphocyte reaction setting. Human DCs were differentiated from CD14+monocytes in the presence of GM-CSF and IL-4 for 7 days. CD4+ T cells isolated from another donor were then co-cultured with the DCs and serial dilutions of anti-PD-L1 blocking antibody. At day 5 post-inoculation, the culture supernatant was assayed for IFNγ production. The results indicated that the HL1210-3 antibodies can dose-dependently promote IFNγ production, suggesting anti-PD-L1 antibody can promote human T cell response (FIG. 4).

1.4. Binding Affinity of HL1210-3 Mouse mAb

Figure 5:
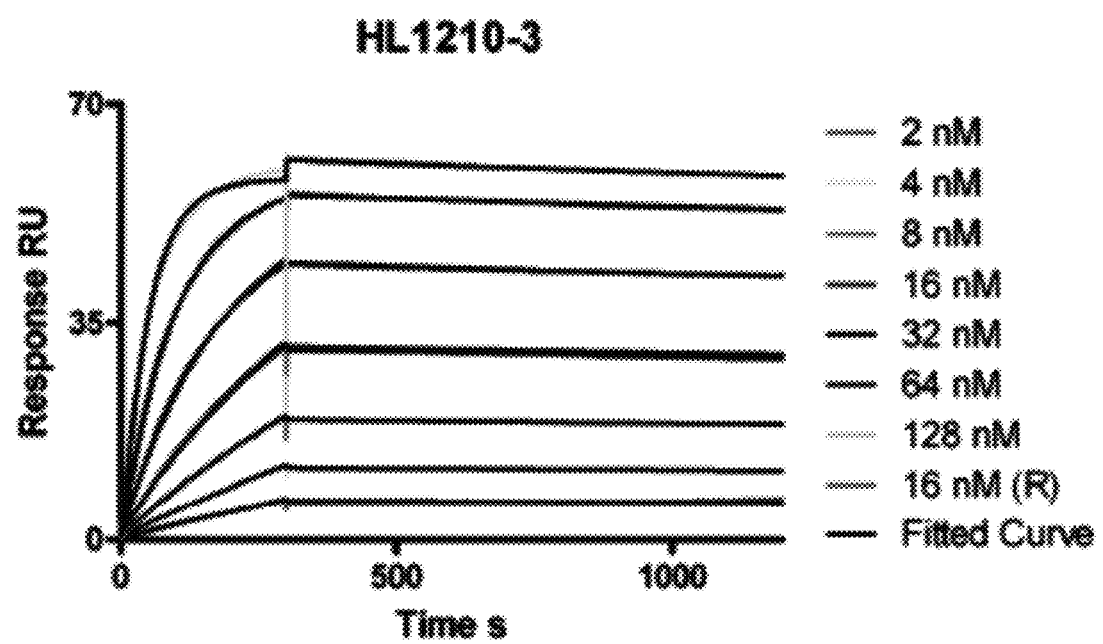
FIG. 5 shows the binding kinetics of HL1210-3 to recombinant PD-1.
Figure 6A:
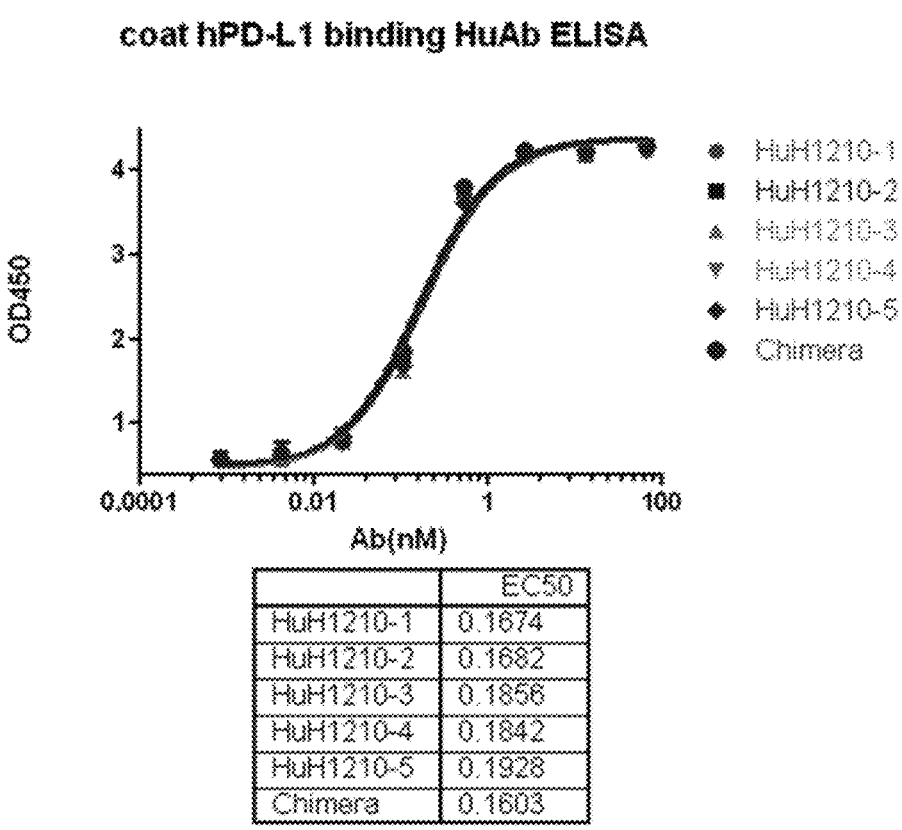
FIGS. 6A-6E show that all tested humanized antibodies had comparable binding efficacy to human PD-L1 in contact to chimeric antibody.
Figure 6B:
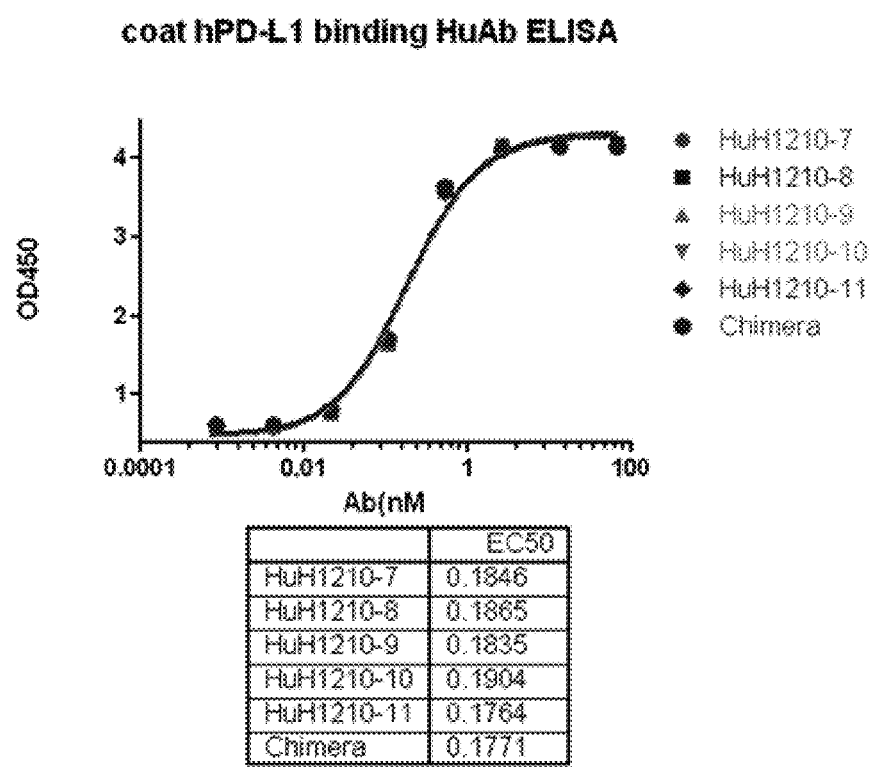
Figure 6C:
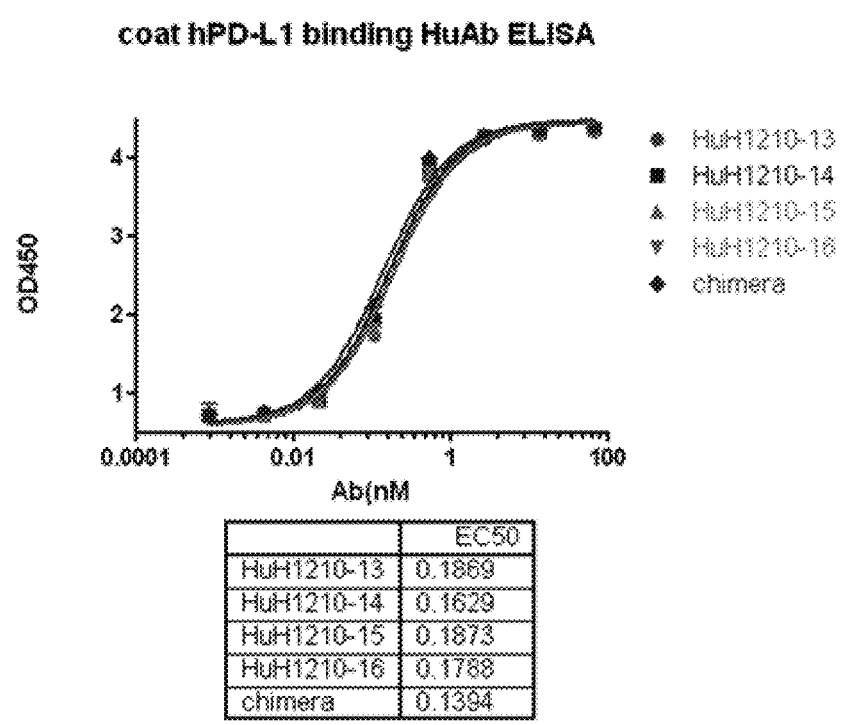
Figure 6D:
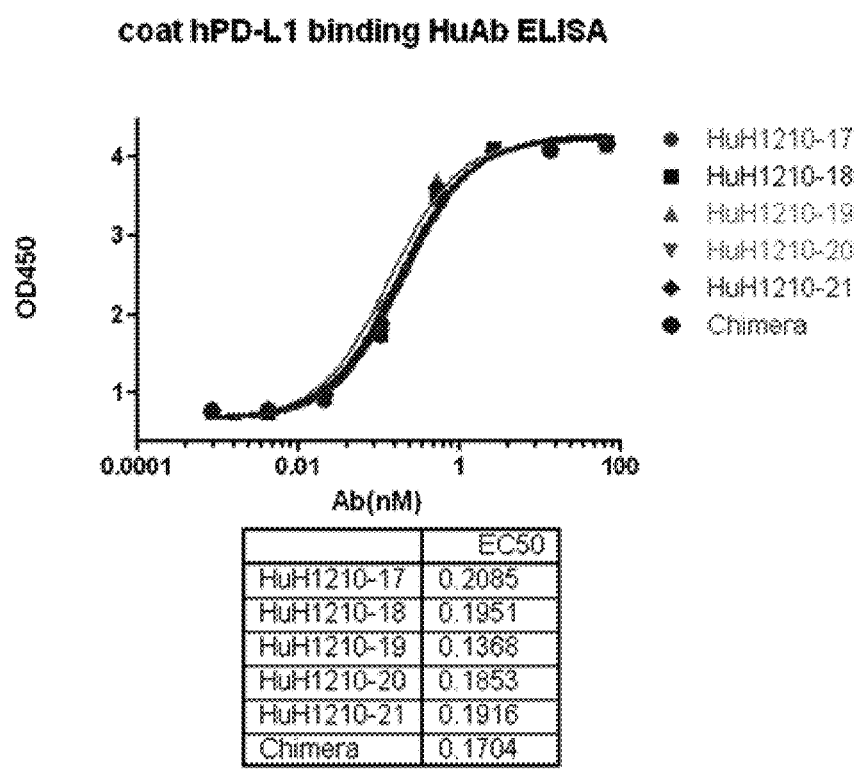
Figure 6E:
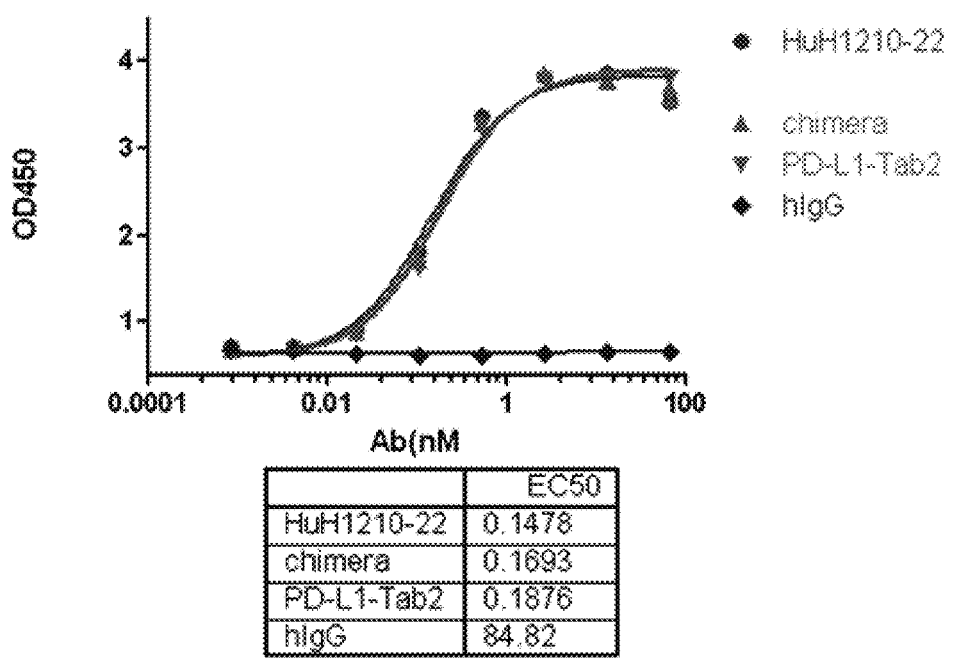

The binding of the HL1210-3 antibodies to recombinant PD-L1 protein (human PD-L1-his taq) was tested with BIACORE™ (GE® Healthcare molecular interaction analysis platform) using a capture method. The HL1210-3 mouse mAb was captured using anti-mouse Fc antibody coated on a CM5 chip. A series dilution of human PD-L1-his taq protein was injected over captured antibody for 3 mins at a flow rate of 25 μg/ml. The antigen was allowed to dissociate for 900s. All the experiment were carried out on a Biacore™ T200. Data analysis was carried out using Biacore™ T200 evaluation software. The results are shown in FIG. 5 and Table 6 below.

TABLE 6

Binding Kinetics of HL1210-3 to recombinant human PD-L1

| Antibody | ka (1/Ms) | kd (1/s) | KD (M) |
| --- | --- | --- | --- |
| HL1210-3 | 1.61E+05 | 4.69E−05 | 2.93E−10 |

1.5. Humanization of the HL1210-3 Mouse mAb

The mAb HL1210-3 variable region genes were employed to create a humanized MAb. In the first step of this process, the amino acid sequences of the VH and VK of MAb HL1210-3 were compared against the available database of human Ig gene (IgG1) sequences to find the overall best-matching human germline Ig gene sequences. For the light chain, the closest human match was the O18/Jk2 and KV1-39*01/KJ2*04 gene, and for the heavy chain the closest human match was the VH3-21 gene. VH3-11, VH3-23, VH3-7*01 and VH3-48 genes were also selected due to their close matches.

Humanized variable domain sequences were then designed where the CDR1 (SEQ ID NO. 4), 2 (SEQ ID NO. 5) and 3 (SEQ ID NO. 6) of the HL1210-3 light chain were grafted onto framework sequences of the O18/Jk2 and KV1-39*01/KJ2*04 gene, and the CDR1 (SEQ ID NO. 1), 2 (SEQ ID NO. 2), and 3 (SEQ ID NO. 3) sequences of the HL1210-3 VH were grafted onto framework sequences of the VH3-21, VH3-11, VH3-23, VH3-48 or VH3-7*01 gene. A 3D model was then generated to determine if there were any framework positions where replacing the mouse amino acid to the human amino acid could affect binding and/or CDR conformation. In the case of the light chain, 22S, 43S, 60D, 63T and 42Q (Kabat numbering, see Table 7) in framework were identified. In the case of the heavy chain, 1E, 37V, 40T, 44S, 49A, 77N, 91I, 94R and 108T in the framework was involved in back-mutations.

TABLE 7

Humanization Design

| Construct | Mutation |
| --- | --- |
| VH Design I: VH3-21/JH6 | |
| Hu1210 VH | Chimera |
| Hu1210 VH.1 | CDR-grafted |
| Hu1210 VH.1a | S49A |
| Hu1210 VH.1b | S49A, G44S, Y91I |
| VH Design II: VH3-11/JH6 | |
| Hu1210 VH.2 | CDR-grafted, Q1E |
| Hu1210 VH.2a | Q1E, S49A |
| Hu1210 VH.2b | Q1E, I37V, S49A, G44S, Y91I |
| VH Design III: VH3-23/JH6 | |
| Hu1210 VH.3 | CDR-grafted, K94R |
| Hu1210 VH.3a | G44S, S49A, Y91I, K94R |
| VH Design IV: VH3-48/JH6 | |
| Hu1210 VH.4 | CDR-grafted |
| Hu1210 VH.4a | S49A |
| Hu1210 VH.4b | S49A, G44S, Y91I |
| Hu1210 VH.4c | D52E, S49A, G44S, Y91I |
| Hu1210 VH.4d | G53A, S49A, G44S, Y91I |
| Hu1210 VH.4e | G53V, S49A, G44S, Y91I |
| VH Design V: VH3-7*01/HJ1*01 | |
| Hu1210 VH.5 | CDR-grafted |
| Hu1210 VH.5a | H91I |
| Hu1210 VH.5b | H91I, H108T |
| Hu1210 VH.5c | H91I, H77N |
| Hu1210 VH.5d | H91I, H77N, H40T |
| VK Design I: O18/Jk2 | |
| Hu1210 Vk | Chimera |
| Hu1210 Vk.1 | CDR-grafted |
| Hu1210 Vk.1a | A43S |
| VK Design II: KV1-39*01/KJ2*04 | |
| Hu1210 Vk.2 | CDR-grafted |
| Hu1210 Vk.2a | L60D, L63T |
| Hu1210 Vk.2b | L60D, L63T, L42Q, L43S |
| Hu1210 Vk.2c | L60D, L63T, L42Q, L43S, T22S |

The amino acid and nucleotide sequences of some of the humanized antibody are listed in Table 8 below.

TABLE 8

Humanized antibody sequences (bold indicates CDR)

| Name | Amino Acid Sequence | SEQ ID NO: |
| --- | --- | --- |
| HL1210-VH | EVKLVESGGDLVKPGGSLKLSCAASGFTFSSYDMSWVRQTPEKSLEWVATIS DGGGYIYYSDSVKGRFTISRDNAKNNLYLQMSSLRSEDTALYICAREFGKRY ALDYWGQGTSVTVSS | 7 |
| Hu1210 VH.1 | EVQLVESGGGLVKPGGSLRLSCAASGFTFSSYDMSWVRQAPGKGLEWVSTIS DGGGYIYYSDSVKGRFTISRDNAKNSLYLQMNSLRAEDTAVYYCAREFGKRY ALDYWGQGTTVTVSS | 8 |
| Hu1210 VH.1a | EVQLVESGGGLVKPGGSLRLSCAASGFTFSSYDMSWVRQAPGKGLEWVATIS DGGGYIYYSDSVKGRFTISRDNAKNSLYLQMNSLRAEDTAVYYCAREFGKRY ALDYWGQGTTVTVSS | 9 |
| Hu1210 VH.1b | EVQLVESGGGLVKPGGSLRLSCAASGFTFSSYDMSWVRQAPGKSLEWVATIS DGGGYIYYSDSVKGRFTISRDNAKNSLYLQMNSLRAEDTAVYICAREFGKRY ALDYWGQGTTVTVSS | 10 |
| Hu1210 VH.2 | EVQLVESGGGLVKPGGSLRLSCAASGFTFSSYDMSWIRQAPGKGLEWVSTIS DGGGYIYYSDSVKGRFTISRDNAKNSLYLQMNSLRAEDTAVYYCAREFGKRY ALDYWGQGTTVTVSS | 11 |

TABLE 8-continued

Humanized antibody sequences (bold indicates CDR)

| | | |
|---|---|---|
| Hu1210 VH.2a | EVQLVESGGGLVKPGGSLRLSCAASGFTFSSYDMSWIRQAPGKGLEWVATIS DGGGYIYYSDSVKGRFTISRDNAKNSLYLQMNSLRAEDTAVYYCAREFGKRY ALDYWGQGTTVTVSS | 12 |
| Hu1210 VH.2b | EVQLVESGGGLVKPGGSLRLSCAASGFTFSSYDMSWVRQAPGKSLEWVATIS DGGGYIYYSDSVKGRFTISRDNAKNSLYLQMNSLRAEDTAVYICAREFGKRY ALDYWGQGTTVTVSS | 13 |
| Hu1210 VH.3 | EVQLLESGGGLVQPGGSLRLSCAASGFTFSSYDMSWVRQAPGKGLEWVSTIS DGGGYIYYSDSVKGRFTTSRDNSKNTLYLQMNSLRAEDTAVYYCAREFGKRY ALDYWGQGTTVTVSS | 14 |
| Hu1210 VH.3a | EVQLLESGGGLVQPGGSLRLSCAASGFTFSSYDMSWVRQAPGKSLEWVATIS DGGGYIYYSDSVKGRFTISRDNSKNTLYLQMNSLRAEDTAVYICAREFGKRY ALDYWGQGTTVTVSS | 15 |
| Hu1210 VH.4 | EVQLVESGGGLVQPGGSLRLSCAASGFTFSSYDMSWVRQAPGKGLEWVSTIS DGGGYIYYSDSVKGRFTISRDNAKNSLYLQMNSLRDEDTAVYYCAREFGKRY ALDYWGQGTTVTVSS | 16 |
| Hu1210 VH.4a | EVQLVESGGGLVQPGGSLRLSCAASGFTFSSYDMSWVRQAPGKGLEWVATIS DGGGYIYYSDSVKGRFTISRDNAKNSLYLQMNSLRDEDTAVYYCAREFGKRY ALDYWGQGTTVTVSS | 17 |
| Hu1210 VH.4b | EVQLVESGGGLVQPGGSLRLSCAASGFTFSSYDMSWVRQAPGKSLEWVATIS DGGGYIYYSDSVKGRFTISRDNAKNSLYLQMNSLRDEDTAVYICAREFGKRY ALDYWGQGTTVTVSS | 18 |
| Hu1210 VH.4c | EVQLVESGGGLVQPGGSLRLSCAASGFTFSSYDMSWVRQAPGKSLEWVATIS EGGGYIYYSDSVKGRFTISRDNAKNSLYLQMNSLRDEDTAVYICAREFGKRY ALDYWGQGTTVTVSS | 19 |
| Hu1210 VH.4d | EVQLVESGGGLVQPGGSLRLSCAASGFTFSSYDMSWVRQAPGKSLEWVATIS DAGGYIYYSDSVKGRFTISRDNAKNSLYLQMNSLRDEDTAVYICAREFGKRY ALDYWGQGTTVTVSS | 20 |
| Hu1210 VH.4e | EVQLVESGGGLVQPGGSLRLSCAASGFTFSSYDMSWVRQAPGKSLEWVATIS DVGGYIYYSDSVKGRFTISRDNAKNSLYLQMNSLRDEDTAVYICAREFGKRY ALDYWGQGTTVTVSS | 21 |
| Hu1210 VH.5 | EVQLVESGGGLVQPGGSLRLSCAASGFTFSSYDMSWVRQAPGKGLEWVATIS DGGGYIYYSDSVKGRFTISRDNAKNSLYLQMNSLRAEDTAVYYCAREFGKRY ALDYWGQGTLVTVSS | 22 |
| HU1210 VH.5a | EVQLVESGGGLVQPGGSLRLSCAASGFTFSSYDMSWVRQAPGKGLEWVATIS DGGGYIYYSDSVKGRFTISRDNAKNSLYLQMNSLRAEDTAVYICAREFGKRY ALDYWGQGTLVTVSS | 23 |
| HU1210 VH.5b | EVQLVESGGGLVQPGGSLRLSCAASGFTFSSYDMSWVRQAPGKGLEWVATIS DGGGYIYYSDSVKGRFTISRDNAKNSLYLQMNSLRAEDTAVYICAREFGKRY ALDYWGQGTTVTVSS | 24 |
| HU1210 VH.5C | EVQLVESGGGLVQPGGSLRLSCAASGFTFSSYDMSWVRQAPGKGLEWVATIS DGGGYIYYSDSVKGRFTISRDNAKNNLYLQMNSLRAEDTAVYICAREFGKRY ALDYWGQGTLVTVSS | 25 |
| HU1210 VH.5d | EVQLVESGGGLVQPGGSLRLSCAASGFTFSSYDMSWVRQTPEKSLEWVATIS DGGGYIYYSDSVKGRFTISRDNAKNNLYLQMNSLRAEDTAVYICAREFGKRY ALDYWGQGTLVTVSS | 26 |
| HL1210-VK | DIVMTQSHKFMSTSVGDRVSISCKASQDVTPAVAWYQQKPGQSPKLLIYSTS SRYTGVPDRFTGSGSGTDFTETISSVQAEDLAVYYCQQHYTTPLTFGAGTKL ELK | 27 |
| Hu1210 VK.1 | DIQMTQSPSSLSASVGDRVTITCKASQDVTPAVAWYQQKPGKAPKLLIYSTS SRYTGVPSRFSGSGSGTDFTETTSSLQPEDIATYYCQQHYTTPLTFGQGTKL EIK | 28 |
| Hu1210 VK.1a | DIQMTQSPSSLSASVGDRVTITCKASQDVTPAVAWYQQKPGKSPKLLIYSTS SRYTGVPSRFSGSGSGTDFTFTISSLQPEDIATYYCQQHYTTPLTFGQGTKL EIK | 29 |
| Hu1210 Vk.2 | DIQMTQSPSSLSASVGDRVTITCKASQDVTPAVAWYQQKPGKAPKLLIYSTS SRYTGVPSRFSGSGSGTDFTLTISSLQPEDFATYYCQQHYTTPLTFGQGTKL EIKR | 30 |

TABLE 8-continued

| | Humanized antibody sequences (bold indicates CDR) | |
|---|---|---|
| Hu1210 Vk.2a | DIQMTQSPSSLSASVGDRVTITCKASQDVTPAVAWYQQKPGKAPKLLIYSTS SRYTGVPDRFTGSGSGTDFTLTISSLQPEDFATYYCQQHYTTPLTFGQGTKL EIKR | 31 |
| Hu1210 Vk.2b | DIQMTQSPSSLSASVGDRVTITCKASQDVTPAVAWYQQKPGQSPKLLIYSTS SRYTGVPDRFTGSGSGTDFTLTISSLQPEDFATYYCQQHYTTPLTFGQGTKL EIKR | 32 |
| Hu1210 Vk.2c | DIQMTQSPSSLSASVGDRVTISCKASQDVTPAVAWYQQKPGQSPKLLIYSTS SRYTGVPDRFTGSGSGTDFTLTISSLQPEDFATYYCQQHYTTPLTFGQGTKL EIKR | 33 |

| Name | Nucleic Acid Sequence | SEQ ID NO: |
|---|---|---|
| HL1210 VH | GAGGTGAAGCTGGTGGAGAGCGGCGGAGATCTGGTGAAGCCTGGCGGCAGCC TGAAGCTGAGCTGTGCCGCCAGCGGCTTCACCTTCAGCAGCTACGACATGAG CTGGGTGAGGCAGACCCCCGAGAAGAGCCTGGAGTGGGTGGCCACCATCAGC GATGGCGGCGGCTACATCTACTACAGCGACAGCGTGAAGGGCAGGTTCACCA TCAGCAGGGACAACGCCAAGAACAACCTGTACCTGCAGATGAGCAGCCTGAG GAGCGAGGACACCGCCCTGTACATCTGCGCCAGGGAGTTCGGCAAGAGGTAC GCCCTGGACTACTGGGGACAGGGCACCAGCGTGACCGTGAGCAGC | 34 |
| Hu1210 VH.1 | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGGTGAGACAGGCCCCTGGCAAAGGCCTGGAGTGGGTGAGCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACTACTGCGCCAGGGAGTTCGGCAAAAGGTAC GCCCTGGACTACTGGGGCCAGGGCACAACCGTGACCGTGAGCAGC | 35 |
| Hu1210 VH.1a | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGGTGAGACAGGCCCCTGGCAAAGGCCTGGAGTGGGTGGCCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACTACTGCGCCAGGGAGTTCGGCAAAAGGTAC GCCCTGGACTACTGGGGCCAGGGCACAACCGTGACCGTGAGCAGC | 36 |
| Hu1210 VH.1b | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGGTGAGACAGGCCCCTGGCAAAAGCCTGGAGTGGGTGGCCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACATCTGCGCCAGGGAGTTCGGCAAATGGTAC GCCCTGGACTACTGGGGCCAGGGCACAACCGTGACCGTGAGCAGC | 37 |
| Hu1210 VH.2 | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGATCAGACAGGCCCCTGGCAAAGGCCTGGAGTGGGTGAGCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACTACTGCGCCAGGGAGTTCGGCAAAAGGTAC GCCCTGGACTACTGGGGCCAGGGCACAACCGTGACCGTGAGCAGC | 38 |
| Hu1210 VH.2a | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGATCAGACAGGCCCCTGGCAAAGGCCTGGAGTGGGTGGCCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACTACTGCGCCAGGGAGTTCGGCAAAAGGTAC GCCCTGGACTACTGGGGCCAGGGCACAACCGTGACCGTGAGCAGC | 39 |
| Hu1210 VH.2b | GAGGTGCAGCTGGTGGAGAGCGGAGGAGGACTGGTGAAGCCCGGAGGCAGCC TGAGACTGAGCTGCGCTGCCAGCGGCTTCACCTTCAGCAGCTACGACATGAG CTGGGTGAGACAGGCCCCTGGCAAAAGCCTGGAGTGGGTGGCCACCATCTCC GATGGCGGCGGCTACATCTATTACTCCGACAGCGTGAAGGGCAGGTTCACCA TCAGCAGGGACAACGCCAAGAACAGCCTGTACCTGCAGATGAACAGCCTGAG GGCCGAGGACACCGCCGTGTACATCTGCGCCAGGGAGTTCGGCAAAAGGTAC GCCCTGGACTACTGGGGCCAGGGCACAACCGTGACCGTGAGCAGC | 40 |
| Hu1210 VH.3 | GAGGTGCAGCTGCTGGAGAGCGGAGGAGGACTGGTGCAACCCGGAGGCAGCC TGAGACTGAGCTGCGCTGCCAGCGGCTTCACCTTCAGCAGCTACGACATGAG CTGGGTGAGACAGGCCCCTGGCAAAGGCCTGGAGTGGGTGAGCACCATCTCC GATGGCGGCGGCTACATCTATTACTCCGACAGCGTGAAGGGCAGGTTCACCA TCAGCAGGGACAACAGCAAGAACACCCTGTACCTGCAGATGAACAGCCTGAG GGCCGAGGACACCGCCGTGTACTACTGCGCCAGGGAGTTCGGCAAAAGGTAC GCCCTGGACTACTGGGGCCAGGGCACAACCGTGACCGTGAGCAGG | 41 |

TABLE 8-continued

| Humanized antibody sequences (bold indicates CDR) | | |
|---|---|---|
| Hu1210 VH.3a | GAGGTGCAGCTGCTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GATGGCGGCGGCTAGATCTATTAGTCCGAGAGCGTGAAGGGGAGGTTCACCA<br>TCAGCAGGGACAACAGCAAGAACACCCTGTACCTGCAGATGAACAGCCTGAG<br>GGCCGAGGACACCGCCGTGTACATCTGCGCCAGGGAGTTCGGCAAAAGGTAC<br>GCCCTGGACTACTGGGGCCAGGGCACAACCGTGACCGTGAGCAGC | 42 |
| Hu1210 VH.4 | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAGGCCTGGAGTGGGTGAGCACCATCTCC<br>GATGGCGGCGGCTACATCTATTACTCCGACAGCGTGAAGGGCAGGTTCACCA<br>TCAGCAGGGACAACGCCAAGAACAGCCTGTACCTGCAGATGAACAGCCTGAG<br>GGATGAGGACACCGCCGTGTACTACTGCGCCAGGGAGTTCGGCAAAAGGTAC<br>GCCCTGGACTACTGGGGCCAGGGCACAACCGTGACCGTGAGCAGC | 43 |
| Hu1210 VH.4a | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GATGGCGGCGGCTAGATCTATTAGTCCGAGAGCGTGAAGGGCAGGTTCACCA<br>TCAGGAGGGACAACGCCAAGAACAGCCTGTACCTGCAGATGAACAGCCTGAG<br>GGATGAGGACACCGCCGTGTACTACTGCGCCAGGGAGTTCGGCAAAAGGTAC<br>GCCCTGGACTACTGGGGCCAGGGCACAACCGTGACCGTGAGCAGC | 44 |
| Hu1210 VH.4b | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GATGGCGGCGGCTACATCTATTACTCCGACAGCGTGAAGGGCAGGTTCACCA<br>TCAGCAGGGACAACGCCAAGAACAGCCTGTACCTGCAGATGAACAGCCTGAG<br>GGATGAGGACACCGCCGTGTACATCTGCGCCAGGGAGTTCGGCAAAAGGTAC<br>GCCCTGGACTACTGGGGCCAGGGCACAACCGTGACCGTGAGCAGC | 45 |
| Hu1210 VH.4c | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GAAGGCGGCGGCTACATCTATTACTCCGACAGCGTGAAGGGCAGGTTCACCA<br>TCAGCAGGGACAACGCCAAGAACAGCCTGTACCTGCAGATGAACAGCCTGAG<br>GGATGAGGACACCGCCGTGTACATCTGCGCCAGGGAGTTCGGCAAAAGGTAC<br>GCCCTGGACTACTGGGGCCAGGGCACAACCGTGACCGTGAGCAGC | 46 |
| Hu1210_VH.4d | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GATGCGGGCGGCTACATCTATTACTCCGACAGCGTGAAGGGCAGGTTCACCA<br>TCAGCAGGGACAACGCCAAGAACAGCCTGTACCTGCAGATGAACAGCCTGAG<br>GGATGAGGACACCGCCGTGTACATCTGCGCCAGGGAGTTCGGCAAAAGGTAC<br>GCCCTGGACTACTGGGGCCAGGGCACAACCGTGACCGTGAGCAGC | 47 |
| Hu1210_VH.4e | GAGGTGCAGCTGGTGGAGAGCGGAGGAGGACTGGTGCAACCCGGAGGCAGCC<br>TGAGACTGAGCTGCGCTGCCAGCGGCTTCACCTTCAGCAGCTACGACATGAG<br>CTGGGTGAGACAGGCCCCTGGCAAAAGCCTGGAGTGGGTGGCCACCATCTCC<br>GATGTTGGCGGCTACATCTATTACTCCGACAGCGTGAAGGGCAGGTTCACCA<br>TCAGCAGGGACAACGCCAAGAACAGCCTGTACCTGCAGATGAACAGCCTGAG<br>GGATGAGGACACCGCCGTGTACATCTGCGCCAGGGAGTTCGGCAAAAGGTAC<br>GCCCTGGACTACTGGGGCCAGGGCACAACCGTGACCGTGAGCAGC | 48 |
| Hu1210 VH.5 | GAGGTGCAGCTGGTGGAGTCCGGAGGAGGCCTGGTGCAACCTGGAGGCTCCC<br>TGAGGCTGTCCTGTGCCGCTTCCGGCTTCACCTTCAGCTCCTACGATATGAG<br>CTGGGTGAGGCAGGCTCCTGGAAAGGGCCTGGAGTGGGTGGCCACCATCTCC<br>GACGGAGGCGGCTACATCTACTACTCCGACTCCGTGAAGGGCAGGTTCACCA<br>TCTCCCGGGACAACGCCAAGAACTCCCTGTACCTGCAGATGAACTCTCTCAG<br>GGCTGAGGACACCGCCGTGTATTACTGCGCCAGGGAGTTTGGCAAGAGGTAC<br>GCCCTGGATTACTGGGGCCAGGGCACACTGGTGACAGTGAGCTCC | 49 |
| Hu1210 VH.5a | GAGGTGCAGCTGGTGGAGTCCGGAGGAGGCCTGGTGCAACCTGGAGGCTCCC<br>TGAGGCTGTCCTGTGCCGCTTCCGGCTTCACCTTCAGCTCCTACGATATGAG<br>CTGGGTGAGGCAGGCTCCTGGAAAGGGCCTGGAGTGGGTGGCCACCATCTCC<br>GACGGAGGCGGCTACATCTACTACTCCGACTCCGTGAAGGGCAGGTTCACCA<br>TCTCCCGGGACAACGCCAAGAACTCCCTGTACCTGCAGATGAACTCTCTCAG<br>GGCTGAGGACACCGCCGTGTATATCTGCGCCAGGGAGTTTGGCAAGAGGTAC<br>GCCCTGGATTACTGGGGCCAGGGCACACTGGTGACAGTGAGCTCC | 50 |
| Hu1210 VH.5b | GAGGTGCAGCTGGTGGAGTCCGGAGGAGGCCTGGTGCAACCTGGAGGCTCCC<br>TGAGGCTGTCCTGTGCCGCTTCCGGCTTCACCTTCAGCTCCTACGATATGAG<br>CTGGGTGAGGCAGGCTCCTGGAAAGGGCCTGGAGTGGGTGGCCACCATCTCC<br>GACGGAGGCGGCTACATCTACTACTCCGACTCCGTGAAGGGCAGGTTCACCA<br>TCTCCCGGGACAACGCCAAGAACAACCTGTACCTGCAGATGAACTCTCTCAG | 51 |

TABLE 8-continued

| | Humanized antibody sequences (bold indicates CDR) | |
|---|---|---|
| | GGCTGAGGACACCGCCGTGTATATCTGCGCCAGGGAGTTTGGCAAGAGGTAC<br>GCCCTGGATTACTGGGGCCAGGGCACACTGGTGACAGTGAGCTCC | |
| Hu1210 VH.5c | GAGGTGCAGCTGGTGGAGTCCGGAGGAGGCCTGGTGCAACCTGGAGGCTCCC<br>TGAGGCTGTCCTGTGCCGCTTCCGGCTTCACCTTCAGCTCCTACGATATGAG<br>CTGGGTGAGGCAGACCCCTGAGAAGAGCCTGGAGTGGGTGGCCACCATCTCC<br>GACGGAGGCGGCTACATCTACTACTCCGACTCCGTGAAGGGCAGGTTCACCA<br>TCTCCCGGGACAACGCCAAGAACAACCTGTACCTGCAGATGAACTCTCTCAG<br>GGCTGAGGACACCGCCGTGTATATCTGCGCCAGGGAGTTTGGCAAGAGGTAC<br>GCCCTGGATTACTGGGGCCAGGGCACACTGGTGACAGTGAGCTCC | 52 |
| Hu1210_VH.5d | GAGGTGCAGCTGGTGGAGTCCGGAGGAGGCCTGGTGCAACCTGGAGGCTCCC<br>TGAGGCTGTCCTGTGCCGCTTCCGGCTTCACCTTCAGCTCCTACGATATGAG<br>CTGGGTGAGGCAGGCTCCTGGAAAGGGCCTGGAGTGGGTGGCCACCATCTCC<br>GACGGAGGCGGCTACATCTACTACTCCGACTCCGTGAAGGGCAGGTTCACCA<br>TCTCCCGGGACAACGCCAAGAACTCCCTGTACCTGCAGATGAACTCTCTCAG<br>GGCTGAGGACACCGCCGTGTATATCTGCGCCAGGGAGTTTGGCAAGAGGTAC<br>GCCCTGGATTACTGGGGCCAGGGCACAACCGTGACAGTGAGCTCC | 53 |
| HL1210 VK | GACATCGTGATGACCCAGAGCCACAAGTTCATGAGCACCAGCGTGGGCGATA<br>GGGTGAGCATCAGCTGCAAGGCCAGCCAGGATGTGACCCCTGCCGTGGCCTG<br>GTACCAGCAGAAGCCCGGCCAGAGCCCCAAGCTGCTGATCTACAGCACCAGC<br>AGCAGGTACACCGGCGTGCCCGACAGGTTCACAGGAAGCGGCAGCGGCACCG<br>ACTTCACCTTCACCATCAGCAGCGTGCAGGCCGAGGACCTGGCCGTGTACTA<br>CTGCCAGCAGCACTACACCACCCCTCTGACCTTCGGCGCCGGCACCAAGCTG<br>GAGCTGAAG | 54 |
| Hu1210 VK.1 | GACATCCAGATGACCCAGAGCCCTAGCAGCCTGAGCGCTAGCGTGGGCGACA<br>GGGTGACCATCACCTGCAAGGCCAGCCAGGATGTGACCCCTGCCGTGGCCTG<br>GTACCAGCAGAAGCCCGGCAAGGCCCCCAAGCTGCTGATCTACAGCACCAGC<br>AGCAGGTACACCGGCGTGCCCAGCAGGTTTAGCGGAAGCGGCAGCGGCACCG<br>ACTTCACCTTCACCATCAGCAGCCTGCAGCCCGAGGACATCGCCACCTACTA<br>CTGCCAGCAGCACTACACCACCCCTCTGACCTTCGGCCAGGGCACCAAGCTG<br>GAGATCAAG | 55 |
| Hu1210 VK.1a | GACATCCAGATGACCCAGAGCCCTAGCAGCCTGAGCGCTAGCGTGGGCGACA<br>GGGTGACCATCACCTGCAAGGCCAGCCAGGATGTGACCCCTGCCGTGGCCTG<br>GTACCAGCAGAAGCCCGGCAAGTCCCCCAAGCTGCTGATCTACAGCACCAGC<br>AGCAGGTACACCGGCGTGCCCAGCAGGTTTAGCGGAAGCGGCAGCGGCACCG<br>ACTTCACCTTCACCATCAGCAGCCTGCAGCCCGAGGACATCGCCACCTACTA<br>CTGCCAGCAGCACTACACCACCCCTCTGACCTTCGGCCAGGGCACCAAGCTG<br>GAGATCAAG | 56 |
| Hu1210 VK.2 | GACATTCAGATGACCCAGTCCCCTAGCAGCCTGTCCGCTTCCGTGGGCGACA<br>GGGTGACCATCACCTGCAAGGCCAGCCAGGACGTGACACCTGCTGTGGCCTG<br>GTATCAACAGAAGCCTGGCAAGGCTCCTAAGCTCCTGATCTACAGCACATCC<br>TCCCGGTACACCGGAGTGCCCTCCAGGTTTAGCGGCAGCGGCTCCGGCACCG<br>ATTTCACCCTGACCATTCCTCCCTGCAGCCCGAGGACTTCGCCACCTACTA<br>CTGCCAGCAGCACTACACCACACCCCTGACCTTCGGCCAGGGCACCAAGCTG<br>GAGATCAAGCGG | 57 |
| Hu1210 VK.2a | GACATTCAGATGACCCAGTCCCCTAGCAGCCTGTCCGCTTCCGTGGGCGACA<br>GGGTGACCATCACCTGCAAGGCCAGCCAGGACGTGACACCTGCTGTGGCCTG<br>GTATCAACAGAAGCCTGGCAAGGCTCCTAAGCTCCTGATCTACAGCACATCC<br>TCCCGGTACACCGGAGTGCCCGACAGGTTTACCGGCAGCGGCTCCGGCACCG<br>ATTTCACCCTGACCATTCCTCCCTGCAGCCCGAGGACTTCGCCACCTACTA<br>CTGCCAGCAGCACTACACCACACCCCTGACCTTCGGCCAGGGCACCAAGCTG<br>GAGATCAAGCGG | 58 |
| Hu1210 VK.2b | GACATTCAGATGACCCAGTCCCCTAGCAGCCTGTCCGCTTCCGTGGGCGACA<br>GGGTGACCATCACCTGCAAGGCCAGCCAGGACGTGACACCTGCTGTGGCCTG<br>GTATCAACAGAAGCCTGGCCAGAGCCCTAAGCTCCTGATCTACAGCACATCC<br>TCCCGGTACACCGGAGTGCCCGACAGGTTTACCGGCAGCGGCTCCGGCACCG<br>ATTTCACCCTGACCATTCCTCCCTGCAGCCCGAGGACTTCGCCACCTACTA<br>CTGCCAGCAGCACTACACCACACCCCTGACCTTCGGCCAGGGCACCAAGCTG<br>GAGATCAAGCGG | 59 |
| Hu1210 VK.2c | GACATTCAGATGACCCAGTCCCCTAGCAGCCTGTCCGCTTCCGTGGGCGACA<br>GGGTGACCATCAGCTGCAAGGCCAGCCAGGACGTGACACCTGCTGTGGCCTG<br>GTATCAACAGAAGCCTGGCCAGAGCCCTAAGCTCCTGATCTACAGCACATCC<br>TCCCGGTACACCGGAGTGCCCGACAGGTTTACCGGCAGCGGCTCCGGCACCG<br>ATTTCACCCTGACCATTCCTCCCTGCAGCCCGAGGACTTCGCCACCTACTA<br>CTGCCAGCAGCACTACACCACACCCCTGACCTTCGGCCAGGGCACCAAGCTG<br>GAGATCAAGCGG | 60 |

The humanized VH and VK genes were produced synthetically and then respectively cloned into vectors containing the human gamma 1 and human kappa constant domains. The pairing of the human VH and the human VK created the 40 humanized antibodies (see Table 9).

To explore the binding kinetics of the humanized antibody, this example performed the affinity ranking by using Octet® Red 96 (a bio-layer interferometry platform). As shown in Table 10, hu1210-3, hu1210-8, hu1210-9, hu1210-14, hu1210-17, hu1210-1 and Hu1210-22 show better affinity, which is comparable with chimeric antibody.

TABLE 9

Humanized antibodies with their VH an VL regions

| VH Vk | Hu1210 VH.1 | Hu1210 VH.1a | Hu1210 VH.1b | Hu1210 VH.2 | Hu1210 VH.2a | Hu1210 VH 2.b | Hu1210 VH |
|---|---|---|---|---|---|---|---|
| Hu1210 Vk.1 | Hu1210-1 | Hu1210-2 | Hu1210-3 | Hu1210-4 | Hu1210-5 | | |
| Hu1210 Vk.1a | Hu1210-7 | Hu1210-8 | Hu1210-9 | Hu1210-10 | Hu1210-11 | | |
| Hu1210 Vk | | | | | | | H1210 chimera |

| VH Vk | Hu1210 VH.3 | Hu1210 VH.3a | Hu1210 VH.4 | Hu1210 VH.4a | Hu1210 VH.4b |
|---|---|---|---|---|---|
| Hu1210 Vk.1 | Hu1210-13 | Hu1210-14 | Hu1210-15 | Hu1210-16 | Hu1210-17 |
| Hu1210 Vk.1a | Hu1210-18 | Hu1210-19 | Hu1210-20 | Hu1210-21 | Hu1210-22 |

| VH VK | Hu1210 VH.5 | HU1210 VH.5a | HU1210 VH.5b | HU1210 VH.5c | HU1210 VH.Sd |
|---|---|---|---|---|---|
| Hu1210 Vk.2 | Hu1210-23 | Hu1210-27 | Hu1210-31 | Hu1210-32 | Hu1210-36 |
| Hu1210 Vk.2a | Hu1210-24 | Hu1210-28 | | Hu1210-33 | Hu1210-37 |
| Hu1210 Vk.2b | Hu1210-25 | Hu1210-29 | | Hu1210-34 | Hu1210-38 |
| Hu1210 Vk.2c | Hu1210-26 | Hu1210-30 | | Hu1210-35 | Hu1210-39 |

| VH Vk | Hu1210 VH.4c | Hu1210 VH.4d | Hu1210 VH.4e |
|---|---|---|---|
| Hu1210 Vk.1 | Hu1210-40 | Hu1210-41 | Hu1210-42 |

1.6. Antigen Binding Properties of Humanized PD-L1 Antibodies

To evaluate the antigen binding activity, the humanized antibodies were subjected to ELISA test. Briefly, microtiter plates were coated with human PD-L1-Fc protein at 0.1 µg/ml in PBS, 100 µl/well at 4° C. overnight, then blocked with 100 µl/well of 5% BSA. Five-fold dilutions of humanized antibodies starting from 10 µg/ml were added to each well and incubated for 1-2 hours at RT. The plates were washed with PBS/Tween® and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. As shown in FIGS. 6A-6E, all the humanized antibodies show comparable binding efficacy to human PD-L1 in contact to chimeric antibody.

Figure 7A:
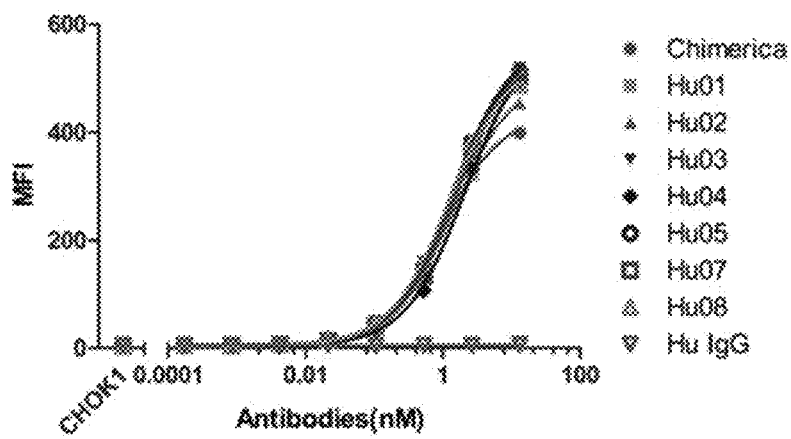
FIGS. 7A-7C shows that all tested humanized antibodies can high efficiently bind to PD-L1 expressed on mammalian cells, comparable with chimeric antibody.
Figure 7B:
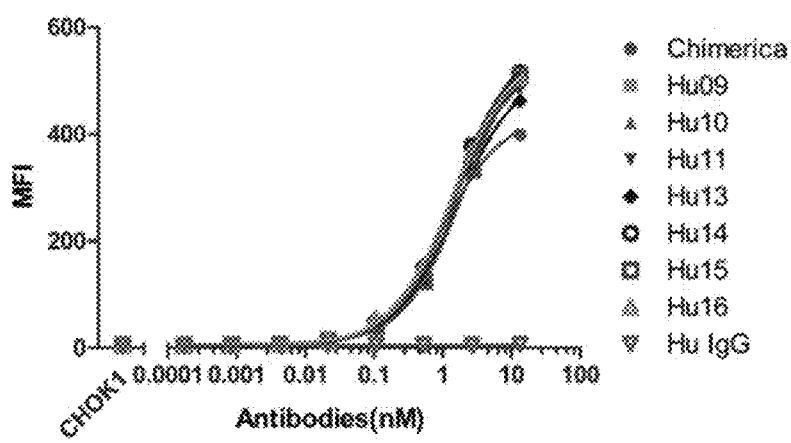
Figure 7C:
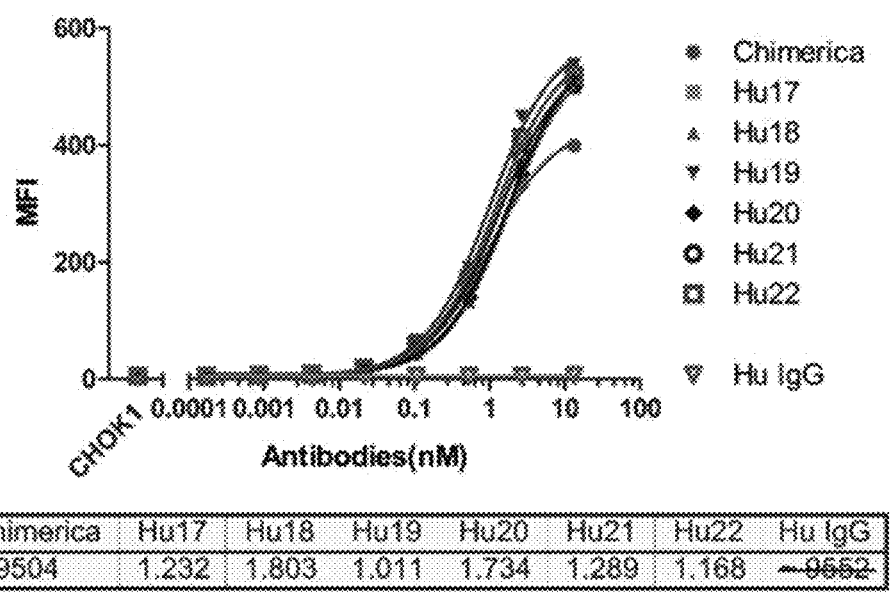

To evaluate the antigen binding property, the humanized antibodies were analyzed for its binding to mammalian expressed PD-L1 by FACS. Briefly, PDL1-CHOK1 cells were firstly incubated with 5-fold serious diluted humanized antibodies starting at 2 µg/ml at RT for 1 hour. After wash by FACS buffer (PBS with 2% FBS), the Alexa Fluor®488-anti-human IgG antibody was added to each well and incubated at RT for 1 hour. The MFI of Alexa Fluor® 488 was evaluated FACSAria™ III. As shown in the FIGS. 7A-7C, all the humanized antibodies can high efficiently bind to PD-L1 expressed on mammalian cells, which was comparable with chimeric antibody.

TABLE 10

Affinity ranking of humanized antibodies

| Antibody | KD (M) | Kon (1/Ms) | kdis(1/s) |
|---|---|---|---|
| Hu1210 (mIgG) | 7.16E−09 | 3.94E+05 | 2.83E−03 |
| H1210 chimera | 1.07E−09 | 1.62E+05 | 1.73E−04 |
| Hu1210-1 | 4.25E−09 | 7.10E+04 | 3.02E−04 |
| Hu1210-2 | 3.23E−09 | 7.78E+04 | 2.51E−04 |
| Hu1210-3 | 2.64E−09 | 8.62E+04 | 2.28E−04 |
| Hu1210-4 | 7.68E−09 | 7.12E+04 | 5.46E−04 |
| Hu1210-5 | 4.83E−09 | 7.93E+04 | 3.83E−04 |
| Hu1210-7 | 4.78E−09 | 8.45E+04 | 4.04E−04 |
| Hu1210-8 | 1.64E−09 | 7.72E+04 | 1.27E−04 |
| Hu1210-9 | 2.33E−09 | 8.37E+04 | 1.95E−04 |
| Hu1210-10 | 7.03E−09 | 8.59E+04 | 6.04E−04 |
| Hu1210-11 | 4.18E−09 | 7.54E+04 | 3.15E−04 |
| Hu1210-13 | 4.36E−09 | 8.38E+04 | 3.66E−04 |
| Hu1210-14 | 2.34E−09 | 8.41E+04 | 1.97E−04 |
| Hu1210-15 | 4.45E−09 | 7.87E+04 | 3.50E−04 |
| Hu1210-16 | 3.14E−09 | 8.41E+04 | 2.64E−04 |
| Hu1210-17 | 2.20E−09 | 8.17E+04 | 1.80E−04 |
| Hu1210-18 | 4.50E−09 | 7.92E+04 | 3.57E−04 |
| Hu1210-19 | 2.50E−09 | 9.03E+04 | 2.25E−04 |
| Hu1210-20 | 4.51E−09 | 8.87E+04 | 4.00E−04 |
| Hu1210-21 | 3.12E−09 | 9.39E+04 | 2.93E−04 |
| Hu1210-22 | 2.56E−09 | 9.00E+04 | 2.30E−04 |

The binding of the humanized antibodies to recombinant PD-L1 protein (human PD-L1-his taq) was tested by BIACORE™ using a capture method. The HL1210-3 mouse mAb were captured using anti-mouse Fc antibody coated on a CM5 chip. A series dilution of human PD-L1-his taq protein was injected over captured antibody for 3 mins at a flow rate of 25 µg/ml. The antigen was allowed to dissociate for 900 s. All the experiments were carried out on a Biacore™ T200. Data analysis was carried out using Biacore™ T200 evaluation software and is shown in Table 11 below.

TABLE 11

Affinity by Biacore

| Antibody | ka (1/Ms) | kd (1/s) | KD (M) |
|---|---|---|---|
| Hu1210-8 | 9.346E+4 | 7.169E-5 | 7.671E-10 |
| Hu1210-9 | 9.856E+4 | 4.528E-5 | 4.594E-10 |
| Hu1210-14 | 1.216E+5 | 5.293E-5 | 4.352E-10 |
| Hu1210-16 | 9.978E+4 | 6.704E-5 | 6.720E-10 |
| Hu1210-17 | 1.101E+5 | 2.128E-5 | 1.933E-10 |
| Hu1210-28 | 1.289E+5 | 1.080E-4 | 8.378E-10 |
| Hu1210-31 | 1.486E+5 | 1.168E-4 | 7.862E-10 |
| Hu1210-36 | 1.461E+5 | 7.852E-5 | 5.376E-10 |
| Hu1210-40 | 8.77E+04 | 1.31E-04 | 1.49E-09 |
| Hu1210-41 | 9.17E+04 | 3.46E-05 | 3.78E-10 |
| Hu1210-42 | 8.68E+04 | 7.53E-05 | 8.67E-10 |
| 1210 Chimera | 1.236E+5 | 3.265E-5 | 2.642E-10 |

1.7. Cross Species Activity

Figure 8:
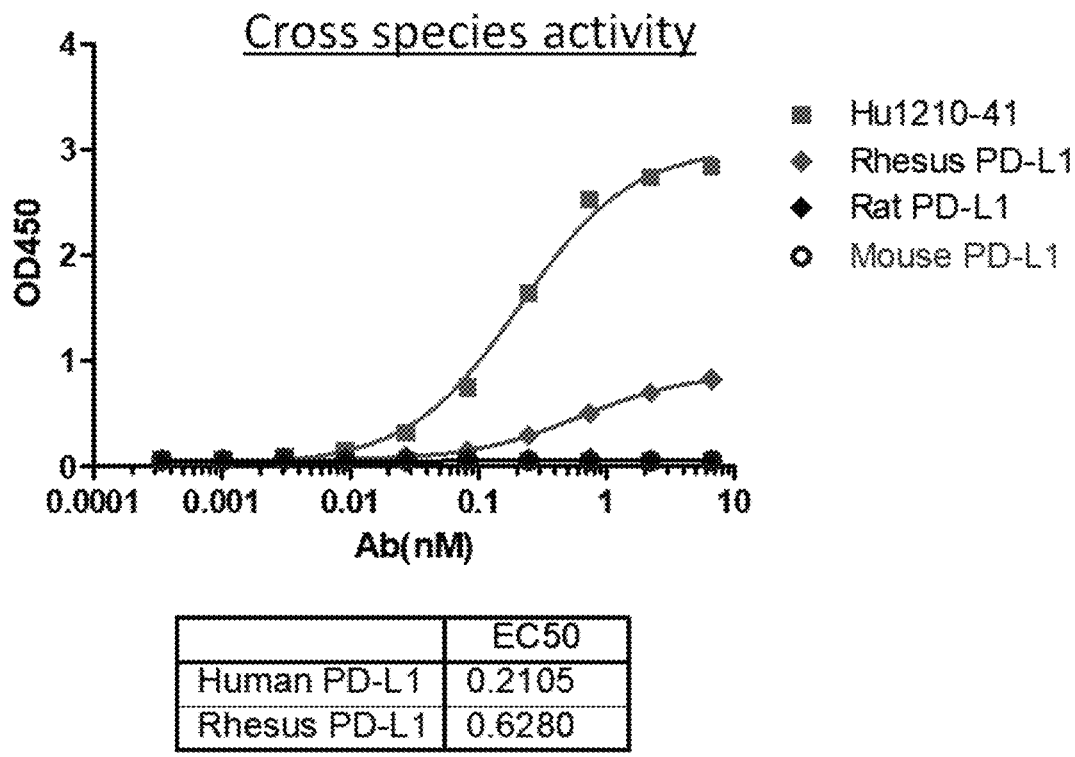
FIG. 8 shows that humanized antibody Hu1210-41 can bind to rhesus PD-L1 with lower affinity and cannot bind to rat and mouse PD-1.

To evaluate the binding of humanized antibodies to huPD-L1, Mouse PD-L1, Rat PD-L1, Rhesus PD-L1, the antibodies were performed for the ELISA testing. Briefly, microtiter plates were coated with human, mouse, rat and rhesus PD-L1-Fc protein at 1 µg/ml in PBS, 100 µl/well at 4° C. overnight, then blocked with 100 µl/well of 5% BSA. Three-fold dilutions of humanized antibodies starting from 1 µg/ml were added to each well and incubated for 1-2 hours at RT. The plates were washed with PBS/Tween® and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. The Hu1210-41 antibody can bind to rhesus PD-L1 with lower affinity and cannot bind to rat and mouse PD-L1 (FIG. 8 & Table 12).

TABLE 12

| | Human | Rhesus | Rat | Mouse |
|---|---|---|---|---|
| EC50 | 0.215 nM | 0.628 nM | No binding | No binding |

Figure 9:
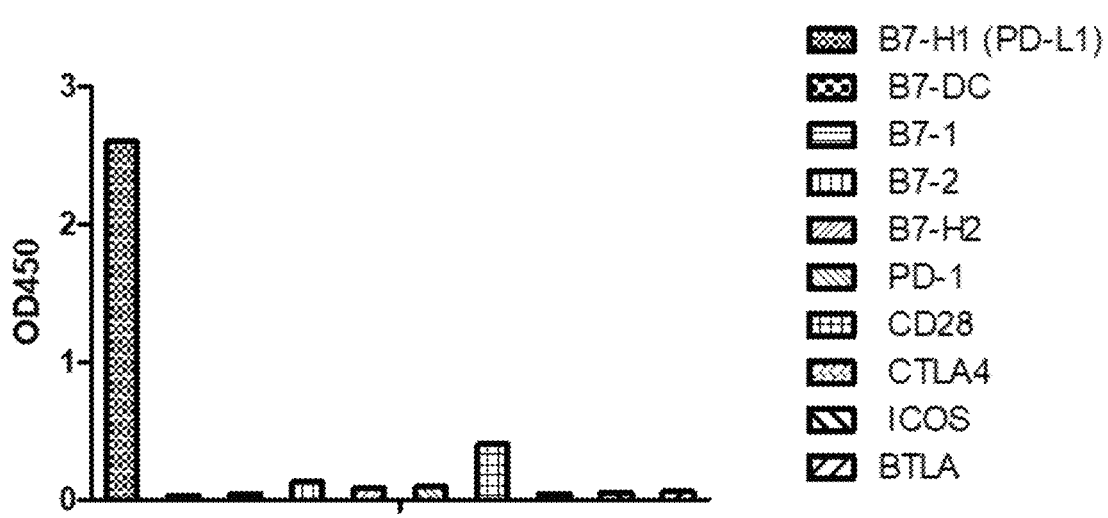
FIG. 9 shows that Hu1210-41 antibody can only specifically binding to B7-H1 (PD-L1), not B7-DC, B7-1, B7-2, B7-H2, PD-1, CD28, CTLA4, ICOS and BTLA.

To evaluate the binding of humanized anti-PD-L1 antibody to human B7 family and other immune checkpoint, the antibody was evaluate for its binding to B7-H1 (PD-L1), B7-DC, B7-1, B7-2, B7-H2, PD-1, CD28, CTLA4, ICOS and BTLA by ELISA. As shown in FIG. 9, the Hu1210-41 antibody can only specifically bind to B7-H1 (PD-L1).

1.8. Activity of Humanized Anti-PD-L1 Antibodies to Block Human PD-L1 to PD-1

Cell Based Receptor Blocking Assay

To evaluate the blocking effect of humanized antibodies on human PD-L1 expressed on mammalian cells to bind to its receptor PD-1, the FACS-based receptor blocking assay was employed. Briefly, PDL1-CHOK1 cells were firstly incubated with 3-fold serious diluted HL1210-3 mouse mAb starting at 20 µg/ml at RT for 1 hour. After wash by FACS buffer (PBS with 2% FBS), the biotin-labeled huPD-1 were added to each well and incubated at RT for 1 hour. Then, the Streptavidin-PE was added to each well for 0.5 hour post twice wash with FACS buffer. The mean florescence intensity (MFI) of PE was evaluated by FACSAria™ III.

$$\% \text{ of inhibition} = \left(1 - \frac{MFI \text{ of testing antibody}}{MFI \text{ of vehicle contori}}\right) \times 100\%$$

As shown in Table 13 below, Hu1210-3, Hu1210-9, Hu1210-8, Hu1210-14, Hu1210-17, Hu1210-19 and Hu1210-22 antibodies show comparable efficacy with chimeric antibody to blocking the binding of PD-L1 to PD-1.

TABLE 13

PD-1 receptor blocking assay

| | Bio-PD1(30 µg/ml) | |
|---|---|---|
| | TOP | EC50 |
| H1210 chimera | 87.16 | 3.961 |
| Hu1210-8 | 86.35 | 4.194 |
| Hu1210-9 | 85.7 | 4.038 |
| Hu1210-16 | 88.02 | 5.436 |
| Hu1210-17 | 80.88 | 4.424 |
| Hu1210-3 | 84.28 | 3.693 |
| Hu1210-14 | 79.56 | 3.572 |
| Hu1210-19 | 87.45 | 4.52 |
| Hu1210-22 | 85.83 | 4.505 |
| Hu1210-27 | 103.9 | 11.48 |
| Hu1210-31 | 92.91 | 6.179 |
| Hu1210-36 | 91.75 | 8.175 |

Receptor Blocking Assay by Using Recombinant Human PD-L1

Figure 10:
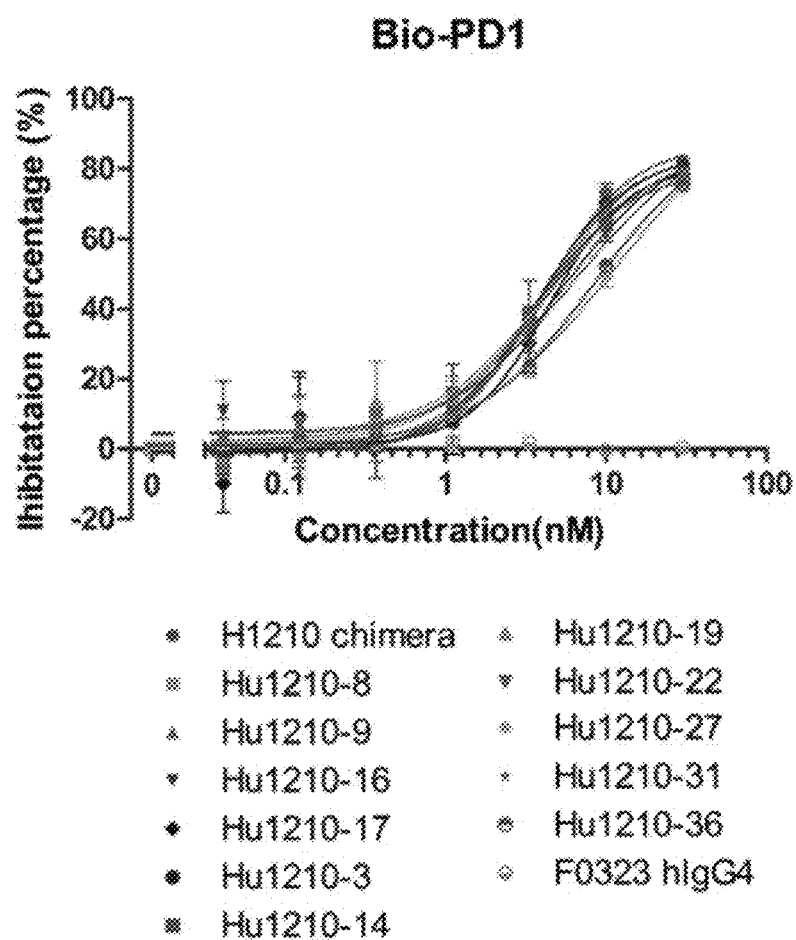
FIG. 10 shows that Hu1210-41 can efficiently inhibit the binding of human PD-L1 to human PD1 and B7-1.
Figure 11:
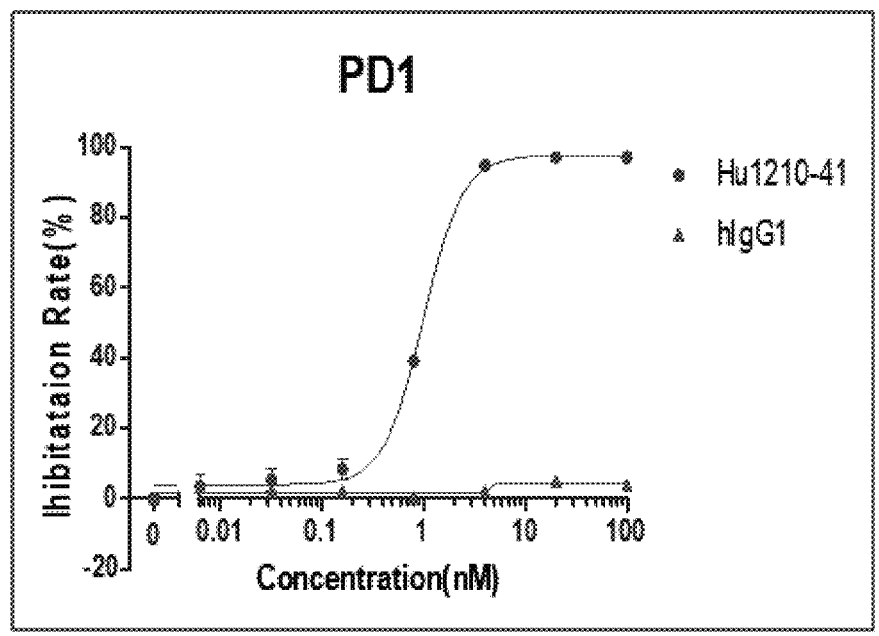
FIG. 11 shows that Hu1210-41 can efficiently inhibit the binding of human PD-L1 to human PD1 and B7-1.
Figure 11:
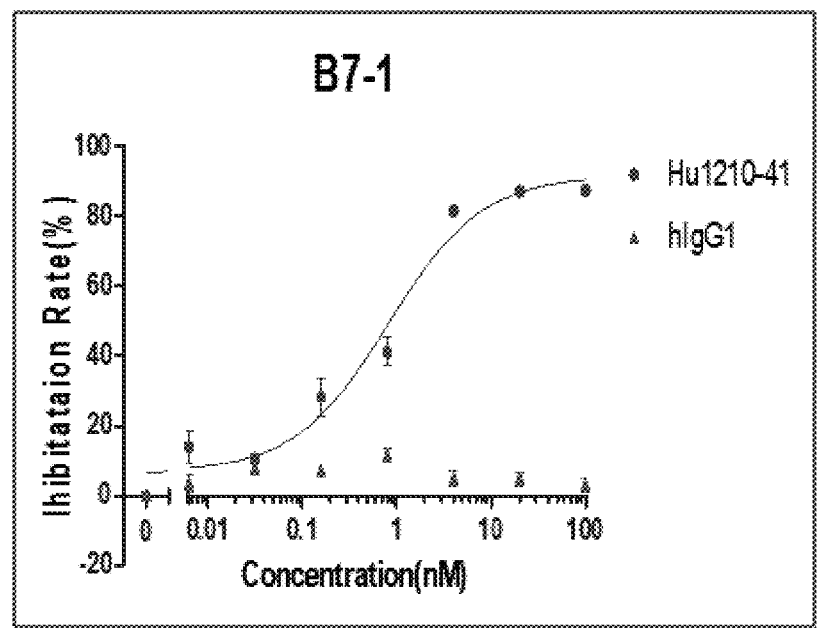

There are two receptors i.e. PD-1 and B7-1 for human PD-L1. To explore the blocking property of humanized PD-L1 antibody to these two proteins, the protein based receptor blocking assay was employed here. Briefly, microtiter plates were coated with human PD-L1-Fc protein at 1 µg/ml in PBS, 100 µl/well at 4° C. overnight, then blocked with 200 µl/well of 5% BSA at 37° C. for 2 hr. 50 µl biotin-labeled human PD-1-Fc or B7-1 protein and 5-fold dilutions of PD-L1 antibodies starting from 100 nM at 50 µl were added to each well and incubated for 1 hour at 37° C. The plates were washed with PBS/Tween® and then incubate with Streptavidin-HRP for 1 hour at 37° C. After washing, the plates were developed with TMB substrate and analyzed by spectrophotometer at OD 450 nm. As shown in FIGS. 10 and 11, Hu1210-41 can efficiently inhibit the binding of human PD-L1 to human PD1 and B7-1.

1.9. Activity of Humanized Anti-PD-L1 Antibody to Promote Human T Cell Immune Response Mixed Lymphocyte Reaction Assay To evaluate the in vitro function of humanized antibodies, the response of human T cells assessed in a mixed lymphocyte reaction setting. Human DCs were differentiated from CD14+monocytes in the presence of GM-CSF and IL-4 for 7 days. CD4+ T cells isolated from another donor were then co-cultured with the DCs and serial dilutions of anti-PD-L1 blocking antibody. At day 5 post-inoculation, the culture supernatant was assayed for IL-2 and IFNγ production. The results indicated that the Hu1210-8, Hu1210-9, Hu1210-16 and Hu1210-17 antibodies can dose-dependently promote IL-2 and IFNγ production, suggesting anti-PD-L1 antibodies can promote human T cell response.

CMV Recall Assay

Figure 12:
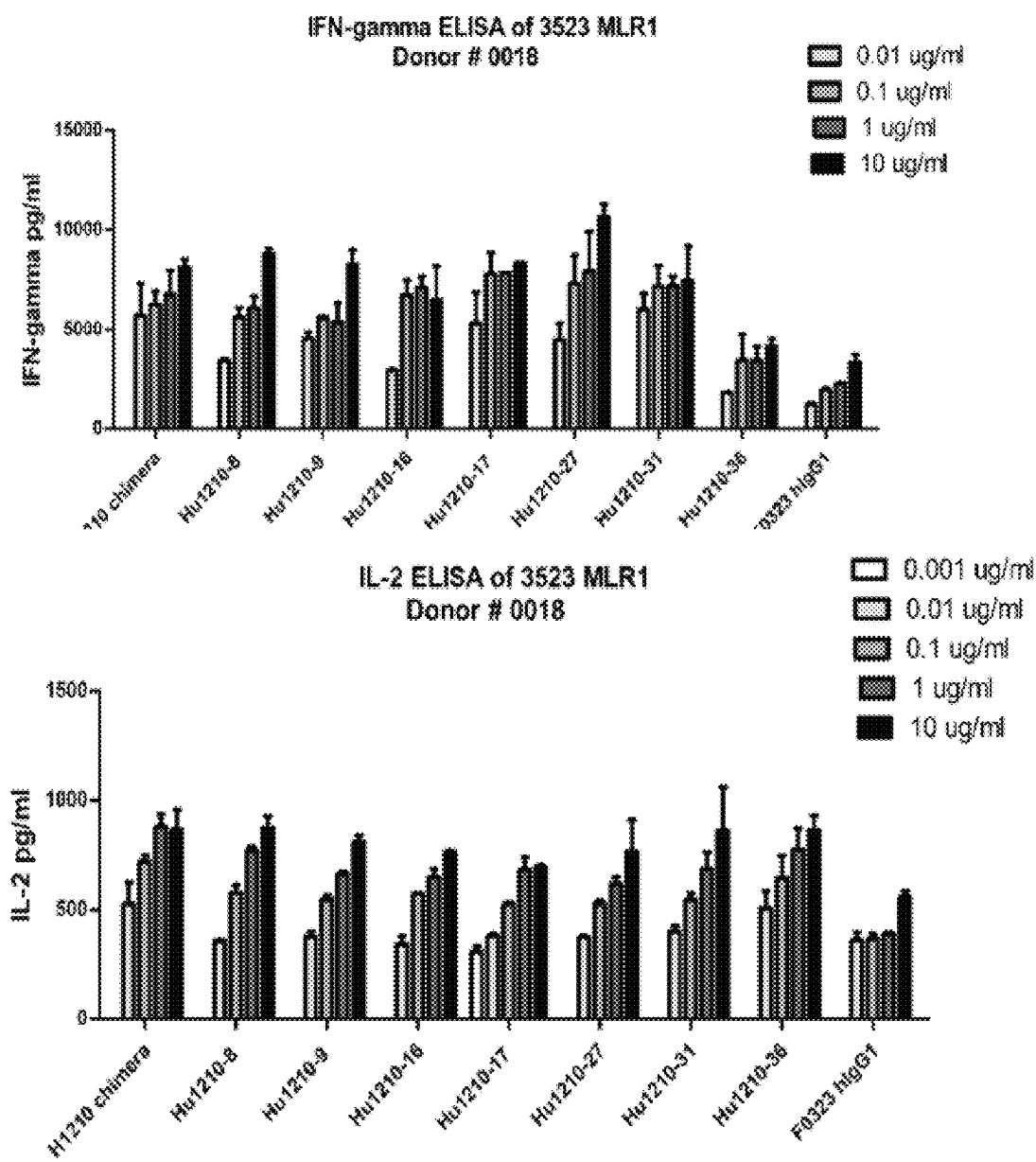
FIG. 12 shows that the Hu1210-8, Hu1210-9, Hu1210-16, Hu1210-17, Hu1210-21 and Hu1210-36 humanized antibodies can dose dependently promote the IFNγ and IL-2 production in mix lymphocyte reaction.
Figure 13:
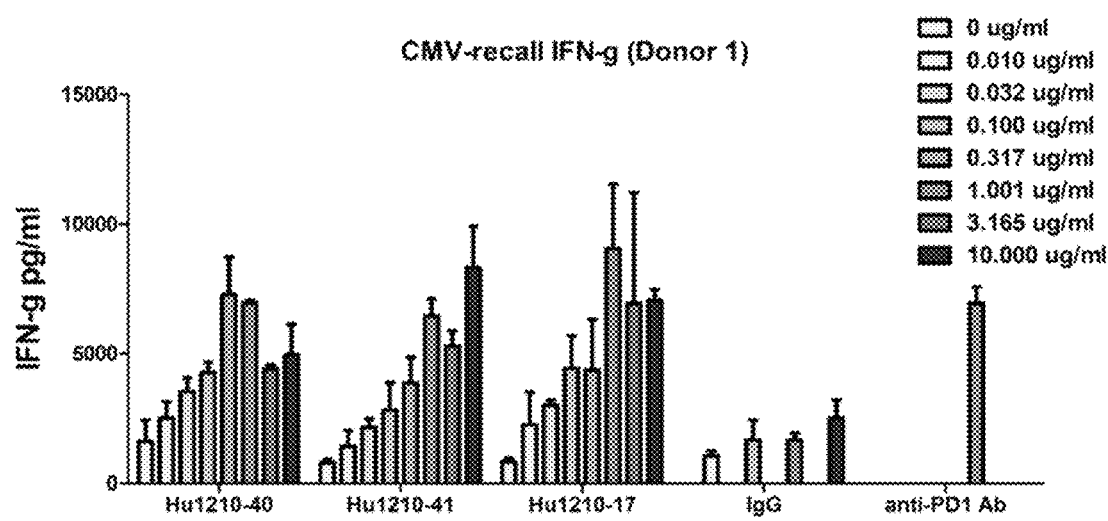
FIG. 13 shows that the Hu1210-40, Hu1210-41 and Hu1210-17 humanized antibodies can dose dependently promote the IFNγ production in CMV recall assay.

To evaluate the in vitro function of humanized antibodies, the response of human T cells assessed in CMV recall assay. Human PBMCs were stimulated with 1 µg/ml CMV antigen in the presence of serious diluted humanized antibodies. As shown in FIGS. 12 and 13 the Hu1210-40, Hu1210-41 and Hu1210-17 can dose dependently promote the IFNγ production.

1.10. Tumor Growth Inhibition by Anti-PD-L1 mAb.

Figure 14:
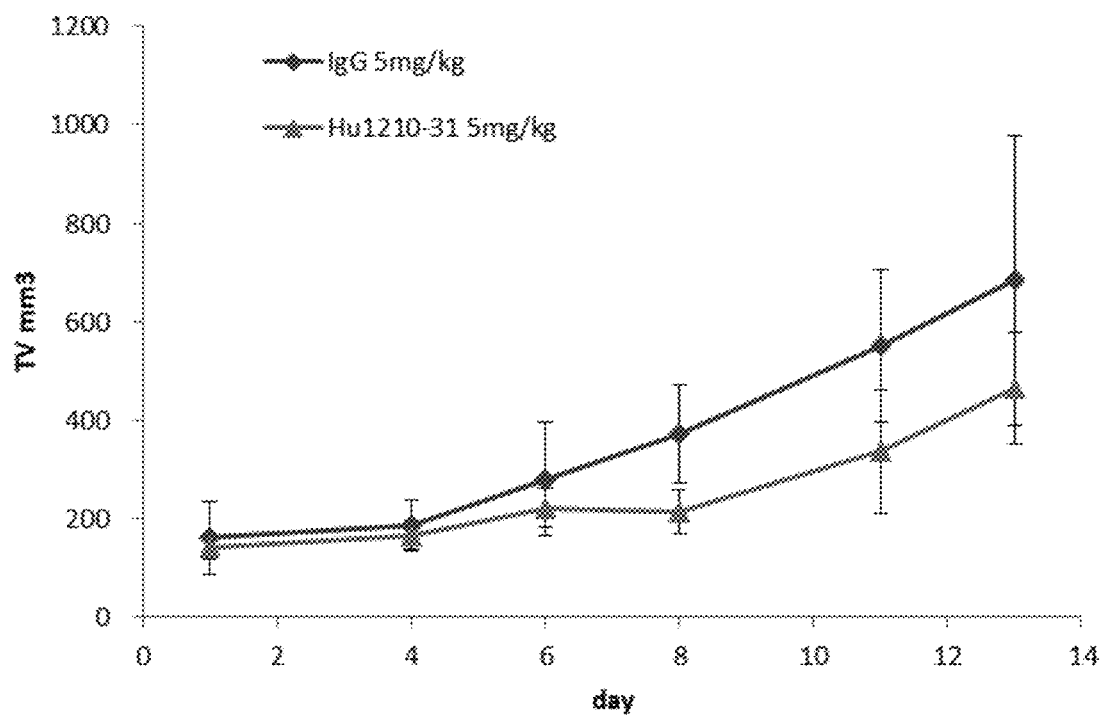
FIG. 14 shows that Hu1210-31 can inhibit the tumor growth by 30% at 5 mg/kg in HCC827-NSG-xenograft model.
Figure 15:
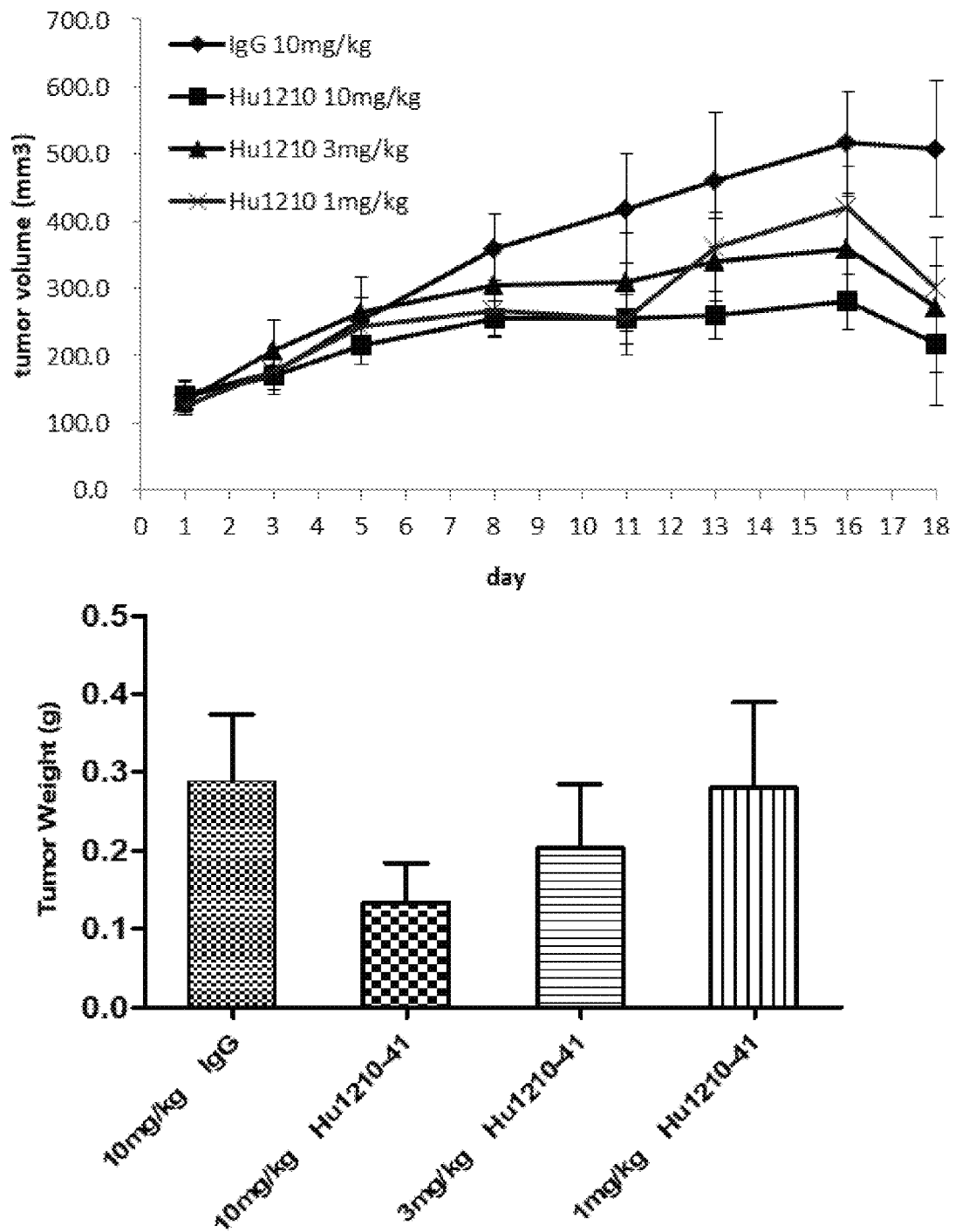
FIG. 15 shows that Hu1210-41 antibody can dose-dependently inhibit the tumor growth in HCC827-NSG-xenograft model, while the tumor weight was also dose-dependently suppressed by Hu1210-41 antibody.

Cells from the human lung adenocarcinoma cell line HCC827 will be grafted into NOD scid gamma (NSG) mice. NSG mice are NOD scid gamma deficient and the most immunodeficient mice making them ideal recipients for human tumor cell and PBMC grafting. 10 days post-graft, human PBMCs will be transplanted into the tumor-bearing mice. Approximately 20 days post-graft, once the tumor volume has reached 100-150 mm³, PD-L1 antibody will be administered to the mice every other day at 5 mg/kg. Tumor volume will be monitored every other day in conjunction with antibody administration. As shown in FIG. 14, Hu1210-31 can inhibit the tumor growth by 30% at 5 mg/kg. Hu1210-41 antibody can dose-dependently inhibit the tumor growth, while the tumor weight was also dose-dependently suppressed by Hu1210-41 antibody (FIG. 15).

1.11. Computer Simulation of Further Variation and Optimization of the Humanized Antibodies It was contemplated that certain amino acid residues within the CDR regions or the framework regions could be changed to further improve or retain the activity and/or stability of the antibodies. Variants were tested, with a computational tool (VectorNTI, available at ebi.ac.uk/tools/msa/clustalo/), with respect to their structural, conformational and functional properties, and those (within the CDR regions) that showed promises are listed in the tables blow.

TABLE 14

VH and VL CDRs and their variants suitable for inclusion in humanized antibodies

| Name | Sequence | SEQ ID NO: |
|---|---|---|
| VH CDR1 | SYDMS | 1 |
|  | TYDMS | 61 |
|  | CYDMS | 62 |
|  | SFDMS | 63 |
|  | SHDMS | 64 |
|  | SWDMS | 65 |
|  | SYDMT | 66 |
|  | SYDMC | 67 |
| VH CDR2 | TISDGGGYIYYSDSVKG | 2 |
|  | TISDGGAYIYYSDSVKG | 68 |
|  | TISDGGPYIYYSDSVKG | 69 |
|  | TISDGGGFIYYSDSVKG | 70 |
|  | TISDGGGHIYYSDSVKG | 71 |
|  | TISDGGGWIYYSDSVKG | 72 |
|  | TISDGGGYIYYSDTVKG | 73 |
|  | TISDGGGYIYYSDCVKG | 74 |
|  | TISDGGGYIYYSDSLKG | 75 |
|  | TISDGGGYIYYSDSIKG | 76 |
|  | TISDGGGYIYYSDSMKG | 77 |
| VH CDR3 | EFGKRYALDY | 3 |
|  | QFGKRYALDY | 78 |
|  | DFGKRYALDY | 79 |
|  | NFGKRYALDY | 80 |
|  | EYGKRYALDY | 81 |
|  | EHGKRYALDY | 82 |
|  | EWGKRYALDY | 83 |
|  | EFAKRYALDY | 84 |
|  | EFPKRYALDY | 85 |
|  | EFGRRYALDY | 86 |
|  | EFGKKYALDY | 87 |
|  | EFGKRFALDY | 88 |
|  | EFGKRHALDY | 89 |
|  | EFGKRWALDY | 90 |
| VL CDR1 | KASQDVTPAVA | 4 |
|  | KATQDVTPAVA | 91 |
|  | KACQDVTPAVA | 92 |
| VL CDR2 | STSSRYT | 5 |
|  | TTSSRYT | 93 |
|  | CTSSRYT | 94 |
|  | SSSSRYT | 95 |
|  | SMSSRYT | 96 |
|  | SVSSRYT | 97 |
|  | STTSRYT | 98 |
|  | STCSRYT | 99 |
|  | STSTRYT | 100 |
|  | STSCRYT | 101 |
|  | STSSKYT | 102 |

TABLE 14-continued

VH and VL CDRs and their variants suitable for inclusion in humanized antibodies

| Name | Sequence | SEQ ID NO: |
|---|---|---|
|  | STSSRFT | 103 |
|  | STSSRHT | 104 |
|  | STSSRWT | 105 |
| VL CDR3 | QQHYTTPLT | 6 |
|  | EQHYTTPLT | 106 |
|  | DQHYTTPLT | 107 |
|  | NQHYTTPLT | 108 |
|  | QEHYTTPLT | 109 |
|  | QDHYTTPLT | 110 |
|  | QNHYTTPLT | 111 |

(in Table 14, hotspot mutation residues an their substitutes are underlined)

1.12. Identification of PD-L1 Epitope

This study was conducted to identify amino acid residues involved in the binding of PD-L1 to the antibodies of the present disclosure.

Figure 16:
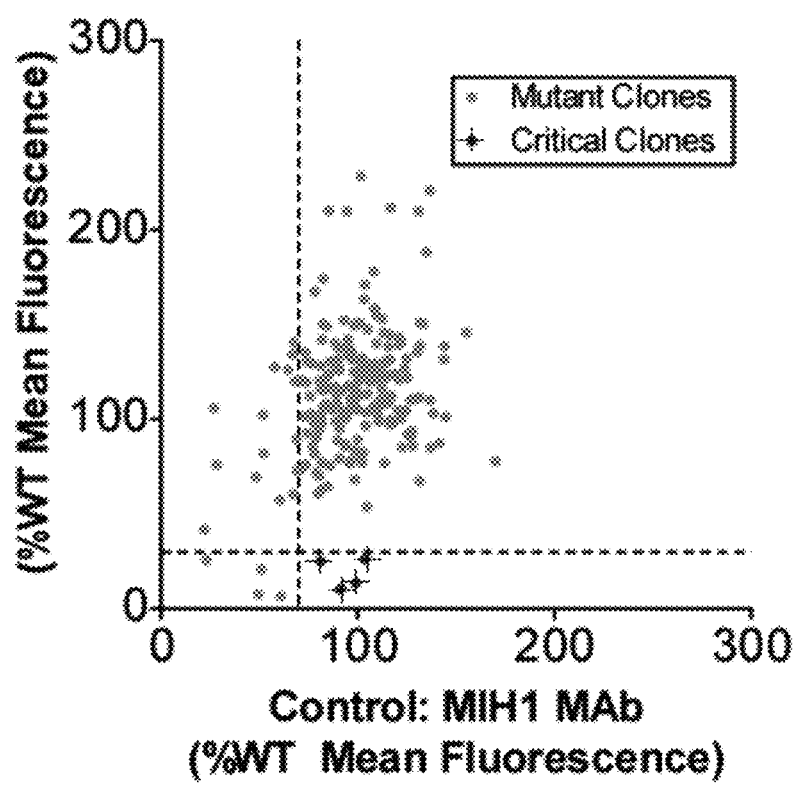
FIG. 16 plots, for each PD-L1 mutant, the mean binding value as a function of expression (control anti-PD-L1 mAb reactivity).

An alanine-scan library of PD-L1 was constructed. Briefly, 217 mutant clones of PD-L1 were generated on Integral Molecular's protein engineering platform. Binding of Hu1210-41 Fab to each variant in the PD-L1 mutation library was determined, in duplicate, by high-throughput flow cytometry. Each raw data point had background fluorescence subtracted and was normalized to reactivity with PD-L1 wild-type (WT). For each PD-L1 variant, the mean binding value was plotted as a function of expression (control anti-PD-L1 mAb reactivity). To identify preliminary critical clones (circles with crosses), thresholds (dashed lines) of >70% WT binding to control MAb and <30% WT reactivity to Hu1210-41 Fab were applied (FIG. 16). Y134, K162, and N183 of PDL1 were identified as required residues for Hu1210-41 binding. The low reactivity of N183A clone with Hu1210-41 Fab suggests that it is the major energetic contributor to Hu1210-41 binding, with lesser contributions by Y134 and K162.

Figure 17:
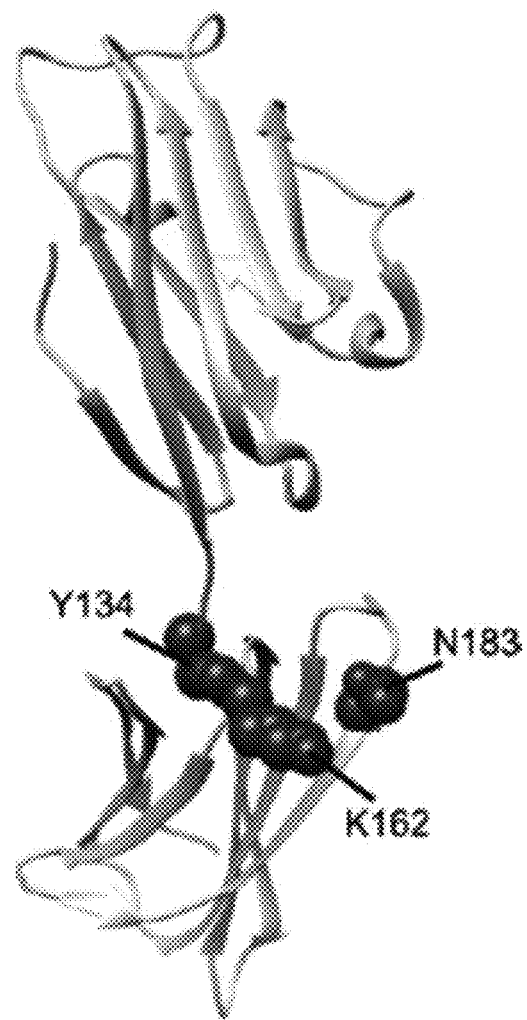
FIG. 17 illustrates the locations of Y134, K162, and N183, the residues (spheres) involved in binding to the anti-PD-L1 Hu1210-41 antibody.

The critical residues (spheres) were identified on a 3D PD-L1 structure, as illustrated in FIG. 17. These residues, Y134, K162, and N183, therefore, constitute an epitope of PD-L1 responsible for binding to antibodies of various embodiments of the present disclosure.

It is interesting to note that Y134, K162, and N183 are all located within the IgC domain of the PD-L1 protein. Both PD-1 and PD-L1's extracellular portions have an IgV domain and an IgC domain. It is commonly known that PD-L1 binds to PD-1 through bindings between their IgV domains. Unlike such conventional antibodies, however, Hu1210-41 binds to the IgC domain, which would have been expected to be ineffective in inhibiting PD-1/PD-L1 binding. This different epitope of Hu1210-41, surprisingly, likely contributes to the excellent activities of Hu1210-41.

1.13. Antibody Engineering of Anti-PDL1 Antibody

Examples 1.13-1.15 attempted to identify further improved antibodies based on Hu1210-41 using mutagenesis.

Four sub-libraries were constructed for antibody engineering of anti-PD-L1 monoclonal antibody, using either of the following strategies. In strategy 1, mutagenesis of heavy chain variable domain VH CDR3 or VL-CDR3 was perform by highly random mutation. In strategy 2, two CDR combination libraries composed of (VH-CDR3, VL-CDR3 and VL-CDR1) or (VH-CDR1, VH-CDR2 and VL-CDR2) were generated by CDR walking with controlled mutation rates.

Bio-Panning: the phage panning methods were adapted by shortening the incubation/binding time prior to the harsh washing condition. Briefly, 100 μl magnetic streptavidin beads (Invitrogen, USA) were blocked with 1 ml of MPBS for 1 hr at room temperature. In another tube, library phage was pre-incubated (5×10^11~12 for each round) with 100 μl magnetic streptavidin beads in 1 ml of MPBS to remove unwanted binders. Magnet particle concentrator was used to separate the phage and beads. The biotinylated PD-L1 protein was added to the phage and incubated 2 h at room temperature, and gently mixed using an over-head shaker. Beads carrying phage from the solution were separated in the magnetic particle concentrator and the supernatant was discarded. The beads were washed with fresh wash buffer, ten times with PBST and ten times with PBS (pH7.4). 0.8 ml, 0.25% Trypsin in PBS (Sigma, USA) was added and incubated for 20 min at 37° C. to elute the phage. The output phage was titrated and rescued for next round panning, decreasing antigen concentration round by round.

ELISA Screening and on/Off Rate Ranking

Clones were picked and induced from the desired panning output; phage ELISA was conducted for primary screening; positive clones were analyzed by sequencing; unique hotspots were found. Table 15 shows the mutations identified. As shown below, the FGK residues in the CDRH3 are hotpot residues producing improved antibodies.

TABLE 15

Mutations in the CDRs

| | CDR-H1 (SEQ No.) | CDR-H2 (SEQ No.) | CDR-H3 (SEQ No.) |
|---|---|---|---|
| WT* | SYDMS (1) | TISDAGGYIYYRDSVKG (526) | EFGKRYALDY (3) |
| B3 | SYDMS (1) | TISDAGGYIYYRDSVKG (526) | EFGKRYALDY (3) |
| C4 | SYDMS (1) | TISDAGGYIYYRDSVKG (526) | EFGKRYALDS (513) |
| B1 | SYDMS (1) | TISDAGGYIYYRDSVKG (526) | EIFNRYALDY (514) |
| B6 | SYDMS (1) | TISDAGGYIYYRDSVKG (526) | ELPWRYALDY (515) |
| C3 | SYDMS (1) | TISDAGGYIYYRDSVKG (526) | ELHFRYALDY (516) |
| C6 | SYDMS (1) | TISDAGGYIYYRDSVKG (526) | ELYFRYALDY (517) |
| A1 | SYDMS (1) | TISDAGGYIYYRDSVKG (526) | ELLHRYALDY (518) |
| A2 | SYDMS (1) | TISDAGGYIYYRDSVKG (526) | ELRGRYALDY (519) |
| A3 | SYDMS (1) | TISDAGGYIYYRDSVKG (526) | EFGKRYALDY (3) |

| | CDR-L1 (SEQ No.) | CDR-L2 (SEQ No.) | CDR-L3 (SEQ No.) |
|---|---|---|---|
| WT* | KASQDVTPAVA (4) | STSSRYT (5) | QQHYTTPLT (6) |
| B3 | KAKQDVTPAVA (520) | STSSRYT (5) | MQHYTTPLT (522) |
| C4 | KASQDVWPAVA (521) | STSSRYT (5) | QQHSTTPLT (523) |
| B1 | KASQDVTPAVA (4) | STSSRYT (5) | QQHYTTPLT (6) |
| B6 | KASQDVTPAVA (4) | STSSRYT (5) | OOHYTTPLT (6) |
| C3 | KASQDVTPAVA (4) | STSSRYT (5) | QQHYTTPLT (6) |
| C6 | KASQDVTPAVA (4) | STSSRYT (5) | OOHYTTPLT (6) |
| A1 | KASQDVTPAVA (4) | STSSRYT (5) | QQHYTTPLT (6) |
| A2 | KASQDVTPAVA (4) | STSSRYT (5) | QQHYTTPLT (6) |
| A3 | KASQDVTPAVA (4) | STSSRYT (5) | QQHSDAPLT (524) |

(*WT differs from Hu1210-41 by a S60R (Kabat numbering) substitution in the heavy chain to improve affinity.)

The amino acid sequences of the variable regions of these antibodies are shown in Table 16 below.

TABLE 16

Antibody sequences

| Name | Sequence | SEQ ID NO: |
|---|---|---|
| WT-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREF GKRYALDYWGQGTTVTVSS | 493 |
| WR-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GRKLEIK | 494 |
| B3-VH | EVQLVESGGGLVQPGGSLRLSCAASGFT6FSSYDMSWVRQAPGKSLEWVAT ISDAGGYIYYRDSVKGRFTISRDNAKNSLYLQMNSLRDEDTAVYICAREF GKRYALDYWGQGTTVTVSS | 495 |
| B3-Vk | DIQMTQSPSSLSASVGDRVTITCKAKQDVTPAVAWYQQKPGKAPKLLIYS TSSRYTGVPSRFSGSGSGTDFTFTISSLQPEDIATYYCMQHYTTPLTFGQ GTKLEIK | 496 |
| C4-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREF GKRYALDSWGQGTTVTVSS | 497 |
| C4-Vk | DIQMTQSPSSLSASVGDRVTITCKASQDVWPAVAWYQQKPGKAPKLLIYS TSSRYTGVPSRFSGSGSGTDFTFTISSLQPEDIATYYCQQHSTTPLTFGQ GTKLEIK | 498 |
| B1-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTACYICAREI FNRYALDYWGQGTTVTVSS | 499 |

TABLE 16-continued

Antibody sequences

| Name | Sequence | SEQ ID NO: |
|---|---|---|
| B1-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GTKLEIK | 500 |
| B6-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREL PWRYALDYWGQGTTVTVSS | 501 |
| B6-Vk | DIQMTQSPSSLSASVGDRVTITCKASQDVTPACAWYQQKPGKAPKLLIYS TSSRYTGVPSRFSGSGSGTDFTFTISSLQPEDIATYYCQQHYTTPLTFGQ GTKLEIK | 502 |
| C3-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTACYICAREL HFRYALDYWGQGTTVTVSS | 503 |
| C3-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GTKLEIK | 504 |
| C6-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREL YFRYALDYWGQGTTVTVSS | 505 |
| C6-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GTKLEIK | 506 |
| A1-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREL LHRYALDYWGQGTTVTVSS | 507 |
| A1-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GTKLEIK | 508 |
| A2-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREL RGRYALDYWGQGTTVTVSS | 509 |
| A2-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHYTTPLTFGQ GTKLEIK | 510 |
| A3-VH | EVQLVESGGGLVQPGGSLRLSCAASGFTFSSYDMSWVRQAPGKSLEWVAT ISDAGGYIYYRDSVKGRFTISRDNAKNSLYLQMNSLRDEDTAVYICAREF GKRYALDYWGQGTTVTVSS | 511 |
| A3-Vk | DIQMTQSPSSLSASVGDRVTITCKASQDVTPAVAWYQQKPGKAPKLLIYS TSSRYTGVPSRFSGSGSGTDFTFTISSLQPEDIATYYCQQHSDAPLTFGQ GTKLEIK | 512 |

1.14. Antigen Binding Properties of the PD-L1 Antibodies

As shown in Tables 15 and 16, totally 9 unique clones were characterized and converted into full-length IgG.

Binding Property to Recombinant Human PD-L1

Figure 18:
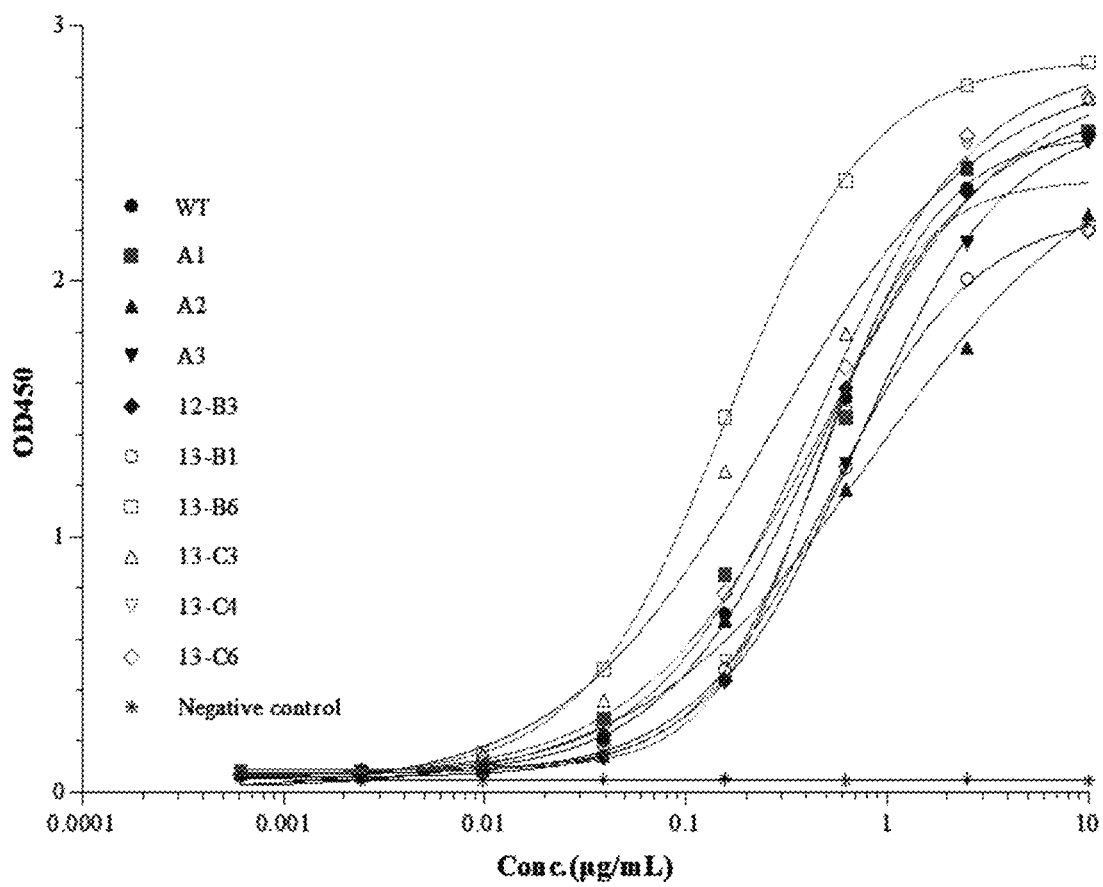
FIG. 18 shows the results of a binding assay (to human PD-L1) for the derived antibodies.

To evaluate the antigen binding activity, the antibodies were subjected to ELISA test. Briefly, microtiter plates were coated with human PD-L1-Fc protein at 2 µg/ml in PBS, 100 µl/well at 4° C. overnight, then blocked with 100 µl/well of 5% BSA. 4-fold dilutions of humanized antibodies starting from 10 µg/ml were added to each well and incubated for 1-2 hours at RT. The plates were washed with PBS/Tween® and then incubate with goat-anti-mouse IgG antibody conjugated with Horse Radish Peroxidase (HRP) for 1 hour at RT. After washing, the plates were developed with TMB substrate and analyzed by spectrophotometer at OD 450-630 nm. As shown in FIG. 18, all the humanized antibodies showed excellent binding efficacy to human PD-L1, and B6 and C3 behaved better than the parental clone WT.

Binding Property to Mammalian Expressed Human PD-L1

Figure 19:
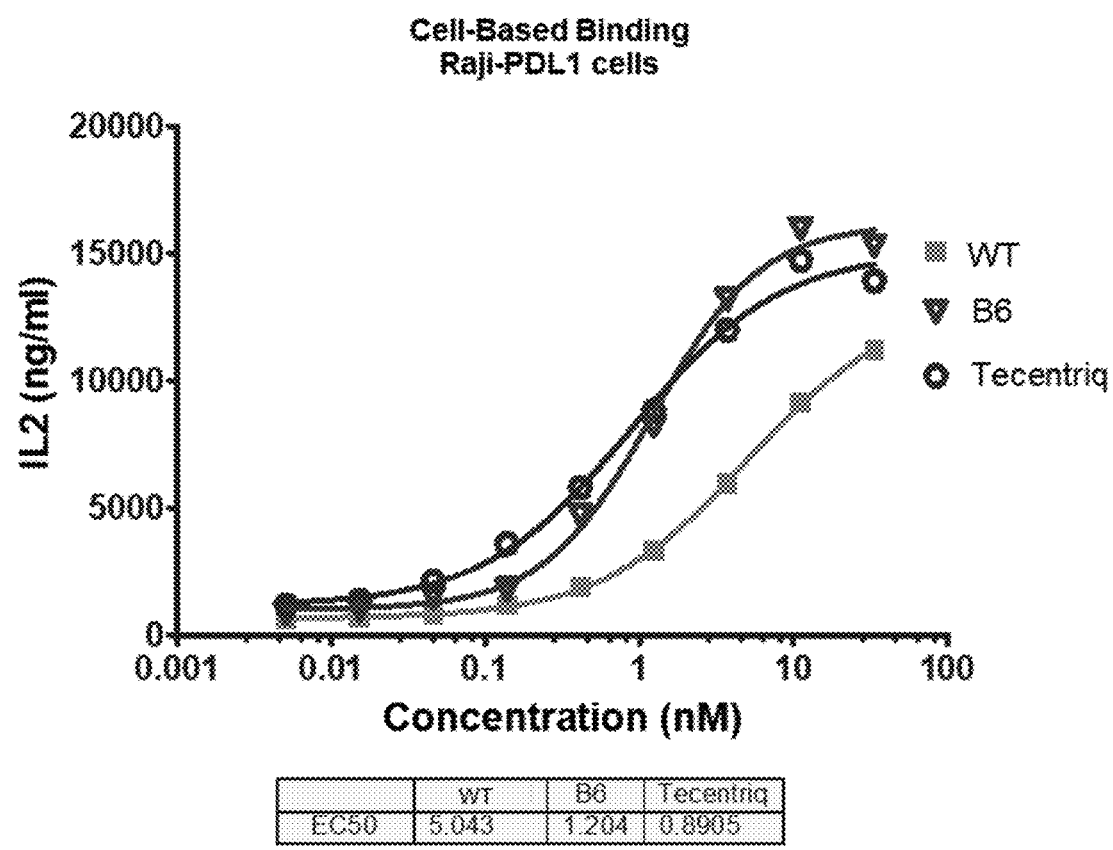
FIG. 19 shows that antibody B6 more highly efficiently bound to PD-L1 expressed on mammalian cells, as compared to the parental antibody and Tecentriq™ (atezolizumab).

To evaluate the antigen binding property, the antibodies were analyzed for its binding to mammalian expressed PD-L1 by FACS. Briefly, PDL1-Raji cells were firstly incubated with 5-fold serious diluted humanized antibodies starting from 2 g/ml at RT for 1 hour. After wash by FACS buffer (PBS with 2% FBS), the Alexa Fluor® 488-anti-human IgG antibody was added to each well and incubated at RT for 1 hour. The MFI of Alexa Fluor® 488 was evaluated by FACSAria™ III. As shown in the FIG. 19, B6 highly efficiently bound to PD-L1 expressed on mammalian cells, which was more potent than the parental antibody WT.

Affinity Ranking of Humanized Antibodies by Biacore™

To explore the binding kinetics of the humanized antibody, this example performed the affinity ranking using Biacore™. As shown Table 17, B6, C3, C6, A1 and A3 showed better affinity than the parent antibody WT.

TABLE 17

Affinity ranking

| Antibody | ka (1/Ms) | kd (1/s) | KD (M) |
|---|---|---|---|
| WT | 1.77E+05 | 4.64E−04 | 2.63E−09 |
| B3 | 1.19E+05 | 2.96E−04 | 2.49E−09 |
| C4 | 1.13E+05 | 5.06E−04 | 4.50E−09 |
| B1 | 1.63E+05 | 2.61E−04 | 1.60E−09 |
| B6 | 2.42E+05 | 2.46E−04 | 1.02E−09 |
| C3 | 2.18E+05 | 2.99E−04 | 1.37E−09 |
| C6 | 2.06E+05 | 3.34E−04 | 1.63E−09 |
| A1 | 2.03E+05 | 2.76E−04 | 1 36E−09 |
| A2 | 1.87E+05 | 4.75E−04 | 2.55E−09 |
| A3 | 2.18E+05 | 3.24E−04 | 1.49E−09 |

1.15. Anti-PDL1 Antibody Cell-Based Function

Figure 20:
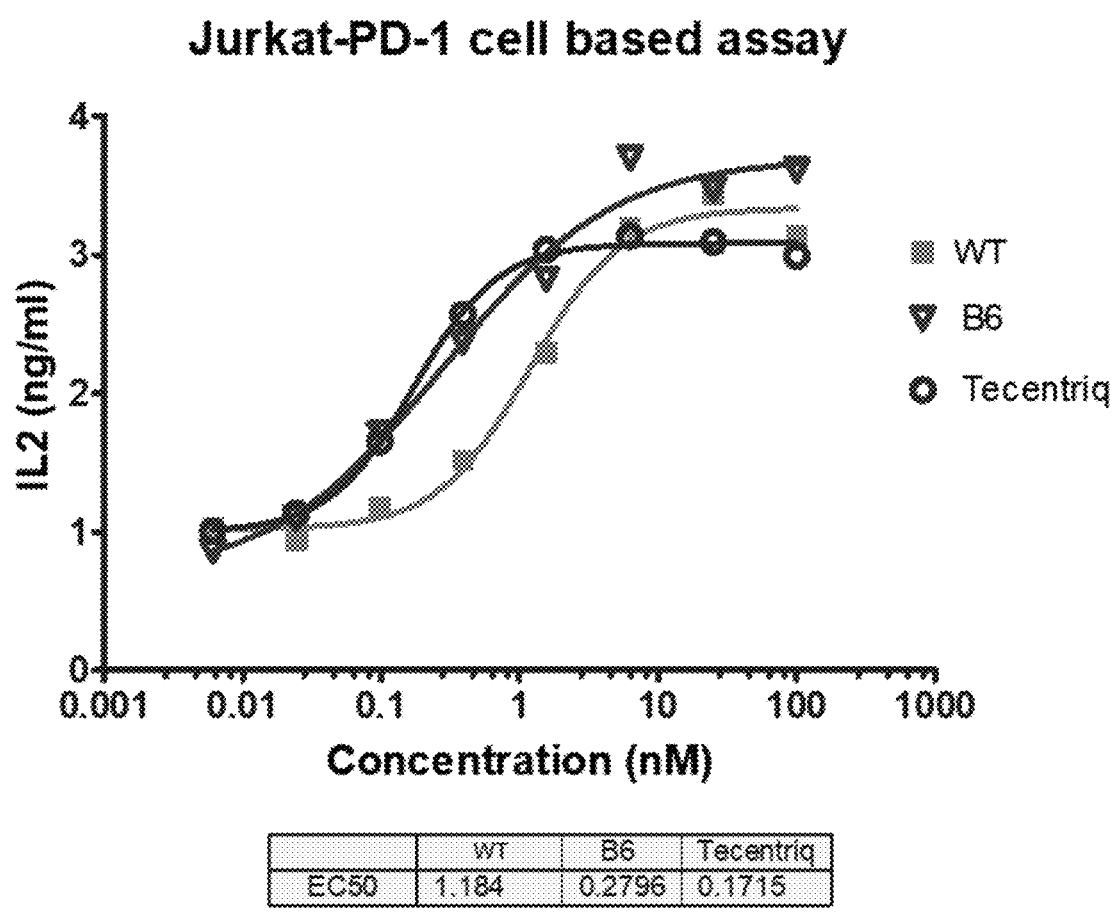
FIG. 20 shows the effects of the antibodies on IL2 production in Jurkat cells in which B6 also exhibited higher potency.

To test the ability of anti-PDL1 antibodies to stimulate T cell response, hPD-1-expressed Jurkat cells were used. Briefly, Jurkat is human T cell leukemia cell line that can produce IL2 upon TCR stimulation. In this assay, Jurkat cells transfected with human PD-1 gene by lentivirus were used as the responder cells. The Raji-PDL1 cells were used as the antigen presenting cells (APC). Staphylococcal Enterotoxins (SE) are used to stimulate TCR signal. In this system, ectopically expressed huPDL1 can suppress SE stimulated IL-2 production by Jurkat cells, while anti-PDL1 antibodies can reverse IL-2 production. In short, APCs ($2.5 \times 10^4$) were co-cultured with PD-1 expressing Jurkat T cells ($1 \times 10^5$) in the presence of SE stimulation. Anti-PDL1 antibodies (starting from 100 nM and 1:4 serially diluted for 8 dose) were added at the beginning of the culture. 48 hr later, culture supernatant was evaluated for IL2 production by ELISA. As shown in FIG. 20, the B6 monoclonal antibody was more potent than parental antibody WT.

Example 2. Preparation of Anti-LAG3 Monoclonal Antibodies 2.1. Screening of Full Human Monoclonal Antibodies Against LAG-3

Figure 21:
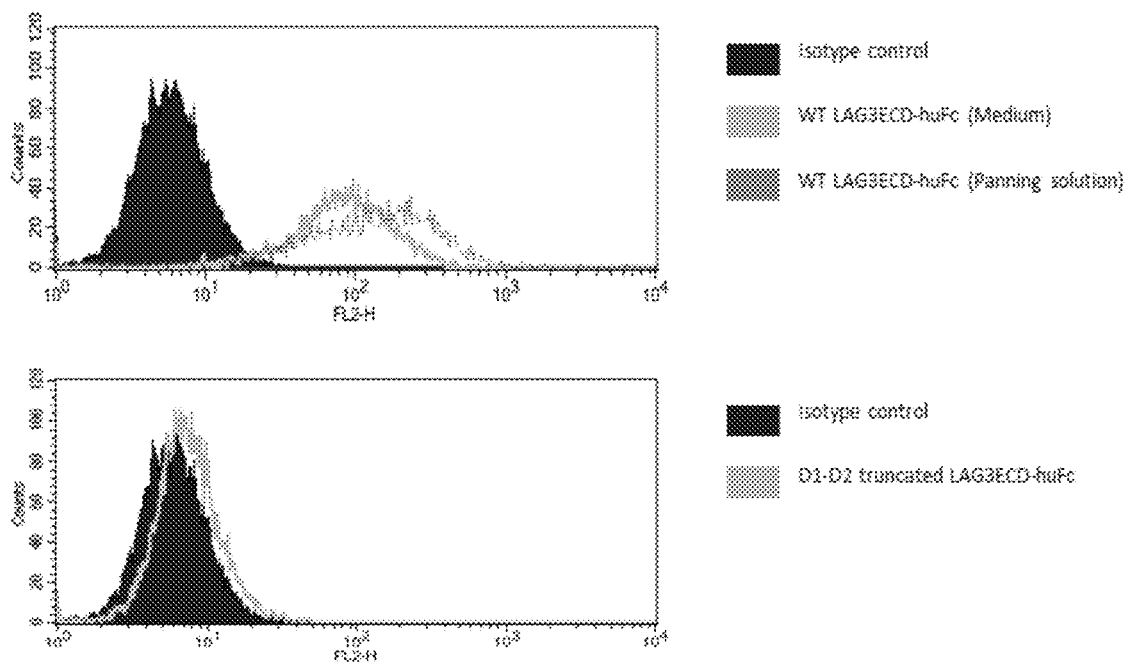
FIG. 21 shows that the D1-D2 domains are important for LAG-3 function. Wildtype (WT) LAG3 extracellular domain (ECD) fusion protein (LAG-3-ECD-huFc) fragments can bind to Daudi cells while D1-D2 truncated LAG-3-ECD-huFc fragments fail to bind Daudi cells.
Figure 22A:
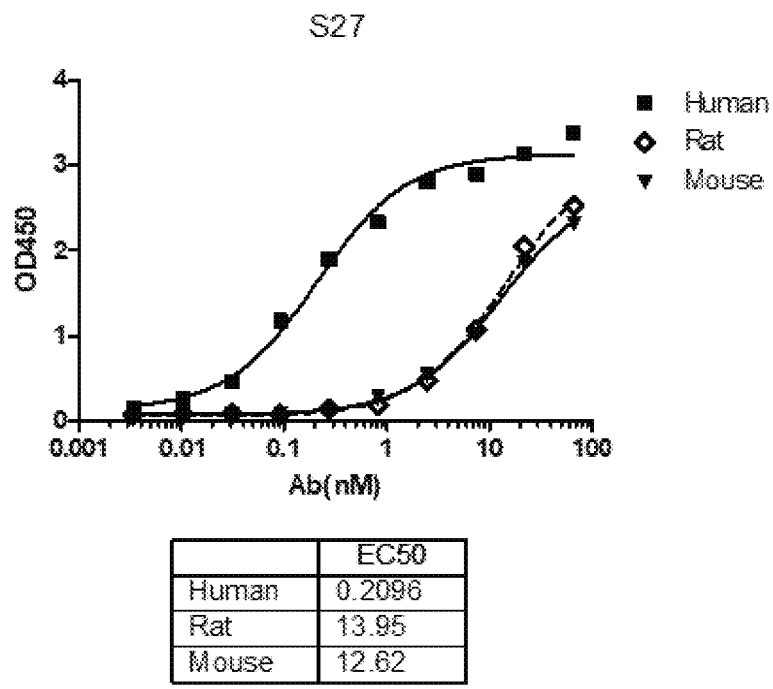
FIGS. 22A-22D show the binding of human anti-LAG3 antibodies to LAG3 protein derived from various species. Anti-LAG-3 antibodies were evaluated for their binding properties to human, rat, and mouse LAG3 through enzyme-linked immunosorbent assay (ELISA).
Figure 22B:
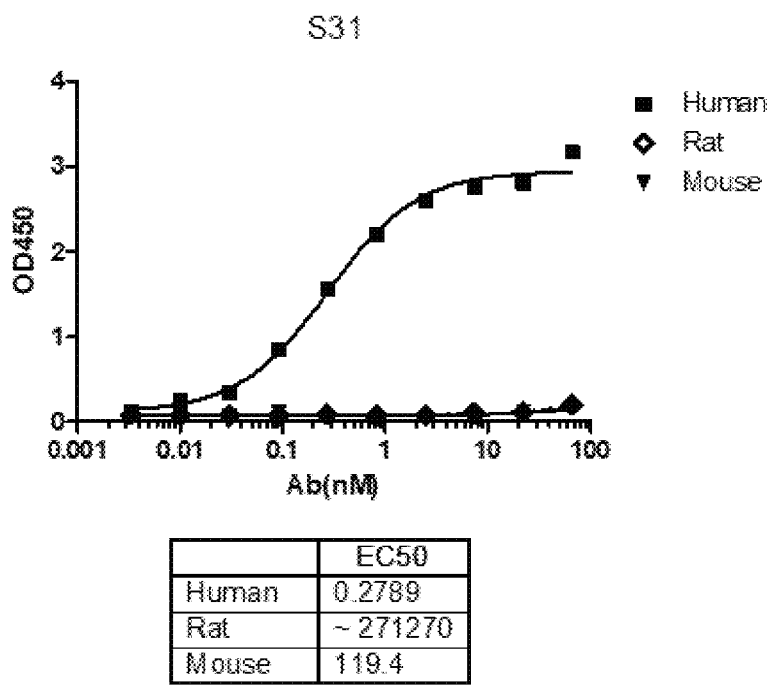
Figure 22C:
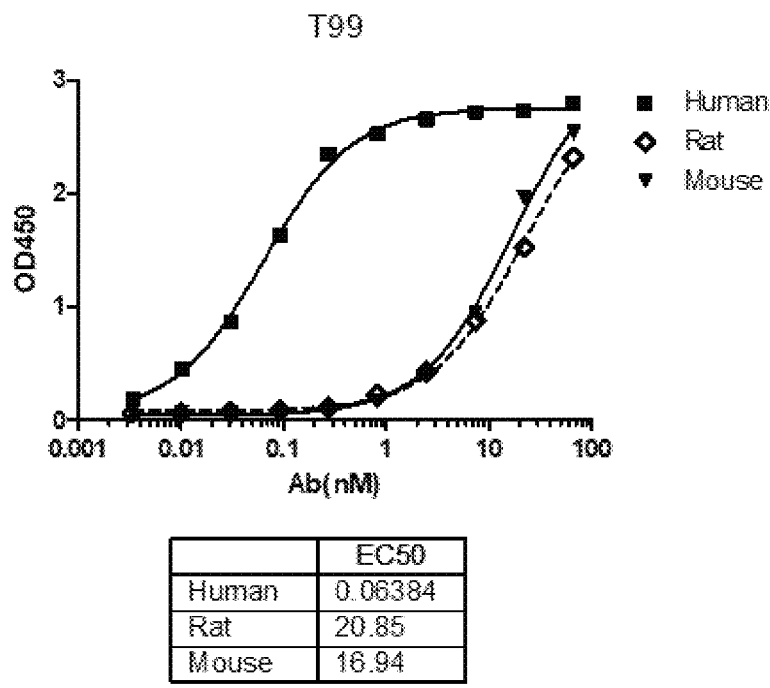
Figure 22D:
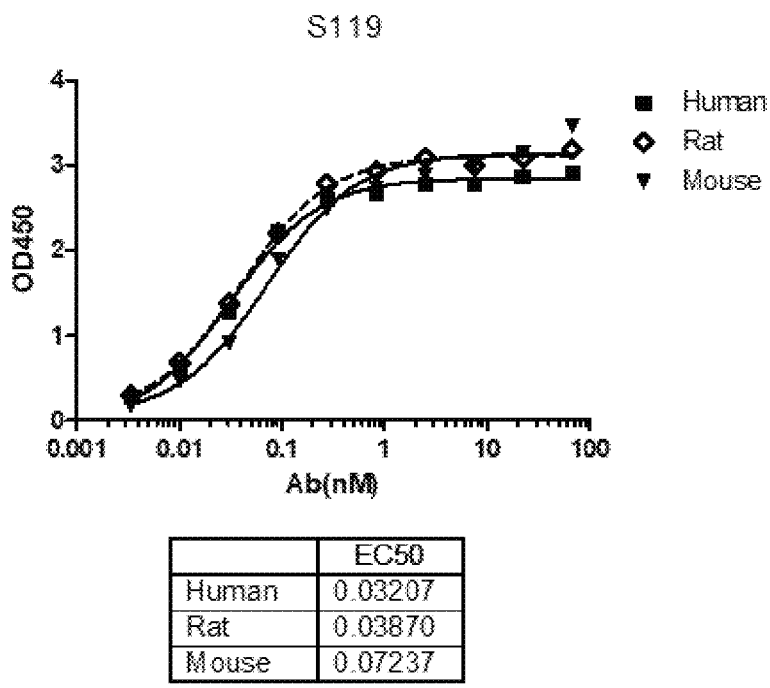

Anti-LAG3 human monoclonal antibodies (α-LAG-3 mAbs) were generated by screening full human Fab phage-display libraries. Wildtype LAG-3-ECD-huFc fragments can bind to Daudi cells while D1-D2 truncated LAG-3-ECD-huFc fragments fail to bind Daudi cells (FIG. 21). Consequently, the D1-D2 domains are critical for LAG-3 function.

Antigens for phage-display library-panning. LAG-3 is a single-pass type I membrane protein which belongs to the immunoglobulin (Ig) superfamily and contains 4 extracellular Ig-like domains (ECD): domain (D)1, D2, D3 and D4. A recombinant human LAG-3-ECD-human IgG1 (LAG-3-huFc) fusion protein or a human D1-D2 truncated LAG-3-ECD-human IgG1 (ΔD1D2-LAG-3-huFc) fusion protein were expressed in a 293T cell system.

Phage library. Ig gene segments in mammals are arranged in groups of variable (V), diversity (D), joining (J), and constant (C) exons. The human Fab phage libraries were construed using the phage vectors, which consists of: 1) all human variable kappa (VK) repertoires; and 2) the VH of VH3-23 and VH1-69 germline genes, respectively, with genetically randomized CDR3 regions from healthy human subjects.

Antigen screening and generation. To select the D1-D2 domain-specific phage binders, the phage libraries were subjected to antigen-based panning.

I) Phage Library Solution Panning Against LAG-3.

293F cells were transfected with a plasmid containing a D1-D2 deleted LAG-3 (ΔD1D2-LAG-3) sequence with a FLAG-tag at the N-terminus. At 3 days post-transfection, the ΔD1D2-LAG-3 293F cells were used for phage library screening. The phage libraries were performed the sequential negative screenings: streptavidin beads, ΔD1D2-LAG-3 transfected 293F cells and biotin-labeled-human IgG1Fc protein. The resulting library was then incubated with biotinylated LAG-3-huFc LAG-3 for 2 hrs under motion, followed by incubation with 100 μL of casein blocked streptavidin-magnetic beads for 15 min. Unbound phages were removed by washing with PBS 5-20 times. The bound phages were then eluted with freshly prepared 100 mM triethylamine (TEA) and neutralized with the addition of Tris-HCl buffer. The resulting phages were labeled as the Output-1 phage libraries. Output-1 phage libraries were subjected to the same screening as described above to generate the Output-2 and subsequent Output-3 phage libraries. Three rounds of phage library screening were performed in total.

II) Phage Library Immunotube Panning Against LAG-3

The phage libraries were used to perform sequential negative screenings: casein-coated immunotubes, ΔD1D2-LAG-3 transfected 293F cells and human IgG1Fc protein. The resulting library was then incubated in LAG3-huFc-coated immunotubes for 2 hrs under motion. Unbound phages were removed by washing with PBST 5-20 times. Similar with cell-based panning, three rounds of phage library screening were performed in total.

Output-3 phage libraries were diluted and plated to grow at 37° C. for 8 hrs and captured by anti-kappa antibody-coated filters overnight at 22° C. Biotinylated LAG-3-huFc (50 nM) and NeutrAvidin-AP conjugate were applied to the filter to detect antigen binding anti-LAG3 phages. Positive phage plaques were picked and eluted into 100 μL of phage elution buffer. About 10-15 μL of eluted phages were then used to infect 1 mL of XL1-Blue competent cells to make a high-titer (HT) phage for phage single point ELISA (SPE) (ELISA immobilized substrate coated with 50 nM of each protein tested). $1 \times 10^{10}$ plaque forming units (pfus) of each phage hit was used for SPE confirmation. The positive clones picked from the filter lift were then tested for LAG-3 antigen binding with LAG-3-huFc and ΔD1D2-LAG-3-huFc. The D1-D2 specific binders were amplified from antigen positive phages by PCR and sequenced. Ig light chain V genes (VL) and VH sequences were analyzed to identify unique sequences and determine sequence diversity.

VL and VH gene sequences of all hits were cloned into expression vectors pFUSE2ss-CLlg-hk (light chain, InvivoGen Cat No. pfuse2ss-hclk) and pFUSEss-CHlg-hG1 (heavy chain, InvivoGen Cat No. pfusess-hchg1). The antibodies were expressed in HEK293 cells and purified using Protein A PLUS-Agarose. Sequences of the antibodies and their CDR regions are provided in the table below.

TABLE 18

| heavy chain variable regions | | |
| --- | --- | --- |
| Antibody No. | VH | SEQ ID NO: |
| NLAG3-HDB169-T03 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGS SWFDYWGQGTLVTVSS | 254 |
| NLAG3-HDB169-T05 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCASSY HGGGYHRYWGQGTLVTVSS | 255 |
| NLAG3-HDB169-T06 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTTSK YSGSALRYWGQGTLVTVSS | 256 |
| NLAG3-HDB169-T07 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDR TGAFDYWGQGTLVTVSS | 257 |

TABLE 18-continued heavy chain variable regions

| Antibody No. | VH | SEQ ID NO: |
|---|---|---|
| NLAG3-HDB169-T08 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARHE TVAGSFDYWGQGTLVTVSS | 258 |
| NLAG3-HDB169-T10 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARTG YYGGNSGAFDIWGQGTMVTVSS | 259 |
| NLAG3-HDB169-T13 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARAG TGMDLVFNSWGQGTLVTVSS | 260 |
| NLAG3-HDB169-T23 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGL ARGDLNFGYWGQGTLVTVSS | 261 |
| NLAG3-HDB169-S24 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTREP HFDYWGQGTLVTVSS | 262 |
| NLAG3-HDB169-S27 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTTAA PGSYYLVFHYWGQGTLVTVSS | 263 |
| NLAG3-HDB169-S31 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDA GPVGYYGMDVWGQGTTVTVSS | 264 |
| NLAG3-HDB169-S32 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAGDG LYGSGSFGYWGQGTPVTVSS | 265 |
| NLAG3-HDB169-S61 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAKDI RWFYGMDVWGQGTTVTVSSw | 266 |
| NLAG3-HDB169-S64 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARHE SGIAGGHFDYWGQGTLVTVSS | 267 |
| NLAG3-HDB169-S86 | QVQLVQSGAEVKKPGSSVKVSCKASGGTFSSYAISWVRQAPGQGLEWMGG IIPIFGTANYAQKFQGRVTITADESTSTAYMELSSLRSELTAVYYCARDA GPVGYYGMDVWGQGTTVTVSS | 268 |
| NLAG3-HDB169-S87 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAKDI RWYYGMDVWGQGTTVTVSS | 269 |
| NLAG3-HDB169-T94 | QVQLVQSGAEVKKPGSSVKVFCKASGGTFSSYAISWVRQAPGQGLEWMGG IIPIFGTANYAQKFQGRVTITADESTSTAYMELSSLRSEDTAVYYCAKGV RGTYQIGYYGMDVWGQGTTVTVSS | 270 |
| NLAG3-HDB169-T97 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARQG TAMALDYWGQGTLVTVSS | 271 |
| NLAG3-HDB169-T99 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCVRDL QDWNYGGAAYWGQGTLVTVSS | 272 |
| NLAG3-HDB169-S103 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDD YYYGQFDSWGQGTLVTVSS | 273 |
| NLAG3-HDB169-S107 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAREI TGTSYTALDSWGQGTLVTVSS | 274 |
| NLAG3-HDB169-S109 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARGH IDGQAAGDYWGQGTLVTVSS | 275 |
| NLAG3-HDB169-S119 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRVPNPPYWGQGTLVTVSS | 276 |
| NLAG3-HDB169-S120 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARSG DRYDFWSGYWGQGTLVTVSS | 277 |
| NLAG3-HDB169-S127 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRVPNPPYWGQGTLVTVSS | 278 |
| NLAG3-HDB169-S128 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCARDA GPCGYYGMDVWGQGTMVTVSS | 279 |
| NLAG3-HDB169-S136 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCTRGQ DSTWYSSFDYWGQGTLVTVSS | 280 |
| NLAG3-HDB169-S139 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST LRLPNPPYWGQGTLVTVSS | 281 |
| NLAG3-HDB169-S150 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAAST TSFYSHGMDVWGQGTTVTVSS | 282 |

TABLE 18-continued heavy chain variable regions

| Antibody No. | VH | SEQ ID NO: |
|---|---|---|
| NLAG3-HDB169-S157 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGALDSWGRGTLVTVSS | 283 |
| NLAG3-HDB169-S164 | QVQLVQSGAEVKKPGSSVKVSCKASGGTFSSYAISWVRQAPGQGLEWMGGIIPIFGTANYAQKFQGRVTFTADESTSTAYMELSSLRSEDTAVYYCARGFTYGDFFFDYWGQGTLVTVSS | 284 |
| NLAG3-HDB169-S177 | QVQLVQSGAEVKKPGSSVKVSCKASGGTFSSYAPSWVRQAPGQGLEWMGGIIPIFGTANYAQKFQGRVTITADESTSTAYMELSSLRSEDTAVYYCARDVRGVTYLGMDVWGQGTTVTVSS | 285 |
| NLAG3-HDB323-S20 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGTLDSWGRGTLVTVSS | 286 |
| NLAG3-HDB323-S21 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRRTPFWGALDSWGRGTLVTVSS | 287 |
| NLAG3-HDB323-S32 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGALDSWGRGTLVTVSS | 288 |
| NLAG3-HDB323-S35 | QLLESGGGLVQPGGSLRLSCLAASGFTFSSYAMSWVRQAPGKGLEWSAISGSGGSTYYADSYTLGRFTLSRDNSKNTLYLQMNSLRAEDTAVYYCAKRKGLGSPTDYYYGMDVWGQGTTVTVSS | 289 |
| NLAG3-HDB323-S52 | QLLESGGGLVQPGGSLRLSCAASGFTFSSYAMSWVRQAPGKGLEWVSAISGSGGSTYYADSVKGRFTTSRDNSKNTLYLQMNSLRAEDTAVYYCARVRKTPFWGALDSWGRGTLVTVSS | 290 |
| NLAG3-HDB323-S55 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGTLDSWGRGSLVTVSS | 291 |
| NLAG3-HDB323-T89 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARPEYDYYYGMDVWGQGTTVTVSS | 292 |
| NLAG3-HDB323-T92 | QLLESGGGLVQPGGSLRLSCAASGFTFSSYAMSWVRQAPGKGLEWVSAISGSGGSTYYADSVKGRFTISRDN3KNTLYLQMNSLRAEDTAVYYCAKGGGSYDYWGQGTLVTVSS | 293 |
| NLAG3-HDB323-T94 | QLLESGGGLVQVGGSLRLSCAASGFTFSSYAMSWVRQAPGKGLEWVSAISGSGGSTYYADSVKGRFTISRDNSKNTLYLQMNSLRAEDTAVYYCARALNGMDVWGQGTMVTVSS | 294 |
| NLAG3-HDB323-S102 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCTRPLQGTAAADSYYYYAMDVWGQGTTVTVSS | 295 |
| NLAG3-HDB323-S103 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARLHSYLSEEFDPWGQGTLVTVSS | 296 |
| NLAG3-HDB323-S107 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRKTPFWGALDSWGRGTLVTVSS | 297 |
| NLAG3-HDB323-S114 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKLSAVNTYIDDWGQGTLVTVSS | 298 |
| NLAG3-HDB323-S135 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVTKTPFWGTLDYWGQGTLVTVSS | 299 |
| NLAG3-HDB323-S143 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVRRTPFWGALDSWGRGTLVTVSS | 300 |
| NLAG3-HDB323-S146 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVSQSPVWGYFDYWGQGMLVTVSS | 301 |
| NLAG3-HDB323-S161 | QLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDGYYDFWSGYSDYWGQGTLVTVSS | 302 |

TABLE 19

Heavy Chain CDRs

| Antibody No. | CDR H1 | SEQ ID NO: | CDR H2 | SEQ ID NO: | CDR H3 | SEQ ID NO: |
|---|---|---|---|---|---|---|
| NLAG3-HDB169-T03 | SYAIS | 116 | GIIPIFGTANYAQKFQG | 118 | ARGSSWFDY | 120 |
| NLAG3-HDB169-T05 | SYAIS | 116 | GIIPIFGTANYAQKFQG | 118 | ASSYHGGGYHRY | 121 |
| NLAG3-HDB169-T06 | SYAIS | 116 | GIIPIFGTANYAQKFQG | 118 | TTSKYSGSALRY | 122 |
| NLAG3-HDB169-T07 | SYAIS | 116 | GIIPIFGTANYAQKFQG | 118 | ARDRTGAFDY | 123 |
| NLAG3-HDB169-T08 | SYAIS | 116 | GIIPIFGTANYAQKFQG | 118 | ARHETVAGSFDY | 124 |
| NLAG3-HDB169-T10 | SYAIS | 116 | GIIPIFGTANYAQKFQG | 118 | ARTGYYGGNSGAFDI | 125 |

TABLE 19-continued

Heavy Chain CDRs

| Antibody No. | CDR H1 | SEQ ID NO: | CDR H2 | SEQ ID NO: | CDR H3 | SEQ ID NO: |
|---|---|---|---|---|---|---|
| NLAG3-HDB169-T13 | SYAIS | 116 | GIIPIFGTANYAQKFQG | 118 | ARAGTGMDLVFNS | 126 |
| NLAG3-HDB169-T23 | SYAIS | 116 | GIIPIFGTANYAQKFQG | 118 | ARGLARGDLNFGY | 127 |
| NLAG3-HDB169-S24 | SYAIS | 116 | GIIPIFGTANYAQKFQG | 118 | TREPHFDY | 128 |
| NLAG3-HDB169-S27 | SYAIS | 116 | GIIPIFGTANYAQKFQG | 118 | TTAAPGSYYLVFHY | 129 |
| NLAG3-HDB169-S31 | SYAIS | 116 | GIIPIFGTANYAQKFQG | 118 | ARDAGPVGYYGMDV | 130 |
| NLAG3-HDB169-S32 | SYAIS | 116 | GIIPIFGTANYAQKFQG | 118 | AGDGLYGSGSFGY | 131 |
| NLAG3-HDB169-S61 | SYAIS | 116 | GIIPIFGTANYAQKFQG | 118 | AKDIRWFYGMDV | 132 |
| NLAG3-HDB169-S64 | SYAIS | 116 | GIIPIFGTANYAQKFQG | 118 | ARHESGIAGGHFDY | 133 |
| NLAG3-HDB169-S86 | SYAIS | 116 | GIIPIFGTANYAQKFQG | 118 | ARDAGPVGYYGMDV | 130 |
| NLAG3-HDB169-S87 | SYAIS | 116 | GIIPIFGTANYAQKFQG | 118 | AKDIRWYYGMDV | 134 |
| NLAG3-HDB169-T94 | SYAIS | 116 | GIIPIFGTANYAQKFQG | 118 | AKGVRGTYQIGYYGMDV | 135 |
| NLAG3-HDB169-T97 | SYAIS | 116 | GIIPIFGTANYAQKFQG | 118 | ARQGTAMALDY | 136 |
| NLAG3-HDB169-T99 | SYAIS | 116 | GIIPIFGTANYAQKFQG | 118 | VRDLQDWNYGGAAY | 137 |
| NLAG3-HDB169-S103 | SYAIS | 116 | GIIPIFGTANYAQKFQG | 118 | ARDDYYYGQFDS | 138 |
| NLAG3-HDB169-S107 | SYAIS | 116 | GIIPIFGTANYAQKFQG | 118 | AREITGTSYTALDS | 139 |
| NLAG3-HDB169-S109 | SYAIS | 116 | GIIPIFGTANYAQKFQG | 118 | ARGHIDGQAAGDY | 140 |
| NLAG3-HDB169-S119 | SYAIS | 116 | GIIPIFGTANYAQKFQG | 118 | AASTLRVPNPPY | 141 |
| NLAG3-HDB169-S120 | SYAIS | 116 | GIIPIFGTANYAQKFQG | 118 | ARSGDRYDFWSGY | 142 |
| NLAG3-HDB169-S127 | SYAIS | 116 | GIIPIFGTANYAQKFQG | 118 | AASTLRVPNPPY | 141 |
| NLAG3-HDB169-S128 | SYAIS | 116 | GIIPIFGTANYAQKFQG | 118 | ARDAGPVGYYGMDV | 130 |
| NLAG3-HDB169-S136 | SYAIS | 116 | GIIPIFGTANYAQKFQG | 118 | TRGQDSTWYSSFDY | 143 |
| NLAG3-HDB169-S139 | SYAIS | 116 | GIIPIFGTANYAQKFQG | 118 | AASTLRLPNPPY | 144 |
| NLAG3-HDB169-S150 | SYAIS | 116 | GIIPIFGTANYAQKFQG | 118 | ATTQTSFYSHGMDV | 145 |
| NLAG3-HDB169-S157 | SYAIS | 116 | GIIPIFGTANYAQKFQG | 118 | ARVRKTPFWGALDS | 146 |
| NLAG3-HDB169-S164 | SYAIS | 116 | GIIPIFGTANYAQKFQG | 118 | ARGFTYGDFIFDY | 147 |
| NLAG3-HDB169-S177 | SYAIS | 116 | GIIPIFGTANYAQKFQG | 118 | ARDVRGVTYLGMDV | 148 |
| NLAG3-HDB323-S20 | SYAMS | 117 | AISGSGGSTYYADSVKG | 119 | ARVRKTPFWGTLDS | 149 |
| NLAG3-HDB323-S21 | SYAMS | 117 | AISGSGGSTYYADSVKG | 119 | ARVRRTPFWGALDS | 150 |
| NLAG3-HDB323-S32 | SYAMS | 117 | AISGSGGSTYYADSVKG | 119 | ARVRKTPFWGALDS | 146 |
| NLAG3-HDB323-S35 | SYAMS | 117 | AISGSGGSTYYADSVKG | 119 | AKRKGLGSPTDYYYGMDV | 151 |
| NLAG3-HDB323-S52 | SYAMS | 117 | AISGSGGSTYYADSVKG | 119 | ARVRKTPFWGALDS | 146 |
| NLAG3-HDB323-S55 | SYAMS | 117 | AISGSGGSTYYADSVKG | 119 | ARVRKTPFWGTLDS | 149 |
| NLAG3-HDB323-T89 | SYAMS | 117 | AISGSGGSTYYADSVKG | 119 | VRPEYDTYYYGMDV | 152 |
| NLAG3-HDB323-T92 | SYAMS | 117 | AISGSGGSTYYADSVKG | 119 | AKGGGSYDY | 153 |
| NLAG3-HDB323-T94 | SYAMS | 117 | AISGSGGSTYYADSVKG | 119 | ARALNGMDV | 154 |
| NLAG3-HDB323-S102 | SYAMS | 117 | AISGSGGSTYYADSVKG | 119 | TRPLQGIAAADSYYYYAMDV | 155 |
| NLAG3-HDB323-S103 | SYAMS | 117 | AISGSGGSTYYADSVKG | 119 | ARLHSYLSEEFDP | 156 |
| NLAG3-HDB323-S107 | SYAMS | 117 | AISGSGGSTYYADSVKG | 119 | ARVRKTPFWGALDS | 146 |
| NLAG3-HDB323-S114 | SYAMS | 117 | AISGSGGSTYYADSVKG | 119 | AKLSAVNTYIDD | 157 |
| NLAG3-HDB323-S135 | SYAMS | 117 | AISGSGGSTYYADSVKG | 119 | ARVTKTPFWGTLDY | 158 |
| NLAG3-HDB323-S143 | SYAMS | 117 | AISGSGGSTYYADSVKG | 119 | ARVRRTPFWGALDS | 150 |
| NLAG3-HDB323-3146 | SYAMS | 117 | AISGSGGSTYYADSVKG | 119 | ARVSQSPVWGYFDY | 159 |
| NLAG3-HDB323-S161 | SYAMS | 117 | AISGSGGSTYYADSVKG | 119 | AKDGYYDFWSGYSDY | 160 |

TABLE 20

Light chain variable regions

| Antibody No. | VL | SEQ ID NO: |
|---|---|---|
| NLAG3-HDB169-T03 | DIQLTQSPSSLSAFVGDRVTITCQANQDIHHYLNWYQQKPGKAPKLLIYD ASILQSGVPSRFSGSGSGTDFTLTISSLQPEDFATYFCQQADSFPITFGQ GTRLEIKR | 303 |
| NLAG3-HDB169-T05 | EIVLTQSPDSLAVSLGERATINCKSSQSVLYSSSNKNYLAWYQQKPGQPP KLLIYWASTRESGVPDRFSGSGSGTDFTLTISSLQPEDFATYYCQQSYST PWTFGPGTKLEIKR | 304 |
| NLAG3-HDB169-T06 | DIQMTQSPDSLAVSLGERATINCKSSQSVLYSSNKNYLAWYQQKPGHPP KLLVYWASTRESGVPARFSASGSGTDFTLAISNLQAEDVAVYYCQQYYST PWTFGQGTKVEIKR | 305 |
| NLAG3-HDB169-T07 | EIVLTQSPLSLPVTPGEPASISCRSSQNLLHSDGYNYLNWYLQKPGQSPQ LLIYLGSNRATGVPDRFSGSGSGTDFTLTISSLQPEDFATYYCQQSYSTP WTFGQGTKVEIKR | 306 |
| NLAG3-HDB169-T08 | DIVMTQSPDSLAVSLGERATINCKSSQSVLYTSNNKNYLAWYQQKPGQPP KLLIYWASTRESGVPDRFSGSGSGTDFTLTISSLQAEDVAIYYCQQYYST PWTFGQGTKLEIKR | 307 |
| NLAG3-HDB169-T10 | AIQLTQSPDSLAVSLGERATINCKSSQSVLYSSNNKNYLAWYQQKPGQPP KLLIYWASTRESGVPDRFSGSGSGTDFTLTISSLQAEDSATYYCQQSFTT PWTFGQGTKVEIKR | 308 |
| NLAG3-HDB169-T13 | DIQMTQSPSSLSASVGDRVTITCQASQDINRYLSWYQQKPGKAPKLLIYD ASNLETGVPSRFSGSASGTDFTFAISSLQPEDIATYYCQQYDNLPPTFGQ GTRLEIKR | 309 |

TABLE 20-continued

Light chain variable regions

| Antibody No. | VL | SEQ ID NO: |
|---|---|---|
| NLAG3-HDB169-T23 | EIVMTQSPSSLSASVGDRVTITCQASQDISNYLNWYQQKPGKAPKLLIYAASSLQSGVPSRFSGSGSGTDFTLTISSLQPEDFASYYCQQSYGSPVTFGQGTKLEIKR | 310 |
| NLAG3-HDB169-S24 | EIVMTQSPSSLSASVGDRVTITCQASQDISNYLNWYQQKPGKAPKLLIYDASNLETGVPSRFSGSGSGTEFTLTISSLRPEDFATYFCQQADSFPITFGQGTRLEIKR | 311 |
| NLAG3-HDB169-S27 | DIQLTQSPSSLSASVGDRVTITCRASQTISSHLNWYQQKPGKAPKVLIYAASSLQSGVPSRFSGSGSGTEFTLTISSLQPDDFATYYCQQGNSFPFTFGPGTKVEIKR | 312 |
| NLAG3-HDB169-S31 | AIRMTQSPSTLSASVGDRVTITCRASQGIAGWLAWYQQKPGKAPKLLIYAASSLQSGVPSRFSGSASGTDFTLTISNLQPEDFATYYCQQAKSFPLTFGGGTKVEIKR | 313 |
| NLAG3-HDB169-832 | DIVMTQSPDSLAVSLGERATINCKSSQSVLYSSNNKNYLAWYQQKPQPPKLLIYWASTRESGVPDRFSGTGSGTDFTLTISSLQAEDVAVYYCQQSYSTPWTFGQGTKLEIK | 314 |
| NLAG3-HDB169-861 | DIVMTQSPSSVSAFVGDRVTITCRASQGVSSWLAWFQQKPGKAPKLLIYAASTLQSGVPSRFSGRGYGTEFTLTISSLQPEDLATYYCQQVKSFPLTFGGGTKVDIKR | 315 |
| NLAG3-HDB169-S64 | DIVMTQSPDSLAVSLGERATINCKSSQSLFYHSNNHNYLAWYQQKPGQPPKLLIYWASTRQSGVPDRFTGSGSGTDFTLTISSLQAEDVAVYYCQQYYNTPWTFGQGTKVEIKR | 316 |
| NLAG3-HDB169-S86 | AIRMTQSPSTLSASVGDRVTITCRASQGIAGWLAWYQQKPGKAPKLLIYAASSLQSGVPSRFSGSASGTDFTLTISNLQPEDFATYYCQQAKSFPLTFGGGTKVEIKR | 317 |
| NLAG3-HDB169-S87 | DIVMTQSPSSVSAFVGDRVTITCRASQGVSSWLAWFQQKPGKAPKLLIYAASTLQSGVPSRFSGRGYGTEFTLTISSLQPEDLATYYCQQVKSFPLTFGGGTKVDIKR | 318 |
| NLAG3-HDB169-T94 | DIVMTQSPSSLSASVGDRVTITCRASQGISSSLAWYQQKPGKAPNLLIYTASTLQNGVPSRFSGSGSGTDFTLTISGLQPEDFATYYCQQTKNFPLTFGQGTRLEIKR | 319 |
| NLAG3-HDB169-T97 | EIVLTQSPDSLAVSLGERATINCKSSQSVLYSSNNKNYLAWYQQRPGQPPKLLISWASTRESGVPDRFSGSGSGADFSLTISSLQAEDVAVYYCQQYYSTPWTFGQGTKLEIKR | 320 |
| NLAG3-HDB169-T99 | VIWMTQSPSSLSASVGDSVTITCQASRDISNSLSWHQQKPGKAPKLLIYAASSLQSGVPSRFSGSGSGTDFTLTISSLQPEDFATYYCQQTKSFPLTFGGGTKVEIKR | 321 |
| NLAG3-HDB169-S103 | EIVMTQSPSSLSASVGDRVTISCRASQSISRYLNWYQQKPGQAPKLLIYAAFSLQSGVPSRFSGSGSGTDFTLTISSLQPEDFATYYCQQSYNTPRTFGQGTKLEIKR | 322 |
| NLAG3-HDB169-S107 | DVVMTQSPSTVSASVGDRITITCRASRSISNWLAWYQQKPGKAPKLLIYAASSLQSGVPSRFSGSGSGTDFTLTISSLQPEDFATYYCQQAKSFPLTFGGGTKVEIK | 323 |
| NLAG3-HDB169-S109 | DIQLTQSPDSLAVSLGERATINCKSSQSVFYRSNQKNYLAWYQQKPGQTPRLLIYGASSRATGIPDRFSGSGSGTDFTLTISSLQPEDFATYYCQQSYRAPWTFGQGTKVEIKR | 324 |
| NLAG3-HDB169-S119 | EIVLTQSPGTLSLSPGERATLSCRASQSVSSYLAWYQQKPGQAPRLLIYGISSRATGIPDRFSGSGSGTDFTLTISSLQPEDFATYYCQQANNFPLTFGGGTKLEIKR | 325 |
| NLAG3-HDB169-S120 | EIVLTQSPSSVSASVGDRVTITCRASRGISSWLAWYQQKPGKAPKLLIYAASTLQSGVPSRFSGSGSGTDFTLTISSLQPEDFATYYCQQAKSFPLTFGGGTKVEIKR | 326 |
| NLAG3-HDB169-S127 | EIVLTQSPGTLSLSPGERATLSCRASQSVSSYLAWYQQKPGQAPRLLIYGISSRATGIPDRFSGSGSGTDFTLTISSLQPEDFATYYCQQANNFPLTFGGGTKLEIKR | 327 |
| NLAG3-HDB169-S128 | AIQMTQSPSSLSASVGDRVTITCRASQGISSWLAWYQQKPGKAPKLLIYAASSLQSGVPSRFSGSGSGTDFTLTISRLQPEDFATYYCQQAKSFPLTFGGGTKVEIKR | 328 |
| NLAG3-HDB169-S136 | AIRMTQSPSSLSASVGDRVTITCRASQSISSYLNWYQQKPGKAPNLLIYAVSTLQSGVPSRFSGSGSGTVFTLTISSLQPEDFATYFCQQGNSFPLTFGGGTKVEIKR | 329 |
| NLAG3-HDB169-S139 | DIQLTQSPSTLSASVGDRVTITCRASQAISNLLAWYQQKPGKPPNLLIYDISTLQNGVPSRFSGSGSGTDFTLTINSLQPEDFAIYYCQQSKNFPVTFGGGTKVEIKR | 330 |
| NLAG3-HDB169-S150 | DIQLTQSPSSVSASVGDRVTITCRASQGISSWLAWYQQKPGKAPKLLIYGASTLQSGVPSRFSGSGSGADYTLTISSLQPEDFATYYCQQANSFPLTFAGGTKLEIKR | 331 |
| NLAG3-HDB169-S157 | DIQLTQSPSSLSASPGDRVTITCRASQGISTWLAWYQQKPGNAPKLLIYAASSLQSGVPSRFSGSKSGTEYTLTISSLQPEDFATYYCQQLESYPLTFGGGTKVEIKR | 332 |
| NLAG3-HDB169-S164 | AIRMTQSPDSLVVSLGERATINCKSSQSVLYSSNNKNYLAWYQQKPGQPPKLLIYWASTRESGVPDRFSGSGSGTDFTLSISSLQAEDVAVYYCQQYYSSPTFGGGTKVEIKR | 333 |
| NLAG3-HDB169-S177 | DVVMTQSPFFLSASVGDRVTITCRASQGIASNLAWYQQKPGKAPKLLIYAASTLQSGVPSRFTGSGSGTEFTLTVTSLQPEDFATYYCQQLKTFPLTFGGGTKVEIKR | 334 |

TABLE 20-continued

Light chain variable regions

| Antibody No. | VL | SEQ ID NO: |
|---|---|---|
| NLAG3-HDB323-S20 | VIWMTQSPSSLSASVGDRVTITCRASQGVSSYLAWYQQKPGKAPKLLIYA ASSLQSGVPSRFSGSGSGTEFTLTISSLQPEDFATYYCQQTNWFPLTFGP GTRLEIKR | 335 |
| NLAG3-HDB323-S21 | DIQMTQSPSSLSTSAGDTVTITCRASQSIYTYLNWYQQKPGKAPNLLIYG ASSLQSGVPSRFSGSGSGTDFTLTISSLQPEDFATYYCQQAQSFPITFGQ GTRLEIKR | 336 |
| NLAG3-HDB323-S32 | VIWMTQSPSSVSASVGDRVTITCRASQGISSWLAWYQQKPGKAPKLLIYA ASSLQSGVPSRFSGSGSGTDFTLTISSLQPEDFATYYCQQAHSFPLTFGG GTKVEIKR | 337 |
| NLAG3-HDB323-S35 | AIQLTQSPSTLSASVGDRVTITCRASQFVSDWLAWYQQKPGKAPKLLIYA ASTLQSGVPSRFSGSGSGTDFTLTISSLQPEDLATYYCLQDYHFPLTFGG GTKLEIKR | 338 |
| NLAG3-HDB323-S52 | DVVMTQSPSSVSASVGDRVTITCRASQDIVNWLAWYQQKPGKAPKLLIYA ASTLESGAPSRFSASGSGTDFTLTISSLQPDDFATYYCQQGHSFPLTFGP GTKLEIKR | 339 |
| NLAG3-HDB323-S55 | DIVMTQSPSSLSASVGDRVTITCRASQSIYTYLNWYQQKPGKAPKLLIYD ASSLQSGVPSRFSGSGYGTEFTLTISGLQPEDFATYYCQQSYIFPLTFGR GTKVEIKR | 340 |
| NLAG3-HDB323-T89 | AIRMTQSPSFVSASVGDRVTIACRASQTISTWLAWYQQKPGKAPKVLISK ASNLQSGVPSRFSGSGSGTEFTLTISSLQPDDFATYYCQQYDTYWTFGQG TKVEIKR | 341 |
| NLAG3-HDB323-T92 | AIRMTQSPSFVSASVGDRVTIACRASQTISTWLAWYQQKPGKAPKVLISK ASNLQSGVPSRFSGSGSGTEFTLTISSLQPDDFATYYCQQYDTYWTFGQG TKVEIKR | 342 |
| NLAG3-HDB323-T94 | DIVMTQSPSFVSASVGDTVTITCRASQGISSYLAWYQQKPGKAPKLLIYA ASTLQSGVPSRFSGSGSGTEFTLTISSLQPEDFATYYCQQLNSYPEFTFG PGTKVEIKR | 343 |
| NLAG3-HDB323-S102 | DIQMTQSPSTLSASVGDRVTITCRASQSIGYWLAWYQQKPGKAPKLLIYR ASSLQSGVPSRFSGSGSATEFTLTITSLQPDDFATYFCQQYSSYWTFGQG TKVEIKR | 344 |
| NLAG3-HDB323-S103 | EIVLTQSPSSLSASVGDTVTITCRATQSISSWLAWYQQKPGKAPQRLISG ASTLQSGVPSRFSGSGSGTEFTLTISGLQPEDFATYYCLQHNTYPFTFGQ GTKVEIKR | 345 |
| NLAG3-HDB323-S107 | DIVMTQSPSSVSASVGDRVTITCRASQGVRNWLAWYQQKPGKAPKLLIYA ASHLQSGVPSRFSGSGSGTDFTLTISSLQTDDFATYYCQQGHSFPLTFGG GTKVEIKR | 346 |
| NLAG3-HDB323-S114 | DIVMTQSPSSVSASVGDRVTITCRASQGVRNWLAWYQQKPGKAPKLLIYA ASHLQSGVPSRFSGSGSGTDFTLTISSLQTDDFATYYCQQGHSFPLTFGG GTKVEIKR | 347 |
| NLAG3-HDB323-S135 | VIWMTQSPSTLSASVGDRVTITCRASQSINNYLAWYQQKPGKAPKLLIYD ASTLQSGVPSRFSGGGSGTDFTLTINSLQPDDFASYYCQQAHSFPFTFGG GTKLEIKR | 348 |
| NLAG3-HDB323-S143 | EIVMTQSPSSVSASVGDRVTITCRASQDITSWLAWYQQKPGKAPKLLIYA ASTLESGVPSRFSGSGSGTDFTLTITGLQPEDFATYYCQQANMFPLTFGG GTKVEIKR | 349 |
| NLAG3-HDB323-S146 | AIRMTQSPSSLSASVGDRVTITCRASQGIYDYLAWYQQKPGKAPSLLIYA ASNLERGVPSRFSGSGSGKYFILTISSLQPEDFATYYCQQANSFPLTFGG GTKVEIKR | 350 |
| NLAG3-HDB323-S161 | AIQLTQSPSSLSASVGDRVTITCRASEGISGWLAWYQQIPGKAPKLLIYA ASSLETGVPSRFSGSGYGTDFTLTISSLQPEDFATYYCQQADSFPFTFGP GTKVEIKR | 351 |

TABLE 21

Light Chain CDRs

| Antibody No. | CDR L1 | SEQ ID NO: | CDR L2 | SEQ ID NO: | CDR L3 | SEQ ID NO: |
|---|---|---|---|---|---|---|
| NLAG3-HDB169-T03 | QANQDIHHYLN | 161 | DASILQS | 196 | QQADSFPIT | 218 |
| NLAG3-HDB169-T05 | KSSQSVLYSSSNKNYLA | 162 | WASTRES | 197 | QQSYSTPWT | 219 |
| NLAG3-HDB169-T06 | KSSQSVLYSSNNKNYLA | 163 | WASTRES | 197 | QQYYSTPWT | 220 |
| NLAG3-HDB169-T07 | RSSQNLLHSDGYNYLN | 164 | LGSNRAT | 198 | QQSYSTPWT | 219 |
| NLAG3-HDB169-T08 | KSSQSVLYTSNNKNYLA | 165 | WASTRES | 197 | QQYYSTPWT | 220 |
| NLAG3-HDB169-T10 | KSSQSVLYSSNNKNYLA | 163 | WASTRES | 197 | QQSFTTPWT | 221 |
| NLAG3-HDB169-T13 | QASQDINRYLS | 166 | DASNLET | 199 | QQYDNLPPT | 222 |
| NLAG3-HDB169-T23 | QASQDISNYLN | 167 | AASSLQS | 200 | QQSYGSPVT | 223 |
| NLAG3-HDB169-S24 | QASQDLSNYLN | 167 | DASNLET | 199 | QQADSFPIT | 218 |
| NLAG3-HDB169-S27 | RASQTISSHLN | 168 | AASSLQS | 200 | QQGNSFPFT | 224 |
| NLAG3-HDB169-S31 | RASQGIAGWLA | 169 | AASSLQS | 200 | QQAKSFPLT | 225 |
| NLAG3-HDB169-S32 | KSSQSVLYSSNNKNYLA | 163 | WASTRES | 197 | QQSYSTPWT | 219 |
| NLAG3-HDB169-S61 | RASQGVSSWLA | 170 | AASTLQS | 201 | QQVKSFPLT | 226 |
| NLAG3-HDB169-S64 | KSSQSLFYHSNNHNYLA | 171 | WASTRQS | #N/A | QQYYNTPWT | 227 |
| NLAG3-HDB169-S86 | RASQGIAGWLA | 169 | AASSLQS | 200 | QQAKSFPLT | 225 |

TABLE 21-continued

Light Chain CDRs

| Antibody No. | CDR L1 | SEQ ID NO: | CDR L2 | SEQ ID NO: | CDR L3 | SEQ ID NO: |
|---|---|---|---|---|---|---|
| NLAG3-HDB169-S87 | RASQGVSSWLA | 170 | AASTLQS | 201 | QQVKSFPLT | 226 |
| NLAG3-HDB169-T94 | RASQGISSSLA | 172 | TASTLQN | 212 | QQTKNFPLT | 228 |
| NLAG3-HDB169-T97 | KSSQSVLYSSNNKNYLA | 163 | WASTRES | 197 | QQYYSTPWT | 220 |
| NLAG3-HDB169-T99 | QASRDISNSLS | 173 | AASSLQS | 200 | QQTKSFPLT | 230 |
| NLAG3-HDB169-S103 | RASQSISRYLN | 174 | AAFSLQS | 202 | QQSYNTPRT | 231 |
| NLAG3-HDB169-S107 | RASRSISNWLA | 175 | AASSLQS | 200 | QQAKSFPLT | 225 |
| NLAG3-HDB169-S109 | KSSQSVFYRSNQKNYLA | 176 | GASSRAT | 203 | QQSYRAPWT | 232 |
| NLAG3-HDB169-S119 | RASQSVSSYLA | 177 | GISSRAT | 204 | QQANNFPLT | 233 |
| NLAG3-HDB169-S120 | RASRGISSWLA | 178 | AASTLQS | 201 | QQAKSFPLT | 225 |
| NLAG3-HDB169-S127 | RASQSVSSYLA | 177 | GISSRAT | 204 | QQANNFPLT | 233 |
| NLAG3-HDB169-S128 | RASQGISSWLA | 179 | AASSLQS | 200 | QQAKSFPLT | 225 |
| NLAG3-HDB169-S136 | RASQSISSYLN | 180 | AVSTLQS | 205 | QQGNSFPLT | 234 |
| NLAG3-HDB169-S139 | RASQAISNLLA | 181 | DISTLQN | 206 | QQSKNFPVT | 235 |
| NLAG3-HDB169-S150 | RASQGISSWLA | 179 | GASTLQS | 207 | QQANSFPLT | 236 |
| NLAG3-HDB169-S157 | RASQGISTWLA | 182 | AASSLQS | 200 | QQLESYPLT | 237 |
| NLAG3-HDB169-S164 | KSSQSVLYSSNNKNYLA | 163 | WASTRES | 197 | QQYYSSPT | 238 |
| NLAG3-HDB169-S177 | RASQGIASNLA | 183 | AASTLQS | 201 | QQLKTFPLT | 239 |
| NLAG3-HDB323-S20 | RASQGVSSYLA | 184 | AASSLQS | 200 | QQTNWFPLT | 240 |
| NLAG3-HDB323-S21 | RASQSIYTYLN | 185 | GASSLQS | 208 | QQAQSFPIT | 241 |
| NLAG3-HDB323-S32 | RASQGISSWLA | 179 | AASSLQS | 200 | QQAHSFPLT | 242 |
| NLAG3-HDB323-S35 | RASQFVSDWLA | 186 | AASTLQS | 201 | LQDYHFPLT | 243 |
| NLAG3-HDB323-S52 | RASQDIVNWLA | 229 | AASTLES | 209 | QQGNSFPLT | 244 |
| NLAG3-HDB323-S55 | RASQSIYTYLN | 185 | DASSLQS | 210 | QQSYIFPLT | 245 |
| NLAG3-HDB323-T89 | RASQTISTWLA | 187 | KASNLQS | 211 | QQYDTYWT | 246 |
| NLAG3-HDB323-T92 | RASQTISTWLA | 187 | KASNLQS | 211 | QQYDTYWT | 246 |
| NLAG3-HDB323-T94 | RASQGISSYLA | 188 | AASTLQS | 201 | QQLNSYPLFT | 247 |
| NLAG3-HDB323-S102 | RASQSIGYWLA | 189 | RASSLQS | 213 | QQYSSYWT | 248 |
| NLAG3-HDB323-S103 | RATQSISSWLA | 190 | GASTLQS | 207 | LQHNTYPFT | 249 |
| NLAG3-HDB323-S107 | RASQGVRNWLA | 191 | AASHLQS | 214 | QQGHSFPLT | 244 |
| NLAG3-HDB323-S114 | RASQGVRNWLA | 191 | AASHLQS | 214 | QQGHSFPLT | 250 |
| NLAG3-HDB323-S135 | RASQSINNYLA | 192 | DASTLQS | 215 | QQAHSFPFT | 251 |
| NLAG3-HDB323-S143 | RASQDITSWLA | 193 | AASTLES | 209 | QQANMFPLT | 252 |
| NLAG3-HDB323-S146 | RASQGIYDYLA | 194 | AASNLER | 216 | QQANSFPLT | 236 |
| NLAG3-HDB323-S161 | RASEGISGMLA | 195 | AASSLET | 217 | QQADSFPFT | 253 |

2.2. The Binding of Human Anti-LAG3 Antibodies to LAG3 Protein Derived from Various Species.

To evaluate the capability of the anti-LAG-3 antibodies to bind to human, rat, and mouse LAG3 the antibodies identified in Example 2.1 were evaluated for their binding property through ELISA. The human, rat and mouse LAG3 ECD-Fc protein were coated to ELISA plate at 1 µg/ml with 100 µl/well. Antibodies from Example 1 were serially diluted with ELISA diluent buffer. To assess binding, LAG-3 antibodies at various concentrations 10 µg/ml, 3.333 µg/ml, 1.111 µg/ml, 0.370 µg/ml, 0.123 µg/ml, 0.041 µg/ml, 0.014 µg/ml, 0.005 µg/ml, 0.0015 µg/ml and 0.0005 µg/ml) were then added to LAG3 antigen coated plate for 1.5 hr RT. The resulting plates were washed and then labeled with anti-human IgG(Fab)-HRP antibody. The S31 can only bind to human LAG3. The S27 and T99 can bind to human LAG3 and rat/mouse LAG3 with lower potency. The S119 antibody can bind to human, rat and mouse LAG3 at high potency (FIGS. 22A-22D).

2.3. The Binding of Human Anti-LAG3 Antibodies to Cell Surface LAG-3 Antigen on Activated Human Primary CD4+ T Cells.

Figure 23:
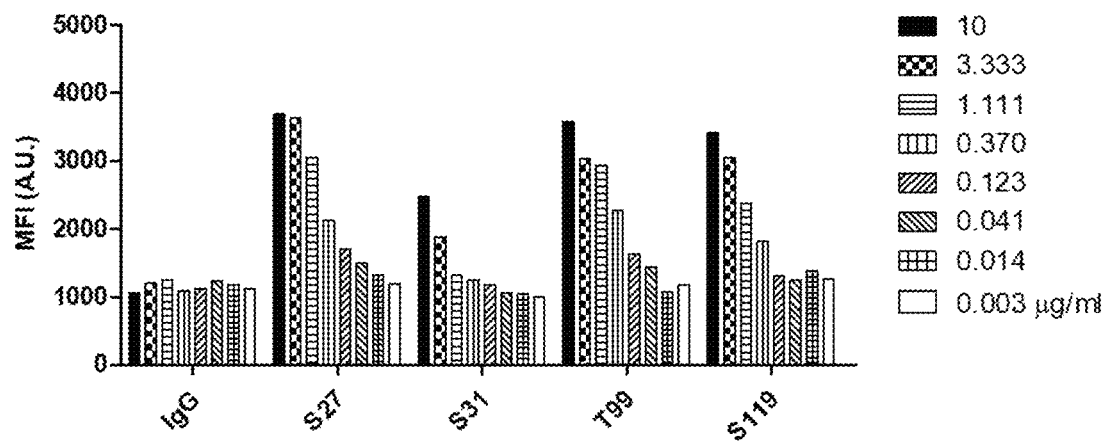
FIG. 23 shows the binding of human anti-LAG3 antibodies to cell surface LAG-3 antigen on activated human primary CD4+ T cells. Anti-LAG-3 antibodies were assessed for binding to cell surface LAG-3 antigen on activated human primary CD4+ T cells at various concentrations (10 µg/ml, 3.333 µg/ml, 1.111 µg/ml, 0.370 µg/ml, 0.123 µg/ml, 0.041 µg/ml, 0.014 µg/ml and 0.005 µg/ml).

LAG-3 is expressed on activated or exhausted T cells. CD4+ T cells were isolated using CD4 magnetic beads. The purified human CD4+ T cells were stimulated with Dynabeads® (magnetic beads) Human T-Activator CD3/CD28 for 72 hrs. Antibodies from Example 2.1 were serially diluted with FACS buffer. To assess binding, LAG-3 antibodies at various concentrations (10 µg/ml, 3.333 µg/ml, 1.111 µg/ml, 0.370 µg/ml, 0.123 µg/ml, 0.041 µg/ml, 0.014 µg/ml and 0.005 µg/ml) were then added to the activated human CD4 T cells in the presence of mouse anti-human LAG3 PE antibody (eBioscience®, clone: 3DS223H) for 30 min on ice. The labeled cells were washed with FACS buffer and subsequently labeled with APC-conjugated anti-human IgG antibodies for 30 min on ice. The resulting cells were washed once with FACS buffer. Labeled cells were evaluated for fluorescence intensity by flow cytometry in a BD FACSCalibur™ flow cytometer. As shown in FIG. 23, the S27, S31, T99 and S119 antibodies can dose-dependently bind to LAG3 expressed on the activated human CD4+ T cells.

Figure 24:
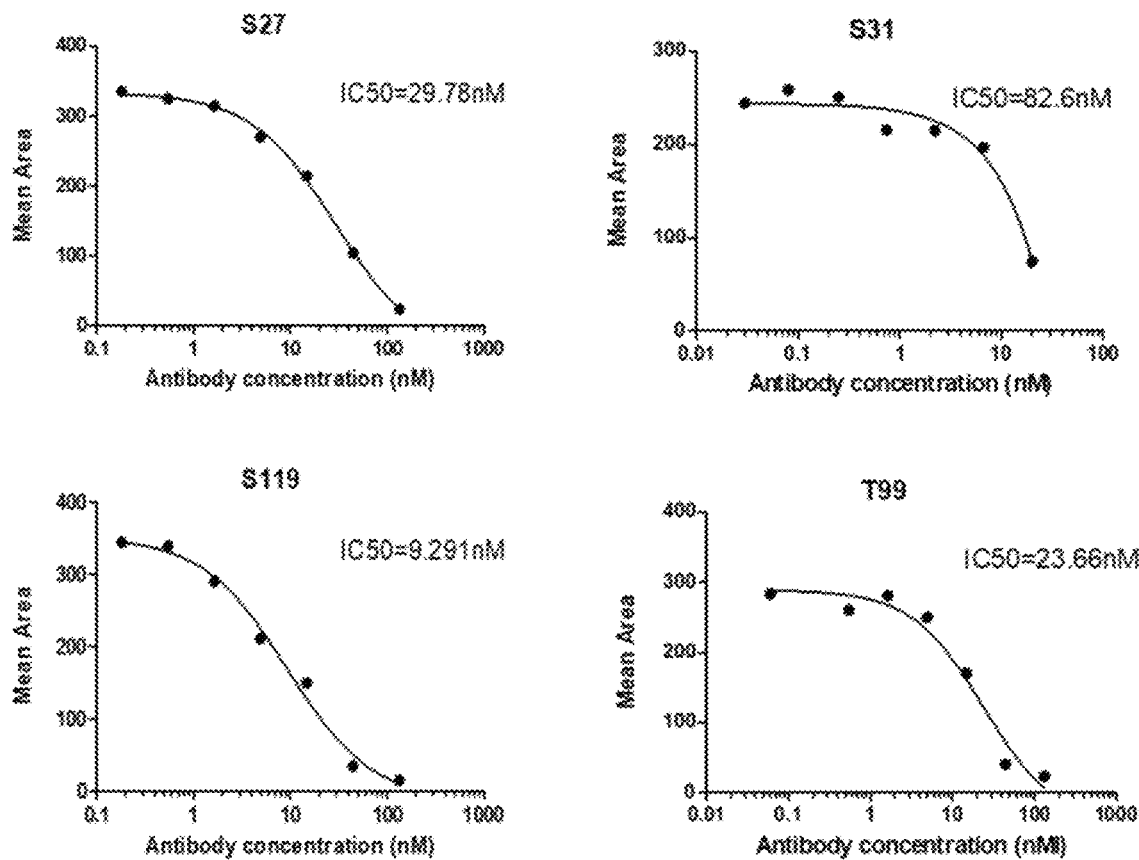
FIG. 24 shows inhibition of soluble LAG-3 (sLAG) binding to MHC class II receptor by anti-LAG-3 antibody. Anti-LAG-3 antibodies were evaluated for their ability to block the binding of sLAG-3 to MHC class II receptor in an in vitro binding assay using biotin-labeled LAG-3-ECD-huFcLAG-3-Fc fusion proteins and Raji cells expressing MHC class II receptor.

2.4. Anti-LAG-3 Antibody Inhibition of Soluble LAG-3 (sLAG) Binding to MHC Class II Receptor To evaluate the ability of anti-LAG-3 antibodies to block the binding of sLAG-3 to MHC class II receptor, an in vitro binding assay was designed using biotin-labeled LAG-3-ECD-huFc fusion proteins and Raji cells expressing MHC class II receptor. Antibodies from Example 1 were serially diluted from 20 µg/mL with FACS buffer and pre-incubated with 6 µg/mL of biotin-LAG-3-ECD-huFcc for 30 min at room temperature. The antibody mixture was then added to FcR blocked Raji cells and incubated for 30 min on ice. Cells were then washed with FACS buffer and subsequently stained with streptavidin PE for 30 min on ice and subsequently washed once with FACS buffer. Labeled cells were evaluated for fluorescence intensity by flow cytometry in a BD FACSCalibur™. As shown in FIG. 24, the S27, S31, S119 and T99 antibodies can dose dependently inhibit the binding of LAG3 to its receptor MHC class II molecules.

2.5. Stimulation of IL-2 Production in Peripheral Blood Mononuclear Cells (PBMCs) by Anti-LAG-3 Antibodies.

Figure 25:
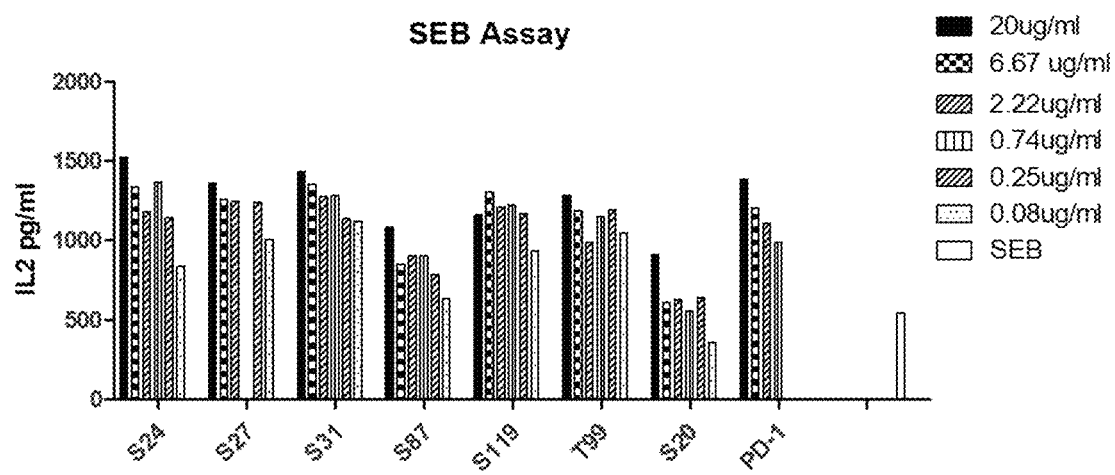
FIG. 25 shows stimulation of IL-2 production in peripheral blood mononuclear cells (PBMCs) by anti-LAG-3 antibodies. Anti-LAG-3 antibodies were administrated into Staphylococcal Enterotoxin B (SEB) stimulated PBMCs at various concentrations starting from 20 µg/ml at 1:3 serial dilution for 6 doses. Three days later, IL-2 concentration in the culture supernatant was evaluated by enzyme-linked immunosorbent assay (ELISA).

Staphylococcal enterotoxin B (SEB) is a superantigen that simultaneously binds to MHC class II antigens and T cell receptors (TCRs), bringing them together in such a way as to induce T cell proliferation and cytokine production. $2 \times 10^5$ PBMCs were stimulated with SEB in the presence of the antibodies from Example 1 at various concentrations starting from 20 µg/ml at 1:3 serial dilutions for 6 doses. Three days later, IL-2 concentration in the culture supernatant was evaluated by ELISA. As shown in FIG. 25, similar to PD-1 antibody, anti-LAG3 antibodies (S24, S27, S31, S87, S119, T99 and S20) can dose dependently enhanced IL-2 production as compared with SEB stimulation only.

2.6. Reversing the Inhibition of Regulatory T Cells ($T_{regs}$) on Effector T Cells ($T_{effs}$) Using Anti-LAG-3 Antibodies.

Figure 26:
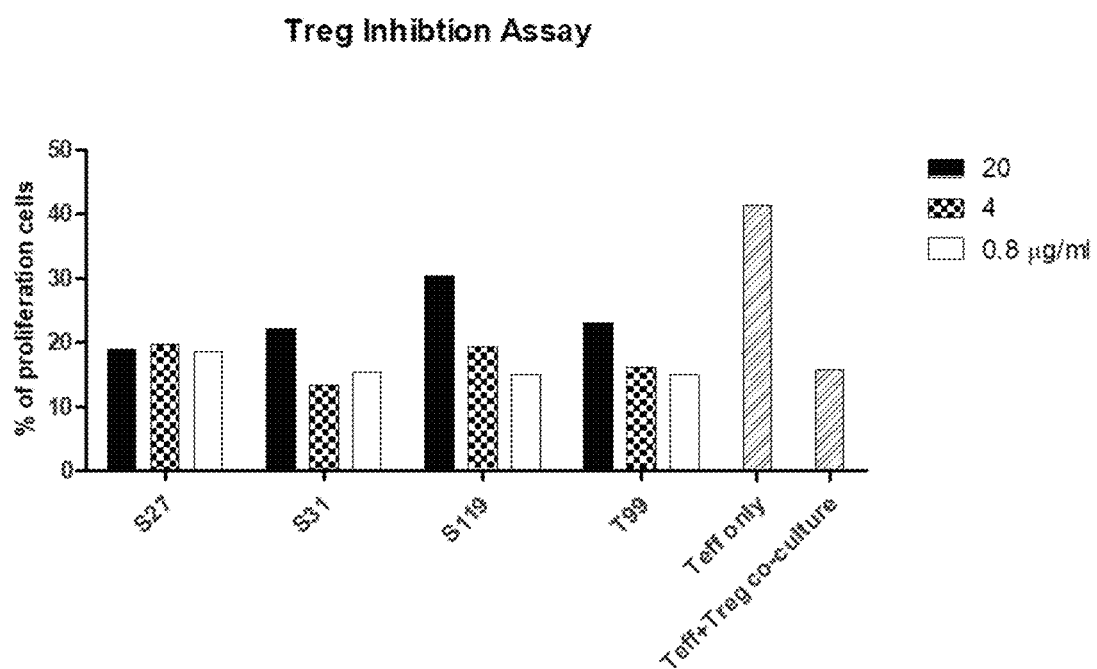
FIG. 26 shows Reversing the suppressive function of regulatory T cells ($T_{regs}$) on effector T cells ($T_{effs}$) using anti-LAG-3 antibodies. To evaluate the ability of anti-LAG-3 antibodies to reverse the suppressive effect of $T_{regs}$ on $T_{effs}$, the antibodies of Example 2.1 were used in an in vitro Tregs suppression assay.

LAG-3 is highly expressed on $T_{regs}$ ($CD4^+CD25^{hi}$) and mediates their suppressive function (Journal of Immunology 184:6545-51, 2010). To evaluate the ability of anti-LAG-3 antibodies on reversing the suppressive effect of $T_{regs}$ on effector T cells ($CD4^+CD25^-CD127^{hi}$), antibodies of Example 1 were used in an in vitro suppression assay. First, $T_{regs}$ ($CD4^+CD25^{hi}CD127^{low}$) and $T_{effs}$ ($CD4^+CD25^-CD127^{hi}$) were FACS-sorted by using a BD FACSAria™ II system. $T_{effs}$ were then labeled with carboxyfluorescein succinimidyl ester (CFSE) and co-cultured with $T_{regs}$ at a 1:1 ratio in the presence of plate bound anti-CD3 antibodies and mitomycin C-treated antigen presenting cells. Anti-LAG-3 antibodies were next added to the cell culture and $T_{effs}$ cell proliferation were tested 5 days later. The results in FIG. 26, indicate that when $T_{regs}$ were co-cultured with effector T cells, effector T cell proliferation and cytokine production was inhibited. S119 and T99 can reverse the inhibition of $T_{effs}$ by $T_{regs}$.

2.7. LAG-3 Antibody BIACORE™ Analysis

The binding of the S20, S24, S27, S31, S87, S119, S120, S128, S136, S161 and T99 antibodies to recombinant his-tag human LAG3-ECD protein was examined by Biacore™ T200 using a capture method. Anti-LAG3 antibodies were captured using anti-human Fc antibody. The anti-human Fc antibody was coated on chip. Serial concentrations of his-tag human LAG3-ECD protein (0-4 nM) were injected over capture antibodies at the flow rate of 30 µl/min. The dissociation phase was 900 s or 550 s. The results are shown in Table 22 below. The Biacore™ results for the anti-LAG3 antibodies have shown that these anti-LAG3 antibodies are high affinity binder to human LAG3.

TABLE 22

| | $K_a$ ($M^{-1} s^{-1}$) | $k_d$ ($s^{-1}$) | $K_D$ (M) |
| --- | --- | --- | --- |
| S20 | 1.65E+05 | 7.33E−06 | 4.43E−11 |
| S24 | 1.79E+06 | 1.20E−02 | 6.73E−09 |
| S27 | 7.04E+06 | 1.10E−04 | 1.56E−11 |
| S31 | 2.08E+06 | 6.25E−05 | 3.00E−11 |
| S87 | 9.28E+05 | 2.33E−06 | 2.51E−12 |
| S119 | 2.17E+07 | 1.49E−04 | 6.87E−12 |
| S120 | 1.40E+06 | 2.64E−03 | 1.88E−09 |
| S128 | 1.00E+06 | 8.17E−04 | 8.15E−10 |
| S136 | 7.98E+05 | 8.27E−05 | 1.04E−10 |
| S161 | 6.20E+05 | 5.53E−04 | 8.92E−10 |
| T99 | 7.62E+06 | 1.70E−04 | 2.24E−11 |

2.8. Generation of Mouse Monoclonal Antibodies Against Human LAG3

This example shows how anti-human-LAG3 mouse monoclonal antibodies were generated using hybridoma technology.

Antigen: Recombinant human LAG-3 fusion proteins were used as the immunogen to raise anti-human LAG-3 antibodies. A fusion protein comprising the entire extracellular region (domains 1-4) of human LAG-3 fused to a mouse immunoglobulin Fc domain (D1-D4 mFc) was used as the immunogen. For the ELISA binding test, a fusion protein comprising entire extracellular region (domains 1-4) or extracellular region without D1-D2 domain of human LAG-3 fused to human immunoglobulin Fc domain (D1-D4 huFc or ΔD1-D2 huFc respectively). The LAG-3 fusion proteins were prepared using standard recombinant DNA techniques.

Immunizations:

The LAG-3 fusion proteins were prepared using standard recombinant DNA techniques. Mice were immunized intraperitoneally (IP) and/or subcutaneously (SC).

The mice were firstly SC immunized 50 mg immunogen and then IP immunized biweekly with 25 µg immunogen. The immune response was monitored by retroorbital bleeds. The plasma was screened by ELISA and cell-based receptor blocking assay (as described below). Mice with sufficient titers of anti-LAG-3 D1-D2 domain immunoglobulin and functional LAG3 blocker were used for fusions. Prior to sacrifice and removal of the spleens, the mice were boosted intraperitoneally with 25 µg of antigen followed by a subsequent boost with 25 µg of antigen. The spleens were used for fusion. The hybridoma supernatant was tested for anti-LAG-3 D1-D2 domain binding and its function to block the binding of LAG3 to its receptor by cell based receptor blocking assay.

Selection of Mice Producing Anti-LAG3 Blocking Antibodies.

To select mice producing anti-LAG3 blocking antibodies, sera from immunized mice was tested for binding to D1-D2 domain by ELISA. Briefly, sera were evaluated for their binding to D1-D4 huFc and its binding to ΔD1-D2 huFc was served as a counter screen. In short, D1-D4 huFc or ΔD1-D2 huFc was coated at 0.5 ug/ml overnight and then blocked by 5% BSA in PBS. The serially diluted sera were incubated with the coated antigen for 1 h at room temperature. The resulting plates were washed with PBS/T and incubated with goat anti-mouse IgG-HRP for 1 h at room temperature. The plates were developed with TMB substrate and analyzed by spectrophotometer at OD 450-630 nm. In parallel, sera were evaluated to their function to blocking the binding of LAG3 to MHCII molecules expressed on Raji cells as described Example 2.4. The mice with high titers specific to LAG3 D1-D2 domain and function to block the binding of LAG3 to Raji cells were selected for fusion and further screening.

Hybridoma clones 122H, 147H and 170H were selected for further analysis and sequencing.

2.9. Binding Properties of Anti-LAG3 Mouse Monoclonal Antibodies

This example tested the binding properties of the anti-LAG3 mouse antibodies to the LAG3 proteins.

D1-D2 specific binders:

To evaluate the binding specificity, the purified 122H, 147H and 170H mouse monoclonal antibodies were subjected to ELISA binding test for D1-D4 huFc and ΔD1-D2 huFc antigens. Briefly, D1-D4 huFc or ΔD1-D2 huFc was coated at 0.5 µg/ml overnight and then blocked by 5% BSA in PBS. The serially diluted antibodies (starting from 1 µg/ml and 1:3 serial dilution for 10 doses) were incubated with the coated antigen for 1 hr at room temperature. The resulting plates were washed with PBS/T and incubated with goat anti-mouse IgG-HRP for 1 h at room temperature. The plates were developed with TMB substrate and analyzed by spectrophotometer at OD 450-630 nm.

Figure 27A:
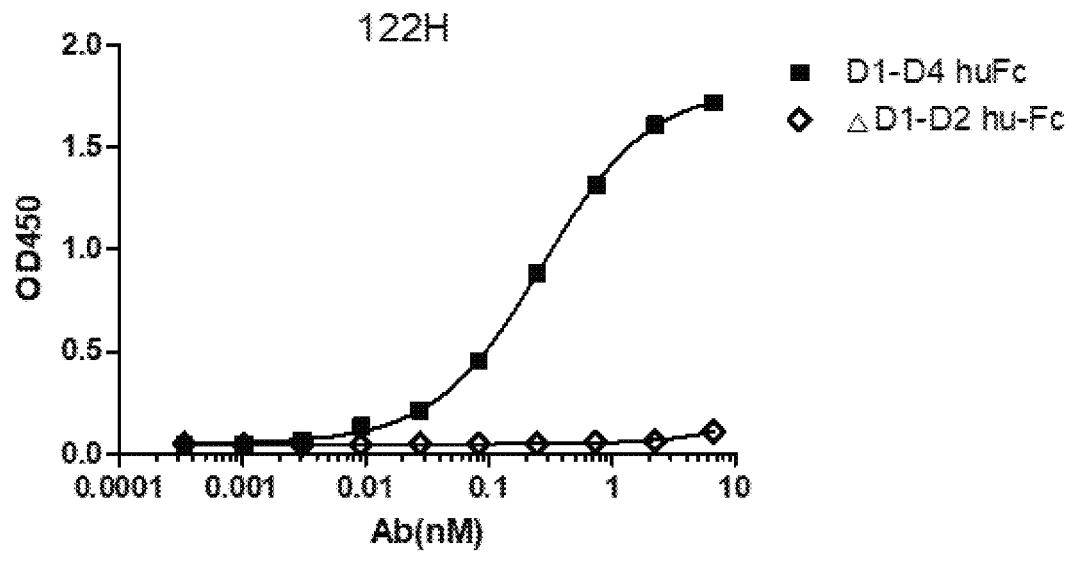
FIGS. 27A-27C show ELISA results showing EC50 of the antibody for binding to full extracellular domain of LAG3 (D1-D4 huFc) but not D1-D2 deleted LAG3 (A D1-D2 huFc), demonstrating that 122H, 147H and 170H are potent and selective binder for D1 and D2 domain of human LAG3.
Figure 27B:
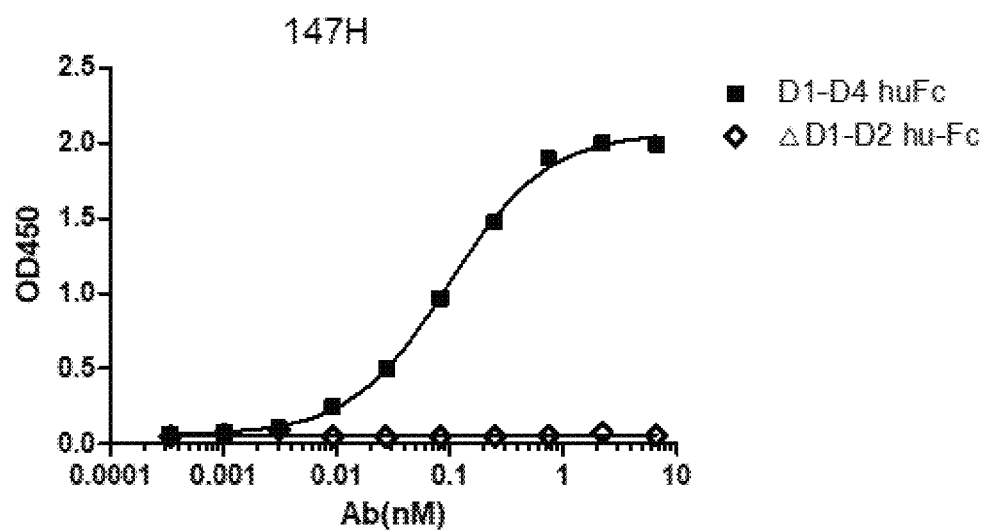
Figure 27C:
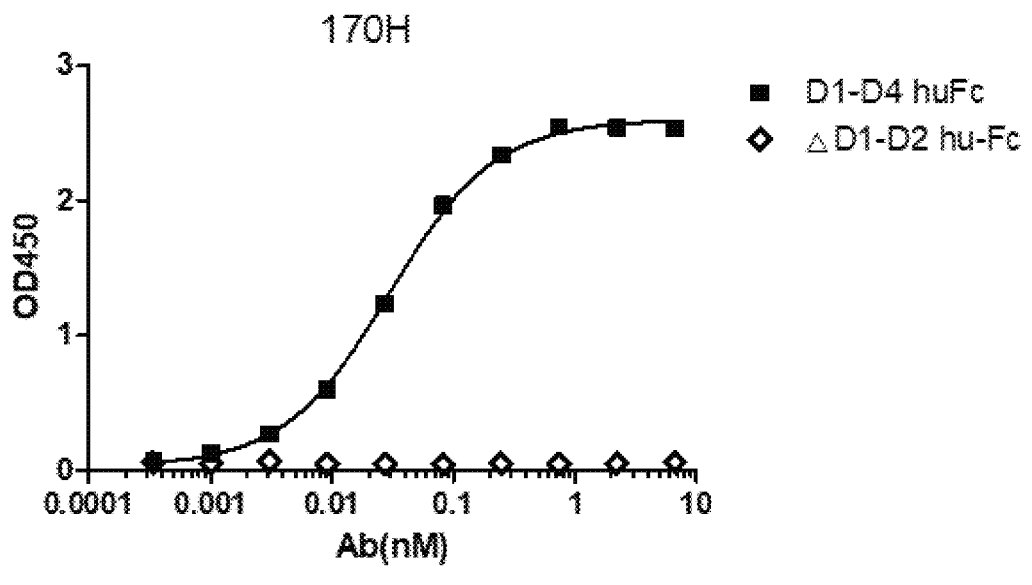

The results of the ELISA are summarized in FIGS. 27A-27C, which show strong binding to full extracellular domain of LAG3 (D1-D4 huFc) but not D1-D2 deleted LAG3 (ΔD1-D2 huFc), confirm that 122H, 147H and 170H are potent and selective binder for D1 and D2 domain of human LAG3.

Figure 28A:
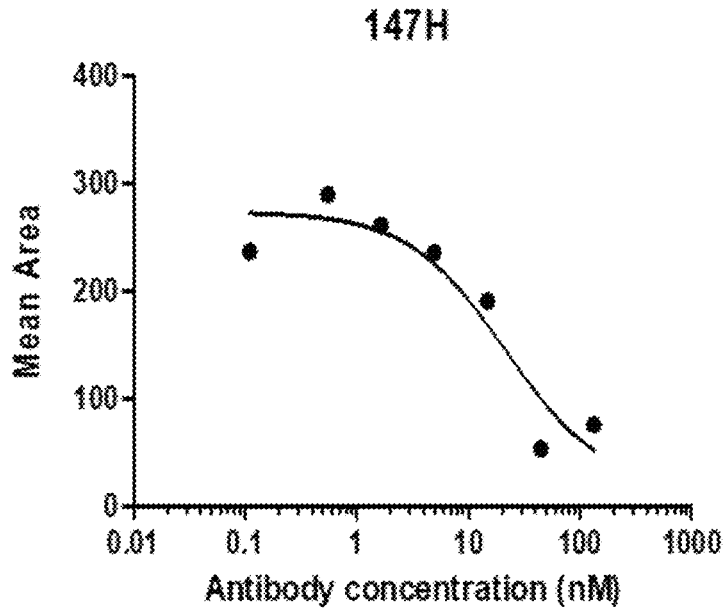
FIGS. 28A-28C show that 122H, 147H and 170H antibodies dose dependently inhibited the binding of LAG3 to its receptor MHC class II molecules.
Figure 28B:
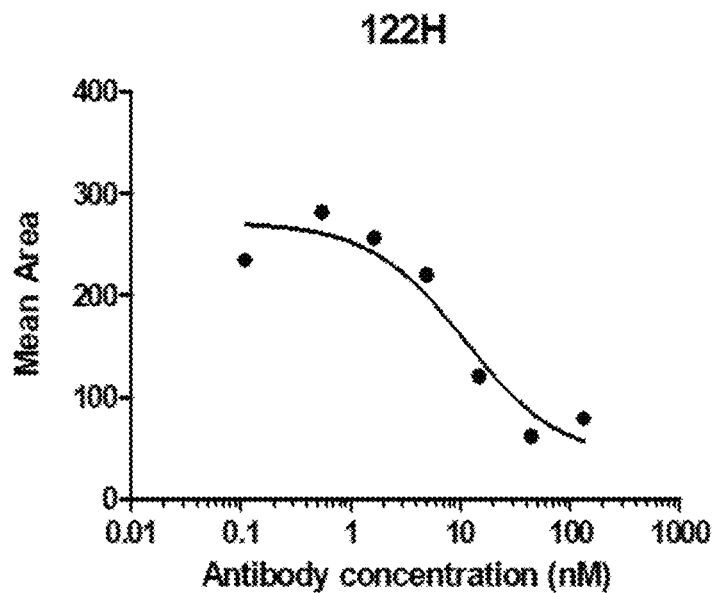
Figure 28C:
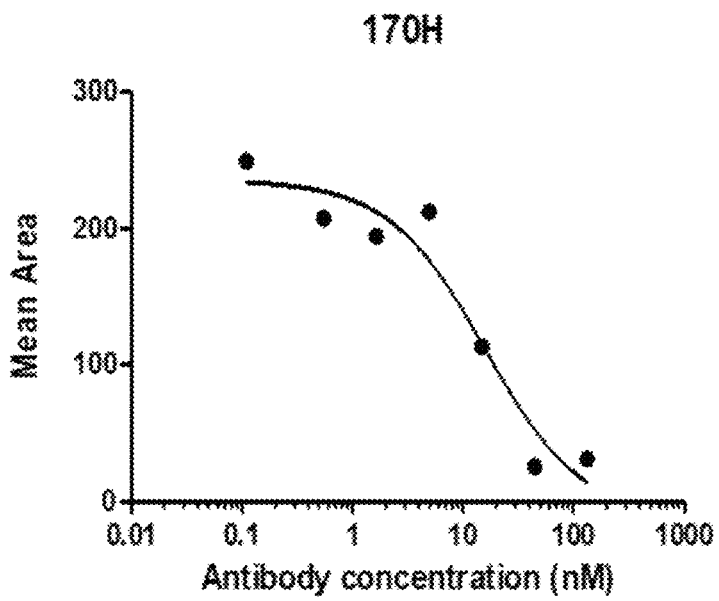
Figure 29:
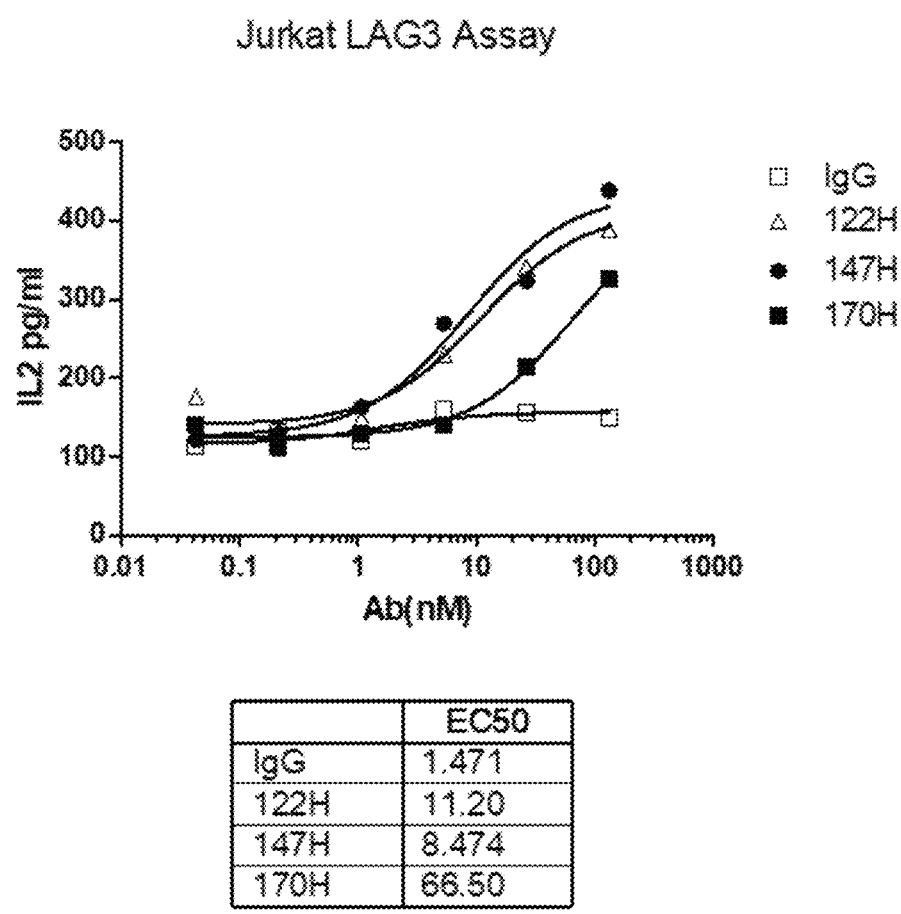
FIG. 29 shows that 122H, 147H and 170H mouse monoclonal antibodies dose dependently promoted IL2 production by Jurkat T cells.

2.10. Functional Properties of Anti-LAG3 Mouse Monoclonal Antibodies Blocking the Binding of LAG3 to its Receptor To evaluate the ability of anti-LAG-3 antibodies to block the binding of sLAG-3 to MHC class II receptor, an in vitro binding assay was designed using biotin-labeled LAG-3-ECD-huFc fusion proteins and Raji cells expressing MHC class II receptor. 122H, 147H and 170H mouse monoclonal antibodies were serially diluted (1:5 for 6 doses) from 20

µg/mL with FACS buffer and pre-incubated with 6 ug/mL of biotin-LAG-3-ECD-huFc for 30 min at room temperature. The antibody mixture was then added to FcR blocked Raji cells and incubated for 30 min on ice. Cells were then washed with FACS buffer and subsequently stained with streptavidin PE for 30 min on ice and subsequently washed once with FACS buffer. Labeled cells were evaluated for fluorescence intensity by flow cytometry in a BD FACSCalibur™. As shown in FIGS. 28A-28C, the 122H, 147H and 170H antibodies can dose dependently inhibit the binding of LAG3 to its receptor MHC class II molecules.

Stimulation of Human T Cell Response by Anti-LAG3 Antibodies

To test the ability of the anti-LAG3 antibodies to stimulated T cell response, Jurkat T cell stimulation assay was used. Jurkat is human T cell leukemia cell line that can produce IL2 upon TCR stimulation. In this assay, Jurkat cells transfected with human LAG3 gene by lentivirus were used as the responder cells. The Raji cells which expressed MHCII was used as the antigen presenting cells (APC). Staphylococcal Enterotoxins (SE) are superantigen, which can crosslink the MHCII molecules and T cell receptor beta (TCRVβ) and stimulate T cell response. SE was used as the stimulator in this assay. In this system, ectopically expressed huLAG3 can suppress SE stimulated IL-2 production by Jurkat cells, while anti-LAG3 antibodies can reverse IL-2 production. In short, APCs ($2.5 \times 10^4$) were co-cultured with LAG3 expressing Jurkat T cells ($1 \times 10^5$) in the presence of SE stimulation. Anti-LAG3 antibodies (starting from 20 µg/ml and 1:5 serially diluted for 6 dose) were added at the beginning of the culture. 48 hr later, culture supernatant was evaluated for IL2 production by ELISA. As shown in FIG. 29, 122H, 147H and 170H mouse monoclonal antibodies can dose dependently promote IL2 production by Jurkat T cells, suggesting they can stimulate TCR stimulation by suppressing LAG3 signal to T cells.

2.11. 147H Mouse mAb Humanization Design

The mAb 147H variable region genes were employed to create a humanized mAb. In the first step of this process, the amino acid sequences of the VH and VK of mAb 147H were compared against the available database of human Ig gene sequences to find the overall best-matching human germline Ig gene sequences. For the light chain, the closest human match was the A19/JK4 gene, and for the heavy chain the closest human match was the VH1-f/JH6 gene. Humanized variable domain sequences were then designed where the CDR1 (SEQ ID NO:243), 2 (SEQ ID NO:244) and 3 (SEQ ID NO:245) of the 147H light chain were grafted onto framework sequences of the A19/JK4 gene, and the CDR1 (SEQ ID NO:240), 2 (SEQ ID NO:241), and 3 (SEQ ID NO:242) sequences of the 147H VH were grafted onto framework sequences of the VH1-f/JH6 gene. A 3D model was then generated to determine if there were any framework positions where replacing the mouse amino acid to the human amino acid could affect binding and/or CDR conformation. In the case of the heavy chain, R71, M69, R66, V67, M48, V37, R38, Y91 and Q1 (Kabat numbering) in human framework were identified and subjected to back-mutation to their mouse counterpart amino acid i.e.: R71A, M69L, R66K, V67A, M48I, V37I, R38K, Y91F and Q1E.

TABLE 23

Mouse antibody sequences

| Antibody chain or domain | Sequences (CDR residues with VH and VL are underlined) | SEQ ID NO: |
| --- | --- | --- |
| 147H VH | QVQLQQSGSELVRPGTSVKISCKAS<u>GYTFTNYWLG</u>WIKQRPGHGLEWIG<u>DIYPGGDYINYNEKFKG</u>KATLSADTSSSTAYMQLSSLTSEDSAVYFCAR<u>PNLPGDY</u>WGQGTSVTVSS | 352 |
| 147H VL | DIVMTQAAFSNPVTLGTSASISC<u>RSSKSLLHSNGITYLY</u>WYLQKPGQSPQLLIY<u>QVSNLAS</u>GVPGRFSGSGSGTDFTLRISRVEAEDVGVYYC<u>AQNLELPWT</u>FGGGTKLEIK | 353 |
| CDRH1 | GYTFTNYWLG | 354 |
| CDRH2 | DIYPGGDYINYNEKFKG | 355 |
| CDRH3 | PNLPGDY | 356 |
| CDRL1 | RSSKSLLHSNGITYLY | 357 |
| CDRL2 | QVSNLAS | 358 |
| CDRL3 | AQNLELPWT | 359 |

The amino acid sequences of the humanized antibodies are listed: 147H-1, 147H-2, 147H-3, 147H-4, 147H-5, 147H-6, 147H-7, 147H-8, 147H-9, 147H-10, 147H-11, 147H-12, 147H-13, and 147H-14, each having a different heavy chain but all share a common light chain.

TABLE 24

Humanized antibodies and back mutations

| Antibody chain | Sequences (CDR underlined; back mutations bold and underlined) | SEQ ID NO: |
| --- | --- | --- |
| 147H-1 VH | QVQLVQSGAEVKKPGASVKVSCKAS<u>GYTFTNYWLG</u>WVRQAPGQGLEWMGD<u>IYPGGDYINYNEKFKG</u>RVTMTRDTSISTAYMELSRLRSDDTAVYYCAR<u>PNLPGDY</u>WGQGTTVTVSS | 360 |

TABLE 24-continued

Humanized antibodies and back mutations

| Antibody chain | Sequences (CDR underlined; back mutations bold and underlined) | SEQ ID NO: |
|---|---|---|
| 147H-2 VH | QVQLVQSGAEVKKPGASVKVSCKASGYTFTNYWLGWVRQAPGQGLEWMGDIYPGGDYINYNEKFKGRVTMTADTSISTAYMELSRLRSDDTAVYYCARPNLPGDYWGQGTTVTVSS | 361 |
| 147H-3 VH | QVQLVQSGAEVKKPGASVKVSCKASGYTFTNYWLGWVRQAPGQGLEWMGDIYPGGDYINYNEKFKGRVTLTADTSISTAYMELSRLRSDDTAVYYCARPNLPGDYWGQGTTVTVSS | 362 |
| 147H-4 VH | QVQLVQSGAEVKKPGASVKVSCKASGYTFTNYWLGWVRQAPGQGLEWMGDIYPGGDYINYNEKFKGKATLTADTSISTAYMELSRLRSDDTAVYYCARPNLPGDYWGQGTTVTVSS | 363 |
| 147H-5 VH | QVQLVQSGAEVKKPGASVKVSCKASGYTFTNYWLGWVRQAPGQGLEWIGDIYPGGDYINYNEKFKGKATLTADTSISTAYMELSRLRSDDTAVYYCARPNLPGDYWGQGTTVTVSS | 364 |
| 147H-6 VH | QVQLVQSGAEVKKPGASVKVSCKASGYTFTNYWLGWIKQAPGQGLEWIGDIYPGGDYINYNEKFKGKATLTADTSISTAYMELSRLRSDDTAVYYCARPNLPGDYWGQGTTVTVSS | 365 |
| 147H-7 VH | QVQLVQSGAEVKKPGASVKVSCKASGYTFTNYWLGWIKQAPGQGLEWIGDIYPGGDYINYNEKFKGKATLTADTSISTAYMELSRLRSDDTAVYFCARPNLPGDYWGQGTTVTVSS | 366 |
| 147H-8 VH | EVQLVQSGAEVKKPGASVKVSCKASGYTFTNYWLGWVRQAPGQGLEWMGDIYPGGDYINYNEKFKGRVTMTRDTSISTAYMELSRLRSDDTAVYYCARPNLPGDYWGQGTTVTVSS | 367 |
| 147H-9 VH | EVQLVQSGAEVKKPGASVKVSCKASGYTFTNYWLGWVRQAPGQGLEWMGDIYPGGDYINYNEKFKGRVTMTADTSISTAYMELSRLRSDDTAVYYCARPNLPGDYWGQGTTVTVSS | 368 |
| 147H-10 VH | EVQLVQSGAEVKKPGASVKVSCKASGYTFTNYWLGWVRQAPGQGLEWMGDIYPGGDYINYNEKFKGRVTLTADTSISTAYMELSRLRSDDTAVYYCARPNLPGDYWGQGTTVTVSS | 369 |
| 147H-11 VH | EVQLVQSGAEVKKPGASVKVSCKASGYTFTNYWLGWVRQAPGQGLEWMGDIYPGGDYINYNEKFKGKATLTADTSISTAYMELSRLRSDDTAVYYCARPNLPGDYWGQGTTVTVSS | 370 |
| 147H-12 VH | EVQLVQSGAEVKKPGASVKVSCKASGYTFTNYWLGWVRQAPGQGLEWIGDIYPGGDYINYNEKFKGKATLTADTSISTAYMELSRLRSDDTAVYYCARPNLPGDYWGQGTTVTVSS | 371 |
| 147H-13 VH | EVQLVQSGAEVKKPGASVKVSCKASGYTFTNYWLGWIKQAPGQGLEWIGDIYPGGDYINYNEKFKGKATLTADTSISTAYMELSRLRSDDTAVYYCARPNLPGDYWGQGTTVTVSS | 372 |
| 147H-14 VH | EVQLVQSGAEVKKPGASVKVSCKASGYTFTNYWLGWIKQAPGQGLEWIGDIYPGGDYINYNEKFKGKATLTADTSISTAYMELSRLRSDDTAVYFCARPNLPGDYWGQGTTVTVSS | 373 |
| 147H VL | DIVMTQSPLSLPVTPGEPASISCRSSKSLLHSNGITYLYWYLQKPGQSPQLLIYQVSNLASGVPDRFSGSGSGTDFTLKISRVEAEDVGVYYCAQNLELPWTFGGGTKVEIK | 374 |

The humanized VH and VK genes were produced synthetically and then respectively cloned into vectors containing the human gamma 1 and human kappa constant domains. The pairing of the human VH and the human VK created 40 humanized antibodies.

2.12. Binding Properties of Anti-LAG3 147H Humanized Monoclonal Antibodies

Affinity Ranking of Humanized Antibodies by Octet® RED96 System

To explore the binding kinetics of the humanized antibody, this example performed the affinity ranking by using Octet® Red 96. As shown in Table 25 below, 147H, 147H-6, 147H-7, 147H-13 and 147H-14 show better affinity.

TABLE 25

| Antibody | KD (M) | kon(1/Ms) | kdis(1/s) |
|---|---|---|---|
| 147H-1 | 3.54E−08 | 1.09E+05 | 3.86E−03 |
| 147H-2 | 3.16E−08 | 9.93E+04 | 3.14E−03 |
| 147H-3 | 3.65E−08 | 9.25E+04 | 3.38E−03 |
| 147H-4 | 3.98E−08 | 8.62E+04 | 3.43E−03 |
| 147H-5 | 3.13E−08 | 9.58E+04 | 3.00E−03 |
| 147H-6 | 1.53E−08 | 1.20E+05 | 1.84E−03 |
| 147H-7 | 1.57E−08 | 1.52E+05 | 2.39E−03 |
| 147H-8 | 3.23E−08 | 1.65E+05 | 5.33E−03 |
| 147H-9 | 6.64E−08 | 6.74E+04 | 4.48E−03 |
| 147H-10 | 8.23E−08 | 4.91E+04 | 4.04E−03 |
| 147H-11 | 4.22E−08 | 1.07E+05 | 4.51E−03 |

TABLE 25-continued

| Antibody | KD (M) | kon(1/Ms) | kdis(1/s) |
|---|---|---|---|
| 147H-12 | 5.52E−08 | 6.23E+04 | 3.44E−03 |
| 147H-13 | 2.16E−08 | 1.08E+05 | 2.34E−03 |
| 147H-14 | 2.32E−08 | 1.08E+05 | 2.50E−03 |

Full Kinetic Affinity of Humanized Antibodies by Octet® RED96 System

To explore the binding kinetics of the humanized antibody, this example further performed the full kinetic affinity testing by running various dose of antigen (50 nM, 25 nM, 12.5 nM, 6.15 nM, 3.125 nM) by using Octet® Red 96. The binding affinity was calculated by software in Octet® RED96 System. As shown in Table 26, 147H-6, 147H-7, 147H-13 and 147H-14 showed comparable affinity with 147H chimeric antibody.

TABLE 26

| Antibody | KD (M) | kon(1/Ms) | kdis(1/s) |
|---|---|---|---|
| 147H chimeric | 2.71E−08 | 8.01E+04 | 2.17E−03 |
| 147H-6 | 2.48E−08 | 1.05E+05 | 2.59E−03 |
| 147H-7 | 2.65E−08 | 1.18E+05 | 3.12E−03 |
| 147H-13 | 1.82E−08 | 1.04E+05 | 1.90E−03 |
| 147H-14 | 2.07E−08 | 9.87E+04 | 2.04E−03 |

Figure 30:
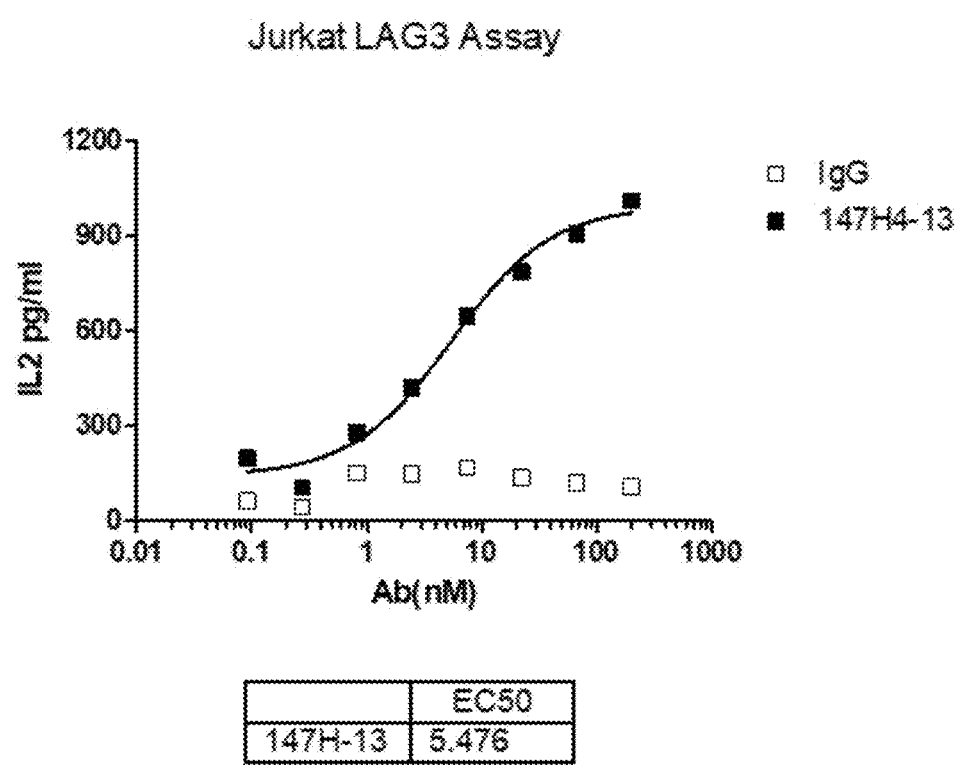
FIG. 30 shows that Humanized monoclonal antibody 147H-13 dose dependently promoted the IL2 production by Jurkat T cells.

2.13. Functional Properties of Anti-LAG3 Mouse Monoclonal Antibodies Stimulation of Human T Cell Response by Anti-LAG3 Antibodies To test the ability of anti-LAG3 antibodies to stimulated T cell response, Jurkat T cell stimulation assay was used as described in Example 12. Anti-LAG3 antibodies (starting from 30 μg/ml and 1:3 serially diluted for 6 doses) were added at the beginning of the culture. 48 hr later, culture supernatant was evaluated for IL2 production by ELISA. As shown in FIG. 30, 147H-13 humanized monoclonal antibodies can dose dependently promote IL2 production by Jurkat T cells, suggesting they can stimulate the TCR stimulation by suppressing LAG3 signal to T cells.

2.14. Affinity Maturation of Anti-LAG3 147H Humanized Monoclonal Antibodies

To improve antigen binding affinity, this example performed affinity maturation of 147H4-13 using phage display technology. Strategy 1: The CDRH3 and CDRL3 of 147H-13 were targeted for codon-based mutagenesis. CDRH3 and CDRL3 were randomized at position H95-H102 and L89-L97 (Kabat numbering), respectively. Strategy 2: Each CDR was targeted for single codon based mutagenesis using CDR walking approach. Then CDRH1, CDRH2, CDRL1 combined to library 1. The CDRH3, CDRL2, CDRL3 combined to library 2.

In both strategies, libraries were subject to three or four rounds of affinity-based solution-phase phage display selection with decreasing concentration of antigen at each round. A relatively high antigen concentration (10 nM) was used for the first round. The antigen concentration was decreased 10-fold each of the subsequent three rounds or 100-fold each the subsequent two rounds to select for high affinity variants. Individual variants from the final round were tested for positive binding to antigen by ELISA screening. Off-rate ranking of individual variants was determined by Octet® Red 96 (Fortebio, USA). Mutations with improved affinity were combined to generate new LAG3 antibodies. Affinity was further confirmed by Biacore™ which suggested N58V of CDR H2 significantly increased Koff, while N91Y of CDR L3 improved Kon.

TABLE 27

Antibody affinity maturation

| No. | Sequence (CDR underlined, mutation bold) |
|---|---|
| 147H 3421 | VH (SEQ ID NO: 375)<br>EVQLVQSGAEVKKPGASVKVSCKASGYTFTNYWLGWIKQAPGQGLEWIGDIYPGGDYINYN<br>EKFKGKATLTADTSISTAYMELSRLRSDDTAVYYCARPNLPKDHWGQGTTVTVSS<br>VL (SEQ ID NO: 376)<br>DIVMTQSPLSLPVTPGEPASISCRSSKSLLHSNAITYLYWYLQKPGQSPQLLIYQVSNLAS<br>GVPDRFSGSGSGTDFTLKISRVEAEDVGVYYCAQNLELPWTFGGGTKVEIK |
| 147H 3422 | VH (SEQ ID NO: 377)<br>EVQLVQSGAEVKKPGASVKVSCKASGYTFTNYWLGWIKQAPGQGLEWIGDIYPGGDYINYN<br>EKFKGKATLTADTSISTAYMEDSRLRSDDTAVYYCARPDLPGDYWGQGTTVTVSS<br>VL (SEQ ID NO: 378)<br>DIVMTQSPLSLPVTPGEPASISCRSSKSLLHSNAITYLYWYLQKPGQSPQLLIYQVSNLAS<br>GVPDRFSGSGSGTDFTLKISKVEAEDVGVYYCAQNLELPWTFGGGTKVEIK |
| 147H 3423 | VH (SEQ ID NO: 379)<br>EVQLVQSGAEVKKPGASVKVSCKASGYTFTNYWLGWIKQAPGQGLEWIGDIYPGGDYINYN<br>EKFKGKATLTADTSISTAYMELSRLRSDDTAVYYCARPGLPKDYWGQGTTVTVSS<br>VL (SEQ ID NO: 380)<br>DIVMTQSPLSLPVTPGEPASISCRSSKSLLHSNAITYLYWYLQKPGQSPQLLIYQVSNLAS<br>GVPDRFSGSGSGTDFTLKISRVEAEDVGVYYCAQNLELPWTFGGGTKVEIK |
| 147H 3424 | VH (SEQ ID NO: 381)<br>EVQLVQSGAEVKKPGASVKVSCKASGYTFTNYWLGWIKQAPGQGLEWIGDIYPGGDYINYN<br>EKFKGKATLTADISISTAYMELSRLRSDDTAVYYCARPNLPKDYWGQGTTVTVSS<br>VL (SEQ ID NO: 382)<br>DIVMTQSPLSLPVTPGEPASISCRSSKSLLHSNAITYLYWYLQKPGQSPQLLIYQVSNLAS<br>GVPDRFSGSGSGTDFTLKISRVEAEDVGVYYCAQNLELPWTFGGGTKVEIK |
| 147H 3425 | VH (SEQ ID NO: 383)<br>EVQLVQSGAEVKKPGASVKVSCKASGYTFTNYWLGWIKQAPGQGLEWIGDIYPGGDYINYN<br>EKFKGKATLTADTSISTAYMELSRLRSDDTAVYYCARPNLPRDYWGQGTTVTVSS |

TABLE 27-continued

Antibody affinity maturation

| No. | Sequence (CDR underlined, mutation bold) |
|---|---|
| | VL (SEQ ID NO: 384)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLELPWT</u>FGGGTKVEIK |
| 147H 3426 | VH (SEQ ID NO: 385)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<b>GLPR</b>DYWGQGTTVTVSS<br>VL (SEQ ID NO: 386)<br>DIVMTQSPLSLPVTPGEPASISC<u>RSSKSLLHSNAITYLY</u>WYLQKPGQS<b>R</b>QLLIY<u>QVSNLAS</u><br>GVPDRFSGSGSGTDFTLKISRVEAEDVGVYYC<u>AQNLELPWT</u>FGGGTKVEIK |
| 147H 3427 | VH (SEQ ID NO: 387)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<b>GLPQ</b>DYWGQGTTVTVSS<br>VL (SEQ ID NO: 388)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLELPWT</u>FGGGTKVEIK |
| 147H 3428 | VH (SEQ ID NO: 389)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<b>DLPK</b>DYWGQGTTVTVSS<br>VL (SEQ ID NO: 390)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLELPWT</u>FGGGTKVEIK |
| 147H 3429 | VH (SEQ ID NO: 391)<br>EVQLVQSGAEVKKPGASVKVSQKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<b>NLPG</b>DYWGQGTTVTVSS<br>VL (SEQ ID NO: 392;<br>DIVMTQSPLSLPVTPGEPASISC<u>RSSKSLLHSNAITYLY</u>WYLQKPGQSPQLLIY<u>QVSNLAS</u><br>GVPDRFSGSGSGTD<b>E</b>TLKISRVEAEDVGVYYC<b>G</b><u>QNLELPWT</u>FGGGTKVEIK |
| 147H 3430 | VH (SEQ ID NO: 393)<br>EVQLVQSGAEV<b>RR</b>PGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<b>NLPG</b>DYWGQGTTVTVSS<br>VL (SEQ ID NO: 394)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLE<b>MP</b>WT</u>FGGGTKVEIK |
| 147H 3431 | VH (SEQ ID NO: 395)<br>EVQLVQSGAEVKKPGASVKVSCRAS<u>GYTFTNYWLG</u>WI<b>R</b>QAPGQGLEWIG<u>DIYPGGDYINYN</u><br><u>EKFKG</u>KATLTADTSISTAYMELSRL<u>R</u>SDDTAVYYCARP<u>NLPGD</u>YWGQGTTVTVSS<br>VL (SEQ ID NO: 396)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<b>G</b><u>QNLE<b>MP</b>WT</u>FGGGTKVEIK |
| 147H 3432 | VH (SEQ ID NO: 397)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<u>NLPGDY</u>WGQGTTVTVSS<br>VL (SEQ ID NO: 398)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQ<b>Y</b>LE<b>E</b>PWT</u>FGGGTKVEIK |
| 147H 3433 | VH (SEQ ID NO: 399)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<u>NLPGDY</u>WGQGTTVTVSS<br>VL (SEQ ID NO: 400)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQ<b>Y</b>LELPWT</u>FGGGTKVEIK |
| 147H 3508 | VH (SEQ ID NO: 401)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<u>NLP<b>KD</b>H</u>WGQGTTVTVSS<br>VL (SEQ ID NO: 402)<br>DIVMTQSPLSLPVTPGEPASISC<u>RSSKSLLHSNAITYLY</u>WYLQKPGQSPQLLIY<u>QVSNLAS</u><br>GVPDRFSGSGSGTD<b>E</b>TLKISRVEAEDVGVYYC<b>G</b><u>QNLELPWT</u>FGGGTKVEIK |
| 147H 3549 | VH (SEQ ID NO: 403)<br>EVQLVQSGAEVKKPGASVKVSCKAS<u>GYTFTNYWLG</u>WIKQAPGQGLEWIG<u>DIYPGGDYINYN</u><br><u>EKFKG</u>KATLTADTSISTAYMELSRL<u>R</u>SDDTAVYYCARP<u>NLP<b>KD</b>H</u>WGQGTTVTVSS<br>VL (SEQ ID NO: 404)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQ<b>Y</b>LE<b>E</b>PWT</u>FGGGTKVEIK |

TABLE 27-continued

Antibody affinity maturation

| No. | Sequence (CDR underlined, mutation bold) |
|---|---|

147H 3550
VH (SEQ ID NO: 405)
EVQLVQSGAEVKKPGASVKVSCKASGYTFTNYWLGWIKQAPGQGLEWIGDIYPGGDYINYN
EKFKGKATLTADTSISTAYMELSRLRSDDTAVYYCARPNLPKDHWGQGTTVTVSS
VL (SEQ ID NO: 406)
DIVMTQSPLSLPVTPGEPASISCRSSKSLLHSNAITYLYWYLQKPGQSPQLLIYQVSNLAS
GVPDRFSGSGSGTDFTLKISRVEAEDVGVYYCAQYLELPWTFGGGTKVEIK 147H 3663
VH (SEQ ID NO: 407)
EVQLVQSGAEVKKPGASVKVSCKASGYTFENYWLGWIKQAPGQGLEWIGDIYPGGDYIVYN
EKFKGKATLTADTSISTAYMELSRLRSDDTAVYYCARPNLPGDYWGQGTTVTVSS
VL (SEQ ID NO: 408)
DIVMTQSPLSLPVTPGEPASISCRSSKSLLHSNAITYLYWYLQKPGQSPQLLIYQVSNLAR
GVPDRFSGSGSGTDFTLKISRVEAEDVGVYYCAQNLELPWTFGGGTKVEIK 147H 3664
VH (SEQ ID NO: 409)
EVQLVQSGAEVKKPGASVKVSCKASGYMFTNYWLGWIKQAPGQGLEWIGDIYPGGDYINYN
EKFKGKATLTADTSISTAYMELSRLRSDDTAVYYCARPNLPGDYWGQGTTVTVSS
VL (SEQ ID NO: 410)
DIVMTQSPLSLPVTPGEPASISCRSSKSLLHSNAITYLYWYLQKPGQSPQLLIYQKSNLAS
GVPDRFSGSGSGTDFTLKISRVEAEDVGVYYCAQNLELPWTFGGGTKVEIK 147H 3665
VH (SEQ ID NO: 411)
EVQLVQSGAEVKKPGASVKVSCKASGYTFDNYWLGWIKQAPGQGLEWIGDIYPGGDIINYN
EKFKGKATLTADTSISTAYMELSRLRSDDTAVYYCARPNLPGDYWGQGTTVTVSS
VL (SEQ ID NO: 412)
DIVMTQSPLSLPVTPGEPASISCRSSKSLLHSNAITYLYWYLQKPGQSPQLLIYQVSNLAV
GVPDRFSGSGSGTDFTLKISRVEAEDVGVYYCAQNLELPWTFGGGTKVEIK 147H 3666
VH (SEQ ID NO: 413)
EVQLVQSGAEVKKPGASVKVSCKASGYTFGNYWLGWIKQAPGQGLEWIGDIYPGGDVINYN
EKFKGKATLTADTSISTAYMELSRLRSDDTAVYYCARPNLPGDYWGQGTTVTVSS
Vl (SEQ ID NO: 414)
DIVMTQSPLSLPVTPGEPASISCRSSKSLLHSNAITYLYWYLQKPGQSPQLLIYQVSNLAL
GVPDRFSGSGSGTDFTLKISRVEAEDVGVYYCAQNLELPWTFGGGTKVEIK 147H 3667
VH (SEQ ID NO: 415)
EVQLVQSGAEVKKPGASVKVSCKASGYTFTNYWLWWIKQAPGQGLEWIGDIFPGGDYINYN
EKFKGKATLTADTSISTAYMELSRLRSDDTAVYYCARPNLPGDYWGQGTTVTVSS
VL (SEQ ID NO: 416)
DIVMTQSPLSLPVTPGEPASISCRSSKSLLHSNAITYLYWYLQKPGQSPQLLIYQVD**NLAS
GVPDRFSGSGSGTDFTLKISRVEAEDVGVYYCAQNLELPWTFGGGTKVEIK 147H 3668
VH (SEQ ID NO: 417)
EVQLVQSGAEVKKPGASVKVSCKASGYTFTNYWLGWIKQAPGQGLEWIGDIYPGGDYIVYN
EKFKGKATLTADTSISTTAYMELSRLRSDDTAVYYCARPNLPGDYWGQGTTVTVSS
VL (SEQ ID NO: 418)
DIVMTQSPLSLPVTPGEPASISCRSSKSLLHSNAITYLYWYLQKPGQSPQLLIYQVSNLAT
GVPDRFSGSGSGTDFTLKISRVEAEDVGVYYCAQNLELPWTFGGGTKVEIK 147H 3669
VH (SEQ ID NO: 419)
EVQLVQSGAEVKKPGASVKVSCKASGYLFTNYWLGWIKQAPGQGLEWIGDIYPGGDYIVYN
EKFKGKATLTADTSISTAYMELSRLRSDDTAVYYCARPNLPGDYWGQGTTVTVSS
VL (SEQ ID NO: 420)
DIVMTQSPLSLPVTPGEPASISCRSSKSLLHSNAITYLYWYLQKPGQSPQLLIYQVSNLAS
GVPDRFSGSGSGTDETLKISRVEAEDVGVYYCAQNLELPWTFGGGTKVEIK 147H 3670
VH (SEQ ID NO: 421)
EVQLVQSGAEVKKPGASVKVSCKASGYTFTNYWLGWIKQAPGQGLEWIGDIYPGGDYINYN
EKFKGKATLTADTSISTAYMELSRLRSDDTAVYYCARPNLPGDYWGQGTTVTVSS
VL (SEQ ID NO: 422)
DIVMTQSPLSLPVTPGEPASISCRSSKSLLHSNAITYLYWYLQKPGQSPQLLIYHVSNLAS
GVPDRFSGSGSGTDFTLKISRVEAEDVGVYYCAQNLELPWTFGGGTKVEIK 147H 3675
VH (SEQ ID NO: 423)
EVQLVQSGAEVKKPGASVKVSCKASGYTFTNYWLWWIKQAPGQGLEWIGDIYPGGDLINYN
EKFKGKATLTADTSISTAYMELSRLRSDDTAVYYCARPNLPGDYWGQGTTVTVSS
VL (SEQ ID NO: 424)
DIVMTQSPLSLPVTPGEPASISCRSSKSLLHSNAITYLYWYLQKPGQSPQLLIYHVSNLAS
GVPDRFSGSGSGTDFTLKISRVEAEDVGVYYCAQNLELPWTFGGGTKVEIK 147H 3676
VH (SEQ ID NO: 425)
EVQLVQSGAEVKKPGASVKVSCKASGYTFTNYWLSWIKQAPGQGLEWIGDIYPGGDHINYN
EKFKGKATLTADTSISTAYMELSRLRSDDTAVYYCARPNLPGDYWGQGTTVTVSS

TABLE 27-continued

Antibody affinity maturation

| No. | Sequence (CDR underlined, mutation bold) |
|---|---|
| | VL (SEQ ID NO: 426)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLELPWT</u>FGGGTKVEIK |
| 147H 3677 | VH (SEQ ID NO: 427)<br>EVQLVQSGAEVKKPGASVKVSCKAS<u>GYTFTNYWLW</u>WIKQAPGQGLEWIGE<u>IYPGGDYITYN</u><br><u>EKFKG</u>KATLTADTSISTAYMELSRLRSDDTAVYYCAR<u>PNLPGDY</u>WGQGTTVTVSS<br>VL (SEQ ID NO: 428)<br>DIVMTQSPLSLPVTPGEPASISC<u>RSSKSLLHSNAITYLY</u>WYLQKPGQSPQLLIY<u>QVSNRAS</u><br>GVPDRFSGSGSGTDFTLKISRVEAEDVGVYYC<u>AQNLELPWT</u>FGGGTKVEIK |
| 147H 3678 | VH (SEQ ID NO: 429)<br>EVQLVQSGAEVKKPGASVKVSCKAS<u>GYTFTNYWLGW</u>IKQAPGQGLEWIG<u>DIYPGGDYINYN</u><br><u>EKFKG</u>KATLTADISISTAYMELSRLRSDDTAVYYCAR<u>PNLPGDY</u>WGQGTTVTVSS<br>VL (SEQ ID NO: 430)<br>DIVMTQSPLSLPVTPGEPASISC<u>RSSKSLLHSNAITYLY</u>WYLQKPGQSPQLLIY<u>QVDNLAS</u><br>GVPDRFSGSGSGTDFTLKISRVEAEDVGVYYC<u>AQNLELPWT</u>FGGGTKVEIK |
| 147H 3679 | VH (SEQ ID NO: 431)<br>EVQLVQSGAEVKKPGASVKVSCKAS<u>GFTFTNYWLGW</u>IKQAPGQGLEWIG<u>DIYPGGDYIVYN</u><br><u>EKFKG</u>KATLTADTSISTAYMELSRLRSDDTAVYYCAR<u>PNLPGDY</u>WGQGTTVTVSS<br>VL (SEQ ID NO: 432)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQNLELPWT</u>FGGGTKVEIK |
| 147H 3790 | VH (SEQ ID NO: 433)<br>EVQLVQSGAEVRRPGASVKVSCKAS<u>GYTTNYWLGW</u>LKQAPGQGLEWIG<u>DIYPGGDYINYN</u><br><u>EKFKG</u>KATLTADTSISTAYMELSRLRSDDTAVYYCAR<u>PNLPKDH</u>WGQGTTVTVSS<br>VL (SEQ ID NO: 434)<br>DIVMTQSPLSLPVTPGEPASISC<u>RSSKSLLHSNAITYLY</u>WYLQKPGQSPQLLIY<u>QVSNLAT</u><br>GVPDRFSGSGSGTDFTLKISRVEAEDVGVYYC<u>AQNLELPWT</u>FGGGTKVEIK |
| 147H 3791 | VH (SEQ ID NO: 435)<br>EVQLVQSGAEVKKPGASVKVSCKAS<u>GYTFTNYWLGW</u>IKQAPGQGLEWIG<u>DIYPGGDYIVYN</u><br><u>EKFKG</u>KATLTADTSISTAYMELSRLRSDDTAVYYCAR<u>PNLPGDY</u>WGQGTTVTVSS<br>VL (SEQ ID NO: 436)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDETLKISRVEAEDVGVYYCG<u>QNLELPWT</u>FGGGTKVEIK |
| 147H 3792 | VH (SEQ ID NO: 437)<br>EVQLVQSGAEVKKPGASVKVSCKAS<u>GYTFTNYWLGW</u>IKQAPGQGLEWIG<u>DIYPGGDYIVYN</u><br><u>EKFKG</u>KATLTADTSISTAYMELSRLRSDDTAVYYCAR<u>PNLPGDY</u>WGQGTTVTVSS<br>VL (SEQ ID NO: 438)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDETLKISKVEAEDVGVYYC<u>AQYLELPWT</u>FGGGTKVEIK |
| 147H 3793 | VH (SEQ ID NO: 439)<br>EVQLVQSGAEVKKPGASVKVSCKAS<u>GYLFTNYWLGW</u>IKQAPGQGLEWIG<u>DIYPGGDYIVYN</u><br><u>EKFKG</u>KATLTADTSISTAYMELSRLRSDDTAVYYCAR<u>PNLPGDY</u>WGQGTTVTVSS<br>VL (SEQ ID NO: 440)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYCG<u>QNLELPWT</u>FGGGTKVEIK |
| 147H 3794 | VH (SEQ ID NO: 441)<br>EVQLVQSGAEVKKPGASVKVSCKAS<u>GYLFTNYWLGW</u>IKQAPGQGLEWIG<u>DIYPGGDYIVYN</u><br><u>EKFKG</u>KATLTADTSISTAYMELSRLRSDDTAVYYCAR<u>PNLPGDY</u>WGQGTTVTVSS<br>VL (SEQ ID NO: 442)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQYLELPWT</u>FGGGTKVEIK |
| 147H 3807 | VH (SEQ ID NO: 443)<br>EVQLVQSGAEVKKPGASVKVSCKAS<u>GYTFTNYWLGW</u>IKQAPGQGLEWIG<u>DIYPGGDYIVYN</u><br><u>EKFKG</u>KATLTADTSISTAYMELSRLRSDDTAVYYCAR<u>PNLPKDH</u>WGQGTTVTVSS<br>VL (SEQ ID NO: 444)<br>DIVMTQSPLSLPVTPGEPASISC<u>RSSKSLLHSQGITYLY</u>WYLQKPGQSPQLLIY<u>QVSNLAS</u><br>GVPDRFSGSGSGTDFTLKISRVEAEDVGVYYC<u>AQYLELPWT</u>FGGGTKVEIK |
| 147H 3807b | VH (SEQ ID NO: 491)<br>EVQLVQSGAEVKKPGASVKVSCKAS<u>GYTFTNYWLGW</u>IKQAPGQGLEWIG<u>DIYPGGDYIVYN</u><br><u>EKFKG</u>KATLTADTSISTAYMELSRLRSDDTAVYYCAR<u>PNLPKDH</u>WGQGTTVTVSS<br>VL (SEQ ID NO: 492)<br>DIVMTQSPLSLPVTPGEPASISC<u>RSSKSLLHSNAITYLY</u>WYLQKPGQSPQLLIY<u>QVSNLAS</u><br>GVPDRFSGSGSGTDFTLKISRVEAEDVGVYYC<u>AQYLELPWT</u>FGGGTKVEIK |

TABLE 27-continued

Antibody affinity maturation

| No. | Sequence (CDR underlined, mutation bold) |
|---|---|
| 147H 3808 | VH (SEQ ID NO: 445)<br>EVQLVQSGAEVKKPGASVKVSCKASGYTFTNYWLGWIKQAPGQGLEWIGDIYPGGDYIVYN<br>EKFKGKATLTADTSISTAYMELSRLRSDDTAVYYCARPNLPKDHWGQGTTVTVSS<br>VL (SEQ ID NO: 446)<br>DIVMTQSPLSLPVTPGEPASISCRSSKSLLHSNAITYLYWYLQKPGQSPQLLIYQVSNLAS<br>GVPDRFSGSGSGTDFTLKISRVEAEDVGVYYCGQYLELPWTFGGGTKVEIK |
| 147H 3809 | VH (SEQ ID NO: 447)<br>EVQLVQSGAEVKKPGASVKVSCKASGYLFTNYWLGWIKQAPGQGLEWIGDIYPGGDYIVYN<br>EKFKGKATLTADTSISTAYMELSRLRSDDTAVYYCARPNLPKDHWGQGTTVTVSS<br>VL (SEQ ID NO: 448)<br>DIVMTQSPLSLPVTPGEPASISCRSSKSLLHSNAITYLYWYLQKPGQSPQLLIYQVSNLAS<br>GVPDRFSGSGSGTDFTLKISRVEAEDVGVYYCAQYLELPWTFGGGTKVEIK |
| 147H 3810 | VH (SEQ ID NO: 449)<br>EVQLVQSGAEVKKPGASVKVSCKASGYLFTNYWLGWIKQAPGQGLEWIGDIYPGGDYIVYN<br>EKFKGKATLTADTSISTAYMELSRLRSDDTAVYYCARPNLPKDHWGQGTTVTVSS<br>VL (SEQ ID NO: 450)<br>DIVMTQSPLSLPVTPGEPASISCRSSKSLLHSNAITYLYWYLQKPGQSPQLLIYQVSNLAT<br>GVPDRFSGSGSGTDFTLKISRVEAEDVGVYYCAQYLELPWTFGGGTKVEIK |
| 147H 3811 | VH (SEQ ID NO: 451)<br>EVQLVQSGAEVKKPGASVKVSCKASGYLFTNYWLGWIKQAPGQGLEWIGDIYPGGDYIVYN<br>EKFKGKATLTADTSISTAYMELSRLRSDDTAVYYCARPNLPKDHWGQGTTVTVSS<br>VL (SEQ ID NO: 452)<br>DIVMTQSPLSLPVTPGEPASISCRSSKSLLHSNAITYLYWYLQKPGQSPQLLIYQVSNLAT<br>GVPDRFSGSGSGTDFTLKISRVEAEDVGVYYCGQYLELPWTFGGGTKVEIK |

TABLE 28

Summary of mutations and mutated CDR regions:

| | Original sequence (SEQ ID NO:_) | Example substitutions (based on kabat numbering) | Example mutated sequences (SEQ ID NO:_) |
|---|---|---|---|
| CDRH1 | GYTFTNYWLG (354) | Y27: F<br>T28: M, L<br>T30: E, D, G<br>S27: W, S | GYTFENYWLG (453)<br>GYMFTNYWLG (454)<br>GYTFDNYWLG (455)<br>GYTFGNYWLG (456)<br>GYTFTNYWLW (457)<br>GYLFTNYWLG (458)<br>GYTFTNYWLS (459)<br>GFTFTNYWLG (460) |
| CDRH2 | DIYPGGDYINYNEKFKG (355) | D50: E<br>Y52: F<br>Y56: I, V, L, H<br>N58: V, T | DIYPGGDYIVYNEKFKG (461)<br>DIYPGGDIINYNEKFKG (462)<br>DIYPGGDVINYNEKFKG (463)<br>DIFPGGDYINYNERHKG (464)<br>DIYPGGDLINYNEKFKG (465)<br>DIYPGGDHINYNEKEKG (466)<br>EIYPGGDYITYNEKFKG (467) |
| CDRH3 | PNLPGDY (356) | N96: D, G<br>G99: K, R, Q<br>Y102: H | PNLPKDH (468)<br>PDLPGDY (469)<br>PGLPKDY (470)<br>PNLPKDY (471)<br>PNLPRDY (472)<br>PGLPRDY (473)<br>PGLPQDY (474)<br>PDLPKDY (475) |
| CDRL1 | RSSKSLLHSNGITYLY (357) | N28: Q | RSSKSLLHSQGITYLY (490) |
| CDRL2 | QVSNLAS (358) | Q50: H<br>V51: K<br>S52: D<br>L54: R<br>S56: R, V, L, T | QVSNLAR (476)<br>QKSNLAS (477)<br>QVSNLAV (478)<br>QVSNLAL (479)<br>QVDNLAS (480) |

TABLE 28-continued

Summary of mutations and mutated CDR regions:

| Original sequence (SEQ ID NO:_) | Example substitutions (based on kabat numbering) | Example mutated sequences (SEQ ID NO:_) |
|---|---|---|
| | | QVSNLAT (481) |
| | | HVSNLAS (482) |
| | | QVSNRAS (483) |
| CDRL3 AQNLELPWT (359) | A89: G<br>N91: Y<br>L94: M, E | GQNLELPWT (484)<br>AQNLEMPWT (485)<br>GQNLEMPWT (486)<br>AQYLEEPWT (487)<br>AQYLELPWT (488)<br>GQYLELPWT (489) |

2.15. Binding Properties of Affinity Matured Anti-LAG3 147H Humanized Monoclonal Antibodies The binding kinetics of affinity matured antibodies to recombinant his-tag human LAG3-ECD protein was examined by Biacore™ T200, as stated in Example 2.7. The results were shown in Table below. The Biacore™ results showed that these anti-LAG3 antibodies had better affinity than parent 147H-13.

TABLE 29

| | KD (M) | kon(1/Ms) | kdis(1/s) |
|---|---|---|---|
| 147H-13 | 1.4E-08 | 2.2E+06 | 3.0E-02 |
| 147H 3421 | 8.1E-09 | 1.4E+06 | 1.2E-02 |
| 147H 3508 | 1.4E-09 | 2.9E+06 | 4.2E-03 |
| 147H 3549 | 9.2E-10 | 7.4E+06 | 6.8E-03 |
| 147H 3550 | 9.8E-10 | 8.7E+06 | 8.5E-03 |
| 147H 3663 | 6.8E-09 | 7.9E+05 | 5.4E-03 |
| 147H 3669 | 8.8E-09 | 7.2E+05 | 6.3E-03 |
| 147H 3790 | 5.9E-09 | 7.7E+05 | 4.5E-03 |
| 147H 3791 | 1.2E-09 | 2.1E+06 | 2.5E-03 |
| 147H 3792 | 5.9E-10 | 4.9E+06 | 2.9E-03 |
| 147H 3793 | 1.3E-09 | 1.8E+06 | 2.3E-03 |
| 147H 3794 | 7.2E-10 | 3.7E+06 | 2.7E-03 |
| 147H 3807b | 5.1E-10 | 4.0E+06 | 2.0E-03 |
| 147H 3808 | 7.5E-10 | 4.3E+06 | 3.2E-03 |
| 147H 3809 | 4.7E-10 | 4.3E+06 | 2.0E-03 |
| 147H 3810 | 4.1E-10 | 4.7E+06 | 1.9E-03 |
| 147H 3811 | 5.9E-10 | 4.9E+06 | 2.9E-03 |

To confirm the capability of affinity matured anti-LAG-3 antibodies binding to human LAG3, 2 antibodies with highest affinity (B3807b and B3810) along with parent antibody 147H-13 were evaluated using ELISA, which was described in Example 2.2. EC50 of B3807b, B3810 along with parent antibody was showed in table below. Both B3807b and B3810 showed superior binding capability than parent antibody 147H-13.

TABLE 30

| Name | EC50 (nM) |
|---|---|
| 147H-13 | 6.5 |
| 147H 3807b | 0.41 |
| 147H 3810 | 0.49 |

Figure 31:
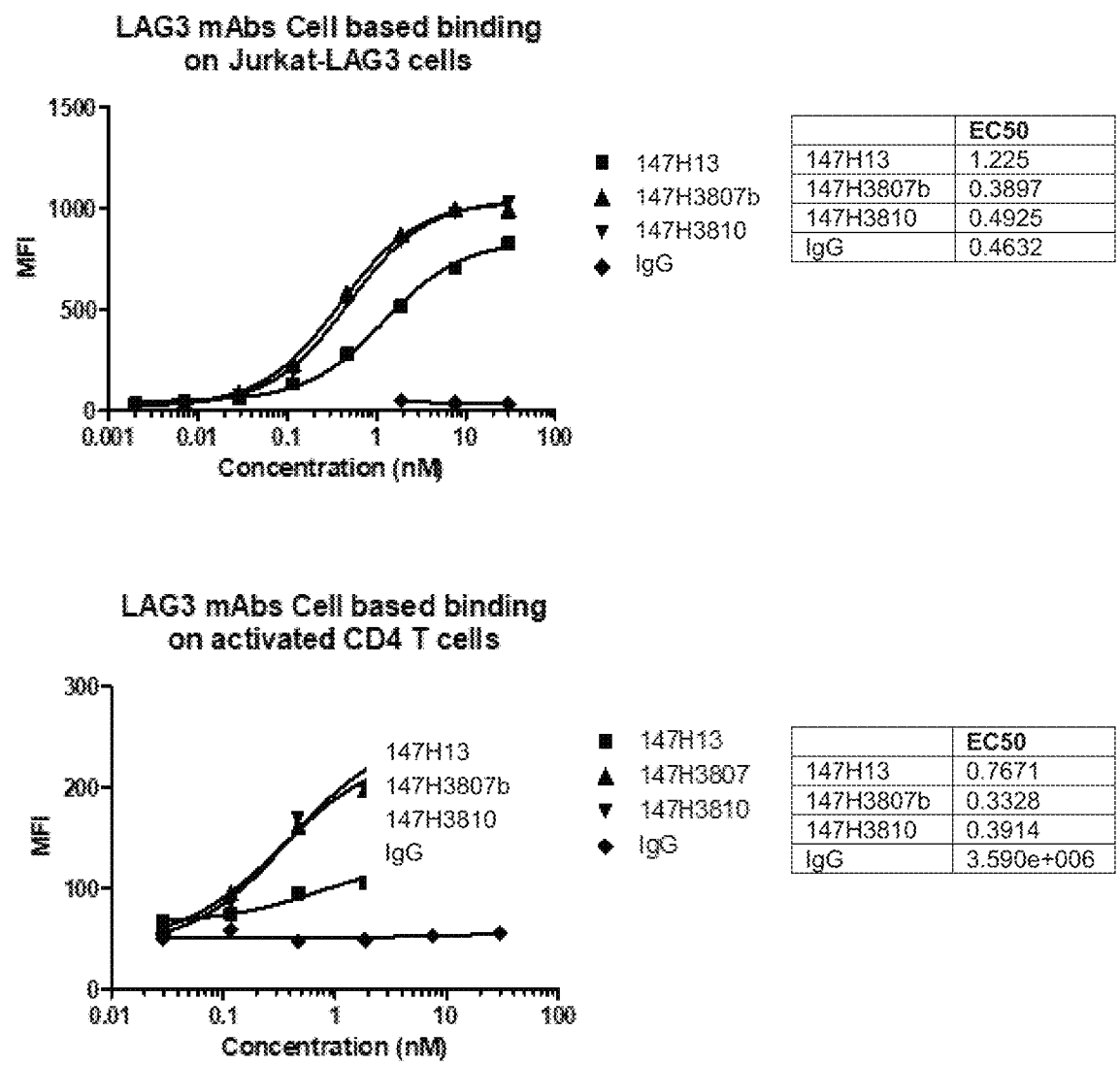
FIG. 31 shows binding curves of anti-LAG3 antibodies on Jurkat-LAG3 cells and activated CD4 T cell.

To further confirm affinity matured anti-LAG-3 antibodies could bind to cell-derived human LAG3, both inducible hLAG3 expressed Jurkat cells and activated PBMCs were used to test the binding capability of B3807b and B3810. In brief, Jurkat cells were resuspended in FACS buffer. Anti-LAG3 antibodies and isotype control were 4-fold serially diluted in FACS buffer with a dose ranging from 20 nM to 30 pM. The serially diluted antibodies were added to the cell suspension and incubated for 30 minutes on ice. Then after removal of unbound antibodies, cells were stained with anti-human IgG conjugated with Alexa Fluor® 633 (Thermo Fisher Scientific®, A21091). Fluorescence measurement was acquired on FACSCelesta™ flow cytometer and analyzed in Flowjo® (Computer software platform for the analysis of flow cytometry data) to determine the mean fluorescence intensities (MFI). To test anti-LAG3 antibodies' ability of binding to native human LAG3, PBMCs from health donor were stimulated with anti-CD3 (BD, 555336) and anti-CD28 (BD, 555725) both at a concentration of 1 ug/ml. Following 3 days' stimulation, cells were harvested and incubated with anti-LAG3 antibodies for 30 mins on ice. The cells were stained with anti-human CD4 and anti-human IgG. Analysis of antibodies binding to CD4+ cells were carried out on FACSCelesta™ flow cytometry. The results of cytometry analysis were summarized in table below which showed EC50 of antibodies binding to cell-derived human LAG3. FIG. 31 is a graph showing the binding curve of anti-LAG3 antibodies. EC50 of tested antibodies was showed below.

TABLE 31

| | EC50 (nM) | | |
|---|---|---|---|
| Cell-based binding assay | 147H-13 | 147H 3807b | 147H 3810 |
| Jurkat-LAG3 | 1.2 | 0.4 | 0.5 |
| Activated CD4 T cells | 0.77 | 0.33 | 0.39 |

2.16. Characterization of Monoclonal Antibody 147H 3807 (B3807)

A. Binding of B3807 to LAG3 Protein

This example evaluated the capability of the anti-LAG-3 antibody 147H 3807 (B3807) to bind to the human LAG3 protein. The streptavidin was coated to an ELISA plate at 2 µg/ml with 100 µl/well. 100 µl of Bio-LAG3 at 1.0 µg/ml was subsequently incubated with streptavidin at RT for 1 hr. B3807, along with a positive control 25F7 and a negative control IgG, were serially diluted with ELISA diluent buffer. To assess binding, the antibodies at various concentrations were added to LAG3 protein-coated plate for 1.5 hr RT. The resulting plates were washed and then labeled with anti-human IgG(Fab)-HRP antibody.

Figure 38:
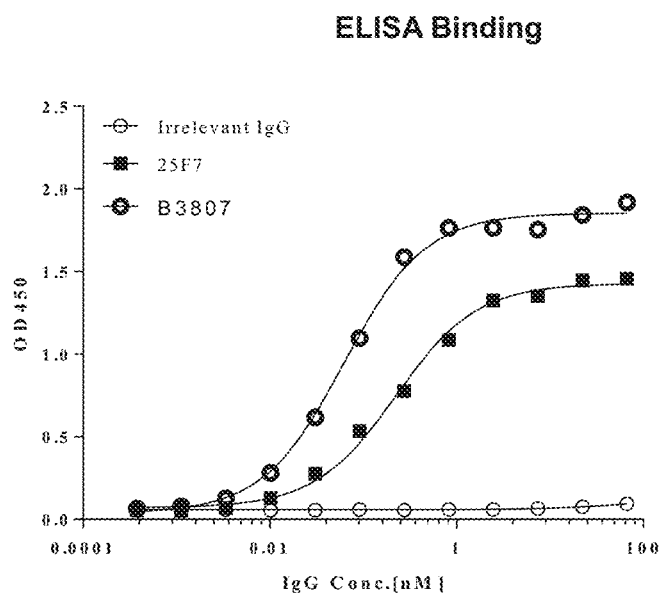
FIG. 38 shows the binding of anti-LAG3 monoclonal antibody B3807 and control antibodies to the human LAG3 protein, through enzyme-linked immunosorbent assay (ELISA).

As shown in FIG. 38, both B3807 and 25F7 bound to human LAG3 in a dose-dependent manner, with B3807 showing a higher potency and lower EC50 (0.06 nM vs. 0.22 nM for 25F7).

B. Biacore™ Analysis

Figure 39:
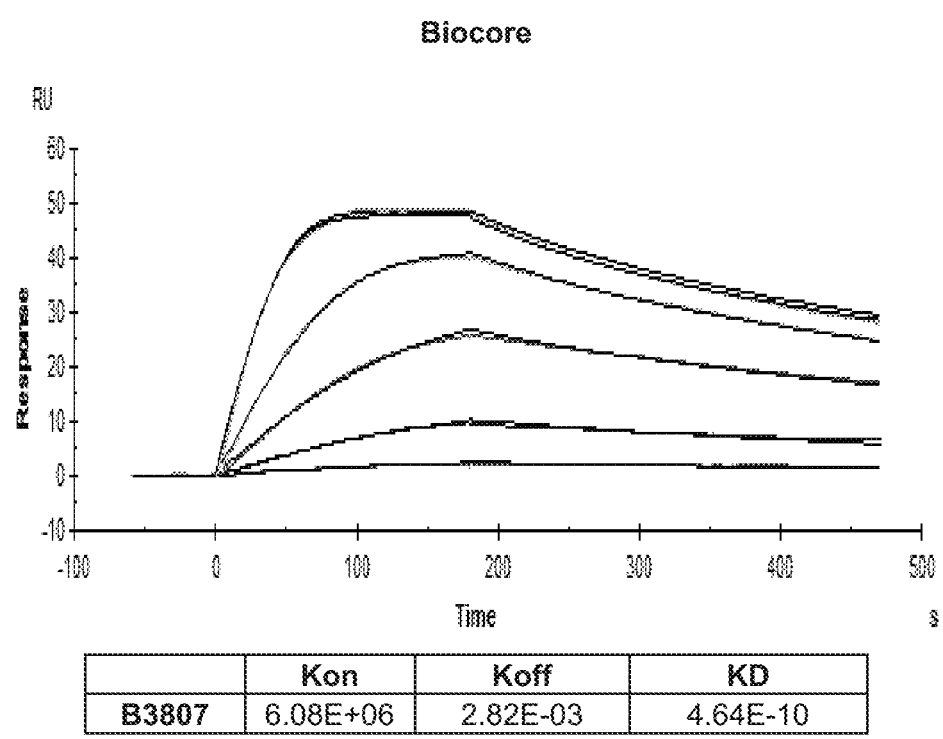
FIG. 39 shows the Biacore™ analysis result for B3807.

The binding of B3807 to recombinant His-tag human LAG3-ECD protein was examined by Biacore™ T200 using a capture method. B3807 was captured using protein A which was immobilized on CM5 sensor chip. Serial concentrations of his-tag human LAG3-ECD protein (0-12 nM) were injected over capture antibodies at the flow rate of 30 μl/min. The dissociation phase was 900 s or 550 s. The results are shown in FIG. 39, demonstrating that B3807 is binding to human LAG3 with high affinity C. Jurkat Cell and PBMC-Based Binding Assays To further confirm that B3807 could bind to cell-derived human LAG3, both inducible human LAG3 expressed Jurkat cells and activated PBMCs were used to test the binding capability of B3807. In brief, Jurkat cells were resuspended in FACS buffer. B3807, 25F7 and isotype control were 3-fold serially diluted in FACS buffer with a dose ranging from 20 nM to 9 pM. The serially diluted antibodies were added to the cell suspension and incubated for 30 minutes on ice. Then after removal of unbound antibodies, cells were stained with Goat anti-human IgG (H+L) cross adsorbed Secondary Antibody conjugated with Alexa Fluor® 633 (Thermo Fisher Scientific®, A21091). Fluorescence measurement was acquired on FACSCelesta™ flow cytometer and analyzed in Flowjo to determine the mean fluorescence intensities (MFI). To test the antibodies' ability of binding to native human LAG3, PBMCs from health donor were stimulated with anti-CD3 (BD, 555336) and anti-CD28 (BD, 555725) both at a concentration of 1 μg/ml. Following 3 days' stimulation, cells were harvested and incubated with anti-LAG3 antibodies for 30 mins on ice. The cells were stained with anti-human CD4 and anti-human IgG. Analysis of antibodies binding to CD4+ cells were carried out on FACSCelesta™ flow cytometer.

Figure 40:
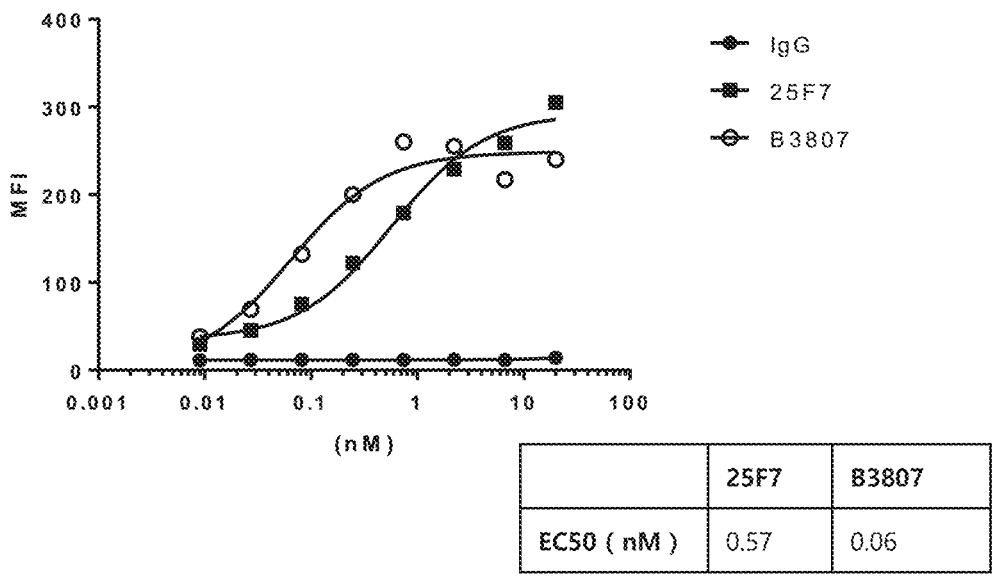
FIG. 40 shows the binding activities of B3807 to human LAG3 on Jurkat and PBMC cells.
Figure 40:
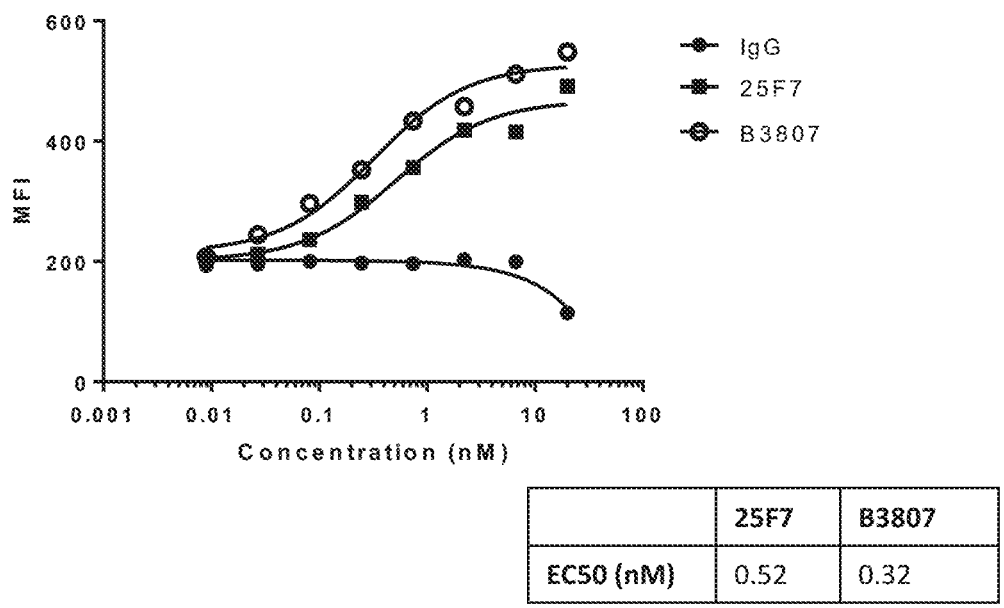

The results of cytometry analysis are presented in FIG. 40. EC50 of tested antibodies are also showed in the figure. In both tests, B3807 exhibited stronger binding capability than the control antibody 25F7.

D. Blocking of LAG3 Binding to MHC Class II

Figure 41:
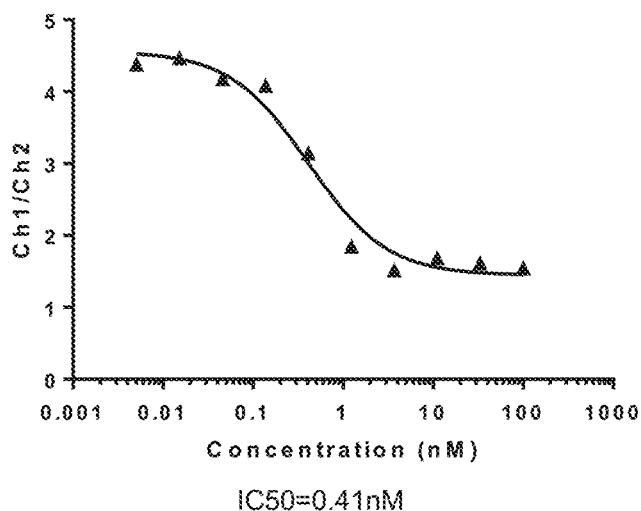
FIG. 41 shows the inhibition of soluble LAG-3 (sLAG) binding to MHC class II receptor by B3807.

To measure the ability of B3807 to block the interaction between human LAG3 and MHCII, the LAG3 and MHC II binding assay (Cisbio®, 64ICP03PEG) was performed utilizing homogeneous TR-FRET technology, following the protocol provided by the kit manufacturer. B3807 was 3-fold diluted ranging from 100 nM to 5 pM (10 points). Fluorescence data was acquired on a PerkinElmer Envision plate reader and a four-parameter dose-response curve was fitted to obtain IC50 of each antibody. IC50 of B3807 was 0.41 nM (FIG. 41) demonstrating potent blocking activity.

Figure 42:
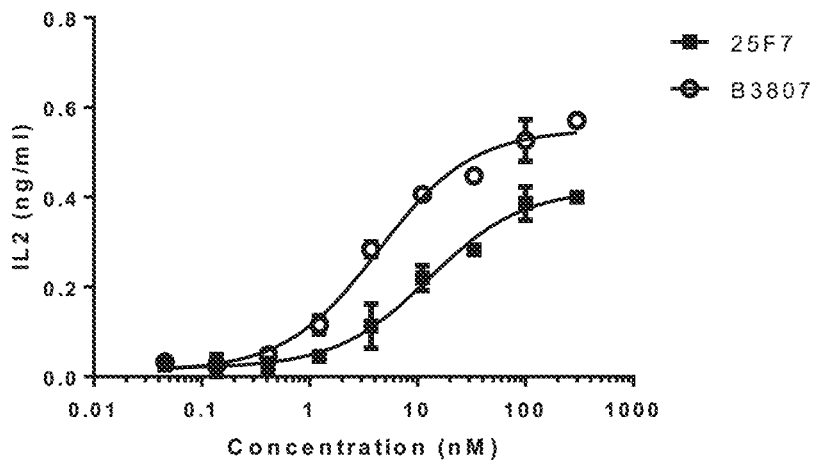
FIG. 42 shows the effects of the B3807 on IL2 production in Jurkat cells.

E. Stimulation of Human T Cell Response To test the ability of anti-LAG3 antibodies to stimulate T cell response, hLAG3-expressed Jurkat cells were used. In each well of 96-well plate, Jurkat cells ($1 \times 10^5$) were incubated with Raji cells ($1 \times 10^4$) in the presence of 0.1 ng/ml SE. B3807 was 3-fold diluted and added to the cells at a final concentration ranging from 100 nM to 50 pm. 48 hours later, IL2 from the culture medium was measured using a homogeneous TR-FRET assay (PerkinElmer, TRF1221M). FIG. 42 shows the curve of B3807 and 25F7 in stimulating IL2 release, in which B3807 outperformed 25F7 by a great margin.

F. IL2 Release in Primary T Cells

Figure 43:
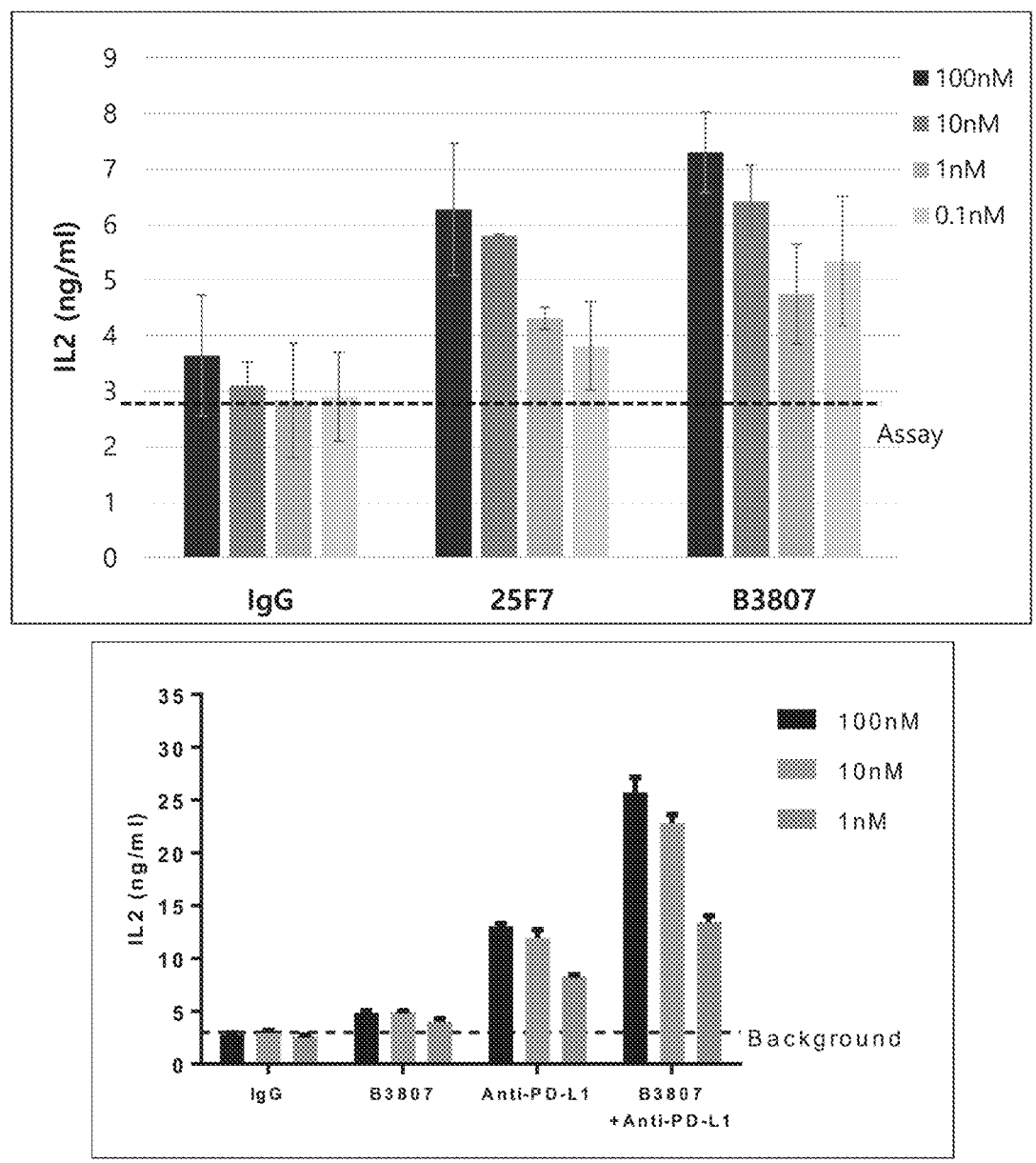
FIG. 43 shows the effects of the B3807, as well as in combination with anti-PD-L1 antibody, on IL2 production in primary T cells.

The antibodies' ability to stimulate T cell response was also tested with hLAG3-expressed primary T cells. At all four tested doses, B3807 outperformed 25F7 (FIG. 43, left panel). When used with an anti-PD-L1 antibody together, the IL2 release profile (FIG. 43, right panel) demonstrated the synergistic effect between the anti-LAG3 antibody B3807 and the anti-PD-L1 antibody.

G. Combinatory Effects with Anti-PD1/Anti-PD-L1 Antibodies in Tumor Regression

Figure 44:
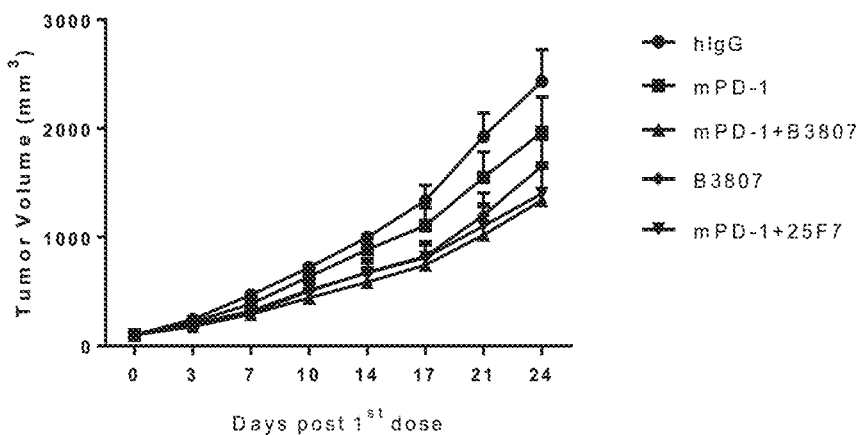
FIG. 44 shows the in vivo results of B3807, alone or in combination with anti-PD-1 or anti-PD-L1 antibodies, in inhibiting tumor growth.
Figure 44:
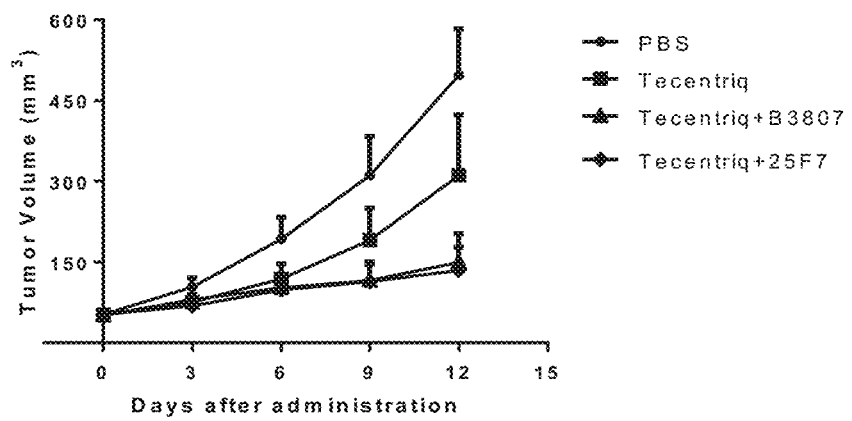

Humanized mice that expressed the extracellular domains of human LAG3 were used. As shown in FIG. 44, left panel, B3807 and 25F7 exhibited some effect in inhibiting the tumor growth when combo with anti-PD-1 antibody.

In the right panel of FIG. 44, however, it is apparent that both B3807 and 25F7 had significant synergistic effect when used together with Tecentriq, a commercially available anti-PD-L1 antibody.

H. Comparison of B3807 with B3807b

The activities of B3807 and B3807b were compared for their ability in promoting IL2 release in Jurkat cells (see experimental procedure in Example 2.16(E)) and in binding to LAG3 on Jurkat cells (see experimental procedure in Example 2.16(C)).

Figure 45:
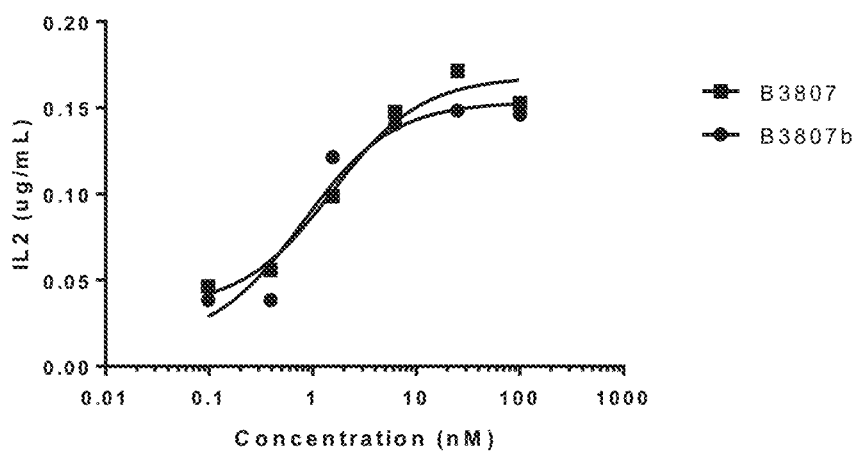
FIG. 45 compares B3807 and B3807b in IL2 release and cell-based binding assays, and demonstrates their high level similarity.
Figure 45:
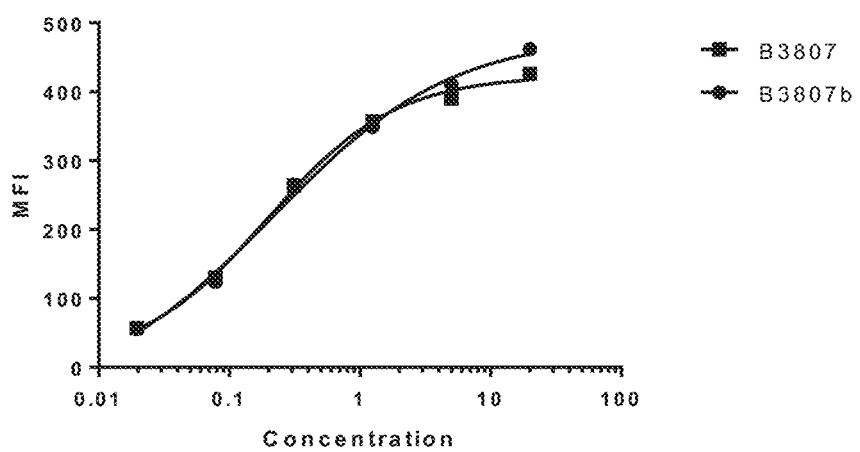

The comparison results are presented in FIG. 45. In both experiments, B3807 and B3807b exhibited highly similar activity profiles, demonstrating that the sequence difference in CDRL1 between these two antibodies did not impact their activities.

Figure 46:
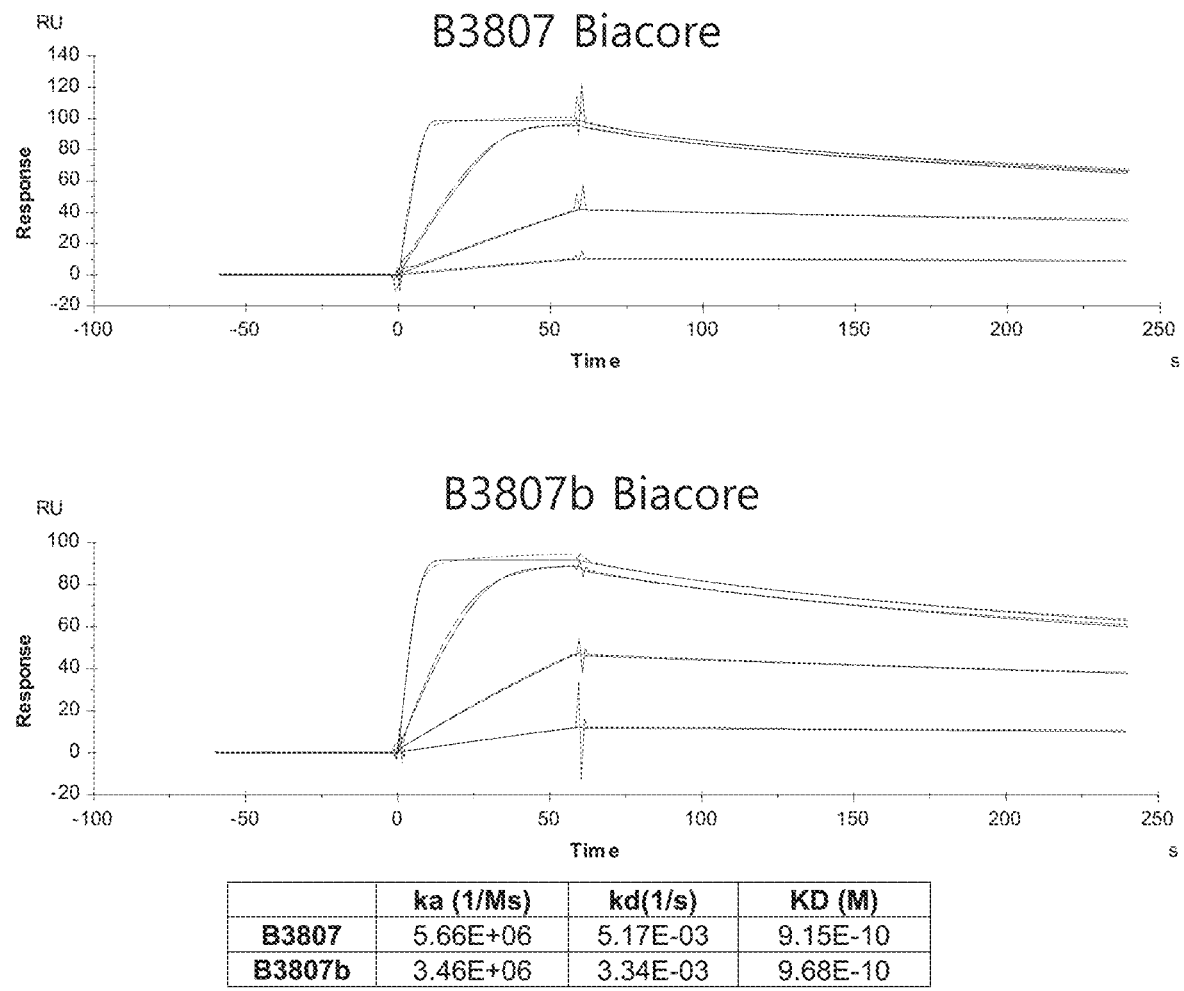
FIG. 46 compares the Biacore™ assay results between B3807 and B3807b.

Also, as shown in FIG. 46, the Biacore™ data (see experimental procedure in Example 2.16(B)) further demonstrate that the great similarity between these two antibodies. B3807 was used in the following examples for further testing and preparing bispecific antibodies.

Example 3. Preparation of Anti-PD-L1/Anti-LAG3 Bispecific Antibodies

Hu1210-41 (Hu1210 VH.4d×Hu1210 Vk.1, see Table 8; hereinafter, "H12") and B6 (see Table 16) clones among the anti-PD-L1 clones prepared in Example 1 and 147H (also called as "147", see Table 23) and 147H 3807 (also called as "147(H3807)"; see Table 27) clones among the anti-LAG3 clones prepared in Example 2 were exemplarily selected, to prepare anti-PD-L1/anti-LAG3 bispecific antibodies in a full-length IgG×scFv form. When PD-L1 is placed in full IgG part, IgG1 with ADCC reduced mutant backbone (N297A mutation; U.S. Pat. Nos. 7,332,581, 8,219,149, etc.) was used, and when LAG3 is placed in full IgG part, IgG4 was used with S241P mutation (Angal et al., *Mol. Immunol.* 30:105-108).

A DNA segment 1 having a nucleotide sequence encoding a heavy chain of an IgG antibody of the anti-PD-L1/anti-LAG3 bispecific antibody was inserted into pcDNA 3.4 (Invitrogen, A14697; plasmid 1), and a DNA segment 2 having a nucleotide sequence encoding a light chain of an IgG antibody of the anti-PD-L1/anti-LAG3 bispecific antibody was inserted into pcDNA 3.4 (Invitrogen, A14697; plasmid 2). Thereafter, a DNA segment 3 encoding a scFv was fused at a part of the DNA segment 1 corresponding to the c-terminus of the Fc region of the IgG antibody inserted into the plasmid 1, using a DNA segment 4 encoding a linker peptide having 10 amino acid lengths consisting of (GGGGS)2, to construct vectors for the expression of bispecific antibodies.

The sequences of the heavy chain, light chain, scFv and DNA segments were summarized in Tables 32 and 33:

TABLE 32

Bispecific antibody comprising the anti-PD-L1 clone in IgG form and the anti-LAG3 clone in scFv form (PD-L1xLAG3)

| | | Amino acid sequence (N'→C') | Nucleotide Sequence (5'→3') |
|---|---|---|---|
| | | H12x147 (bispecific antibody comprising the anti-PD-L1 H12 done in IgG form and the anti-LAG3 147 clone in scFv form) | |
| Heavy Chain | Heavy chain of H12 | EVQLVESGGGLVQPGGSLRLSCAASGFTFSSYDMSWVRQAPGKSLEWVATISDAGGYIYYSDSVKGRETISRDNAKNSLYLQMNSLRDEDTAVYICAREFGKRYALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 528) | GAGGTGCAGCTGGTGGAGAGCGGAGGAGGACTGGTGCAACCCGGAGGCAGCCTGAGACTGAGCTGCGCTGCCAGCGGCTTCACCTTCAGCAGCTACGACATGAGCTGGGTGAGACAGGCCCCTGGCAAAAGCCTGGAGTGGGTGGCCACCATCTCCGATGCGGGCGGCTACATCTATTACTCCGACAGCGTGAYGGGCAGGTTCACCATCAGCAGGGACAACGCCAAGAACAGCCTGTACCTGCAGATGAACAGCCTGAGGGATGAGGACACCGCCGTGTACATCTGCGCCAGGGAGTTCGGCAAAAGGTACGCCCTGGACTACTGGGGCCAGGHCACAACCGTGACCGTGAGCAGCgctAgcAccAAgGGCCCCTCTGTGTTCCCTCTGGCCCCTTCCTCTAAATCCACCTCTGGCGAACCGCTGCTCTGGGCTGTCTGGTCAAGGACTACTTCCCTGAGCCCGTGACCGTGTCTTGGAATTCTGGCGCTCTGACCAGCGGAGTGCACACCTTTCCAGCTGTGCTGCAGTCCTCCGGCCTGTACTCTCTGTCCTCTGTCGTGACAGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCTCCATGTCCTGCTCCAGAACTGCTGGGCGGACCCTCCGTGTTCCTGTTCCCTCCAAAGCCTAAGGACACCCTGATGATCTCCCGGACCCCTGAAGTGACCTGCGTGGTGGATGTGTCCCACGAGGATCCCGAAGTGCACAACGCCAAGACCAAGCCTAGAGAGGAACAGTACgccTCCACCTACCGGGTGGTGTCCGTGCTGACCGTTCTGCACCAGGATTGGCTGAACGGCAAAGAGTACAAGTGCAAGGTGTCCAACAAGGCCCTGCCCCTATCGAAAAGACCATCTCTAAGGCCAAGGGCCAGCCCCGGGAACCTCAAGTGTACACCTTGCCTCCCAGCCGGGAAGAGATGACCAAGAACCAGGTGTCCCTGACCTGCCTGGTTAAGGGCTTC |
| | Linker | GSGSGSGSGSGSGSGS (SEQ ID NO: 529) | |
| | scFv of 147 | VL | DIVMTQSPLSLPVTPGEPASISCRSSKSLLHSNGITYLYWYLQKPGQSPQLLIYQVSNLASGVPDRFSGSGSGTDFTLKISRVEAEDVGVYYCAQNLELPWTFGCGTKVEIKR (SEQ ID NO: 530) | TACCCCTCCGATATCGCCGTGGAATGGGAGTCTAATGCCAGCCTGAGAACAACTACAAGACCACACCTCCTGTGCTGGACTCCGACGGCTCATTCTTCCTGTACTCCAAGCTGACCGTGGACAAGTCCAGATGGCAGCAGGGCAACGTGTTCTCCTGCTCCGTGATGCACGAGGCCCTGCACAATCACTACACCCAGAAGTCCCTGTCTCTGTCCCCTGGCAAAGGCTCCGGATCTGGTTCTGGATCCGGAAGCGGTTCTGGCAGCGGCTCTGGATCTGACATCGTGATGACCCAGTCTCCACTGAGCCTGCCTGTGACACCTGGCGAGCCTGCTTCCATCTCCTGCCGGTCCTCTAAGTCCCTGCTGCACTCTAACGGCATCACCTACCTGTAC |
| | | Linker | GGGGSGGGSGGGGSGGGGS (SEQ ID NO: 531) | |
| | | VH | EVQLVQSGAEVKKPGASVKVSCKASGYTFTNYWLGWIKQAPGQCLEWIGDIYPGGDYINYNEKFKGKATLTADTSISTAYMELSRLRSDDTAVYYCARPNLPGDYWGQGTTVTVSS* (SEQ ID NO: 532) | TGGTATCTGCAGAAGCCCGGCCAGTCTCCTCAGCTGCTGATCTACCAGGTGTCCAACCTGGCTTCTGGCGTGCCCGATAGATTCTCCGGTAGCGGATCTGGAACCGACTTCACCCTGAAGATCTCGAGAGTGGAAGCCGAGGACGTGGGCGTGTACTACTGTGCTCAGAACCTGGAACTGCCCTGGACCTTTGGCTGTGGCACCAAGGTGGAAATCAAGAGAGGCGGCGGAGGATCTGGCGGAGGTGGAAGCGGAGGCGGAGGAAGCGGTGGCGGCGGATCTGAAGTTCAGTTGGTTCAGTCTGGCGCCGAAGTGAAGAAACCTGGCGCCTCTGTGAAGGTGTCCTGCAAGGCTTCCGGCTACACCTTTACCAACTACTGGCTCGGCTGGATCAAGCAGGCCCCTGGACAGTGTCTGGAATGGATCGGCGACATCTACCCTGGCGGCGACTACATCAACTACAACGAGAAGTTCAAGGGCAAAGCTAGCCTGACCGCCGACACCTCTATCTCCACCGCCTACATGGAACTGTCCCGGCTGAGATCTGACGACACCGCCGTGTACTATTGCGCCAGACCTAACCTGCCTGGCGACTATTGGGCCAGGGCACAACAGTGACCGTGTCCTCTTAA (SEQ ID NO: 533) |

TABLE 32-continued

Bispecific antibody comprising the anti-PD-L1 clone in IgG form and
the anti-LAG3 clone in scFv form (PD-L1xLAG3)

| | | Amino acid sequence (N'→C') | Nucleotide Sequence (5'→3') |
|---|---|---|---|
| Light chain | Light chain of H12 | DIQMTQSPSSLSASV GDRVTITCKASQDVT PAVAWYQQKPGKAPK LLIYSTSSRYTGVPS RFSGSGSGTDFTETI SSLQPEDIATYYCQQ HYTTPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC* (SEQ ID NO: 534) | GACATCCAGATGACCCAGAGCCCTAGCAGCCTG AGCGCTAGCGTGGGCGACAGGGTGACCATCACC TGCAAGGCCAGCCAGGATGTGACCCCTGCCGTG GCCTGGTACCAGCAGAAGCCCGGCAAGGCCCCC AAGCTGCTGATCTACAGCACCAGCAGCAGGTAC ACCGGCGTGCCCAGCAGGTTTAGCGGAAGCGGC AGCGGCACCGACTTCACCTTCACCATGAGCAGC CTGCAGCCCGAGGACATCGCCACCTACTACTGC CAGCAGCACTACACCACCCCTCTGACCTTCGGC CAGGGCACCAAGCTGGAGATCAAGAGAACCGTG GCCGCTCCCTCCGTGTTCATCTTCCCACCATCT GACGAGCAGCTGAAGTCCGGCACCGCTTCTGTC GTGTGCCTGCTGAACAACTTCTACCCTCGGGAA GCCAAGGTGCAGTGGAAGGTGGACAATGCCCTG CAGTCCGGCAACTCCCAAGAGTCTGTGACCGAG CAGGACTCCAAGGACAGCACCTACTCCCTGTCC TCTACCCTGACCCTGTCCAAGGCCGACTAGGAG AAGCACAAGGTGTACGCCTGCGAAGTGACCCAC CAGGGACTGTCTAGCCCCGTGACCAAGTCCTTC AACAGAGGCGAGTGCTGA (SEQ ID NO: 535) |

H12x147 (H3807)
(bispecific antibody comprising the anti-PD-L1 H12 clone in IgG form
and the anti-LAG3 147(H3807) done in scFv form)

| | | Amino acid sequence | Nucleotide Sequence |
|---|---|---|---|
| Heavy Chain | Heavy chain of H12 | EVQLVESGGGLVQPG GSLRLSCAASGFTFS SYDMSWVRQAPGKSL EWVATISDAGGYIYY SDSVKGRFTISRDNA KNSLYLQMNSLRDEL TAVYICAREFGKRYA LDYWGQGTTVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPELLGGP SVFLFPPKPKDTLMI SRTPEVTCVVVDVSH EDPEVKFNWYVDGVE VHNAKTKPREEQYAS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 528) | GAGGTGCAGCTGGTGGAGAGCGGAGGAGGACTG GTGCAACCCGGAGGCAGCCTGAGACTGAGCTGC GCTGCCAGCGGCTTCACCTTCAGCAGCTACGAC ATGAGCTGGGTGAGACAGGCCCCTGGCAAAAGC CTGGAGTGGGTGGCCACCATCTCCGATGCGGGC GGCTACATCTATTACTCCGACAGCGTGAAGGGC AGGTTCACCATCAGCAGGGACAACGCCAAGAAC AGCCTGTACCTGCAGATGAACAGCCTGAGGGAT GAGGACACCGCCGTGTACATCTGCGCCAGGGAG TTCGGCAAAAGGTACGCCCTGGACTACTGGGGC CAGGGCACAACCGTGACCGTGAGCAGCgctAgc AccAAgGGCCCCTCTGTGTTCCCTCTGGCCCCT TCCTCTAAATCCACCTCTGGCGGAACCGCTGCT CTGGGCTGTCTGGTCAAGGACTACTTCCCTGAG CCCGTGACCGTGTCTTGGAATTCTGGCGCTCTG ACCAGCGGAGTGCACACCTTTCCAGCTGTGCTG CAGTCCTCCGGCCTGTACTCTCTGTCCTCTGTC GTGACAGTGCCTTCCAGCTCTCTGGGCACCCAG ACCTACATCTGCAACGTGAACCACAAGCCCTCC AACACCAAGGTGGACAAGAAGGTGGAACCCAAG TCCTGCGACAAGACCCACACCTGTCCTCCATGT CCTGCTCCAGAACTGCTGGGCGGACCCTCCGTG TTCCTGTTCCCTCCAAAGCCTAAGGACACCCTG ATGATCTCCCGGACCCCTGAAGTGACCTGCGTG GTGGTGGATGTGTCCCACGAGGATCCCGAAGTG AAGTTCAATTGGTACGTGGACGGCGTGGAAGTG CACAACGCCAAGACCAAGCCTAGAGAGGAAGAG TACgccTCCACCTACCGGGTGGTGTCCGTGCTG ACCGTTCTGCACCAGGATTGGCTGAACGGCAAA GAGTACAAGTGCAAGGTGTCCAACAAGGCCCTG CCTGCCCCTATCGAAAAGACCATCTCTAAGGCC |
| | Linker | GSGSGSGSGSGSGSG SGS (SEQ ID NO: 529) | AAGGGCCAGCCCCGGGAACCTCAAGTGTACACC TTGCCTCCCAGCCGGGAAGAGATGACCAAGAAC CAGGTGTCCCTGACCTGCCTGGTTAAGGGCTTC |
| | scFv of 147(H3807) | VL DIVMTQSPLSLPVTP GEPASISCRSSKSLL HSQGITYLYWYLQKP GQSPQLLIYQVSNLA SGVPDRFSGSGSGTD FTLKISRVEAEDVGV YYCAQYLELPWTFGC GTKVEIKR (SEQ ID NO: 536) | TACCCCTCCGATATCGCCGTGGAATGGGAGTCT AACGGCCAGCCCGAGAACAACTACAAGACCACC CCTCCTGTGCTGGACTCCGACGGCTCATTCTTC CTGTACTCCAAGCTGACCGTGGACAAGTCTCGG TGGCAGCAGGGCAACGTGTTCTCCTGCTCTGTG ATGCACGAGGCCCTGCACAACTACTACCAGCAG GTGCAACCCGGAGGCAGCCTGAGCTGAGCTGC AAGTCCCTGTCCCTGTCTCCCGGCAAAGGCTCC GGATCTGGTTCTGGATCCGGAAGCGGTTCTGGC |
| | Linker | GGGGSGGGGSGGGGS GGGGS (SEQ ID NO: 531) | AGCGGCTCTGGATCTGACATTGTGATGACCCAG AGCCCCCTGAGCCTCCCCGTGACCCCTGGAGAA CCCGCCAGCATAAGCTGCAGATCCTCCAAAAGC |

TABLE 32-continued

Bispecific antibody comprising the anti-PD-L1 clone in IgG form and the anti-LAG3 clone in scFvform (PD-L1xLAG3)

| | | Amino acid sequence (N'→C') | Nucleotide Sequence (5'→3') |
|---|---|---|---|
| | VH | EVQLVQSGAEVKKPG ASVKVSCKASGYTFT NYWLGWIKQAPGQCL EWIGDIYPGGDYIVY NEKFKGKATLTADTS ISTAYMELSRLRSDD TAVYYCARPNLPKDR WGQGTTVTVSS* (SEQ ID NO: 537) | CTGCTGCACTCCCAGGGAATAACCTACCTGTAT TGGTACCTGCAGAAACCCGGCCAATCCCCCAA CTCCTGATATACCAAGTGTCCAACCTGGCCTCC GGCGTGCCCGACAGATTCTCCGGCTCCGGCAGC GGTACCGACTTCACCCTCAAAATCTCCAGAGTG GAAGCAGAAGACGTCGGCGTGTACTACTGCGCC CAGTACCTGGAACTGCCCTGGACCTTCGGCtgt GGCACCAAGGTGGAAATCAAGAGAGGCGGCGGA GGAAGCGGAGGCGGCGGTTCTGGTGGTGGCGGT AGCGGAGGTGGTGGATCTGAGGTGCAGCTGGTG CAGAGCGGAGCAGAGGTGAAGAAGCCAGGGGCC AGCGTGAAGGTGAGCTGTAAGGCTAGTGGGTAC ACATTTACAAACTATTGGCTGGGATGGATTAAG CAGGCCCCAGGCCAAtgcCTGGAGTGGATAGGA GACATATACCCCGGAGGAGACTATATCGTGTAC AACGAGAAGTTCAAGGGCAAGGCCACACTCACC GCTGATACAAGCATCAGCACCGCCTACATGGAG CTGAGCCGACTGAGAAGCGACGACACAGCAGTG TATTACTGCGCCAGACCCAACCTGCCCAAGGAC CACTGGGGACAAGGCACCACCGTGACCGTGAGC AGCtga (SEQ ID NO: 538) |
| Light chain | Light chain of H12 | DIQMTQSPSSLSASV GDRVTITCKASQDVT PAVAWYQQKPGKAPK LLIYSTSSRYTGVPS RFSGSGSGTDFTFTI SSLQPEDIATYYCQQ HYTTPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC* (SEQ ID NO: 534) | GACATCCAGATGACCCAGAGCCCTAGCAGCCTG AGCGCTAGCGTGGGCGACAGGGTGACCATCACC TGCAAGGCCAGCCAGGATGTGACCCCTGCCGTG GCCTGGTACCAGCAGAAGCCCGGCAAGGCCCCC AAGCTGCTGATCTACAGCACCAGCAGCAGGTAC ACCGGCGTGCCCAGCAGGTTTAGCGGAAGCGGC AGCGGCACCGACTTCACCTTCACCATCAGCAGC CTGCAGCCCGAGGACATCGCCACCTACTACTGC CAGCAGCACTACACCACCCCTCTGACCTTCGGC CAGGGCACCAAGCTGGAGATCAAGAGAACCGTG GCCGCTCCCTCCGTGTTCATCTTCCCACCATCT GACGAGCAGCTGAAGTCCGGCACCGCTTCTGTC GTGTGCCTGCTGAACAACTTCTACCCTCGGGAA GCCAAGGTGCAGTGGAAGGTGGACAATGCCCTG CAGTCCGGCAACTCCCAAGAGTCTGTGACCGAG CAGGACTCCAAGGACAGCACCTACTCCCTGTCC TCTACCCTGACCCTGTCCAAGGCCGACTACGAG AAGCACAAGGTGTACGCCTGCGAAGTGACCCAC CAGGGACTGTCTAGCCCCGTGACCAAGTCCTTC AACAGAGGCGAGTGCTGA (SEQ ID NO:535) |

B6x147
(bispecific antibody comprising the anti-PD-L1 B6 clone in IgG form and the anti-LAG3 147 clone in scFv form)

| | | | |
|---|---|---|---|
| Heavy Chain | Heavy chain of B6 | EVQLVESGGGLVQPG GSLRLSCAASGFTFS SYDMSWVRQAPGKSL EWVATISDAGGYIYY RDSVKGRFTISRDNA KNSLYLQMNSLRDED TAVYICARELPWRYA LDYWGQGTTVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPELLGGP SVFLFPPKPKDTLMI SRTPEVTCVVVDVSH EDPEVKFNWYVDGVE VHNAKTKPREEQYAS TYRVVSVLTVLHQDW LNGKEYKCKVSNKAL PAPIEKTISKAKGQP REPQVYTLPPSREEM TKNQVSLTCLVKGFY | GAAGTGCAGCTGGTTGAATCTGGCGGCGGATTG GTTCAGCCTGGCGGATCTCTGAGACTGTCTTGT GCCGCCTCCGGCTTCACCTTCTCCAGCTACGAT ATGTCCTGGGTCCGACAGGCCCCTGGCAAGTCT TTGGAATGGGTCGCCACCATCTCTGACGCTGGC GGCTACATCTACTACCGGGACTCTGTGAAGGGC AGATTCACCATCAGCCGGGACAACGCCAAGAAC TCCCTGTACCTGCAGATGAACAGCCTGCGCGAC GAGGATACCGCCGTGTACATCTGTGCTAGAGAG CTGCCTTGGAGATACGCCCTGGATTATTGGGGC CAGGGCACCACAGTGACCGTGTCCTCTGCTTCT ACCAAGGGACCCAGCGTGTTCCCTCTGGCTCCT TCCAGCAAGTCTACCTCTGGCGGAACAGCTGCT CTGGGCTGCCTGGTCAAGGACTACTTTCCTGAG CCTGTGACAGTGTCCTGGAACTCTGGCGCTCTG ACATCTGGCGTGCACACCTTTCCAGCAGTGCTG CAGTCCTCCGGCCTGTACTCTCTGTCCTCTGTC GTGACCGTGCCTTCCAGCTCTCTGGGCACCCAG ACCTACATCTGCAACGTGAACCACAAGCCCTCC AACACCAAGGTGGACAAGAAGGTGGAACCCAAG TCCTGCGACAAGACCCACACCTGTCCTCCATGT CCTGCTCCAGAACTGCTGGGCGGACCCTCCGTG TTCCTGTTCCCTCCAAAGCCTAAGGACACCCTG ATGATCTCCCGGACCCCTGAAGTGACCTGCGTG GTGGTGGATGTGTCCCACGAGGATCCCGAAGTG |

TABLE 32-continued

Bispecific antibody comprising the anti-PD-L1 clone in IgG form and the anti-LAG3 clone in scFvform (PD-L1xLAG3)

| | | | Amino acid sequence (N'→C') | Nucleotide Sequence (5'→3') |
|---|---|---|---|---|
| | | | PSDIAVEWESNGQPE NNYKTTPPVLDSDGS FFLYSKLTVDKSRWQ QGNVFSCSVMHEALH NHYTQKSLSLSPGK (SEQ ID NO: 539) | AAGTTCAATTGGTACGTGGACGGCGTGGAAGTG CACAACGCCAAGACCAAGCCTAGAGAGGAACAG TACgccTCCACCTACCGGGTGGTGTCCGTGCTG ACCGTTCTGCACCAGGATTGGCTGAACGGCAAA GAGTACAAGTGCAAGGTGTCCAACAAGGCCCTG CCTGCCCCTATCGAAAAGACCATCTCTAAGGCC |
| | Linker | | GSGSGSGSGSGSGSG SGS (SEQ ID NO: 529) | AAGGGCCAGCCCCGGGAACCTCAAGTGTACACC TTGCCTCCCAGCCGGGAAGAGATGACCAAGAAC CAGGTGTCCCTGACCTGCCTGGTTAAGGGCTTC |
| | scFv of 147 | VL | DIVMTQSPLSLPVTP GEPASISCRSSKSLL HSNGITYLYWYLQKP GQSPQLLIYQVSNLA SGVPDRFSGSGSGTD FTLKISRVEAEDVGV YYCAQNLELFWTFGC GTKVEIKR (SEQ ID NO: 530) | TACCCCTCCGATATCGCCGTGGAATGGGAGTCT AATGGCCAGCCTGAGAACAACTACAAGACCACA CCTCCTGTGCTGGACTCCGACGGCTCATTCTTC CTGTACTCCAAGCTGACCGTGGACAAGTCCAGA TGGCAGCAGGGCAACGTGTTCTCCTGCTCCGTG ATGCACGAGGCCCTGCACAATCACTACACCCAG AAGTCCCTGTCTCTGTCCCCTGGCAAAGGCTCC GGATCTGGTTCTGGATCGGAAGCGGTTCTGGC AGCGGCTCTGGATCTGACATCGTGATGACCCAG |
| | | Linker | GGGGSGGGGSGGGGS GGGS (SEQ ID NO: 531) | TCTCCACTGAGCCTGCCTGTGACACCTGGCGAG CCTGCTTCCATCTCCTGCCGGTCCTCTAAGTCC CTGCTGCACTCTAACGGCATCACCTACCTGTAC |
| | | VH | EVQLVQSGAEVKKPG ASVKVSCKASGYTFT NYWLGWIKQAPGQCL EWIGDIYPGGDYINY NEKFKGKATLTADTS ISTAYMELSRLRSDD TAVYYCARPNLPGDY WGQGTTVTVSS* (SEQ ID NO: 532) | TGGTATCTGCAGAAGCCCGGCCAGTCTCCTCAG CTGCTGATCTACCAGGTGTCCAACCTGGCTTGT GGCGTGCCCGATAGATTCTCCGGTAGCGGATCT GGAACCGACTTCACCCTGAAGATCTCCAGAGTG GAAGCCGAGGACGTGGGCGTGTACTACTGTGCC CAGAACCTGGAACTGCCCTGGACCTTTGGCTGT GGCACCAAGGTGGAAATCAAGAGAGGCGGCGGA GGATCTGGCGGAGGTGGAAGCGGAGGCGGAGGA AGCGGTGGCGGCGGATCTGAAGTTCAGTTGGTT CAGTCTGGCGCCGAAGTGAAGAAACCTGGCGCC TCTGTGAAGGTGTCCTGCAAGGCTTCCGGCTAC ACCTTTACCAACTACTGGCTCGGCTGGATCAAG CAGGCCCCTGGACAGTGTCTGGAATGGATCGGC GACATCTACCCTGGCGGCGACTACATCAACTAC AACGAGAAGTTCAAGGGCAAAGCTACCCTGACC GCCGACACCTCTATCTCCACCGCCTACATGGAA CTGTCCCGGCTGAGATCTGACGACACCGCCGTG TACTATTGCGCCAGACCTAACCTGCCTGGCGAC TATTGGGGCCAGGGCACAACAGTGACCGTGTCC TCTTAA (SEQ ID NO: 540) |
| Light chain | Light chain of B6 | | DIQMTQSPSSLSASV GDRVTITCRASQDVT PAVAWYQQKPGKAPK LLIYSTSSRYTGVPS RFSGSGSGTDFTFTI SSLQPEDIATYYCQQ HYTTPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC* (SEQ ID NO: 534) | GACATCCAGATGACCCAGAGCCCTAGCAGCCTG AGCGCTAGCGTGGGCGACAGGGTGACCATCACC TGCAAGGCCAGCCAGGATGTGACCCCTGCCGTG GCCTGGTACCAGCAGAAGCCCGGCAAGGCCCCC AAGCTGCTGATCTACAGCACCAGCAGCAGGTAC ACCGGCGTGCCCAGCAGGTTTAGCGGAAGCGGC AGCGGCACCGACTTCACCTTCACCATCAGCAGC CTGCAGCCCGAGGACATCGCCACCTACTACTGC CAGCAGCACTACACCACCCCTCTGACCTTCGGC CAGGGCACCAAGCTGGAGATCAAGAGAACCGTG GCCGCTCCCTCCGTGTTCATCTTCCCACCATCT GACGAGCAGCTGAAGTCCGGCACCGCTTCTGTC GTGTGCCTGCTGAACAACTTCTACCCTCGGGAA GCCAAGGTGCAGTGGAAGGTGGACAATGCCCTG CAGTCCGGCAACTCCCAAGAGTCTGTGACCGAG CAGGACTCCAAGGACAGCAGCTACTCCCTGTCC TCTACCCTGACCCTGTCCAAGGCCGACTACGAG AAGCACAAGGTGTACGCCTGCGAAGTGACCCAC CAGGGACTGTCTAGCCCCGTGACCAAGTCCTTC AACAGAGGCGAGTGCTGA (SEQ ID NO: 535) |

B6x147(H3807)
(bispecific antibody comprising the anti-PD-L1 B6 clone in igG form and the anti-LAG3 147(H3807) done in sc-Fv form)

| | | | | |
|---|---|---|---|---|
| Heavy Chain | Heavy chain of B6 | | EVQLVESGGGLVQPG GSLRLSCAASGFTFS SYDMSWVRQAPGKSL EWVATISDAGGYIYY RDSVKGRFTISRDNA | GAAGTGCAGCTGGTTGAATCTGGCGGCGGATTG GCCGCCTCCGGCTTCACCTTCTCCAGCTACGAT ATGTCCTGGGTCCGACAGGCCCCTGGCAAGTCT TTGGAATGGGTCGCCACCATCTCTGACGCTGGC GGCTACATCTACTACCGGGACTCTGTGAAGGGC |

TABLE 32-continued

Bispecific antibody comprising the anti-PD-L1 clone in IgG form and the anti-LAG3 clone in scFvform (PD-L1xLAG3)

| | | | Amino acid sequence (N'→C') | Nucleotide Sequence (5'→3') |
|---|---|---|---|---|
| | | | KNSLYLQMNSLRDED TAVYICARELPWRYA LDYWGQGTTVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPELLGGP SVFLFPPKPKDTLMI SRTPEVTCVVVDVSH EDPEVKFNWYVDGVE VHNAKTKPREEQYAS TYRVVSVLTVLHQDW LNGKEYKCKVSNKAL PAPIEKTISKAKGQP REPQVYTLPPSREEM TKNQVSLTCLVKGFY PSDIAVLWESNGQPE NNYKTTPPVLDSDGS FFLYSKLTVDKSRWQ QGNVFSCSVMHEALH NHYTQKSLSLSPGK (SEQ ID NO: 539) | AGATTCACCATCAGCCGGGACAACGCCAAGAAC TCCCTGTACCTGCAGATGAACAGCCTGCGCGAC GAGGATACCGCCGTGTACATCTGTGCTAGAGAG CTGCCTTGGAGATACGCCCTGGATTATTGGGGC CAGGGCACCACAGTGACCGTGTCCTCTGCTTCT ACCAAGGGACCCAGCGTGTTCCCTCTGGCTCCT TCCAGCAAGTCTACCTCTGGCGGAACAGCTGCT CTGGGCTGCCTGGTCAAGGACTACTTTCCTGAG CCTGTGACAGTGTCCTGGARCTCTGGCGCTCTG ACATCTGGCGTGCACACCTTTCCAGCAGTGCTG CAGTCCTCCGGCCTGTACTCTCTGTCCTCTGTC GTGACCGTGCCTTCCAGCTCTCTGGGCACCCAG ACCTACATCTGCAACGTGAACCACAAGCCCTCC AACACCAAGGTGGACAAGAAGGTGGAACCCAAG TCCTGCGACAAGACCCACACCTGTCCTCCATGT CCTGCTCCAGAACTGCTGGGCGGACCCTCCGTG TTCCTGTTCCCTCCAAAGCCTAAGGACACCCTG ATGATCTCCCGGACCCCTGAAGTGACCTGCGTG GTGGTGGATGTGTCCCACGAAGAGATCCCGAAGTG AAGTTCAATTGGTACGTGGACGGCGTGGAAGTG CACAACGCCAAGACCAAGCCTAGAGAGGAACAG TACgccTCCACCTACCGGGTGGTGTCCGTGCTG ACCGTTCTGCACCAGGATTGGCTGAACGGCAAA GAGTACAAGTGCAAGGTGTCCAACAAGGCCCTG CCTGCCCCTATCGAAAAGACCATCTCTAAGGCC AAGGGCCAGCCCCGGGAACCTCAAGTGTACACC |
| | Linker | | GSGSGSGSGSGSGSG SGS (SEQ ID NO: 529) | TTGCCTCCCAGCCGGGAAGAGATGACCAAGAAC CAGGTGTCCCTGACCTGCCTGGTTAAGGGCTTC GTTCAGCCTGGCGGATCTCTGAGACTGTCTTGT |
| | scFv of 147(H3807) | VL | DIVMTQSPLSLPVTP GEPASISCRSSKSLL HSQGITYLYWYLQKP GQSPQLLIYQVSNLA SGVPDRFSGSGSGTD FTLKISRVEAEDVGV YYCAQYLELPWTFGC GTKVEIKR (SEQ ID NO: 536) | CCTCCTGTGCTGGACTCCGACGGCTCATTCTTC CTGTACTCCAAGCTGACCGTGGACAAGTCTCGG TGGCAGCAGGGCAACGTGTTCTCCTGCTCTGTG ATGCACGAGGCCCTGCACAACCACTACACCCAG AAGTCCCTGTCCCTGTCTCCCGGCAAAGGCTCC GGATCTGGTTCTGGATCCGGAAGCGGTTCTGGC AGCGGCTCTGGATCTGACATTGTGATGACCCAG AGCCCCCTGAGCCTCCCCGTGACCCCTGGAGAA CCCGCCAGCATAAGCTGCAGATCCTCCAAAAGC |
| | | Linker | GGGGSGGGGSGGGGS GGGGS (SEQ ID NO: 531) | CTGCTGCACTCCCAGGGAATAACCTACCTGTAT TGGTACCTGCAGAAACCCGGCCAATCCCCCCAA CTCCTGATATACCAAGTGTCCAACCTGGCCTCC |
| | | VH | EVQLVQSGAEVKKPG ABVKVSCKASGYTFT NYWLGWIKQAPGQCL EWIGDIYPGGDYIVY NEKFKGKATLTADTS ISTAYMELSRLRSDD TAVYYCARPNLPKDH WGQGTTVTVSS* (SEQ ID NO: 537) | GGCGTGCCCGACAGATTCTCCGGCTCCGGCAGC GGTACCGACTTCACCCTCAAAATCTCCAGAGTG GAAGCAGAAGACGTCGGCGTGTACTACTGCGCC CAGTACCTGGAACTGCCCTGGACCTTCGGCtgt GGCACCAAGGTGGAAATCAAGAGAGGCGGCGGA GGAAGCGGAGGCGGCGGTTCTGGTGGTGGCGGT AGCGGAGGTGGTGGATCTGAGGTGCAGCTGGTG CAGAGCGGAGCAGAGGTGAAGAAGCCAGGGGCC AGCGTGAAGGTGAGCTGTAAGGCTAGTGGGTAC ACATTTACAAACTATTGGCTGGGATGGATTAAG CAGGCCCCAGGCCAATgcCTGGAGTGGATAGGA GACATATACCCCGGAGGAGACTATATCGTGTAC AACGAGAAGTTCAAGGGCAAGGCCACACTCACC GCTGATACARGCATCAGCACCGCCTACATGGAG CTGAGCCGACTGAGAAGCGACGACACAGCAGTG TATTACTGCGCCAGACCCAACCTGCCCAAGGAC CACTGGGGACAAGGCACCACCGTGACCGTGAGC AGCtga (SEQ ID NO: 541) |
| Light chain | Light chain of B6 | | DIQMTQSPSSLSASV GDRVTITCKASQDVT PAVAWYQQRPGKAPK LLIYSTSSRYTGVPS RFSGSGSGTDFTFTI SSLQPEDIATYYCQQ HYTTPLTFGQGTKLE IKRTVAAPSVFIFPP SDEQLKSGTASVVCL LNNFYPREAKVQWKV DNALQSGNSQESVTE QDSKDSTYSLSSTLT | GACATCCAGATGACCCAGAGCCCTAGCAGCCTG AGCGCTAGCGTGGGCGACAGGGTGACCATCACC TGCAAGGCCAGCCAGGATGTGACCCCTGCCGTG GCCTGGTACCAGCAGAAGCCCGGCAAGGCCCCC AAGCTGCTGATCTACAGCACCAGCAGCAGGTAC ACCGGCGTGCCCAGCAGGTTTAGCGGAAGCGGC AGCGGCACCGACTTCACCTTCACCATCAGCAGC CTGCAGCCCGAGGACATCGCCACCTACTACTGC CAGCAGCACTACACCACCCCTCTGACCTTCGGC CAGGGCACCAAGCTGGAGATCAAGAGAACCGTG GCCGCTCCCTCCGTGTTCATCTTCCCACCATCT GACGAGCAGCTGAAGTCCGGCACCGCTTCTGTC |

TABLE 32-continued

Bispecific antibody comprising the anti-PD-L1 clone in IgG form and
the anti-LAG3 clone in scFvform (PD-L1xLAG3)

| | Amino acid sequence (N'→C') | Nucleotide Sequence (5'→3') |
|---|---|---|
| | LSKADYEKHKVYACE VTHQGLSSPVTKSFN RGEC* (SEQ ID NO: 534) | GTGTGCCTGCTGAACAACTTCTACCCTCGGGAA GCCAAGGTGCAGTGGAAGGTGGACAATGCCCTG CAGTCCGGCAACTCCCAAGAGTCTGTGACCGAG CAGGACTCCAAGGACAGCACCTACTCCCTGTCC TCTACCCTGACCCTGTCCAAGGCCGACTACGAG AAGCACAAGGTGTACGCCTGCGAAGTGACCCAC CAGGGACTGTCTAGCCCCGTGACCAAGTCCTTC AACAGAGGCGAGTGCTGA (SEQ ID NO: 535) |

TABLE 33

Bispecific antibody comprising the anti-LAG3 clone in IgG form and
the anti-PD-L1 clone in scFvform (LAG3XPD-L1)

| | | Amino acid sequence (N'→C') | Nucleotide Sequence (5'→3') |
|---|---|---|---|

147xH12
(bispecific antibody comprising the anti-LAG3 147 clone in gG form
and the anti-PD-L1 H12 clone in scFv form)

| Heavy Chain | Heavy chain of 147 | EVQLVQSGAEVKKPG ABVKVSCKASGYTFT NYWLGWIKQAPGQGL EWIGDIYPGGDYINY NEKFKGKATLTADTS ISTAYMELSRLRSDD TAVYYCARPNLPGDY WGQGTTVTVSSASTK GPSVFPLAPCSRSTS ESTAALGCLVKDYFP EPVTVSWNSGALTSG VHTFPAVLQSSGLYS LSSVVTVPSSSLGTK TYTCNVDHKPSNTKV DKRVESKYGPPCPPC PAPEFLGGPSVFLFP PKPKDTLMISRTPEV TCVVVDVSQEDPEVQ FNWYVDGVEVHNAKT KPREEQFNSTYRVVS VLTVLHQDWLNGKEY KCKVSNKGLPSSIEK TISKAKGQPREPQVY TLPPSQEEMTKNQVS LTCLVKGFYPSDIAV EWESNGQPENNYKTT PPVLDSDGSFFLYSR LTVDKSRWQEGNVFS CSVMHEALHNHYTQK SLSLSLGK (SEQ ID NO: 542) | GAGGTGCAGCTGGTGCAGAGCGGAGCAGAGGTG AAGAAGCCAGGGGCCAGCGTGAAGGTGAGCTGT AAGGCTAGTGGGTACACATTTACAAACTATTGG CTGGGATGGATTAAGCAGGCCCCAGGCCAAGGA CTGGAGTGGATAGGAGACATATACCCCGGAGGA GACTATATCAATTACAACGAGAAGTTCAAGGGC AAGGCCACACTCACCGCTGATACAAGCATCAGC ACCGCCTACATGGAGCTGAGCCGACTGAGAAGC GACGACACAGCAGTGTATTACTGCGCCAGACCC AACCTGCCCGGCGACTACTGGGGACAAGGCACC ACCGTGACCGTGTCTTCCgctAgcAccAAgggc ccctccgtgttccctctggccccAtgctcccgg tccAcctccgAgtccAccgccgctctgggctgt ctggtgAAggActActtccctgAgcccgtgAcc gtgAgctggAActctggcgccctgAcctccggc gtgcAcAccttccctgccgtgctgcAgtcctcc ggcctgtActccctgtcctccgtggtgAccgtg ccttcctcctccctgggcAccAAgAcctAcAcc tgcAAcgtggAccAcAAgccttccAAcAccAAg gtggAcAAgcgggtggAgtccAAgtAcggccct ccttgccctcctgccctgccctgAgttcctg ggcggAccctccgtgttcctgttccctcctAAg cctAAggAcAccctgAtgAtctcccggAcccct gAggtgAcctgcgtggtggtggAcgtgtcccAg gAAgAtcctgAggtcAgttcAAttggtAcgtg gAtggcgtggAggtgcAcAAcgccAAgAccAAg cctcgggAggAAcAgttcAActccAcctAccgg gtggtgtctgtgctgAccgtgctgcAccAggAc tggctgAAcggcAAggAAtAcAAgtgcAAggtc AgcAAcAAgggcctgccctcctccAtcgAgAAA AccAtctccAAggccAAgggcAgcctcgcgAg |
| | Linker | GGGGSGGGGSGGGGS (SEQ ID NO: 543) | cctcAggtgtAcAccctgcctcctAgccAggAA gAgAtgAccAagAAtcAggtgtccctgAcAtgc |
| | scFv of H12 | VL DIQMTQSPSSLSASV GDRVTITCKASQDVT PAVAWYQQKPGKAPK LLIYTSSRITGVPS RFSGSGSGTDFTFTI SSLQPEDIATYYCQQ HYTTPLTFGCGTKLE IKR (SEQ ID NO: 544) | ctggtgAAgggcttctAcccttccgAtAtcgcc gtggAgtgggAgAgcAAcggccAgcAgAgAAc AActAcAAgAcccctgtgctggActcc gAcggctccttcttcctgtActccAggctgAcc gtggAcAAgtcccggtggcAggAAggcAAcgtc ttttcctgctccgtgAtgcAcgAggccctgcAc AAccActAcAcccAgAAgtccctgtccctgtct ctgggcAAgGGTGGAGGTGGGTCTGGGGGTGGC GGGTCAGGTGGAGGAGGTTCAGACATCCAGATG |
| | Linker | GGGGSGGGGSGGGGS GGGGS (SEQ ID NO: 531) | ACCCAGAGCCCTAGCAGCCTGAGCGCTAGCGTG GGCGACAGGGTGACCATCACCTGCAAGGCCAGC CAGGATGTGACCCCTGCCGTGGCCTGGTACCAG |
| | VH | EVQLVESGGGLVQPG GSLRLSCAASGFTFS SYDMSWVRQAPGKCL EWVATISDAGGYIYY | CAGAAGCCCGGCAAGGCCCCAAGCTGCTGATC TACAGCACCAGCAGCAGGTACACCGGCGTGCCC AGCAGGTTTAGCGGAAGCGGCAGCGGCACCGAC TTCACCTTCACCATCAGCAGCCTGCAGCCCGAG |

TABLE 33-continued

Bispecific antibody comprising the anti-LAG3 clone in IgG form and the anti-PD-L1 clone in scFv form (LAG3XPD-L1)

| | | Amino acid sequence (N'→C') | Nucleotide Sequence (5'→3') |
|---|---|---|---|
| | | SDSVKGRETTSRDNA KNSLYLQMNSLRDED TAVYICAREFGKRYA LDYWGQGTTVTVSS (SEQ ID NO: 545) | GACATCGCCACCTACTACTGCCAGCAGCACTAC ACCACCCCTCTGACCTTCGGCtgtGGCACCAAG CTGGAGATCAAGAGAGGTGGAGGCGGCTCAGGG GGGGGTGGATCAGGGGGAGGAGGATCAGGGGGA GGCGGTAGTGAGGTGCAGCTGGTGGAGAGCGGA GGAGGACTGGTGCAACCCGGAGGCAGCCTGAGA CTGAGCTGCGCTGCCAGCGGCTTCACCTTCAGC AGCTACGACATGAGCTGGGTGAGACAGGCCCCT GGCAAAtgtCTGGAGTGGGTGGCCACCATCTCC GATGCGGGCGGCTACATCTATTACTCCGACAGC GTGAAGGGCAGGTTCACCATCAGCAGGGACAAC GCCAAGAACAGCCTGTACCTGCAGATGAACAGC CTGAGGGATGAGGACACCGCCGTGTACATCTGC GCCAGGGAGTTCGGCAAAAGGTACGCCCTGGAC TACTGGGGCCAGGGCACAACCGTGACCGTGAGC AGCtga (SEQ ID NO: 546) |
| Light chain | Light chain of 147 | DIVMTQSPLSLPVTP GEPASISCRSSKSLL HSNGITYLYWYLQKP GQSPQLLIYQVSNLA SGVPDRFSGSGSGTD FTLKISRVEAEDVGV YYCAQNLELPWTFGG GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC (SEQ ID NO: 547) | GACATTGTGATGACCCAGAGCCCCCTGAGCCTC CCCGTGACCCCTGGAGAACCCGCCAGCATAAGC TGCAGATCCTCCAAAAGCCTGCTGCACTCCAAC GGAATAACCTAGCTGTATTGGTACCTGCAGAAA CCCGGCCAATCCCCCCAACTCCTGATATACCAA GTGTCCAACCTGGCCTCCGGCGTGCCCGACAGA TTCTCCGGCTCCGGCAGCGGTACCGACTTCACC CTCAAAATCTCCAGAGTGGAAGCAGAAGACGTC GGCGTGTACTACTGCGCCCAGAATCTGGAACTG CCCTGGACCTTCGGCGGCGGCACCAAGGTGGAA ATCAAGAGAACCGTGGCCGCTCCCTCCGTGTTC ATCTTCCCACCATCTGACGAGCAGCTGAAGTCC GGCACCGCTTCTGTCGTGTGCCTGCTGAACAAC TTCTACCCTCGGGAAGCCAAGGTGCAGTGGAAG GTGGACAATGCCCTGCAGTCCGGCAACTCCCAA GAGTCTGTGACCGAGCAGGACTCCAAGGACAGC ACCTACTCCCTGTCCTCTACCCTGACCCTGTCC AAGGCCGACTACGAGAAGCACAAGGTGTACGCC TGCGAAGTGACCCACCAGGGACTGTCTAGCCCC GTGACCAAGTCCTTCAACAGAGGCGAGTGCTGA (SEQ ID NO: 548) |

147xB6
(bispecific antibody comprising the anti-LAG3 147 clone in igG form and the anti-PD-L1 B6 clone in scFv form)

| | | | |
|---|---|---|---|
| Heavy Chain | Heavy chain of 147 | EVQLVQSGAEVKKPG ASVKVSCKASGYTFT NYWLGWIKQAPGQGL EWIGDIYPGGDYINY NEKFKGKATLTADTS ISTAYMELSRLRSDD TAVYYCARPNLPGDY WGQGTTVTVSSASTK GPSVFPLAPCSRSTS ESTAALGCLVKDYFP EPVTVSWNSGALTSG VHTFPAVLQSSGLYS LSSVVTVPSSSLGTK TYTCNVDHKPSNTKV DKRVESKYGPPCPPC PAPEFLGGPSVFLFP PKPKDTLMISRTPEV TCVVVDVSQEDPEVQ FNWYVDGVEVHNAKT KPREEQFNSTYRVVS VLTVLHQDWLNGKEY KCKVSNKGLPSSIEK TISKAKGQPREPQVY TLPPSQEEMTKNQVS LTCLVKGFYPSDIAV EWESNGQPENNYKTT PPVLDSDGSFFLYSR | GAGGTGCAGCTGGTGCAGAGCGGAGCAGAGGTG AAGAAGCCAGGGGCCAGCGTGAAGGTGAGCTGT AAGGCTAGTGGGTACACATTTACAAACTATTGG CTGGGATGGATTAAGCAGGCCCCAGGCCAAGGA CTGGAGTGGATAGGAGACATATACCCCGGAGGA GACTATATCAATTACAACGAGAAGTTCAAGGGC AAGGCCACACTCACCGCTGATACAAGCATCAGC ACCGCCTACATGGAGCTGAGCCGACTGAGAAGC GACGACACAGCAGTGTATTACTGCGCCAGACCC AACCTGCCCGGCGACTACTGGGGACAAGGCACC ACCGTGACCGTGTCTTCCgctAgcAccAAgggc ccctccgtgttccctctgccccAtgctcccggg tccAcctccgAgtccAccgccgctctgggctgt ctggtgAAggActActtccctgAgcccgtgAcc gtgAgctggAActctggcgccctgAcctccggc gtgcAcAccttccctgccgtgctgcAgtcctcc ggcctgtActccctgtcctccgtggtgAccgtg ccttcctcctccctgggcAccAAgAcctAcAcc tgcAAcgtggAccAcAAgcctccAAcAccAAg gtggAcAAgcgggtggAgtccAAgtAcggccct ccttgccctcctgccctgccctgAgttcctg ggcggAcccccgtgttcctgttccctcctAAg cctAAggAcAccctgAtgAtctcccggAccct gAggtgAcctgcgtggtggtggAcgtgtcccAg gAAgAtcctgAggtccAgttcAAttggtAcgtg gAtggcgtggAggtgcAcAAcgccAAgAcAAg cctcgggAggAAcAgttcAActccAcctAccgg |

TABLE 33-continued

Bispecific antibody comprising the anti-LAG3 clone in IgG form and
the anti-PD-L1 clone in scFvform (LAG3XPD-L1)

| | | Amino acid sequence (N'→C') | Nucleotide Sequence (5'→3') |
|---|---|---|---|
| | | LTVDKSRWQEGNVFS CSVMHEALHNHYTQK SLSLSLGK (SEQ ID NO: 542) | gAgAtgAccAagAAtcAggtgtccctgAcAtgc ctggtgAAgggcttctAcccttccgAtATCGCC AccAtctccAAggccAAgggccAgcctcgcgAg cctcAggtgtAcAcctgcctcctAgccAggAA |
| | Linker | GGGGSGGGGSGGGGS (SEQ ID NO: 543) | gAgAtgAccAagAAtcAGGtgtccctgAcAtgc ctggtgAAgggcttctAcccttccgAtATCGCC |
| | scFv of VL B6 | DIQMTQSPSSLSASV GDRVTITCKASQDVT PAVAWYQQKPGKAPK LLIYSTSSRYTGVPS RFSGSGSGTDFTFTI SSLQPEDIATYYCQQ HYTTPLTFGCGTKLE IKR (SEQ ID NO: 544) | GTGGAATGGGAGAGCAATGGCCAGCCTGAGAAC AACTACAAGACAACCCCTCCTGTGCTGGACTCC GACGGCTCCTTCTTTCTGTACTCTCGCCTGACC GTGGACAAGTCCAGATGGCAAGAGGGCAACGTG TTCTCCTGCTCCGTGATGCACGAGGCCCTGCAC AATCACTACACCCAGAAGTCCCTGTCTCTGTCC CTCGGAAAAGGCGGCGGAGGATCTGGCGGAGGC GGTAGCGGTGGTGGCGGATCTGATATTCAGATG ACCCAGTCTCCTTCCAGCCTGTCCGCTTCTGTG |
| | Linker | GGGGSGGGGSGGGGS GGGGS (SEQ ID NO: 531) | GGCGACAGAGTGACCATCACATGCAAGGCCAGC CAGGATGTGACCCCTGCTGTGGCTTGGTATCAG CAGAAGCCTGGCAAGGCCCCTAAGCTGCTGATC |
| | VH | EVQLVESGGGLVQPG GSLRLSCAASGFTFS SYDMSWVRQAPGKCL EWVATISDAGGYIYY RDSVKGRFTISRDNA KNSLYLQMNSLRDED TAVYICARELPWRYA LDYWGQGTTVTVSS* (SEQ ID NO: 549) | TACTCCACCTCCTCCAGATACACAGGCGTGCCC TCCAGATTCTCCGGCTCTGGCTCTGGCACCGAC TTTACCTTTACAATCTCCAGCCTGCAGCCTGAG GACATTGCCACCTACTACTGCCAGCAGCACTAC ACCACACCTCTGACCTTTGGCTGCGGCACCAAG CTGGAAATCAAGAGAGGTGGCGGAGGAAGCGGA GGCGGCGGTTCAGGTGGCGGTGGTTCAGGCGGT GGTGGATCTGAAGTTCAGCTGGTGGAATCTGGC GGCGGATTGGTTCAACCAGGCGGCTCTCTGAGA CTGTCTTGTGCCGCTTCCGGCTTCACCTTCTCC AGCTACGACATGTCCTGGGTCCGACAGGCCCCT GGAAAGTGTCTGGAATGGGTCGCCACCATCTCT GACGCTGGCGGCTACATCTACTACCGGGACTCT GTGAAGGGCAGATTCACCATCAGCCGGGACAAT GCCAAGAACTCCCTGTACCTGCAGATGAACAGT CTGCGCGACGAGGACACCGCCGTGTACATCTGT GCTAGAGAGCTGCCTTGGCGCTACGCCCTGGAT TATTGGGGCCAGGGCACAACAGTGACAGTGTCC TCTTGA (SEQ ID NO: 550) |
| Light chain | Light chain of 147 | DIVMTQSPLSLPVTP GEPASISCRSSKSLL HSNGITYLYWYLQKP GQSPQLLIYQVSNLA SGVPDRESGSGSGTL FTLKISRVEAEDVGV YYCAQNLELPWTFGG GTKVEIKRTVAAPSV FIFPPSDEQLKSGTA SVVCLLNNFYPREAR VQWKVDNALQSGNSQ ESVTEQDSKDSTYSL SSTLTLSKADYEKHK VYACEVTHQGLSSPV TKSFNRGEC (SEQ ID NO: 547) | GACATTGTGATGACCCAGAGCCCCCTGAGCCTC CCCGTGACCCCTGGAGAACCCGCCAGCATAAGC TGCAGATCCTCCAAAAGCCTGCTGCACTCCAAC GGAATAACCTACCTGTATTGGTACCTGGAGAAA CCCGGCCAATCCCCCAACTCCTGATATACCAA GTGTCCAACCTGGCCTCCGGCGTGCCCGACAGA TTCTCCGGCTCCGGCAGCGGTACCGACTTCACC CTCAAAATCTCCAGAGTGGAAGCAGAAGACGTC GGCGTGTAGTACTGCGCCCAGAATCTGGAACTG CCCTGGACCTTCGGCGGCGGCACCAAGGTGGAA ATCAAGAGAACCGTGGCCGCTCCCTCCGTGTTC ATCTTCCCACCATCTGACGAGCAGCTGAAGTCC GGCACCGCTTCTGTCGTGTGCCTGCTGAACAAC TTCTACCCTCGGGAAGCCAAGGTGCAGTGGAAG GTGGACAATGCCCTGCAGTCCGGCAACTCCCAA GAGTCTGTGACCGAGCAGGACTCCAAGGACAGC ACCTACTCCCTGTCCTCTACCCTGACCCTGTCC AAGGCCGACTACGAGAAGCACAAGGTGTACGCC TGCGAAGTGACCCACCAGGGACTGTCTAGCCCC GTGACCAAGTCCTTCAACAGAGGCGAGTGCTGA (SEQ ID NO: 548) |

147(H3807)xH12
(bispecific antibody comprising the anti-LAG3 147(H3807) clone in IgG form
and the anti-PD-L1 HI 2 done in ScFvform)

| | | | |
|---|---|---|---|
| Heavy Chain | Heavy chain of 147(H3807) | EVQLVQSGAEVKKPG ASVKVSCKASGYTFT NYWLGWIKQAPGQGL EWIGDIYPGGDYIVY NEKFKGKATLTADTS ISTAYMELSRLSDD TAVYYCARPNLPKDH WGQGTTVTVSSASTK GPSVFPLAPCSRSTS | GAGGTGCAGCTGGTGCAGAGCGGAGCAGAGGTG AAGAAGCCAGGGGCCAGCGTGAAGGTGAGCTGT AAGGCCACACTCACCGCTGATACAAGCATCAGC CTGGGATGGATTAAGCAGGCCCCAGGCCAGGA CTGGAGTGGATAGGAGACATATACCCCGGAGGA GACTATATCgtgTACAACGAGAAGTTCAAGGGC AAGGCCACACTCACCGCTGATACAAGCATCAGC ACCGCCTACATGGAGCTGAGCCGACTGAGAAGC GACGACACAGCAGTGTATTACTGCGCCAGACCC |

TABLE 33-continued

Bispecific antibody comprising the anti-LAG3 clone in IgG form and the anti-PD-L1 clone in scFv form (LAG3XPD-L1)

| | | Amino acid sequence (N'→C') | Nucleotide Sequence (5'→3') |
|---|---|---|---|
| | | ESTAALGCLVKDYFP EPVTVSWNSGALTSG VHTFPAVLQSSGLYS LSSVVTVPSSSLGTK TYTCNVDHKPSNTKV DKRVESKYGPPCPPC PAPEFLGGPSVFLFP PKPKDTLMISRTPEV TCVVVDVSQEDPEVQ FNWYVDGVEVHNAKT KPREEQFNSTYRVVS VLTVLHQDWLNGKEY KCKVSNKGLPSSIEK TISKAKGQPREPQVY TLPPSQEEMTKNQVS LTCLVKGFYPSDIAV EWESNGQPENNYKTT PPVLDSDGSFFLYSR LTVDKSRWQEGNVFS CSVMHEALHNHYTQK SLSLSLGK (SEQ ID NO: 551) | AACCTGCCCAAGGACCACTGGGGACAAGGCACC ACCGTGACCGTGTCTTCCgctAgcAccAAgggc ccctccgtgttccctctggccccAtgctccgg tccAcctccgAgtccAccgccgctctgggctgt ctggtgAAggActActtccctgAgcccgtgAcc gtgAgctggAActctggcgccctgAcctccggc gtgcAcAccttccctgccgtgctgcAgtcctcc ggcctgtActccctgtcctccgtggtgAccgtg ccttcctcctccctgggcAccAAgAcctAcAcc tgcAAcgtggAccAcAAgccttccAAcAccAAg gtggAcAAgcgggtggAgtccAAgtAcggccct ccttgccctccctgccctgccctgAgttcctg ggcggAccctccgtgttcctgttccctcctAAg cctAAggAcAccctgAtgAtctcccggAccccct gAggtgAcctgcgtggtggtggAcgtgtcccAg gAAgAtcctgAggtccAgttcAAttggtAcgtg gAtggcgtggAggtgcAcAAcgccAAgAccAAg cctcgggAggAAcAgttcAActccAcctAccgg gtggtgtctgtgctgAccgtgctgcAccAggAc tggctgAAcggcAAggAAtAcAAgtgcAAggtc AgcAAcAAgggcctgccctcctccAtcgAgAAA AccAtctccAAggccAAgggccAgcctcgcgAg |
| | Linker | GGGGSGGGGSGGGGS (SEQ ID NO: 543) | cctcAggtgtAcAccctgcctcctAgccAggAA gAgAtgAccAAgAAtcAggtgtccctgAcAtgc |
| | scFv of VL H12 | DIQMTQSPSSLSASV GDRVTITCKASQDVT PAVAWYQQKPGKAPK LLIYSTSSRYTGVPS RFSGSGSGTDFTFTI SSLQPEDIATYYCQQ HYTTPLTFGCGTKLE IKR (SEQ ID NO: 544) | ctggtgAAgggcttctAccccttccgAtAtcgcc gtggAgtgggAgAgcAAcggcAgccAgAgAAc AActAcAAgAccAcccctcctgtgctggActcc gAcggctccttcttcctgActccAggctgAcc gtggAcAAgtcccggtggcAggAAggcAAcgtc ttttcctgctccgtgAtgcAcgAggccctgcAc AAccActAcAcccAgAAgtccctgtccctgtct ctgggcAAgGGTGGAGGTGGTCTGGGGGTGGC |
| | Linker | GGGGSGGGGSGGGGS GGGGS (SEQ ID NO: 531) | GGGTCAGGTGGAGGAGGTTCAGACATCCAGATG ACCCAGAGCCCTAGCAGCCTGAGCGCTAGCGTG GGCGACAGGGTGACCATCACCTGCAAGGCCAGC CAGGATGTGACCCCTGCCGTGGCCTGGTACCAG |
| | VH | EVQLVESGGGLVQPG GSLRLSCAASGFTFS SYDMSWVRQAPGKCL EWVATISDAGGYIYY SDSVKGRETISRDNA KNSLYLQMNSLRDED TAVYICAREFGKRYA LDYWGQGTTVTVSS (SEQ ID NO: 545) | CAGAAGCCCGGCAAGGCCCCCAAGCTGCTGATC TACAGCACCAGCAGCAGGTACACCGGCGTGCCC AGCAGGTTTAGCGGAAGCGGCAGCGGCACCGAC TTCACCTTCACCATCAGCAGCCTGCAGCCCGAG GACATCGCCACCTACTACTGCCAGCAGCACTAC ACCACCCCTCTGACCTTCGGCtgtGGCACCAAG CTGGAGATCAAGAGAGGTGGAGGCGGCTCAGGG GGGGGTGGATCAGGGGGGAGGAGGATCAGGGGGA GGCGGTAGTGAGGTGCAGCTGGTGGAGAGCGGA GGAGGACTGGTGCAACCCGGAGGCAGCCTGAGA CTGAGCTGCGCTGCCAGCGGCTTCACCTTCAGC AGCTACGACATGAGCTGGGTGAGACAGGCCCCT GGCAAAtgtCTGGAGTGGGTGGCCACCATCTCC GATGCGGGCGGCTACATCTATTACTCCGACAGC GTGAAGGGCAGGTTCACCATCAGCAGGGACAAC GCCAAGAACAGCCTGTACCTGCAGATGAACAGC CTGAGGGATGAGGACACCGCCGTGTACATCTGC GCCAGGGAGTTCGGCAAAAGGTACGCCCTGGAC TACTGGGGCCAGGGCACAACCGTGACCGTGAGC AGCtga (SEQ ID NO: 552) |
| Light chain | Light chain of 147(H3807) | DIVMTQSPLSLPVTP GEPASISCRSSKSLL HSQGITYLYWYLQKP GQSPQLLIYQVSNLA SGVPDRFSGSGSGTD FTLKISRVEAEDVGV YYCAQYLELPWTFGG GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC* (SEQ ID NO: 553) | GACATTGTGATGACCCAGAGCCCCCTGAGCCTC CCCGTGACCCCTGGAGAACCCGCCAGCATAAGC TGCAGATCCTCCAAAAGCCTGCTGCACTCCcag GGAATAACCTACCTGTATTGGTACCTGCAGAAA CCCGGCCAATCCCCCCAACTCCTGATATACCAA GTGTCCAACCTGGCCTCCGGCGTGCCCGACAGA TTCTCCGGCTCCGGCAGCGGGTACCGACTTCACC CTCAAAATCTCCAGAGTGGAAGCAGAAGACGTC GGCGTGTACTACTGCGCCCAGtacCTGGAACTG CCCTGGACCTTCGGCGGCGGCACCAAGGTGGAA ATCAAGAGAACCGTGGCCGCTCCCTCCGTGTTC ATCTTCCCACCATCTGACGAGCAGCTGAAGTCC GGCACCGCTTCTGTCGTGTGCCTGCTGAACAAC TTCTACCCTCGGGAAGCCAAGGTGCAGTGGAAG GTGGACAATGCCCTGCAGTCCGGCAACTCCCAA GAGTCTGTGACCGAGCAGGACTCCAAGGACAGC |

TABLE 33-continued

Bispecific antibody comprising the anti-LAG3 clone in IgG form and the anti-PD-L1 clone in scFvform (LAG3XPD-L1)

| | | Amino acid sequence (N'→C') | Nucleotide Sequence (5'→3') |
|---|---|---|---|
| | | | ACCTACTCCCTGTCCTCTACCCTGACCCTGTCC AAGGCCGACTACGAGAAGCACAAGGTGTACGCC TGCGAAGTGACCCACCAGGGACTGTCTAGCCCC GTGACCAAGTCCTTCAACAGAGGCGAGTGCTGA (SEQ ID NO: 554) |

147(H3807)xB6
(bispecific antibody comprising the anti-LAG3 147(H2 3807) done in IgG form and the anti-PD-L1 B6 done in ScFv form)

| Heavy Chain | Heavy chain of 147(H3807) | EVQLVQSGAEVKKPG ASVKVSCKASGYTFT NYWLGWIKQAPGQGL EWIGDIYPGGDYIVY NEKFKGKATLTADTS ISTAYMELSRLRSDD TAVYYCARPNLPKDH WGQGTTVTVSSASTK GPSVFPLAPCSRSTS ESTAALGCLVKDYFP EPVTVSWNSGALTSG VHTFPAVLQSSGLYS LSSVVTVPSSSLGTK TYTCNVDHKPSNTKV DKRVESKYGPPCPPC PAPEFLGGPSVFLFP PKPKDTLMISRTPEV TCVVVDVSQEDPEVQ FNWYVDGVEVHNAKT KPREEQFNSTYRVVS VLTVLHQDWLNGKEY KCKVSNKGLPSSIEK TISKAKGQPREPQVY TLPPSQEEMTKNQVS LTCLVKGFYPSDIAV EWESNGQPENNYKTT PPVLDSDGSFFLYSR LTVDKSRWQEGNVFS CSVMHEALHNHYTQK SLSLSLGK (SEQ ID NO: 551) | GAGGTGCAGCTGGTGCAGAGCGGAGCAGAGGTG AAGAAGCCAGGGGCCAGCGTGAAGGTGAGCTGT AAGGCTAGTGGGTACACATTTACAAACTATTGG CTGGGATGGATTAAGCAGGCCCCAGGCCAAGGA CTGGAGTGGATAGGAGACATATACCCCGGAGGA GACTATATCgtgTACAACGAGAAGTTCAAGGGC AAGGCCACACTCACCGCTGATACAAGCATCAGC ACCGCCTACATGGAGCTGAGCCGACTGAGAAGC GACGACACAGTGTATTACTGCGCCAGACCC AACCTGCCCAAGGACCACTGGGGACAAGGCACC ACCGTGACCGTGTCTTCCgctAgcAccAAgggc ccctccgtgttccctctggccccAtgctcccgg tccAcctccgAgtccAccgccgctctgggctgt ctggtgAAggActActtccctgAgcccgtgAcc gtgAgctggAActctggcgccctgAcctccggc gtgcAccttccctgccgtgctgcAgtcctcc ggcctgtActccctgtcctccgtggtgAccgtg ccttcctcctccctgggcAccAAgAcctAcAcc tgcAAcgtggAccAcAAgccttccAAcAccAAg gtggAcAAgcgggtggAgtccAAgtAcggccct ccttgccctcctgcctgccctgAgttcctg ggcggAccctccgtgttcctgttccctcctAAg cctAAggAcAccctgAtgAtctcccggAccct gAggtgAcctgcgtggtggtggAcgtgtcccAg gAAgAtcctgAggtccAgttcAAttggtAcgtg gAtggcgtggAggtgcAcAAcgccAAgAccAAg cctcgggAggAAcAgttcAActccAcctAccgg gtggtgtctgtgctgAccgtgctgcAccAggAc tggctgAAcggcAAggAAtAcAAgtgcAAggtc AgcAAcAAgggcctgcctcctccAtcgAgAAA AccAtctccAAggccAAgggccAgcctcgcgAg cctcAggtgtAcAccctgcctcctAgccAggAA gAgAtgAccAAgAAtcAggtgtccctgAcAtgc ctggtgAAgggcttctAccctTccgAtATCGCC |
| | Linker | GGGGSGGGGSGGGGS (SEQ ID NO: 543) | |
| | scFv of VL B6 | DIQMTQSPSSLSASV GDRVTITCKASQDVT PAVAWYQQKPGKAPK LLIYSTSSRYTGVPS RFSGSGSGTDFTFTI SSLQPEDIATYYCQQ HYTTPLTFGCGTKLE IKR (SEQ ID NO: 544) | GTGGAATGGGAGAGCAATGGCCAGCCTGAGAAC AACTACAAGACAACCCCTCCTGTGCTGGACTCC GACGGCTCCTTCTTTCTGTACTCTCGCCTGACC GTGGACAAGTCCAGATGGCAAGAGGGCAACGTG TTCTCCTGCTCCGTGATGCACGAGGCCCTGCAC AATCACTACACCCAGAAGTCCCTGTCTCTGTCC CTCGGAAAAGGCGGCGGAGGATCTGGCGGAGGC GGTAGCGGTGGTGGCGGATCTGATATTCAGATG |
| | Linker | GGGGSGGGGSGGGGS GGGGS (SEQ ID NO: 531) | ACCCAGTCTCCTTCCAGCCTGTCCGCTTCTGTG GGCGACAGAGTGACCATCACATGCAAGGCCAGC CAGGATGTGACCCCTGCTGTGGCTTGGTATCAG |
| | VH | EVQLVESGGGLVQPG GSLRLSCAASGFTFS SYDMSWVRQAPGKCL EWVATISDAGGYIYY RDSVKGRFTISRDNA KNSLYLQMNSLRDED TAVYICARELPWRYA LDYWGQGTTVTVSS* (SEQ ID NO: 549) | CAGAAGCCTGGCAAGGCCCCTAAGCTGCTGATC TACTCCACCTCCTCCAGATACACAGGCGTGCCC TCCAGATTCTCCGGCTCTGGCTCTGGCACCGAC TTTACCTTTACAATCTCCAGCCTGCAGCCTGAG GACATTGCCACCTACTACTGCCAGCAGCACTAC ACCACACCTCTGACCTTTGGCTGCGGCACCAAG CTGGAAATCAAGAGAGGTGGCGGAGGAAGCGGA GGCGGCGGTTCAGGTGGCGGTGGTTCAGGCGGT GGTGGATCTGAAGTTCAGCTGGTGGAATCTGGC GGCGGATTGGTTCAACCAGGCGGCTCTCTGAGA CTGTCTTGTGCCGCTTCCGGCTTCACCTTCTCC AGCTACGACATGTCCTGGGTCCGACAGGCCCCT GGAAAGTGTCTGGAATGGGTCGCCACCATCTCT GACGCTGGCGGCTACATCTACTACCGGGACTCT GTGAAGGGCAGATTCACCATCAGCCGGGACAAT GCCAAGAACTCCCTGTACCTGCAGATGAACAGT CTGCGCGACGAGGACACCGCCGTGTACATCTGT |

TABLE 33-continued

Bispecific antibody comprising the anti-LAG3 clone in IgG form and
the anti-PD-L1 clone in scFvform (LAG3XPD-L1)

| | | Amino acid sequence (N'→C') | Nucleotide Sequence (5'→3') |
|---|---|---|---|
| | | | GCTAGAGAGCTGCCTTGGCGCTACGCCCTGGAT TATTGGGGCCAGGGCACAACAGTGACAGTGTCC TCTTGA (SEQ ID NO: 555) |
| Light chain | Light chain of 147(H3807) | DIVMTQSPLSLPVTP GEPASISCRSSKSLL HSQGITYLYWYLQKP GQSPQLLIYQVSNLA SGVPDRFSGSGSGTD FTLKISRVEAEDVGV YYCAQYLELPWTFGG GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC* (SEQ ID NO: 553) | GACATTGTGATGACCCAGAGCCCCCTGAGCCTC CCCGTGACCCCTGGAGAKCCCGCCAGCATAAGC TGCAGATCCTCCAAAAGCCTGCTGCACTCCcag GGAATAACCTACCTGTATTGGTACCTGCAGAAA CCCGGCCAATCCCCCCAACTCCTGATATACCAA GTGTCCAACCTGGCCTCCGGCGTGCCCGACAGA TTCTCCGGCTCCGGCAGCGGTACCGACTTCACC CTCAAAATCTCCAGAGTGGAAGCAGAAGACGTC GGCGTGTACTACTGCGCCCAGtAcCTGGAACTG CCCTGGACCTTCGGCGGCGGCACCAAGGTGGAA ATCAAGAGAACCGTGGCCGCTCCCTCCGTGTTC ATCTTCCCACCATCTGACGAGCAGCTGAAGTCC GGCACCGCTTCTGTCGTGTGCCTGCTGAACAAC TTCTACCCTCGGGAAGCCAAGGTGCAGTGGAAG GTGGACAATGCCCTGCAGTCCGGCAACTCCCAA GAGTCTGTGACCGAGCAGGACTCCAAGGACAGC ACCTACTCCCTGTCCTCTACCCTGACCCTGTCC AAGGCCGACTACGAGAAGCACAAGGTGTACGCC TGCGAAGTGACCCACCAGGGACTGTCTAGCCCC GTGACGAAGTCCTTCAACAGAGGCGAGTGCTGA (SEQ ID NO: 554) |

The constructed vectors were transiently expressed in ExpiCHO-S™ cells (Chinese hamster ovary cells) (Thermo Fisher Scientific®, A29127) using ExpiFectamine™ CHO Transfection Kit (Thermo Fisher Scientific®, A29129), cultured in ExpiCHO™ Expression medium (Thermo Fisher Scientific®, A29100-01) under the conditions of 30 to 37° C. for 7 to 15 days in a C02 incubator equipped with rotating shaker. Plasmid DNA (250 µg) and ExpiFectamin™ CHO Reagent (800 µL) were mixed with Opti-MEM® I medium (Minimal Essential Medium) (20 mL final volume) and allowed to stand at room temperature for 5 min. The mixed solution was added to 6×10⁶ ExpiCHO™ cells cultured in ExpiCHO™ Expression Medium and gently mixed in a shaker incubator at 37° C. with a humidified atmosphere of 8% C02 in air. At 18 hours post-transfection, 1 0.5 mL of ExpiFectamin™ CHO Transfection Enhancer 1 and 60 mL of ExpiFectamin™ CHO Transfection Feed were added to each flask.

Each BsAb was purified from the cell culture supernatant by recombinant Protein A affinity chromatography (Hitrap Mabselect Sure, GE® Healthcare, 28-4082-55) and gel filtration chromatography with a HiLoad® 26/200 Superdex® 200 prep grade size exclusion chromatography column (GE® Healthcare, 28-9893-36). SDS-PAGE (NuPage® 4-12% Bis-Tris gel, NP0321) and size exclusion HPLC (Agilent®, 1200 series) analysis with SE-HPLC column (SWXL SE-HPLC column, TOSOH®, G3000SWXL) were performed to detect and confirm the size and purity of each BsAb. Purified proteins were concentrated in PBS by ultrafiltration using a Amicon Ultra 15 30K device (Merck®, UFC903096), and protein concentrations were estimated using a Nanodrop® spectrophotometer (Thermo Fisher Scientific®, Nanodrop® One). When a two-vector system is applied, the ratio between light to heavy chain could be 1:1 to 1:3 by weight. Alternatively, a one-vector system that contains both chains in one single vector can also be used.

The prepared anti-PD-L1/anti-LAG3 bispecific antibodies are named as H12×147, H12×147(H3807), B6×147, and B6×147(H3807), 147×H12, 147(H3807)×H12, 147×B6, and 147(H3807)×B6, respectively, wherein the former refers to the clone in the IgG form and the latter refers to the clone in the scFv form.

Example 4. Characterization of Bispecific Antibodies H12×147 and 147×H12

4.1. Binding of the Bispecific Antibodies

To evaluate the binding activity to PD-L1 and LAG3 of the bispecific antibodies (BsAb; H12×147 and 147×H12) prepared in Example 3, the BsAb were subjected to ELISA test. Briefly, microtiter plates were coated with each of human PD-L1-Fc protein (Sinobio, 10084-H02H) and human LAG3-His protein (Sinobio, 16498-H08H) at 0.5 µg/ml in PBS, 100 µl/well at 4° C. overnight, then blocked with 100 µl/well of 5% BSA. Four-fold dilutions of each of the BsAbs starting from 100 nM were added to each well and incubated for 1-2 hours at RT. The plates were washed with PBS/Tween® and then incubate with goat-anti-human IgG antibody conjugated with Horse Radish Peroxidase (HRP) (Pierce™, cat #31413) for 1 hour at RT. After washing, the plates were developed with TMB substrate and analyzed by spectrophotometer at OD 450-630 nm. The results are shown in FIG. 33. As shown in FIG. 33, all the BsAbs tested can bind to both of human PD-L1 and human LAG3 proteins with high activities.

4.2. Binding Affinity of Bispecific Antibodies

The binding affinities of bispecific antibodies PD-L1 and LAG3 of the bispecific antibodies (BsAb; 147×H12, 147H3807×B6 and B6×147H3807) prepared in Example 3 to PD-L1 protein and human LAG3 protein were tested with BIACORE™ using a capture method.

The results are shown in Table 34.

TABLE 34

| Antibody | Human PD-L1 (KD (M)) | Human LAG3 (KD (M)) |
|---|---|---|
| 147xH12 | 2.74E-08 | 1.35E-08 |
| 147H3807xB6 | 5.94E-09 | 1.63E-09 |
| B6x147H3807 | 1.18E-09 | 8.87E-09 |

As shown in Table 34 and FIG. 33, the bispecific antibody tested display relatively high binding affinities to both of human PD-L1 and human LAG3 proteins.

Figure 34:
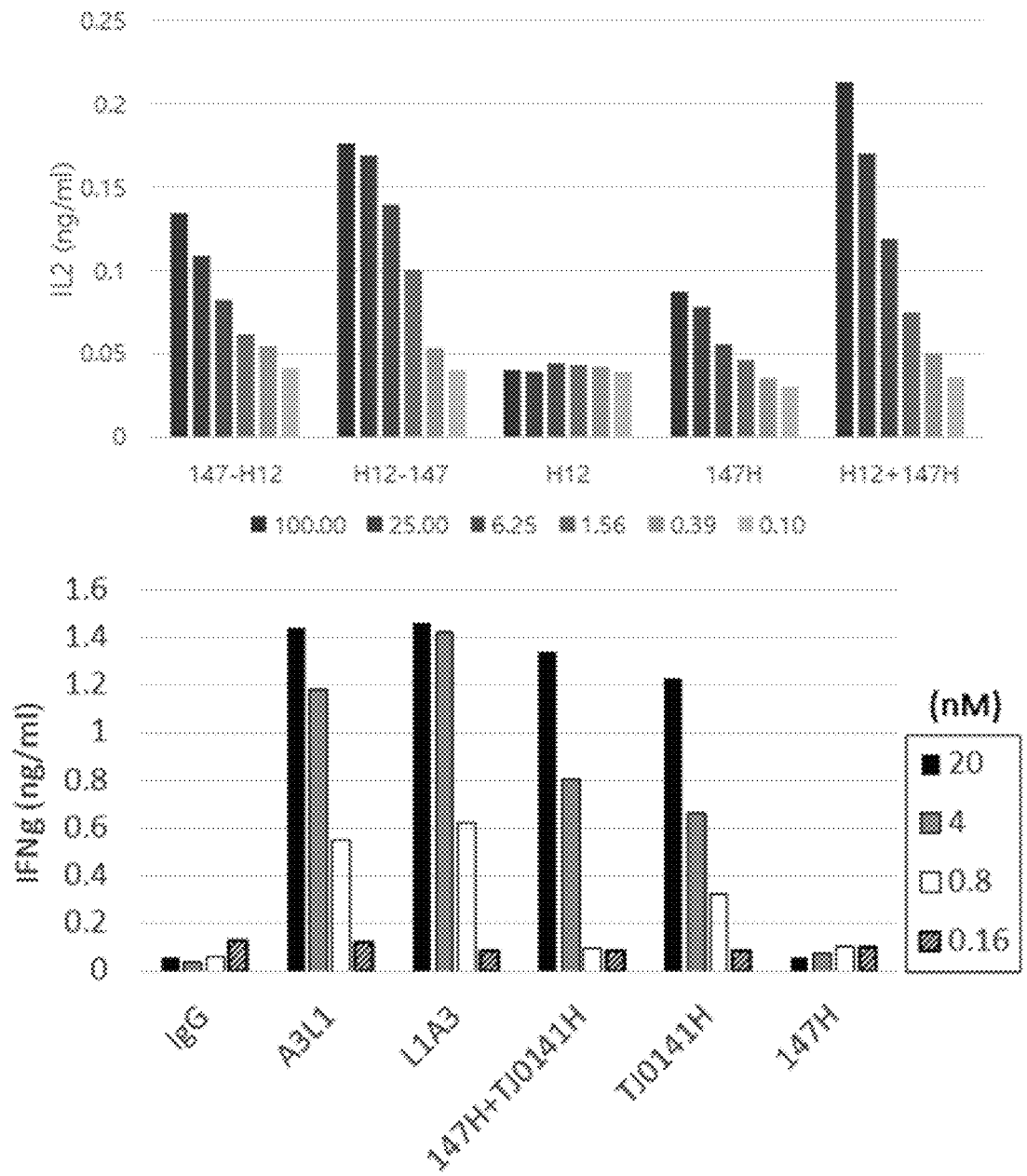
FIG. 34 shows the SEE assay results for the anti-PD-L1/anti-LAG3 bispecific antibody according to an embodiment. It also shows graphs illustrating the T-cell promoting activities of the anti-PD-L1/anti-LAG3 bispecific antibody according to an embodiment.

In addition, SEE assay was conducted, and the obtained results are shown in FIG. 34, the results indicating that the bispecific antibody tested inhibits the binding between MHC II and LAG3, thereby increasing T cell activity by MHC II and TCR.

4.3. Activity of the Bispecific Antibodies to Promote Human T Cell Immune Response To test the ability of bispecific antibodies to stimulated T cell response, Jurkat cell activation assay was used. Jurkat cells transfected with human Lag3 and Pd1 by lentivirus were used as the responder cells. Raji cells which overexpressed PDL1 was used as the antigen presenting cells (APC). Staphylococcal enterotoxins E (SEE) are superantigen, which was used as the stimulator in this assay. In this system, ectopically expressed huLAG3 and huPD-1 can suppress SE stimulated IL-2 production by Jurkat cells, while anti-LAG3 and anti-PD-L1 antibodies can reverse IL-2 production. In short, Raji ($1 \times 10^4$) were co-cultured with Jurkat T cells ($1 \times 10^5$) in the presence of superantigen. Bispecific antibodies and their counterpart monoantibodies (starting from 100 nM diluted for 6 dose) were added to the mixed culture. 48 hrs later, supernatant was collected for IL2 production. As shown in FIG. 34 (upper panel), bispecific antibodies (147xH12 (labeled as 147-H12) and H12x147 (labeled as H12-147)) can dose dependently promote IL2 production by Jurkat cells.

To further evaluate in vitro function of bispecific antibodies towards primary T cells, mixed lymphocyte reaction was performed. Human dendritic cells (DCs) were differentiated from CD14+ monocytes in the presence of GM-CSF and IL-4 for 7 days. CD4+ T cells isolated from another donor were then co-cultured with the DCs and serially diluted antibodies. 5 days after mixed culture, the culture supernatant was assayed for IFNγ production. The results in FIG. 34 (lower panel) indicated that both bispecific antibodies (147xH12 (labeled as A3L1) and H12x147 (labeled as L1A3) can significantly promote IFNγ production.

4.4. Tumor Growth Inhibition of the Bispecific Antibodies (In Vivo Assay)

Double humanized mice that express the extracellular domain of human PD-1 and human LAG3 were used. Mouse colon adenocarcinoma cells (MC38) were engineered to express human PD-L1. Double humanized mice (hLAG3/hPD-1) were subcutaneously implanted with $5 \times 10^5$ MC38-hPD-L1 cells on day 0. On day 10, mice with an average tumor volume of 137 mm³ were selected and randomized into four treatment groups (N=7/group). Mouse were intraperitoneally administered isotype control (5 mg/kg), H12 (anti-PD-L1 antibody, 5 mg/kg), 147H (anti-LAG3 antibody, 5 mg/kg) and 147xH12 (6.6 mg/kg) every other day for 8 doses, starting from day 10.

Figure 35:
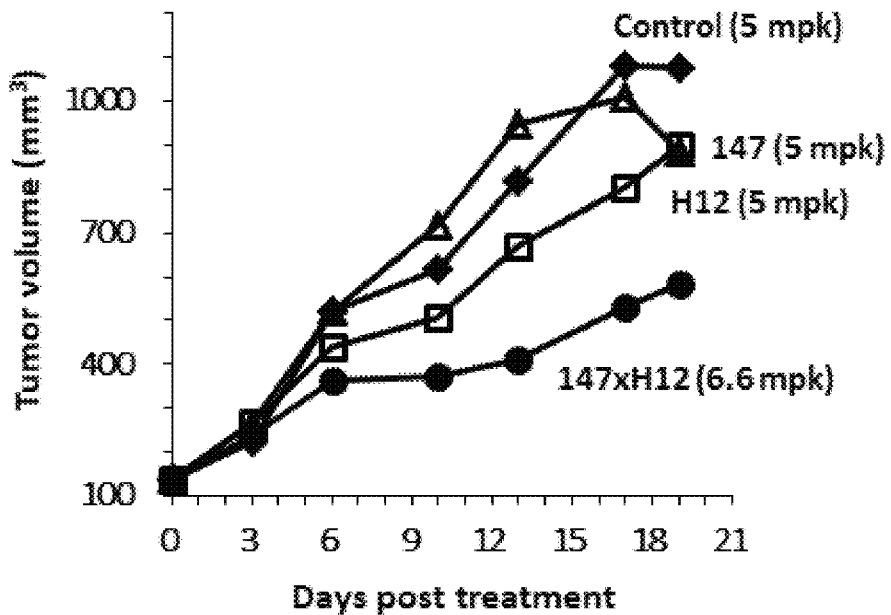
FIG. 35 shows a graph illustrating tumor growth inhibition effect of the anti-PD-L1/anti-LAG3 bispecific antibody according to an embodiment.

Tumor volumes were monitored by caliper measurement twice per week for the duration of the experiment (29 days). Neither H12 nor 147H showed tumor inhibition at 5 mg/kg. By contrast, 147xH12 demonstrated robust inhibition of MC38 tumor growth, with a TGI of 67.7% at the end of the study (FIG. 35).

Example 5. Characterization of Bispecific Antibodies 147xH12 and 147(H3807)xH12

5.1. Binding of the Bispecific Antibodies

To evaluate the binding activity to LAG3 of the bispecific antibodies (BsAb; 147xH12 and 147(H3807)xH12) prepared in Example 3, the BsAbs were subjected to ELISA test. Briefly, microtiter plates were coated with human LAG3-His protein (Sinobio, 16498-H08H) at 0.5 µg/ml in PBS, 100 µl/well at 4° C. overnight, then blocked with 100 µl/well of 5% BSA. Four-fold dilutions of each of the BsAbs starting from 100 nM were added to each well and incubated for 1-2 hours at RT. The plates were washed with PBS/Tween® and then incubate with goat-anti-human IgG antibody conjugated with Horse Radish Peroxidase (HRP) (Pierce™, cat #31413) for 1 hour at RT. After washing, the plates were developed with TMB substrate and analyzed by spectrophotometer at OD 450-630 nm. As shown in FIG. 33, the BsAbs 147(H3807)xH12 displays more improved binding activity to human LAG3 protein.

Figure 36:
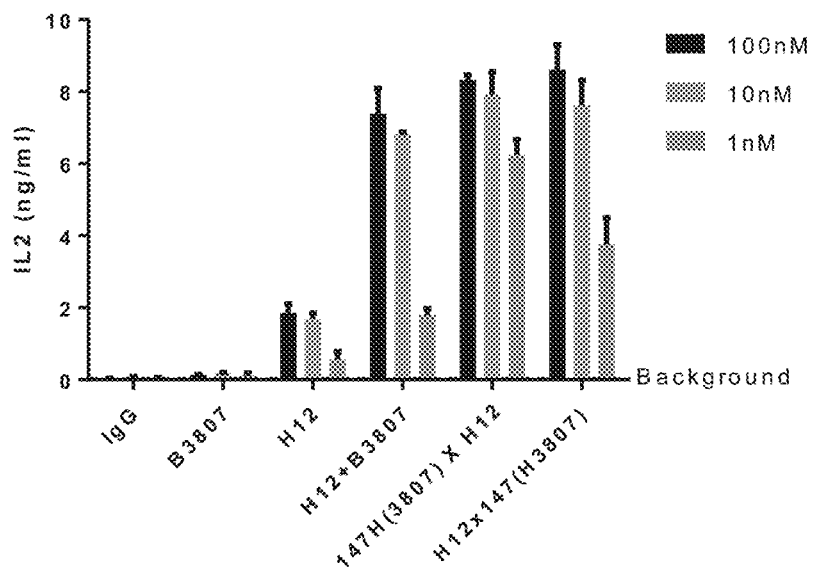
FIG. 36 shows graphs illustrating the T-cell promoting activities of the anti-PD-L1/anti-LAG3 bispecific antibody according to an embodiment.

5.2. Activity of the Bispecific Antibodies to Promote Human T Cell Immune Response The effect of bispecific antibodies prepared in Example 3 was further studied using PBMCs from healthy donors. In brief, human DCs were differentiated from CD14+ monocytes for 7 days. Purified CD4+ T cells isolated from another donor was stimulated by anti-CD3/CD28 for 2 days. Serially diluted antibodies were then added to DC and T cell co-culture in the presence of superantigen and incubated for 5 days and the culture medium was collected for IL-2 level. As showed in FIG. 36, bispecific antibodies could significantly stimulate IL-2 production in primary CD4+ T cells, which was superior than combination of their corresponding monoantibodies. Data are shown as mean values from triplicate wells ±SD.

Figure 37:
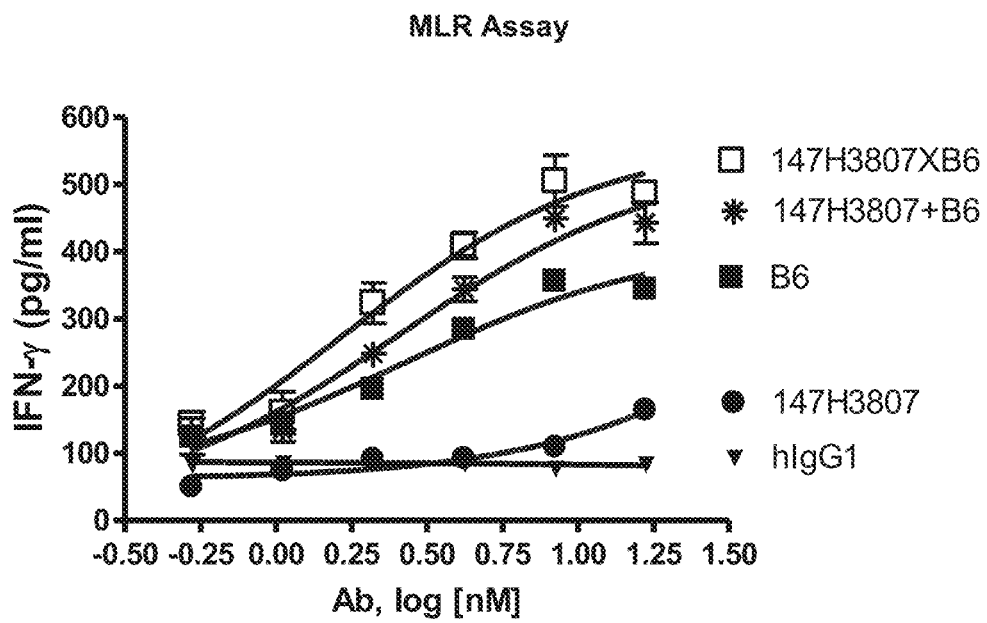
FIG. 37 shows graphs illustrating the T-cell promoting activities of the anti-PD-L1/anti-LAG3 bispecific antibody according to an embodiment.

Moreover, the effect of bispecific antibodies prepared in Example 3 was studied using PBMCs from healthy donors. In brief, human DCs were differentiated from CD14+ monocytes for 5 days, followed by LPS treatment for maturation. Pan T cells were isolated from another donor PBMC. Serially diluted antibodies were then added to mature DC and T cell co-culture and incubated for 5 days and the culture medium was collected for IFNγ level. As showed in FIG. 37, bispecific antibodies could significantly stimulate IFNγ production in primary pan T cells, which was superior than combination of their corresponding monoantibodies. Data are shown as mean values from duplicate wells ±SD.

5.3. Developability of Bispecific Antibodies

The developability regarding the physicochemical properties to PD-L1 and LAG-3 bispecific antibodies (BsAb; B6x147H3807 and 147(H3807)xB6) was assessed. The quality attributes for the BsAbs were evaluated by several analytical methods. Briefly, the purity was measured by Size exclusion-high performance liquid chromatography (SE-HPLC) and both of the BsAbs showed the high purity over 99%. The thermal stability by Protein thermal shift (PTS) with fluorescence labeled Real time-polymerase chain reaction (RT-PCR) was analyzed. Their melting temperature was observed over 67° C. which indicated that the test articles have stable structural integrity. To evaluate solubility of the molecules, the proteins were concentrated to 20 mg/mL using ultrafiltration (Amicon Ultra-15 spin concentrator). As a result, the visible particles were not observed by visual inspection and no increment of aggregates was confirmed by SE-HPLC. The Isoelectric point (pI) of each bsabs measured by capillary isoelectric focusing (cIEF) were 8.26 and 8.35, respectively. This pI range is appropriate to proceed downstream process and formulation development. Overall, as shown in Table 19. It showed that the tested BsAbs(B6× 147H3807 and 147(H3807)×B6) have proper physicochemical properties for the successful development.

TABLE 35

| Content | Method | B6×147H3807 | 147(H3807)×B6 |
|---|---|---|---|
| Purity | SEC | 99.8 | 99.8 |
| Thermal Stability | PTS | 61.8 77.7 | 62.0 71.6 |
| Solubility | Visual inspection | Easy to concentrate up to 20 mg/mL, clear | Easy to concentrate up to 20 mg/mL, clear |
| pI | cIEF | 8.56 | 7.65 |

Example 6. The Effect of B3807 on Inhibition of the Binding of FGL1 to LAG3

This example tested the anti-LAG3 antibody B3807's activity in inhibiting the binding between LAG3 and Fibrinogen-like Protein 1 (FGL1).

It was recently reported that Fibrinogen-like Protein 1 (FGL1) is another functional ligand of LAG3, apart from MHC-II (Cell. 2019; 176:1-14). FGL-1 is secreted from liver and highly produced by cancer cells. FGL-1 inhibits antigen-specific T cell activation and inversely, blockade of FGL-1 potentiates anti-tumor response. Interaction between FGL-1 and LAG3 may represent another mechanism for immune evasion.

Figure 47:
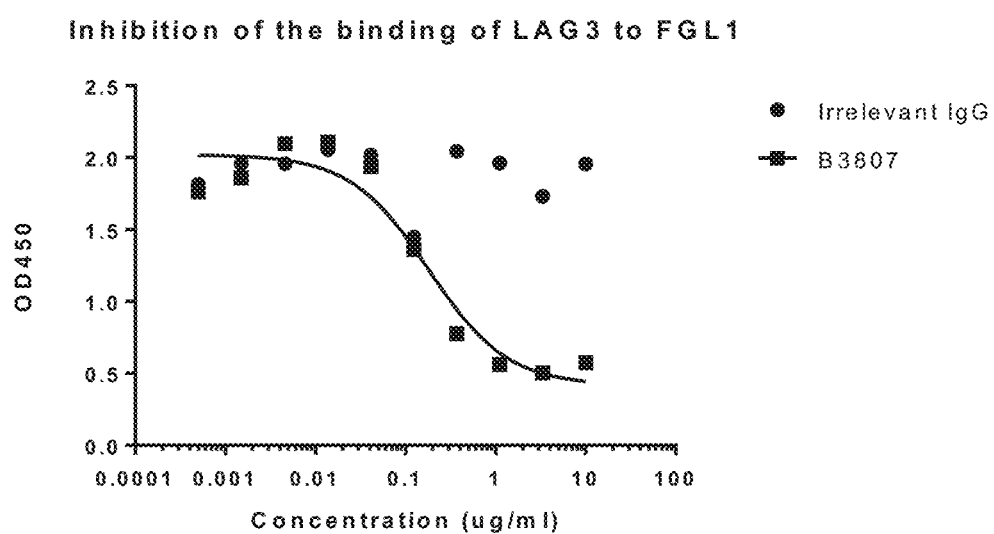
FIG. 47 demonstrates that B3807 effectively inhibited the binding between soluble LAG-3 and FGL1.

Recombinant FGL-1 were coated on a 96 well plated at a concentration of 1 µg/ml and incubated overnight at 4° C. Serially diluted anti-LAG3 antibody B3807 (starting from 10 µg/ml and 1:3 dilution) and biotin-labeled LAG3-ECD (2 µg/ml) were incubated with FGL-1 coated wells at room temperature for 2 hours. After extensive washing with the wash buffer, streptavidin-HRP was added. As shown in FIG. 47, B3807 dose-dependently inhibited the binding of FGL-1 to LAG3 protein.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. An anti-PD-L1/anti-LAG3 bispecific antibody, comprising an anti-PD-L1 antibody or an antigen-binding fragment thereof and an anti-LAG3 antibody or an antigen-binding fragment thereof, wherein
the anti-PD-L1 antibody or antigen-binding fragment thereof comprises:
a VH CDR1 having the amino acid sequence of SEQ ID NO: 1; a VH CDR2 having the amino acid sequence of SEQ ID NO: 525; a VH CDR3 having the amino acid sequence of SEQ ID NO: 3; a VL CDR1 having the amino acid sequence of SEQ ID NO: 4; a VL CDR2 having the amino acid sequence of SEQ ID NO: 5; and a VL CDR3 having the amino acid sequence of SEQ ID NO: 6; or
a VH CDR1 having the amino acid sequence of SEQ ID NO: 1; a VH CDR2 having the amino acid sequence of SEQ ID NO: 526; a VH CDR3 having the amino acid sequence of SEQ ID NO: 515; a VL CDR1 having the amino acid sequence of SEQ ID NO: 4; a VL CDR2 having the amino acid sequence of SEQ ID NO: 5; and a VL CDR3 having the amino acid sequence of SEQ ID NO: 6; and
the anti-LAG3 antibody or antigen-binding fragment thereof comprises;
a VH CDR1 having the amino acid sequence of SEQ ID NO: 354; a VH CDR2 having the amino acid sequence of SEQ ID NO: 355; a VH CDR3 having the amino acid sequence of SEQ ID NO: 356; a VL CDR1 having the amino acid sequence of SEQ ID NO: 357; a VL CDR2 having the amino acid sequence of SEQ ID NO: 358; and a VL CDR3 having the amino acid sequence of SEQ ID NO: 359; or
a VH CDR1 having the amino acid sequence of SEQ ID NO: 354; a VH CDR2 having the amino acid sequence of SEQ ID NO: 461; a VH CDR3 having the amino acid sequence of SEQ ID NO: 468; a VL CDR1 having the amino acid sequence of SEQ ID NO: 490; a VL CDR2 having the amino acid sequence of SEQ ID NO: 358; and a VL CDR3 having the amino acid sequence of SEQ ID NO: 488.

2. The anti-PD-L1/anti-LAG3 bispecific antibody of claim 1, wherein the anti-PD-L1 antibody or antigen-binding fragment thereof comprises a heavy chain variable region comprising the amino acid sequence selected from the group consisting of SEQ ID NOS: 20, 501, 545, and 549, or a polypeptide having at least 90% sequence identity to the amino acid sequence selected from the group consisting of SEQ ID NOS: 20, 501, 545, and 549.

3. The anti-PD-L1/anti-LAG3 bispecific antibody of claim 1, wherein the anti-PD-L1 antibody or antigen-binding fragment thereof comprises a light chain variable region comprising the amino acid sequence selected from the group consisting of SEQ ID NOS: 27-33, 494, 500, 502, 504, 506, 508, 510, 512, and 544, or a peptide having at least 90% sequence identity to the amino acid sequence selected from the group consisting of SEQ ID NOS: 27-33, 494, 500, 502, 504, 506, 508, 510, 512, and 544.

4. The anti-PD-L1/anti-LAG3 bispecific antibody of claim 1, wherein the anti-LAG3 antibody or antigen-binding fragment thereof comprises a heavy chain variable region comprising the amino acid sequence selected from the group consisting of SEQ ID NOS: 352, 360-373, 391, 393, 395, 397, 399, 421, 429, 443, 445, 491, 532, and 537, or a polypeptide having at least 90% sequence identity to the amino acid sequence selected from the group consisting of SEQ ID NOS: 352, 360-373, 391, 393, 395, 397, 399, 421, 429, 443, 445, 491, 532, and 537.

5. The anti-PD-L1/anti-LAG3 bispecific antibody of claim 1, wherein the anti-LAG3 antibody or antigen-binding fragment thereof comprises a light chain variable region comprising the amino acid sequence selected from the group consisting of SEQ ID NOS: 353, 374, 444, 530, and 536, or a peptide having at least 90% sequence identity to the amino acid sequence selected from the group consisting of SEQ ID NOS: 353, 374, 444, 530, and 536.

6. A pharmaceutical composition for treating a disease associated with PD-L1, LAG3, or both thereof, comprising the anti-PD-L1/anti-LAG3 bispecific antibody of claim 1 and a pharmaceutically acceptable carrier.

7. The pharmaceutical composition of claim 6, wherein the disease associated with PD-L1, LAG3, or both thereof is cancer or infection.

8. The pharmaceutical composition of claim 7, wherein the cancer is a solid tumor.

9. The pharmaceutical composition of claim 7, wherein the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

* * * * *